(12) United States Patent
Penaflor-Aspuria et al.

(10) Patent No.: US 11,648,296 B2
(45) Date of Patent: May 16, 2023

(54) IL-2 ORTHOLOGS AND METHODS OF USE

(71) Applicant: Synthekine, Inc., Menlo Park, CA (US)

(72) Inventors: Paul-Joseph Penaflor-Aspuria, Redwood City, CA (US); Scott Alan McCauley, San Francisco, CA (US); Martin Oft, Palo Alto, CA (US); Steve Kauder, San Carlos, CA (US)

(73) Assignee: Synthekine, Inc., Menlo Park, CA (US)

( * ) Notice: Subject to any disclaimer, the term of this patent is extended or adjusted under 35 U.S.C. 154(b) by 162 days.

(21) Appl. No.: 17/119,923

(22) Filed: Dec. 11, 2020

(65) Prior Publication Data

US 2021/0196796 A1 Jul. 1, 2021

Related U.S. Application Data

(60) Provisional application No. 62/948,066, filed on Dec. 13, 2019.

(51) Int. Cl.
*A61K 38/20* (2006.01)
*C07K 14/55* (2006.01)
*C12N 15/85* (2006.01)
*A61K 39/395* (2006.01)
*C12N 5/0783* (2010.01)
*A61K 35/17* (2015.01)

(52) U.S. Cl.
CPC .......... *A61K 38/2013* (2013.01); *A61K 35/17* (2013.01); *A61K 39/3955* (2013.01); *C07K 14/55* (2013.01); *C12N 5/0636* (2013.01); *C12N 15/85* (2013.01)

(58) Field of Classification Search
CPC .......................... C07K 14/55; A61K 38/2013
See application file for complete search history.

(56) References Cited

U.S. PATENT DOCUMENTS

| | | | |
|---|---|---|---|
| 4,902,502 A | 2/1990 | Nitecki | |
| 5,037,644 A | 8/1991 | Shaked et al. | |
| 6,955,807 B1 | 10/2005 | Shanafelt | |
| 10,869,887 B2 | 12/2020 | Garcia et al. | |
| 11,439,664 B2 | 9/2022 | Garcia et al. | |
| 2003/0166163 A1 | 9/2003 | Gillies et al. | |
| 2003/0171267 A1 | 9/2003 | Rosen | |
| 2006/0199250 A1 | 9/2006 | Zhao et al. | |
| 2011/0250213 A1 | 10/2011 | Tsao et al. | |
| 2013/0017168 A1 | 1/2013 | Gillies et al. | |
| 2014/0255360 A1 | 9/2014 | Spencer et al. | |
| 2014/0349402 A1 | 11/2014 | Cooper et al. | |
| 2018/0228842 A1 | 8/2018 | Garcia et al. | |
| 2019/0083635 A1 | 3/2019 | Xie et al. | |
| 2020/0024319 A1 | 1/2020 | Butz et al. | |
| 2021/0069243 A1 | 3/2021 | Garcia et al. | |

FOREIGN PATENT DOCUMENTS

| | | |
|---|---|---|
| JP | 2005-511707 A | 4/2005 |
| WO | 1999-047178 A1 | 9/1999 |
| WO | 2003-048334 A2 | 6/2003 |
| WO | 2005-086751 A2 | 9/2005 |
| WO | 2016/025385 A1 | 2/2016 |
| WO | 2017-044464 A1 | 3/2017 |
| WO | 2019-173773 A1 | 9/2019 |
| WO | 2020/131547 A1 | 6/2020 |

OTHER PUBLICATIONS

Bork P. Powers and pitfalls in sequence analysis: the 70% hurdle. Genome research. Apr. 1, 2000;10(4):398-400.
Bowie et al. Deciphering the message in protein sequences: tolerance to amino acid substitutions. Science. Mar. 16, 1990;247(4948):1306-10.
Burgess et al. Possible dissociation of the heparin-binding and mitogenic activities of heparin-binding (acidic fibroblast) growth factor-1 from its receptor-binding activities by site-directed mutagenesis of a single lysine residue. The Journal of Cell Biology. Nov. 1990; 111(5):2129-38.
Calvello et al. Conservation/Mutation in the splice sites of cytokine receptor genes of mouse and human. International journal of evolutionary biology. 2013;2013.
Cochran et al. Improved mutants from directed evolution are biased to orthologous substitutions. Protein Engineering, Design and Selection. Jun. 1, 2006;19(6):245-53.
Ho et al. Decoupling the functional pleiotropy of stem cell factor by tuning c-Kit signaling. Cell. Mar. 9, 2017;168(6):1041-52.
Imler et al. Identification of three adjacent amino acids of interleukin-2 receptor beta chain which control the affinity and the specificity of the interaction with interleukin-2. The EMBO Journal. Jun. 1992;11(6):2047-53.
Lazar et al. Transforming growth factor alpha: mutation of aspartic acid 47 and Teucine 48 results in different biological activities. Molecular and Cellular Biology. Mar. 1988;8(3):1247-52.
Mitra et al. Interleukin-2 activity can be fine tuned with engineered receptor signaling clamps. Immunity. May 19, 2015;42(5):826-38.
Ring et al. Mechanistic and structural insight into the functional dichotomy between IL-2 and IL-15. Nature immunology. Dec. 2012;13(12):1187-95.

(Continued)

*Primary Examiner* — Prema M Mertz
(74) *Attorney, Agent, or Firm* — Kilpatrick Townsend & Stockton LLP

(57) ABSTRACT

The present disclosure relates to hIL2 orthogonal ligands ("IL2 orthologs") that specifically and selectively bind to the extracellular domain (ECD) a transmembrane polypeptide comprising of a modified hCD122 polypeptide. The binding of the hIL2 ortholog to the modified hCD122 polypeptide participates in the transduction pathway of intracellular signaling resulting in a biological activity of the native intracellular signaling patterns associated with hIL2 binding to either the intermediate or high affinity hIL2 receptor but which exhibits selectivity to an engineered cell expressing an hCD122 orthogonal receptor. The hIL2 orthologs of the present invention exhibit significantly reduced binding relative to their binding to the extracellular domain of wild type hCD122, either alone or when hCD122 is present in the form of an endogenous high or intermediate affinity hIL2 receptors.

2 Claims, 2 Drawing Sheets
Specification includes a Sequence Listing.

(56) References Cited

OTHER PUBLICATIONS

Shi et al. A novel cytokine receptor-ligand pair: identification, molecular characterization, and in vivo immunomodulatory activity. Journal of Biological Chemistry. Jun. 23, 2000;275(25):19167-76.
Sockolosky et al. Selective targeting of engineered T cells using orthogonal IL-2 cytokine-receptor complexes. Science. Mar. 2, 2018;359(6379):1037-42.
Wang et al. Structure of the Quaternary Complex of Interleukin-2 with Its α, β, and γc Receptors. Science. Nov. 18, 2005;310(5751):1159-63.
International Search Report in PCT/US2020/064677, dated Jun. 11, 2021, 5 pages.

| Dilution | cRPMI | | Vector | | wt IL2 | | Ortho SQVLKA | | -QVLKA | | S-VLKA | |
|---|---|---|---|---|---|---|---|---|---|---|---|---|
| 1:2 | 4582 | 5502 | 7372 | 8334 | 59986 | 19396 | 30464 | 15150 | 49218 | 21842 | 33692 | 5742 |
| 1:4 | 4714 | 4316 | 3044 | 3668 | 12746 | 13468 | 11098 | 11066 | 31776 | 34946 | 6288 | 8070 |
| 1:8 | 4516 | 4176 | 5760 | 6734 | 28444 | 9692 | 9602 | 9554 | 56882 | 73468 | 6924 | 7742 |
| 1:16 | 4504 | 4334 | 4926 | 8212 | 6472 | 7176 | 7026 | 7336 | 142450 | 75880 | 7868 | 5462 |
| 1:32 | 4272 | 4132 | 7118 | 8280 | 5382 | 5682 | 5978 | 5832 | 122808 | 124322 | 7696 | 5210 |
| 1:64 | 4348 | 4804 | 5720 | 6360 | 4798 | 5088 | 5206 | 5142 | 105022 | 137826 | 6660 | 6216 |
| 1:128 | 4108 | 3988 | 5602 | 5622 | 5056 | 4622 | 4914 | 4778 | 59304 | 117444 | 7696 | 5312 |
| 1:256 | 3866 | 3620 | 4102 | 4934 | 3836 | 4026 | 4342 | 4150 | 55526 | 57762 | 4496 | 5202 |

| Dilution | SQ-LKA | | SQV-KA | | SQVL-A | | SQVLK- | | SQ--- | | SQVL-- | |
|---|---|---|---|---|---|---|---|---|---|---|---|---|
| 1:2 | 10764 | 13306 | 47696 | 46348 | 51424 | 49952 | 13970 | 17548 | 16084 | 17372 | 9548 | 10946 |
| 1:4 | 9400 | 8222 | 46432 | 45610 | 59212 | 49680 | 10534 | 10292 | 11614 | 15426 | 9022 | 7298 |
| 1:8 | 7054 | 6610 | 43264 | 67642 | 58170 | 78272 | 7700 | 7174 | 7758 | 7268 | 5318 | 5902 |
| 1:16 | 6204 | 6436 | 55630 | 57530 | 49876 | 50880 | 6478 | 5880 | 6946 | 6406 | 5562 | 5494 |
| 1:32 | 6256 | 6150 | 55312 | 55912 | 63280 | 78256 | 5922 | 5196 | 6210 | 5776 | 5166 | 5406 |
| 1:64 | 5184 | 5834 | 52090 | 49596 | 46482 | 67102 | 5216 | 4948 | 5940 | 5280 | 4712 | 5692 |
| 1:128 | 5004 | 5564 | 48420 | 45432 | 45584 | 48968 | 6814 | 4372 | 5528 | 5610 | 4474 | 5536 |
| 1:256 | 4582 | 4898 | 34646 | 35200 | 36750 | 38390 | 5084 | 4090 | 4856 | 4194 | 4022 | 3864 |

| Dilution | E15S | | H16Q | | L19V | | D20L | | Q22K | | M23A | |
|---|---|---|---|---|---|---|---|---|---|---|---|---|
| 1:2 | 55892 | 47318 | 47334 | 46676 | 47674 | 81520 | 55876 | 44486 | 42676 | 57192 | 34236 | 71222 |
| 1:4 | 58318 | 69066 | 63932 | 76272 | 53646 | 62220 | 32440 | 39404 | 54496 | 55070 | 49604 | 64798 |
| 1:8 | 52790 | 53136 | 65906 | 53744 | 54926 | 53008 | 25266 | 26438 | 53660 | 64794 | 99422 | 56882 |
| 1:16 | 52778 | 51862 | 61672 | 52938 | 69172 | 53090 | 20922 | 19774 | 55288 | 68238 | 62768 | 57410 |
| 1:32 | 53860 | 52056 | 53886 | 53486 | 55092 | 54306 | 16396 | 16948 | 59236 | 54700 | 49510 | 62506 |
| 1:64 | 74250 | 52570 | 53740 | 52760 | 53490 | 53484 | 13888 | 13578 | 55508 | 55886 | 48394 | 55166 |
| 1:128 | 49874 | 51810 | 59880 | 51668 | 52660 | 51362 | 10976 | 10758 | 49452 | 50652 | 60894 | 53280 |
| 1:256 | 49050 | 46764 | 49806 | 49412 | 45868 | 44574 | 7402 | 8066 | 50556 | 47254 | 60946 | 59830 |

FIGURE 1

| Dilution | cRPMI | | Vector | | wt IL2 | | SQVLKA | | SQ---- | | SQVL-- | |
|---|---|---|---|---|---|---|---|---|---|---|---|---|
| 1:2 | 2666 | 3148 | 2950 | 3476 | 41162 | 38624 | 7118 | 17448 | 52618 | 53136 | 25228 | 31626 |
| 1:4 | 1698 | 2792 | 3876 | 4800 | 48786 | 45854 | 12276 | 14314 | 56536 | 116136 | 25802 | 24276 |
| 1:8 | 1634 | 2352 | 3362 | 4422 | 47422 | 42624 | 10078 | 10440 | 62520 | 100868 | 43468 | 19542 |
| 1:16 | 1622 | 2376 | 2900 | 3800 | 47830 | 47588 | 6874 | 6832 | 57362 | 53676 | 17938 | 13476 |
| 1:32 | 1560 | 2352 | 3114 | 3940 | 49522 | 47238 | 5140 | 4560 | 60008 | 60754 | 8844 | 8582 |
| 1:64 | 1638 | 2378 | 2922 | 3664 | 51976 | 51758 | 2708 | 3424 | 63328 | 65272 | 6610 | 6610 |
| 1:128 | 1324 | 1694 | 2658 | 3454 | 46496 | 38448 | 2954 | 2798 | 58076 | 54914 | 4586 | 3510 |
| 1:256 | 1356 | 1890 | 2340 | 2820 | 40836 | 38378 | 2570 | 2168 | 54902 | 52958 | 3312 | 2760 |

| Dilution | -QVLKA | | S-VLKA | | SQ-LKA | | SQV-KA | | SQVL-A | | SQVLK- | |
|---|---|---|---|---|---|---|---|---|---|---|---|---|
| 1:2 | 27860 | 26694 | 32376 | 39778 | 18214 | 18440 | 44696 | 44806 | 18164 | 22326 | 30462 | 30164 |
| 1:4 | 27078 | 28510 | 29854 | 35212 | 16900 | 17688 | 56056 | 66316 | 16604 | 18740 | 24370 | 24036 |
| 1:8 | 21790 | 19682 | 22476 | 23392 | 9924 | 10036 | 55412 | 53920 | 11258 | 10776 | 16958 | 19096 |
| 1:16 | 15852 | 14168 | 17246 | 17918 | 6462 | 7212 | 56762 | 56182 | 7532 | 8468 | 12810 | 12750 |
| 1:32 | 10352 | 9946 | 11578 | 12016 | 4428 | 4976 | 53884 | 54960 | 5304 | 4704 | 7778 | 8474 |
| 1:64 | 6540 | 6442 | 7734 | 7872 | 3402 | 4014 | 49418 | 49494 | 4112 | 3664 | 4928 | 5896 |
| 1:128 | 4318 | 3974 | 4920 | 5204 | 2996 | 3378 | 39968 | 40972 | 3472 | 2910 | 3498 | 3588 |
| 1:256 | 2668 | 2590 | 3142 | 3130 | 2530 | 2708 | 32954 | 30902 | 2676 | 2324 | 2464 | 2344 |

| Dilution | E15S | | H16Q | | L19V | | D20L | | Q22K | | M23A | |
|---|---|---|---|---|---|---|---|---|---|---|---|---|
| 1:2 | 37836 | 31900 | 36490 | 36266 | 38304 | 59930 | 30120 | 28990 | 47732 | 68380 | 68260 | 49560 |
| 1:4 | 51694 | 46472 | 64182 | 51028 | 53174 | 52014 | 31652 | 50990 | 88958 | 61880 | 75688 | 86020 |
| 1:8 | 65172 | 47002 | 77768 | 52702 | 69270 | 89708 | 39540 | 31698 | 55850 | 48910 | 67274 | 54922 |
| 1:16 | 54266 | 46466 | 56022 | 80314 | 71858 | 74098 | 22654 | 19582 | 127496 | 81180 | 83420 | 94216 |
| 1:32 | 50374 | 47988 | 54360 | 51512 | 53692 | 68826 | 13190 | 13768 | 61896 | 66682 | 71432 | 78414 |
| 1:64 | 49978 | 58592 | 50462 | 51136 | 52308 | 65382 | 9024 | 9220 | 54220 | 61146 | 53978 | 63666 |
| 1:128 | 52480 | 63522 | 51174 | 51986 | 51450 | 52204 | 6108 | 6122 | 53766 | 47934 | 61958 | 50838 |
| 1:256 | 55904 | 47146 | 50528 | 53008 | 50066 | 49420 | 4024 | 4532 | 68434 | 49338 | 55482 | 54446 |

FIGURE 2

SEQUENCE LISTING

```
<160> NUMBER OF SEQ ID NOS: 438

<210> SEQ ID NO 1
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser Asp Phe Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
    210

<210> SEQ ID NO 2
<211> LENGTH: 524
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 2

```
Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65              70                  75                  80

Arg Val Leu Cys Arg Glu Gly Val Arg Trp Arg Val Met Ala Ile Gln
            85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser Asp Phe Phe Glu Arg His Leu Glu Phe Glu Ala Arg
130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
            195                 200                 205

Ala Leu Gly Lys Asp Thr Ile Pro Trp Leu Gly His Leu Leu Val Gly
        210                 215                 220

Leu Ser Gly Ala Phe Gly Phe Ile Ile Leu Val Tyr Leu Leu Ile Asn
225                 230                 235                 240

Cys Arg Asn Thr Gly Pro Trp Leu Lys Lys Val Leu Lys Cys Asn Thr
                245                 250                 255

Pro Asp Pro Ser Lys Phe Phe Ser Gln Leu Ser Ser Glu His Gly Gly
            260                 265                 270

Asp Val Gln Lys Trp Leu Ser Ser Pro Phe Pro Ser Ser Ser Phe Ser
            275                 280                 285

Pro Gly Gly Leu Ala Pro Glu Ile Ser Pro Leu Glu Val Leu Glu Arg
290                 295                 300

Asp Lys Val Thr Gln Leu Leu Leu Gln Gln Asp Lys Val Pro Glu Pro
305                 310                 315                 320

Ala Ser Leu Ser Ser Asn His Ser Leu Thr Ser Cys Phe Thr Asn Gln
                325                 330                 335

Gly Tyr Phe Phe Phe His Leu Pro Asp Ala Leu Glu Ile Glu Ala Cys
            340                 345                 350

Gln Val Tyr Phe Thr Tyr Asp Pro Tyr Ser Glu Glu Asp Pro Asp Glu
        355                 360                 365

Gly Val Ala Gly Ala Pro Thr Gly Ser Ser Pro Gln Pro Leu Gln Pro
370                 375                 380

Leu Ser Gly Glu Asp Asp Ala Tyr Cys Thr Phe Pro Ser Arg Asp Asp
385                 390                 395                 400
```

```
Leu Leu Leu Phe Ser Pro Ser Leu Gly Gly Pro Ser Pro Pro Ser
            405                 410                 415

Thr Ala Pro Gly Gly Ser Gly Ala Gly Glu Arg Met Pro Pro Ser
            420                 425                 430

Leu Gln Glu Arg Val Pro Arg Asp Trp Asp Pro Gln Pro Leu Gly Pro
        435                 440                 445

Pro Thr Pro Gly Val Pro Asp Leu Val Asp Phe Gln Pro Pro Glu
    450                 455                 460

Leu Val Leu Arg Glu Ala Gly Glu Glu Val Pro Asp Ala Gly Pro Arg
465                 470                 475                 480

Glu Gly Val Ser Phe Pro Trp Ser Arg Pro Pro Gly Gln Gly Glu Phe
                485                 490                 495

Arg Ala Leu Asn Ala Arg Leu Pro Leu Asn Thr Asp Ala Tyr Leu Ser
                500                 505                 510

Leu Gln Glu Leu Gln Gly Gln Asp Pro Thr His Leu
            515                 520

<210> SEQ ID NO 3
<211> LENGTH: 524
<212> TYPE: PRT
<213> ORGANISM: Homo sapiens

<400> SEQUENCE: 3

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr Ile Pro Trp Leu Gly His Leu Leu Val Gly
    210                 215                 220

Leu Ser Gly Ala Phe Gly Phe Ile Ile Leu Val Tyr Leu Leu Ile Asn
225                 230                 235                 240
```

```
Cys Arg Asn Thr Gly Pro Trp Leu Lys Lys Val Leu Lys Cys Asn Thr
            245                 250                 255

Pro Asp Pro Ser Lys Phe Phe Ser Gln Leu Ser Ser Glu His Gly Gly
            260                 265                 270

Asp Val Gln Lys Trp Leu Ser Ser Pro Phe Pro Ser Ser Ser Phe Ser
            275                 280                 285

Pro Gly Gly Leu Ala Pro Glu Ile Ser Pro Leu Glu Val Leu Glu Arg
            290                 295                 300

Asp Lys Val Thr Gln Leu Leu Gln Gln Asp Lys Val Pro Glu Pro
305                 310                 315                 320

Ala Ser Leu Ser Ser Asn His Ser Leu Thr Ser Cys Phe Thr Asn Gln
            325                 330                 335

Gly Tyr Phe Phe Phe His Leu Pro Asp Ala Leu Glu Ile Glu Ala Cys
            340                 345                 350

Gln Val Tyr Phe Thr Tyr Asp Pro Tyr Ser Glu Glu Asp Pro Asp Glu
            355                 360                 365

Gly Val Ala Gly Ala Pro Thr Gly Ser Ser Pro Gln Pro Leu Gln Pro
            370                 375                 380

Leu Ser Gly Glu Asp Asp Ala Tyr Cys Thr Phe Pro Ser Arg Asp Asp
385                 390                 395                 400

Leu Leu Leu Phe Ser Pro Ser Leu Leu Gly Gly Pro Ser Pro Pro Ser
            405                 410                 415

Thr Ala Pro Gly Gly Ser Gly Ala Gly Glu Arg Met Pro Pro Ser
            420                 425                 430

Leu Gln Glu Arg Val Pro Arg Asp Trp Asp Pro Gln Pro Leu Gly Pro
            435                 440                 445

Pro Thr Pro Gly Val Pro Asp Leu Val Asp Phe Gln Pro Pro Pro Glu
            450                 455                 460

Leu Val Leu Arg Glu Ala Gly Glu Glu Val Pro Asp Ala Gly Pro Arg
465                 470                 475                 480

Glu Gly Val Ser Phe Pro Trp Ser Arg Pro Pro Gly Gln Gly Glu Phe
            485                 490                 495

Arg Ala Leu Asn Ala Arg Leu Pro Leu Asn Thr Asp Ala Tyr Leu Ser
            500                 505                 510

Leu Gln Glu Leu Gln Gly Gln Asp Pro Thr His Leu
            515                 520

<210> SEQ ID NO 4
<211> LENGTH: 133
<212> TYPE: PRT
<213> ORGANISM: Homo sapiens

<400> SEQUENCE: 4

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80
```

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 5
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Pro Thr Ser Ser Ser Thr Lys Lys Thr Gln Leu Gln Leu Ser Gln Leu
1               5                   10                  15

Leu Val Leu Leu Lys Ala Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
        130

<210> SEQ ID NO 6
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Pro Thr Ser Ser Ser Thr Lys Lys Thr Gln Leu Gln Leu Ser His
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95
```

```
Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 7
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Pro Thr Ser Ser Ser Thr Lys Lys Thr Gln Leu Gln Leu Ser Gln
1               5                   10                  15

Leu Leu Leu Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 8
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Pro Thr Ser Ser Ser Thr Lys Lys Thr Gln Leu Gln Leu Ser Gln
1               5                   10                  15

Leu Leu Val Asp Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110
```

```
Thr Ile Val Glu Phe Leu Asn Arg Trp Ile Thr Phe Cys Gln Ser Ile
        115                 120                 125

Ile Ser Thr Leu Thr
    130

<210> SEQ ID NO 9
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Pro Thr Ser Ser Ser Thr Lys Lys Thr Gln Leu Gln Leu Ser Gln
1               5                   10                  15

Leu Leu Val Leu Leu Gln Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 10
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Pro Thr Ser Ser Ser Thr Lys Lys Thr Gln Leu Gln Leu Ser Gln
1               5                   10                  15

Leu Leu Val Leu Leu Lys Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125
```

Ile Ser Thr Leu Thr
    130

<210> SEQ ID NO 11
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ala Pro Thr Ser Ser Ser Thr Lys Lys Thr Gln Leu Gln Leu Ser His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 12
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Pro Thr Ser Ser Ser Thr Lys Lys Thr Gln Leu Gln Leu Glu Gln
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 13
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Pro Thr Ser Ser Ser Thr Lys Lys Thr Gln Leu Gln Leu Glu His
1               5                   10                  15

Leu Leu Val Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 14
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Pro Thr Ser Ser Ser Thr Lys Lys Thr Gln Leu Gln Leu Glu His
1               5                   10                  15

Leu Leu Leu Leu Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 15

<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Pro Thr Ser Ser Ser Thr Lys Lys Thr Gln Leu Gln Leu Glu His
1               5                   10                  15
Leu Leu Leu Asp Leu Lys Met Ile Leu Asn Gly Ile Asn Asn Tyr Lys
                20                  25                  30
Asn Pro Lys Leu Thr Arg Met Leu Thr Phe Lys Phe Tyr Met Pro Lys
            35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr
        130

<210> SEQ ID NO 16
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Pro Thr Ser Ser Ser Thr Lys Lys Thr Gln Leu Gln Leu Glu His
1               5                   10                  15
Leu Leu Leu Asp Leu Gln Ala Ile Leu Asn Gly Ile Asn Asn Tyr Lys
                20                  25                  30
Asn Pro Lys Leu Thr Arg Met Leu Thr Phe Lys Phe Tyr Met Pro Lys
            35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr
        130

<210> SEQ ID NO 17
<211> LENGTH: 133
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 17

Ala Pro Thr Ser Ser Ser Thr Lys Lys Thr Gln Leu Gln Leu Ser Gln
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 18
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Pro Thr Ser Ser Ser Thr Lys Lys Thr Gln Leu Gln Leu Ser Gln
1               5                   10                  15

Leu Leu Val Leu Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 19
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 19

```
Ala Pro Thr Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 20
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Pro Thr Ser Ser Thr Lys Lys Thr Gln Leu Gln Leu Ser Gln Leu
1               5                   10                  15

Leu Val Leu Leu Lys Ala Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
        130
```

<210> SEQ ID NO 21
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Ala Thr Ser Ser Ser Thr Lys Lys Thr Gln Leu Gln Leu Ser Gln Leu
1               5                   10                  15

Leu Val Leu Leu Lys Ala Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
    130
```

<210> SEQ ID NO 22
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Ala Pro Ser Ser Thr Lys Lys Thr Gln Leu Gln Leu Ser Gln Leu
1               5                   10                  15

Leu Val Leu Leu Lys Ala Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
    130
```

<210> SEQ ID NO 23
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

Ala Pro Cys Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 24
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Pro Ala Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 25
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Pro Gly Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 26
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Pro Gln Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 27
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ala Pro Glu Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 28
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ala Pro Asn Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 29
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Ala Pro Asp Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130
```

<210> SEQ ID NO 30
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Ala Pro Arg Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130
```

<210> SEQ ID NO 31
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Ala Pro Lys Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 32
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Ala Pro Pro Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 33
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Ala Pro Thr Ser Ser Thr Lys Lys Thr Gln Leu Gln Leu Ser Gln Leu
1               5                   10                  15

Leu Val Leu Leu Lys Ala Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
                115                 120                 125

Ser Thr Leu Thr
    130

<210> SEQ ID NO 34
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ala Pro Thr Ser Ser Thr Lys Lys Thr Gln Leu Gln Leu Ser Gln Leu
1               5                   10                  15

Leu Val Leu Leu Lys Ala Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
                115                 120                 125

Ser Thr Leu Thr
    130

<210> SEQ ID NO 35
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ala Pro Thr Ser Ser Thr Lys Lys Thr Gln Leu Gln Leu Ser Gln Leu
1               5                   10                  15

Leu Val Leu Leu Lys Ala Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
    130

<210> SEQ ID NO 36
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ala Pro Thr Ser Ser Lys Lys Thr Gln Leu Gln Leu Ser Gln Leu
1               5                   10                  15

Leu Val Leu Leu Lys Ala Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
    130

<210> SEQ ID NO 37
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ala Pro Thr Ser Ser Ser Thr Lys Thr Gln Leu Gln Leu Ser Gln Leu
1               5                   10                  15

Leu Val Leu Leu Lys Ala Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
    130

<210> SEQ ID NO 38
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Pro Thr Ser Ser Ser Thr Lys Thr Gln Leu Gln Leu Ser Gln Leu
1               5                   10                  15

Leu Val Leu Leu Lys Ala Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
    130

<210> SEQ ID NO 39
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Ala Pro Thr Ser Ser Thr Lys Lys Thr Gln Leu Leu Ser Gln Leu
1               5                   10                  15

Leu Val Leu Leu Lys Ala Ile Leu Asn Gly Ile Asn Asn Tyr Lys Asn
            20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Leu Lys Pro
 50                  55                  60

Leu Glu Glu Val Leu Asn Leu Ala Gln Ser Lys Asn Phe His Leu Arg
65                   70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Cys Gln Ser Ile Ile
                115                 120                 125

Ser Thr Leu Thr
        130
```

<210> SEQ ID NO 40
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Ala Pro Thr Ser Ser Thr Lys Lys Thr Gln Leu Trp Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
65                   70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
        130
```

<210> SEQ ID NO 41
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

Ala Pro Thr Ser Ser Thr Lys Lys Thr Gln Leu Gln Ser Gln Leu
1               5                   10                  15

Leu Val Leu Leu Lys Ala Ile Leu Asn Gly Ile Asn Asn Tyr Lys Asn
            20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Cys Gln Ser Ile Ile
                115                 120                 125

Ser Thr Leu Thr
            130

<210> SEQ ID NO 42
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ala Pro Thr Ser Ser Thr Lys Lys Thr Gln Leu Gln Met Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
            130

<210> SEQ ID NO 43
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ala Pro Thr Ser Ser Ser Thr Lys Lys Thr Gln Leu Gln Trp Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 44
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ala Pro Thr Ser Ser Ser Thr Lys Lys Thr Gln Leu Gln Leu Lys Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 45
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ala Pro Thr Ser Ser Ser Thr Lys Lys Thr Gln Leu Gln Leu Thr Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 46
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ala Pro Thr Ser Ser Ser Thr Lys Lys Thr Gln Leu Gln Leu Ser Leu
1               5                   10                  15

Leu Val Leu Leu Lys Ala Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
    130

<210> SEQ ID NO 47
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ala Pro Thr Ser Ser Ser Thr Lys Lys Thr Gln Leu Gln Leu Ser Asn
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 48
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ala Pro Thr Ser Ser Ser Thr Lys Lys Thr Gln Leu Gln Leu Ser Gln
1               5                   10                  15

Leu Gly Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 49
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ala Pro Thr Ser Ser Ser Thr Lys Lys Thr Gln Leu Gln Leu Ser Gln
1               5                   10                  15

Leu Met Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 50
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ala Pro Thr Ser Ser Ser Thr Lys Lys Thr Gln Leu Gln Leu Ser Gln
1               5                   10                  15

Leu Phe Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 51
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ala Pro Thr Ser Ser Ser Thr Lys Lys Thr Gln Leu Gln Leu Ser Gln
1               5                   10                  15

Leu Glu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 52
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ala Pro Thr Ser Ser Ser Thr Lys Lys Thr Gln Leu Gln Leu Ser Gln
1               5                   10                  15

Leu His Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 53
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ala Pro Thr Ser Ser Ser Thr Lys Lys Thr Gln Leu Gln Leu Ser Gln
1               5                   10                  15

Leu Trp Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 54
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Ala Pro Thr Ser Ser Ser Thr Lys Lys Thr Gln Leu Gln Leu Ser Gln
1               5                   10                  15

Leu Lys Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 55
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Ala Pro Thr Ser Ser Ser Thr Lys Lys Thr Gln Leu Gln Leu Ser Gln
1               5                   10                  15

Leu Gln Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 56
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Ala Pro Thr Ser Ser Ser Thr Lys Lys Thr Gln Leu Gln Leu Ser Gln
1               5                   10                  15

Leu Ser Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 57
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 57

Ala Pro Thr Ser Ser Thr Lys Lys Thr Gln Leu Gln Leu Ser Gln
1               5                   10                  15

Leu Val Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 58
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Ala Pro Thr Ser Ser Thr Lys Lys Thr Gln Leu Gln Leu Ser Gln
1               5                   10                  15

Leu Ile Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 59
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 59

Ala Pro Thr Ser Ser Thr Lys Lys Thr Gln Leu Gln Leu Ser Gln
1               5                   10                  15

Leu Tyr Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 60
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Ala Pro Thr Ser Ser Thr Lys Lys Thr Gln Leu Gln Leu Ser Gln
1               5                   10                  15

Leu His Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 61
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ala Pro Thr Ser Ser Ser Thr Lys Lys Thr Gln Leu Gln Leu Ser Gln
1               5                   10                  15

Leu Asp Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 62
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ala Pro Thr Ser Ser Ser Thr Lys Lys Thr Gln Leu Gln Leu Ser Gln
1               5                   10                  15

Leu Thr Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 63
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Ala Pro Thr Ser Ser Thr Lys Lys Thr Gln Leu Gln Leu Ser Gln
1               5                   10                  15

Leu Leu Leu Leu Lys Ala Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
    130
```

<210> SEQ ID NO 64
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 64

```
Ala Pro Thr Ser Ser Thr Lys Lys Thr Gln Leu Gln Leu Ser Gln
1               5                   10                  15

Leu Leu Ile Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 65
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

```
Ala Pro Thr Ser Ser Thr Lys Lys Thr Gln Leu Gln Leu Ser Gln
1               5                   10                  15

Leu Leu Val Leu Lys Ala Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
            115                 120                 125

Ser Thr Leu Thr
    130
```

<210> SEQ ID NO 66
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Ala Pro Thr Ser Ser Thr Lys Lys Thr Gln Leu Gln Leu Ser Gln
1               5                   10                  15

Leu Leu Val Ser Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
    130
```

<210> SEQ ID NO 67
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

Ala Pro Thr Ser Ser Ser Thr Lys Lys Thr Gln Leu Gln Leu Ser Gln
1               5                   10                  15

Leu Leu Val Leu Leu Phe Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 68
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ala Pro Thr Ser Ser Ser Thr Lys Lys Thr Gln Leu Gln Leu Ser Gln
1               5                   10                  15

Leu Leu Val Leu Leu Glu Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 69
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ala Pro Thr Ser Ser Thr Lys Lys Thr Gln Leu Gln Leu Ser Gln
1               5                   10                  15

Leu Leu Val Leu Leu Gly Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 70
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ala Pro Thr Ser Ser Thr Lys Lys Thr Gln Leu Gln Leu Ser Gln
1               5                   10                  15

Leu Leu Val Leu Leu Ala Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 71
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Ala Pro Thr Ser Ser Ser Thr Lys Lys Thr Gln Leu Gln Leu Ser Gln
1               5                   10                  15

Leu Leu Val Leu Leu Leu Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 72
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ala Pro Thr Ser Ser Ser Thr Lys Lys Thr Gln Leu Gln Leu Ser Gln
1               5                   10                  15

Leu Leu Val Leu Leu Met Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 73
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Ala Pro Thr Ser Ser Ser Thr Lys Lys Thr Gln Leu Gln Leu Ser Gln
1               5                   10                  15

Leu Leu Val Leu Leu Phe Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 74
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Ala Pro Thr Ser Ser Ser Thr Lys Lys Thr Gln Leu Gln Leu Ser Gln
1               5                   10                  15

Leu Leu Val Leu Leu Trp Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 75
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Ala Pro Thr Ser Ser Thr Lys Lys Thr Gln Leu Gln Leu Ser Gln
1               5                   10                  15

Leu Leu Val Leu Leu Ser Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 76
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Ala Pro Thr Ser Ser Thr Lys Lys Thr Gln Leu Gln Leu Ser Gln
1               5                   10                  15

Leu Leu Val Leu Leu Val Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 77
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Ala Pro Thr Ser Ser Thr Lys Lys Thr Gln Leu Gln Leu Ser Gln
1               5                   10                  15

Leu Leu Val Leu Leu Ile Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 78
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Ala Pro Thr Ser Ser Thr Lys Lys Thr Gln Leu Gln Leu Ser Gln
1               5                   10                  15

Leu Leu Val Leu Leu Tyr Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 79
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Ala Pro Thr Ser Ser Ser Thr Lys Lys Thr Gln Leu Gln Leu Ser Gln
1               5                   10                  15

Leu Leu Val Leu Leu His Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 80
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Ala Pro Thr Ser Ser Ser Thr Lys Lys Thr Gln Leu Gln Leu Ser Gln
1               5                   10                  15

Leu Leu Val Leu Leu Arg Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 81
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Ala Pro Thr Ser Ser Thr Lys Lys Thr Gln Leu Gln Leu Ser Gln
1               5                   10                  15

Leu Leu Val Leu Leu Asn Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 82
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ala Pro Thr Ser Ser Thr Lys Lys Thr Gln Leu Gln Leu Ser Gln
1               5                   10                  15

Leu Leu Val Leu Leu Asp Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 83
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Ala Pro Thr Ser Ser Ser Thr Lys Lys Thr Gln Leu Gln Leu Ser Gln
1               5                   10                  15

Leu Leu Val Leu Leu Thr Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 84
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Ala Pro Thr Ser Ser Ser Thr Lys Lys Thr Gln Leu Gln Leu Ser Gln
1               5                   10                  15

Leu Leu Val Leu Leu Lys Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
    130

<210> SEQ ID NO 85
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Ala Pro Thr Ser Ser Thr Lys Lys Thr Gln Leu Gln Leu Ser Gln
1               5                   10                  15

Leu Leu Val Leu Leu Lys Trp Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 86
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Ala Pro Thr Ser Ser Thr Lys Lys Thr Gln Leu Gln Leu Ser Gln
1               5                   10                  15

Leu Leu Val Leu Leu Lys His Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 87
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Ala Pro Thr Ser Ser Ser Thr Lys Lys Thr Gln Leu Gln Leu Ser Gln
1               5                   10                  15

Leu Leu Val Leu Leu Lys Tyr Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 88
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Ala Pro Thr Ser Ser Ser Thr Lys Lys Thr Gln Leu Gln Leu Ser Gln
1               5                   10                  15

Leu Leu Val Leu Leu Lys Phe Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 89
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Ala Pro Thr Ser Ser Thr Lys Lys Thr Gln Leu Gln Leu Ser Gln
1               5                   10                  15

Leu Leu Val Leu Leu Lys Gln Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 90
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Ala Pro Thr Ser Ser Thr Lys Lys Thr Gln Leu Gln Leu Ser Gln
1               5                   10                  15

Leu Leu Val Leu Leu Lys Ser Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 91
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Ala Pro Thr Ser Ser Thr Lys Lys Thr Gln Leu Gln Leu Ser Gln
1               5                   10                  15

Leu Leu Val Leu Leu Lys Val Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 92
<211> LENGTH: 133
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 92

Ala Pro Thr Ser Ser Thr Lys Lys Thr Gln Leu Gln Leu Ser Gln
1               5                   10                  15

Leu Leu Val Leu Leu Lys Leu Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 93
<211> LENGTH: 133
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 93

Ala Pro Thr Ser Ser Ser Thr Lys Lys Thr Gln Leu Gln Leu Ser Gln
1               5                   10                  15

Leu Leu Val Leu Leu Lys Thr Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 94
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
            115                 120                 125

Ser Thr Leu Thr
        130

<210> SEQ ID NO 95
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Lys Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 96
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Ser Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 97
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Trp Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 98
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Gly Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 99
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Leu Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 100
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Val Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 101
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 102
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
    130

<210> SEQ ID NO 103
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Ile Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 104
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys Tyr Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 105
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Asn Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 106
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala His Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 107
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 108
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 109
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Val
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 110
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
    130

<210> SEQ ID NO 111
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Ile Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 112
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Asp Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 113
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Tyr Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 114
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Val Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 115
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Val Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 116
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
    130

<210> SEQ ID NO 117
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Ala Pro Thr Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Glu Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 118
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 118

```
Ala Pro Thr Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Gln Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 119
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 119

```
Ala Pro Thr Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Arg Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130
```

<210> SEQ ID NO 120
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

```
Ala Pro Thr Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Lys Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130
```

<210> SEQ ID NO 121
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 121

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 122
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Gln Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 123
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Ala Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 124
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Cys Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 125
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Asn Ile Val Glu Phe Leu Asn Arg Trp Ile Thr Phe Cys Gln Ser Ile
        115                 120                 125

Ile Ser Thr Leu Thr
        130

<210> SEQ ID NO 126
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 127
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 128
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys His Ser Ile
        115                 120                 125

Ile Ser Thr Leu Thr
        130

<210> SEQ ID NO 129
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Met Ser Ile
            115                 120                 125

Ile Ser Thr Leu Thr
        130

<210> SEQ ID NO 130
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Lys Ser Ile
            115                 120                 125

Ile Ser Thr Leu Thr
        130

<210> SEQ ID NO 131
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Ala Pro Thr Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Cys Ser Ile
        115                 120                 125

Ile Ser Thr Leu Thr
        130

<210> SEQ ID NO 132
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Ala Pro Thr Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Asp Ser Ile
        115                 120                 125

Ile Ser Thr Leu Thr
        130

<210> SEQ ID NO 133
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Glu Ser Ile
        115                 120                 125

Ile Ser Thr Leu Thr
        130

<210> SEQ ID NO 134
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gly Ser Ile
        115                 120                 125

Ile Ser Thr Leu Thr
        130

<210> SEQ ID NO 135
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Ile Ser Ile
        115                 120                 125

Ile Ser Thr Leu Thr
        130

<210> SEQ ID NO 136
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Arg Ser Ile
        115                 120                 125

Ile Ser Thr Leu Thr
        130

<210> SEQ ID NO 137
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Ser Ser Ile
        115                 120                 125

Ile Ser Thr Leu Thr
        130

<210> SEQ ID NO 138
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
        115                 120                 125

Ile Ser Thr Leu Thr
        130

<210> SEQ ID NO 139
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Gly Gly Ser Gly
1               5

<210> SEQ ID NO 140
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Gly Ser Gly Gly
1               5

<210> SEQ ID NO 141
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Ser Gly Ser Gly
1               5

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Ser Gly Gly Gly
1               5

<210> SEQ ID NO 143
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Gly Gly Gly Ser Gly
1               5

<210> SEQ ID NO 144
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Gly Gly Gly Ser
1               5

<210> SEQ ID NO 145
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Gly Gly Gly Ser
1               5

<210> SEQ ID NO 146
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Gly Ser Gly
1

<210> SEQ ID NO 147
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Gly Ser Gly Gly
1               5

<210> SEQ ID NO 148
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Ser Gly Ser Gly
1               5

<210> SEQ ID NO 149
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Ser Gly Gly Gly
1               5

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 150

Gly Gly Gly Gly Ser Gly
1               5

<210> SEQ ID NO 151
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Ser Ser Ser Gly
1               5

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asp Ile Cys Leu Pro Arg Trp Gly Cys Leu Trp
1               5                   10

<210> SEQ ID NO 153
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
tatagtcagc gccacccatg tacaggatgc aactcctgtc                          40

<210> SEQ ID NO 154
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
tatagggccc tatcaagtca gtgttgagat g                                   31

<210> SEQ ID NO 155
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
caaagaaaac acagctacaa ctggagcagt tactggtgct cttaaaggc                49

<210> SEQ ID NO 156
<211> LENGTH: 49
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 156
gcctttaaga gcaccagtaa ctgctccagt tgtagctgtg ttttctttg                49

<210> SEQ ID NO 157
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
cagctacaac tgagccattt actggtgctc ttaaa                               35

<210> SEQ ID NO 158
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
tttaagagca ccagtaaatg gctcagttgt agctg                               35

<210> SEQ ID NO 159
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
ctgagccagt tactgctgct cttaaaggcc                                     30

<210> SEQ ID NO 160
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
ggcctttaag agcagcagta actggctcag                                     30

<210> SEQ ID NO 161
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
aactgagcca gttactggtg gatttaaagg ccattttgaa tg                       42

<210> SEQ ID NO 162
<211> LENGTH: 42
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 162
cattcaaaat ggcctttaaa tccaccagta actggctcag tt                         42

<210> SEQ ID NO 163
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tgagccagtt actggtgctc ttacaggcca ttttga                               36

<210> SEQ ID NO 164
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
tcaaaatggc ctgtaagagc accagtaact ggctca                               36

<210> SEQ ID NO 165
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
ctggtgctct taaagatgat tttgaatgga attaa                                35

<210> SEQ ID NO 166
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
ttaattccat tcaaaatcat ctttaagagc accag                                35

<210> SEQ ID NO 167
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
cacagctaca actgtcgcat ttactgctgg                                      30

<210> SEQ ID NO 168
<211> LENGTH: 30
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 168
ccagcagtaa atgcgacagt tgtagctgtg                                        30

<210> SEQ ID NO 169
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
gctacaactg gagcagttac tgctggattt ac                                     32

<210> SEQ ID NO 170
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gtaaatccag cagtaactgc tccagttgta gc                                     32

<210> SEQ ID NO 171
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
ctggagcatt tactggtgga tttacagatg attttg                                 36

<210> SEQ ID NO 172
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
caaaatcatc tgtaaatcca ccagtaaatg ctccag                                 36

<210> SEQ ID NO 173
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
gagcatttac tgctgctatt acagatgatt ttg                                    33

<210> SEQ ID NO 174
<211> LENGTH: 33
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 174
caaaatcatc tgtaatagca gcagtaaatg ctc                                33

<210> SEQ ID NO 175
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
catttactgc tggatttaaa gatgattttg aatgg                              35

<210> SEQ ID NO 176
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
ccattcaaaa tcatctttaa atccagcagt aaatg                              35

<210> SEQ ID NO 177
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ctggagcatt tactgctgga tttacaggcg attttgaatg gaattaataa ttaca        55

<210> SEQ ID NO 178
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
tgtaattatt aattccattc aaaatcgcct gtaaatccag cagtaaatgc tccag        55

<210> SEQ ID NO 179
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
caaagaaaac acagctacaa ctgagccagt tactgctgga tttacagatg              50

<210> SEQ ID NO 180
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
catctgtaaa tccagcagta actggctcag ttgtagctgt gttttctttg            50

<210> SEQ ID NO 181
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
ccattcaaaa tcatctgtaa gagcaccagt aactggctca gttgtagctg            50

<210> SEQ ID NO 182
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
caactgagcc agttactggt gctcttaaag gccattttga atggaattaa taattacaag    60

<210> SEQ ID NO 183
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
cttgtcacaa acagtcctac ttcaagttc                                   29

<210> SEQ ID NO 184
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
gaacttgaag taggactgtt tgtgacaag                                   29

<210> SEQ ID NO 185
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
cacaaacagt gcaacttcaa gttctac                                     27

```
<210> SEQ ID NO 186
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
gtagaacttg aagttgcact gtttgtg                                    27

<210> SEQ ID NO 187
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
caaacagtgc accttcaagt tctacaaag                                  29

<210> SEQ ID NO 188
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
ctttgtagaa cttgaaggtg cactgtttg                                  29

<210> SEQ ID NO 189
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
caaacagtgc accttgttca agttctaca                                  29

<210> SEQ ID NO 190
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
tgtagaactt gaacaaggtg cactgtttg                                  29

<210> SEQ ID NO 191
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
caaacagtgc acctgcttca agttctac                                   28
```

```
<210> SEQ ID NO 192
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
gtagaacttg aagcaggtgc actgtttg                                         28

<210> SEQ ID NO 193
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
caaacagtgc acctggttca agttctac                                         28

<210> SEQ ID NO 194
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
gtagaacttg aaccaggtgc actgtttg                                         28

<210> SEQ ID NO 195
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
caaacagtgc acctcagtca agttctacaa ag                                    32

<210> SEQ ID NO 196
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
ctttgtagaa cttgactgag gtgcactgtt tg                                    32

<210> SEQ ID NO 197
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
caaacagtgc acctgagtca agttctacaa ag                                    32

<210> SEQ ID NO 198
```

```
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
ctttgtagaa cttgactcag gtgcactgtt tg                                      32

<210> SEQ ID NO 199
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
caaacagtgc acctaattca agttctacaa ag                                      32

<210> SEQ ID NO 200
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
ctttgtagaa cttgaattag gtgcactgtt tg                                      32

<210> SEQ ID NO 201
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
aaacagtgca cctgattcaa gttctacaaa g                                       31

<210> SEQ ID NO 202
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
ctttgtagaa cttgaatcag gtgcactgtt tg                                      32

<210> SEQ ID NO 203
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
caaacagtgc acctaggtca agttctacaa ag                                      32

<210> SEQ ID NO 204
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
ctttgtagaa cttgacctag gtgcactgtt tg                                    32

<210> SEQ ID NO 205
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
caaacagtgc acctaagtca agttctacaa ag                                    32

<210> SEQ ID NO 206
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
ctttgtagaa cttgacttag gtgcactgtt tg                                    32

<210> SEQ ID NO 207
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
caaacagtgc acctccttca agttctac                                         28

<210> SEQ ID NO 208
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
gtagaacttg aaggaggtgc actgtttg                                         28

<210> SEQ ID NO 209
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
cagtgcacct actagttcta caaaga                                           26

<210> SEQ ID NO 210
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 210
tctttgtaga actagtaggt gcactg                                          26

<210> SEQ ID NO 211
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
gtgcacctac ttcatctaca aagaaaac                                        28

<210> SEQ ID NO 212
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
gttttctttg tagatgaagt aggtgcac                                        28

<210> SEQ ID NO 213
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
cacctacttc aagtacaaag aaaacacag                                       29

<210> SEQ ID NO 214
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
ctgtgttttc tttgtacttg aagtaggtg                                       29

<210> SEQ ID NO 215
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
ctacttcaag ttctaagaaa acacagct                                        28

<210> SEQ ID NO 216
<211> LENGTH: 28
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 216
agctgtgttt tcttagaact tgaagtag                                      28

<210> SEQ ID NO 217
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
cttcaagttc tacaaaaaca cagctacaac                                    30

<210> SEQ ID NO 218
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
gttgtagctg tgttttgta gaacttgaag                                     30

<210> SEQ ID NO 219
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
caagttctac aaagacacag ctacaactg                                     29

<210> SEQ ID NO 220
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
cagttgtagc tgtgtctttg tagaacttg                                     29

<210> SEQ ID NO 221
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
gaaaacacag ctactgagcc agttactg                                      28

<210> SEQ ID NO 222
<211> LENGTH: 28
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 222
cagtaactgg ctcagtagct gtgttttc                              28

<210> SEQ ID NO 223
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
gaaaacacag ctatggctga gccagttac                             29

<210> SEQ ID NO 224
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
gtaactggct cagccatagc tgtgttttc                             29

<210> SEQ ID NO 225
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
aaacacagct acaaagccag ttactggtgc                            30

<210> SEQ ID NO 226
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
gcaccagtaa ctggctttgt agctgtgttt                            30

<210> SEQ ID NO 227
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
aaacacagct acaaatgagc cagttactg                             29

<210> SEQ ID NO 228
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
cagtaactgg ctcatttgta gctgtgttt                                         29

<210> SEQ ID NO 229
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
aaacacagct acaatggagc cagttactgg                                        30

<210> SEQ ID NO 230
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
ccagtaactg gctccattgt agctgtgttt                                        30

<210> SEQ ID NO 231
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
cacagctaca actgaagcag ttactggtgc                                        30

<210> SEQ ID NO 232
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
gcaccagtaa ctgcttcagt tgtagctgtg                                        30

<210> SEQ ID NO 233
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
cacagctaca actgacccag ttactggtgc tc                                     32

<210> SEQ ID NO 234
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
gagcaccagt aactgggtca gttgtagctg tg                                    32

<210> SEQ ID NO 235
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
gctacaactg agcttactgg tgctctta                                         28

<210> SEQ ID NO 236
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
taagagcacc agtaagctca gttgtagc                                         28

<210> SEQ ID NO 237
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
gctacaactg agcaacttac tggtgctc                                         28

<210> SEQ ID NO 238
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
gagcaccagt aagttgctca gttgtagc                                         28

<210> SEQ ID NO 239
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
aactgagcca gttaggggtg ctcttaaagg                                       30

<210> SEQ ID NO 240
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 240
cctttaagag cacccctaac tggctcagtt    30

<210> SEQ ID NO 241
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 241
caactgagcc agttaatggt gctcttaaag gc    32

<210> SEQ ID NO 242
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 242
gcctttaaga gcaccattaa ctggctcagt tg    32

<210> SEQ ID NO 243
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 243
aactgagcca gttattcgtg ctcttaaagg c    31

<210> SEQ ID NO 244
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 244
gcctttaaga gcacgaataa ctggctcagt t    31

<210> SEQ ID NO 245
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 245
caactgagcc agttagaggt gctcttaaag gc    32

<210> SEQ ID NO 246

```
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
gcctttaaga gcacctctaa ctggctcagt tg                                   32

<210> SEQ ID NO 247
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
actgagccag ttacacgtgc tcttaaaggc                                      30

<210> SEQ ID NO 248
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
gcctttaaga gcacgtgtaa ctggctcagt                                      30

<210> SEQ ID NO 249
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
aactgagcca gttatgggtg ctcttaaagg                                      30

<210> SEQ ID NO 250
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
cctttaagag cacccataac tggctcagtt                                      30

<210> SEQ ID NO 251
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
caactgagcc agttaaaggt gctcttaaag gc                                   32

<210> SEQ ID NO 252
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
gcctttaaga gcacctttaa ctggctcagt tg                                    32

<210> SEQ ID NO 253
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
ctgagccagt tacaggtgct cttaaag                                          27

<210> SEQ ID NO 254
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
ctttaagagc acctgtaact ggctcag                                          27

<210> SEQ ID NO 255
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
caactgagcc agttaagcgt gctcttaaag gc                                    32

<210> SEQ ID NO 256
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
gcctttaaga gcacgcttaa ctggctcagt tg                                    32

<210> SEQ ID NO 257
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
caactgagcc agttagtggt gctcttaaag g                                     31

<210> SEQ ID NO 258
<211> LENGTH: 31
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 258
cctttaagag caccactaac tggctcagtt g                                    31

<210> SEQ ID NO 259
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
caactgagcc agttaatcgt gctcttaaag gc                                   32

<210> SEQ ID NO 260
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
gcctttaaga gcacgattaa ctggctcagt tg                                   32

<210> SEQ ID NO 261
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
caactgagcc agttatacgt gctcttaaag gc                                   32

<210> SEQ ID NO 262
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
gcctttaaga gcacgtataa ctggctcagt tg                                   32

<210> SEQ ID NO 263
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
ctgagccagt tacacgtgct cttaaagg                                        28

<210> SEQ ID NO 264
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 264
cctttaagag cacgtgtaac tggctcag                                              28

<210> SEQ ID NO 265
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
caactgagcc agttagacgt gctcttaaag gc                                         32

<210> SEQ ID NO 266
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
gcctttaaga gcacgtctaa ctggctcagt tg                                         32

<210> SEQ ID NO 267
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
caactgagcc agttaacggt gctcttaaag gc                                         32

<210> SEQ ID NO 268
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
gcctttaaga gcaccgttaa ctggctcagt tg                                         32

<210> SEQ ID NO 269
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
ctgagccagt tactgctctt aaaggccatt                                            30

<210> SEQ ID NO 270
<211> LENGTH: 30
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 270
aatggccttt aagagcagta actggctcag                                          30

<210> SEQ ID NO 271
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
ctgagccagt tactgatcct cttaaaggcc at                                       32

<210> SEQ ID NO 272
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
atggccttta agaggatcag taactggctc ag                                       32

<210> SEQ ID NO 273
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
gccagttact ggtgttaaag gccattttg                                           29

<210> SEQ ID NO 274
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
caaaatggcc tttaacacca gtaactggc                                           29

<210> SEQ ID NO 275
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
gccagttact ggtgtcctta aaggccattt tg                                       32

<210> SEQ ID NO 276
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
caaaatggcc tttaaggaca ccagtaactg gc                                32

<210> SEQ ID NO 277
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
tactggtgct cttattcgcc attttgaatg g                                 31

<210> SEQ ID NO 278
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
ccattcaaaa tggcgaataa gagcaccagt a                                 31

<210> SEQ ID NO 279
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
tactggtgct cttagaggcc attttgaatg g                                 31

<210> SEQ ID NO 280
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
ccattcaaaa tggcctctaa gagcaccagt a                                 31

<210> SEQ ID NO 281
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
ttactggtgc tcttaggggc cattttgaat gg                                32

<210> SEQ ID NO 282
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
ccattcaaaa tggcccctaa gagcaccagt aa                                    32

<210> SEQ ID NO 283
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
tactggtgct cttagcggcc attttgaatg                                       30

<210> SEQ ID NO 284
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
cattcaaaat ggccgctaag agcaccagta                                       30

<210> SEQ ID NO 285
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
tactggtgct cttactggcc attttgaatg                                       30

<210> SEQ ID NO 286
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
cattcaaaat ggccagtaag agcaccagta                                       30

<210> SEQ ID NO 287
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
tactggtgct cttaatggcc attttgaatg                                       30

-continued

```
<210> SEQ ID NO 288
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
cattcaaaat ggccattaag agcaccagta                                    30

<210> SEQ ID NO 289
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
tactggtgct cttattcgcc attttgaatg g                                  31

<210> SEQ ID NO 290
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
ccattcaaaa tggcgaataa gagcaccagt a                                  31

<210> SEQ ID NO 291
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
tactggtgct cttatgggcc attttgaatg                                    30

<210> SEQ ID NO 292
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
cattcaaaat ggcccataag agcaccagta                                    30

<210> SEQ ID NO 293
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
tactggtgct cttaagcgcc attttgaatg g                                  31

<210> SEQ ID NO 294
```

```
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
ccattcaaaa tggcgcttaa gagcaccagt a                                 31

<210> SEQ ID NO 295
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
tactggtgct cttagtggcc attttgaatg                                   30

<210> SEQ ID NO 296
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
cattcaaaat ggccactaag agcaccagta                                   30

<210> SEQ ID NO 297
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
tactggtgct cttaatcgcc attttgaatg g                                 31

<210> SEQ ID NO 298
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
ccattcaaaa tggcgattaa gagcaccagt a                                 31

<210> SEQ ID NO 299
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
tactggtgct cttatacgcc attttgaatg g                                 31

<210> SEQ ID NO 300
<211> LENGTH: 31
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
ccattcaaaa tggcgtataa gagcaccagt a                                    31

<210> SEQ ID NO 301
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
tactggtgct cttacacgcc attttgaatg g                                    31

<210> SEQ ID NO 302
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
ccattcaaaa tggcgtgtaa gagcaccagt a                                    31

<210> SEQ ID NO 303
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
tactggtgct cttacgggcc attttgaatg                                      30

<210> SEQ ID NO 304
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
cattcaaaat ggcccgtaag agcaccagta                                      30

<210> SEQ ID NO 305
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
ctggtgctct taacgccat tttgaatgg                                        29

<210> SEQ ID NO 306
<211> LENGTH: 29
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 306
ccattcaaaa tggcgtttaa gagcaccag                                        29

<210> SEQ ID NO 307
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
tactggtgct cttagacgcc attttgaatg g                                     31

<210> SEQ ID NO 308
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
ccattcaaaa tggcgtctaa gagcaccagt a                                     31

<210> SEQ ID NO 309
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
tactggtgct cttaacggcc attttgaatg g                                     31

<210> SEQ ID NO 310
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
ccattcaaaa tggccgttaa gagcaccagt a                                     31

<210> SEQ ID NO 311
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
ctggtgctct taaagatttt gaatggaatt aa                                    32

<210> SEQ ID NO 312
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 312
ttaattccat tcaaaatctt taagagcacc ag                                32

<210> SEQ ID NO 313
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
ctggtgctct taaagtggat tttgaatgga at                                32

<210> SEQ ID NO 314
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
attccattca aaatccactt taagagcacc ag                                32

<210> SEQ ID NO 315
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
tggtgctctt aaagcacatt ttgaatggaa                                   30

<210> SEQ ID NO 316
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
ttccattcaa aatgtgcttt aagagcacca                                   30

<210> SEQ ID NO 317
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
ggtgctctta aagtacattt tgaatggaa                                    29

<210> SEQ ID NO 318
<211> LENGTH: 29
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 318
ttccattcaa aatgtacttt aagagcacc                                      29

<210> SEQ ID NO 319
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
ctggtgctct taaagttcat tttgaatgga at                                  32

<210> SEQ ID NO 320
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
attccattca aaatgaactt taagagcacc ag                                  32

<210> SEQ ID NO 321
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
tggtgctctt aaagcagatt ttgaatgg                                       28

<210> SEQ ID NO 322
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
ccattcaaaa tctgctttaa gagcacca                                       28

<210> SEQ ID NO 323
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
ggtgctctta aagagcattt tgaatgga                                       28
```

<210> SEQ ID NO 324
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
tccattcaaa atgctcttta agagcacc                                       28

<210> SEQ ID NO 325
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
ggtgctctta aaggtcattt tgaatggaa                                      29

<210> SEQ ID NO 326
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
ttccattcaa aatgaccttt aagagcacc                                      29

<210> SEQ ID NO 327
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
ctggtgctct taaagctcat tttgaatgga at                                  32

<210> SEQ ID NO 328
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
attccattca aaatgagctt taagagcacc ag                                  32

<210> SEQ ID NO 329
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
ggtgctctta aagaccattt tgaatgg                                        27

<210> SEQ ID NO 330
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 330
ccattcaaaa tggtctttaa gagcacc                                          27

<210> SEQ ID NO 331
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 331
ggccattttg aatattaata attacaag                                         28

<210> SEQ ID NO 332
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 332
cttgtaatta ttaatattca aaatggcc                                         28

<210> SEQ ID NO 333
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 333
ggccattttg aataaaatta ataattac                                         28

<210> SEQ ID NO 334
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 334
gtaattatta attttattca aaatggcc                                         28

<210> SEQ ID NO 335
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 335
ggccattttg aattcaatta ataattac                                         28

<210> SEQ ID NO 336
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 336
gtaattatta attgaattca aaatggcc     28

<210> SEQ ID NO 337
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 337
atcccaaact cacctggatg ctcacattt     29

<210> SEQ ID NO 338
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 338
aaatgtgagc atccaggtga gtttgggat     29

<210> SEQ ID NO 339
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 339
atcccaaact caccgggatg ctcacattt     29

<210> SEQ ID NO 340
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 340
aaatgtgagc atcccggtga gtttgggat     29

<210> SEQ ID NO 341
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 341
ccaaactcac caggctgctc acatttaag     29

<210> SEQ ID NO 342

<210> SEQ ID NO 342
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 342
cttaaatgtg agcagcctgg tgagtttgg                                      29

<210> SEQ ID NO 343
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 343
ccaaactcac cagggtgctc acatttaag                                      29

<210> SEQ ID NO 344
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 344
cttaaatgtg agcaccctgg tgagtttgg                                      29

<210> SEQ ID NO 345
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 345
ccaggatgct cacaaagaag ttttacatgc c                                   31

<210> SEQ ID NO 346
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 346
ggcatgtaaa acttctttgt gagcatcctg g                                   31

<210> SEQ ID NO 347
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 347
tgcccaagaa ggccgaactg aaacatct                                       28

<210> SEQ ID NO 348
<211> LENGTH: 28

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
agatgtttca gttcggcctt cttgggca                                        28

<210> SEQ ID NO 349
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
gcccaagaag gccatagaac tgaaacatc                                       29

<210> SEQ ID NO 350
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
gatgtttcag ttctatggcc ttcttgggc                                       29

<210> SEQ ID NO 351
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
ccacagaact gaaatatctt cagtgtcta                                       29

<210> SEQ ID NO 352
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352
tagacactga agatatttca gttctgtgg                                       29

<210> SEQ ID NO 353
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353
gctaaattta gctaacagca aaaactttc                                       29

<210> SEQ ID NO 354
<211> LENGTH: 29
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 354
gaaagttttt gctgttagct aaatttagc                                           29

<210> SEQ ID NO 355
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
ctaaatttag ctcacagcaa aaactttc                                            28

<210> SEQ ID NO 356
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356
gaaagttttt gctgtgagct aaatttag                                            28

<210> SEQ ID NO 357
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 357
gtgctaaatt tagcttcaag caaaaacttt c                                        31

<210> SEQ ID NO 358
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
gaaagttttt gcttgaagct aaatttagca c                                        31

<210> SEQ ID NO 359
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
caaaaacttt cacttcagac ccagggactt                                          30

<210> SEQ ID NO 360
<211> LENGTH: 30
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 360
aagtccctgg gtctgaagtg aaagttttg                                     30

<210> SEQ ID NO 361
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
caaaaacttt cacgtaagac ccagggac                                      28

<210> SEQ ID NO 362
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
gtccctgggt cttacgtgaa agttttg                                       28

<210> SEQ ID NO 363
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
aaaaactttc acttacccag ggacttaatc                                    30

<210> SEQ ID NO 364
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
gattaagtcc ctgggtaagt gaaagttttt                                    30

<210> SEQ ID NO 365
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
aactttcact taatacccag ggactta                                       27

<210> SEQ ID NO 366
<211> LENGTH: 27
<212> TYPE: DNA
<213> ORGANISM: Artificial Sequence
<220> FEATURE:

<223> OTHER INFORMATION: Description of Artificial Sequence: Synthetic
     primer

<400> SEQUENCE: 366
taagtccctg ggtattaagt gaaagtt                                        27

<210> SEQ ID NO 367
<211> LENGTH: 31
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 367
aaaactttca cttagaccccc agggacttaa t                                  31

<210> SEQ ID NO 368
<211> LENGTH: 31
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 368
attaagtccc tggggtctaa gtgaaagttt t                                   31

<210> SEQ ID NO 369
<211> LENGTH: 31
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 369
aaaactttca cttataccccc agggacttaa t                                  31

<210> SEQ ID NO 370
<211> LENGTH: 31
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 370
attaagtccc tggggtataa gtgaaagttt t                                   31

<210> SEQ ID NO 371
<211> LENGTH: 29
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 371
taagacccag ggacgtaatc agcaatatc                                      29

<210> SEQ ID NO 372
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
gatattgctg attacgtccc tgggtctta                                    29

<210> SEQ ID NO 373
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
gacccaggga cttagtcagc aatatcaac                                    29

<210> SEQ ID NO 374
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
gttgatattg ctgactaagt ccctgggtc                                    29

<210> SEQ ID NO 375
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
gggacttaat cagcatcaac gtaatagt                                     28

<210> SEQ ID NO 376
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
actattacgt tgatgctgat taagtccc                                     28

<210> SEQ ID NO 377
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
gggacttaat cagcgagatc aacgtaatag                                   30

<210> SEQ ID NO 378
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
ctattacgtt gatctcgctg attaagtccc                                    30

<210> SEQ ID NO 379
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
gggacttaat cagccagatc aacgtaatag                                    30

<210> SEQ ID NO 380
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
ctattacgtt gatctggctg attaagtccc                                    30

<210> SEQ ID NO 381
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
cagcaatatc aaccgaatag ttctggaac                                     29

<210> SEQ ID NO 382
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 382
gttccagaac tattcggttg atattgctg                                     29

<210> SEQ ID NO 383
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
tcagcaatat caacaagata gttctggaac t                                  31

-continued

<210> SEQ ID NO 384
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 384
agttccagaa ctatcttgtt gatattgctg a                              31

<210> SEQ ID NO 385
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
gcaatatcaa cgtattcgtt ctggaactaa ag                             32

<210> SEQ ID NO 386
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
ctttagttcc agaacgaata cgttgatatt gc                             32

<210> SEQ ID NO 387
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387
tagttctgga actacaggga tctgaaaca                                 29

<210> SEQ ID NO 388
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 388
tgtttcagat ccctgtagtt ccagaacta                                 29

<210> SEQ ID NO 389
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 389
ctgaaacaac attcgcgtgt gaatatgctg                                30

<210> SEQ ID NO 390

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 390
cagcatattc acacgcgaat gttgtttcag                                          30

<210> SEQ ID NO 391
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 391
gtgtgaatat gcttgtgaga cagcaacc                                            28

<210> SEQ ID NO 392
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
ggttgctgtc tcacaagcat attcacac                                            28

<210> SEQ ID NO 393
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
gatgagacag caaacattgt agaatttc                                            28

<210> SEQ ID NO 394
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
gaaattctac aatgtttgct gtctcatc                                            28

<210> SEQ ID NO 395
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
gatggattac ctttgctcaa agcatcatc                                           29

<210> SEQ ID NO 396
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
gatgatgctt tgagcaaagg taatccatc                                       29

<210> SEQ ID NO 397
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
atggattacc ttttctcaaa gcatcatctc                                      30

<210> SEQ ID NO 398
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398
gagatgatgc tttgagaaaa ggtaatccat                                      30

<210> SEQ ID NO 399
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
ttaccttttg tcacagcatc atctcaac                                        28

<210> SEQ ID NO 400
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400
gttgagatga tgctgtgaca aaaggtaa                                        28

<210> SEQ ID NO 401
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
ggattacctt ttgtatgagc atcatctcaa c                                    31

<210> SEQ ID NO 402
<211> LENGTH: 31
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 402
gttgagatga tgctcataca aaaggtaatc c                                    31

<210> SEQ ID NO 403
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403
ggattacctt ttgtaaaagc atcatctc                                        28

<210> SEQ ID NO 404
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404
gagatgatgc ttttacaaaa ggtaatcc                                        28

<210> SEQ ID NO 405
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
ggattacctt ttgttgcagc atcatctcaa c                                    31

<210> SEQ ID NO 406
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406
gttgagatga tgctgcaaca aaaggtaatc c                                    31

<210> SEQ ID NO 407
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407
ggattacctt ttgtgacagc atcatctcaa c                                    31

<210> SEQ ID NO 408
<211> LENGTH: 31
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 408
gttgagatga tgctgtcaca aaaggtaatc c                                          31

<210> SEQ ID NO 409
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409
ggattacctt ttgtgaaagc atcatctca                                             29

<210> SEQ ID NO 410
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410
tgagatgatg ctttcacaaa aggtaatcc                                             29

<210> SEQ ID NO 411
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
ggattacctt ttgtggaagc atcatctcaa c                                          31

<210> SEQ ID NO 412
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412
gttgagatga tgcttccaca aaaggtaatc c                                          31

<210> SEQ ID NO 413
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 413
ggattacctt ttgtataagc atcatctcaa c                                          31

<210> SEQ ID NO 414
<211> LENGTH: 31
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 414
gttgagatga tgcttataca aaaggtaatc c                                           31

<210> SEQ ID NO 415
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 415
ggattacctt tgtcgaagc atcatctcaa c                                            31

<210> SEQ ID NO 416
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 416
gttgagatga tgcttcgaca aaaggtaatc c                                           31

<210> SEQ ID NO 417
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
ggattacctt tgttcaagc atcatctcaa c                                            31

<210> SEQ ID NO 418
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 418
gttgagatga tgcttgaaca aaaggtaatc c                                           31

<210> SEQ ID NO 419
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 419
ggattacctt tgtacaagc atcatctcaa c                                            31

<210> SEQ ID NO 420
<211> LENGTH: 31
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 420
gttgagatga tgcttgtaca aaaggtaatc c                                  31

<210> SEQ ID NO 421
<211> LENGTH: 20
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 421

Met Tyr Arg Met Gln Leu Leu Ser Cys Ile Ala Leu Ser Leu Ala Leu
1               5                   10                  15

Val Thr Asn Ser
            20

<210> SEQ ID NO 422
<211> LENGTH: 133
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 422

Ala Pro Thr Ser Ser Ser Thr Lys Lys Thr Gln Leu Gln Leu Glu Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 423
<211> LENGTH: 133
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES

```
<222> LOCATION: (1)..(1)
<223> OTHER INFORMATION: A or not present
<220> FEATURE:
<221> NAME/KEY: MOD_RES
<222> LOCATION: (2)..(2)
<223> OTHER INFORMATION: P or not present
<220> FEATURE:
<221> NAME/KEY: MOD_RES
<222> LOCATION: (3)..(3)
<223> OTHER INFORMATION: T, C, A, G, Q, E, N, D, R, K, P, or not present
<220> FEATURE:
<221> NAME/KEY: MOD_RES
<222> LOCATION: (4)..(4)
<223> OTHER INFORMATION: S or not present
<220> FEATURE:
<221> NAME/KEY: MOD_RES
<222> LOCATION: (5)..(5)
<223> OTHER INFORMATION: S or not present
<220> FEATURE:
<221> NAME/KEY: MOD_RES
<222> LOCATION: (6)..(6)
<223> OTHER INFORMATION: S or not present
<220> FEATURE:
<221> NAME/KEY: MOD_RES
<222> LOCATION: (7)..(7)
<223> OTHER INFORMATION: T or not present
<220> FEATURE:
<221> NAME/KEY: MOD_RES
<222> LOCATION: (8)..(8)
<223> OTHER INFORMATION: K or not present
<220> FEATURE:
<221> NAME/KEY: MOD_RES
<222> LOCATION: (9)..(9)
<223> OTHER INFORMATION: K or not present
<220> FEATURE:
<221> NAME/KEY: MOD_RES
<222> LOCATION: (13)..(13)
<223> OTHER INFORMATION: Q, W, or not present
<220> FEATURE:
<221> NAME/KEY: MOD_RES
<222> LOCATION: (14)..(14)
<223> OTHER INFORMATION: L, M, W, or not present
<220> FEATURE:
<221> NAME/KEY: MOD_RES
<222> LOCATION: (15)..(15)
<223> OTHER INFORMATION: E, K, D, T, A, S, Q, H, or not present
<220> FEATURE:
<221> NAME/KEY: MOD_RES
<222> LOCATION: (16)..(16)
<223> OTHER INFORMATION: H, N, Q, or not present
<220> FEATURE:
<221> NAME/KEY: MOD_RES
<222> LOCATION: (18)..(18)
<223> OTHER INFORMATION: L, R, G, M, F, E, H, W, K, Q, S, V, I, Y, H, D,
      or T
<220> FEATURE:
<221> NAME/KEY: MOD_RES
<222> LOCATION: (19)..(19)
<223> OTHER INFORMATION: L, A, V, I, or not present
<220> FEATURE:
<221> NAME/KEY: MOD_RES
<222> LOCATION: (20)..(20)
<223> OTHER INFORMATION: D, T, S, M, L, or not present
<220> FEATURE:
<221> NAME/KEY: MOD_RES
<222> LOCATION: (22)..(22)
<223> OTHER INFORMATION: Q, F, E, G, A, L, M, F, W, K, S, V, I, Y, H, R,
      N, D, T, F, or not present
<220> FEATURE:
<221> NAME/KEY: MOD_RES
<222> LOCATION: (23)..(23)
<223> OTHER INFORMATION: M, A, W, H, Y, F, Q, S, V, L, T, or not present
<220> FEATURE:
<221> NAME/KEY: MOD_RES
<222> LOCATION: (27)..(27)
<223> OTHER INFORMATION: G, K, S, or not present
<220> FEATURE:
<221> NAME/KEY: MOD_RES
<222> LOCATION: (38)..(38)
```

-continued

```
<223> OTHER INFORMATION: R, W, or G
<220> FEATURE:
<221> NAME/KEY: MOD_RES
<222> LOCATION: (39)..(39)
<223> OTHER INFORMATION: M, L, or V
<220> FEATURE:
<221> NAME/KEY: MOD_RES
<222> LOCATION: (42)..(42)
<223> OTHER INFORMATION: F or K
<220> FEATURE:
<221> NAME/KEY: MOD_RES
<222> LOCATION: (51)..(51)
<223> OTHER INFORMATION: T, I, or not present
<220> FEATURE:
<221> NAME/KEY: MOD_RES
<222> LOCATION: (55)..(55)
<223> OTHER INFORMATION: H or Y
<220> FEATURE:
<221> NAME/KEY: MOD_RES
<222> LOCATION: (74)..(74)
<223> OTHER INFORMATION: Q, N, H, or S
<220> FEATURE:
<221> NAME/KEY: MOD_RES
<222> LOCATION: (80)..(80)
<223> OTHER INFORMATION: L, F, or V
<220> FEATURE:
<221> NAME/KEY: MOD_RES
<222> LOCATION: (81)..(81)
<223> OTHER INFORMATION: R, I, D, Y, T, or not present
<220> FEATURE:
<221> NAME/KEY: MOD_RES
<222> LOCATION: (85)..(85)
<223> OTHER INFORMATION: L or V
<220> FEATURE:
<221> NAME/KEY: MOD_RES
<222> LOCATION: (86)..(86)
<223> OTHER INFORMATION: I or V
<220> FEATURE:
<221> NAME/KEY: MOD_RES
<222> LOCATION: (89)..(89)
<223> OTHER INFORMATION: I or V
<220> FEATURE:
<221> NAME/KEY: MOD_RES
<222> LOCATION: (91)..(91)
<223> OTHER INFORMATION: V, R, or K
<220> FEATURE:
<221> NAME/KEY: MOD_RES
<222> LOCATION: (92)..(92)
<223> OTHER INFORMATION: I or F
<220> FEATURE:
<221> NAME/KEY: MOD_RES
<222> LOCATION: (97)..(97)
<223> OTHER INFORMATION: K or Q
<220> FEATURE:
<221> NAME/KEY: MOD_RES
<222> LOCATION: (104)..(104)
<223> OTHER INFORMATION: M or A
<220> FEATURE:
<221> NAME/KEY: MOD_RES
<222> LOCATION: (109)..(109)
<223> OTHER INFORMATION: D, C, or a non-natural amino acid with an
      activated side chain
<220> FEATURE:
<221> NAME/KEY: MOD_RES
<222> LOCATION: (113)..(113)
<223> OTHER INFORMATION: T or N
<220> FEATURE:
<221> NAME/KEY: MOD_RES
<222> LOCATION: (125)..(125)
<223> OTHER INFORMATION: C, A, or S
<220> FEATURE:
<221> NAME/KEY: MOD_RES
<222> LOCATION: (126)..(126)
<223> OTHER INFORMATION: Q, H, M, K, C, D, E, G, I, R, S, or T
<220> FEATURE:
<221> NAME/KEY: MOD_RES
<222> LOCATION: (130)..(130)
<223> OTHER INFORMATION: S, T, or R
```

<400> SEQUENCE: 423

Xaa Xaa Xaa Xaa Xaa Xaa Xaa Xaa Xaa Thr Gln Leu Xaa Xaa Xaa Xaa
1               5                   10                  15

Leu Xaa Xaa Xaa Leu Xaa Xaa Ile Leu Asn Xaa Ile Asn Asn Tyr Lys
            20                  25                  30

Asn Pro Lys Leu Thr Xaa Xaa Leu Thr Xaa Lys Phe Tyr Met Pro Lys
            35                  40                  45

Lys Ala Xaa Glu Leu Lys Xaa Leu Gln Cys Leu Glu Glu Glu Leu Lys
50                  55                  60

Pro Leu Glu Glu Val Leu Asn Leu Ala Xaa Ser Lys Asn Phe His Xaa
65                  70                  75                  80

Xaa Pro Arg Asp Xaa Xaa Ser Asn Xaa Asn Xaa Xaa Val Leu Glu Leu
                85                  90                  95

Xaa Gly Ser Glu Thr Thr Phe Xaa Cys Glu Tyr Ala Xaa Glu Thr Ala
            100                 105                 110

Xaa Ile Val Glu Phe Leu Asn Arg Trp Ile Thr Phe Xaa Xaa Ser Ile
            115                 120                 125

Ile Xaa Thr Leu Thr
    130

<210> SEQ ID NO 424
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(10)
<223> OTHER INFORMATION: This region may encompass 1-10 residues
<220> FEATURE:
<221> NAME/KEY: SITE
<222> LOCATION: (11)..(20)
<223> OTHER INFORMATION: This region may encompass 1-10 residues
<220> FEATURE:
<221> NAME/KEY: SITE
<222> LOCATION: (21)..(30)
<223> OTHER INFORMATION: This region may encompass 1-10 residues
<220> FEATURE:
<221> NAME/KEY: SITE
<222> LOCATION: (31)..(40)
<223> OTHER INFORMATION: This region may encompass 1-10 residues
<220> FEATURE:
<221> NAME/KEY: SITE
<222> LOCATION: (41)..(50)
<223> OTHER INFORMATION: This region may encompass 1-10 residues
<220> FEATURE:
<221> NAME/KEY: SITE
<222> LOCATION: (51)..(60)
<223> OTHER INFORMATION: This region may encompass 1-10 residues
<220> FEATURE:
<221> NAME/KEY: SITE
<222> LOCATION: (61)..(70)
<223> OTHER INFORMATION: This region may encompass 1-10 residues
<220> FEATURE:
<221> NAME/KEY: SITE
<222> LOCATION: (71)..(80)
<223> OTHER INFORMATION: This region may encompass 1-10 residues
<220> FEATURE:
<221> NAME/KEY: SITE
<222> LOCATION: (81)..(90)
<223> OTHER INFORMATION: This region may encompass 1-10 residues
<220> FEATURE:
<221> NAME/KEY: SITE
<222> LOCATION: (91)..(100)
<223> OTHER INFORMATION: This region may encompass 1-10 residues
<220> FEATURE:
<221> NAME/KEY: SITE

```
<222> LOCATION: (101)..(110)
<223> OTHER INFORMATION: This region may encompass 1-10 residues
<220> FEATURE:
<221> NAME/KEY: SITE
<222> LOCATION: (111)..(120)
<223> OTHER INFORMATION: This region may encompass 1-10 residues
<220> FEATURE:
<221> NAME/KEY: SITE
<222> LOCATION: (121)..(130)
<223> OTHER INFORMATION: This region may encompass 1-10 residues
<220> FEATURE:
<221> NAME/KEY: SITE
<222> LOCATION: (131)..(140)
<223> OTHER INFORMATION: This region may encompass 1-10 residues
<220> FEATURE:
<221> NAME/KEY: SITE
<222> LOCATION: (141)..(150)
<223> OTHER INFORMATION: This region may encompass 1-10 residues
<220> FEATURE:
<221> NAME/KEY: SITE
<222> LOCATION: (151)..(160)
<223> OTHER INFORMATION: This region may encompass 1-10 residues
<220> FEATURE:
<221> NAME/KEY: SITE
<222> LOCATION: (161)..(170)
<223> OTHER INFORMATION: This region may encompass 1-10 residues
<220> FEATURE:
<221> NAME/KEY: SITE
<222> LOCATION: (171)..(180)
<223> OTHER INFORMATION: This region may encompass 1-10 residues
<220> FEATURE:
<221> NAME/KEY: SITE
<222> LOCATION: (181)..(190)
<223> OTHER INFORMATION: This region may encompass 1-10 residues
<220> FEATURE:
<221> NAME/KEY: SITE
<222> LOCATION: (191)..(200)
<223> OTHER INFORMATION: This region may encompass 1-10 residues
<220> FEATURE:
<221> NAME/KEY: SITE
<222> LOCATION: (1)..(200)
<223> OTHER INFORMATION: This sequence may encompass 1-10 "(Gly)m(Ser)o"
      repeating units, wherein m = 1 to 10, o = 1 to 10
<220> FEATURE:
<223> OTHER INFORMATION: See specification as filed for detailed
      description of substitutions and preferred embodiments

<400> SEQUENCE: 424

Gly Gly Gly Gly Gly Gly Gly Gly Gly Ser Ser Ser Ser Ser Ser
1               5                   10                  15

Ser Ser Ser Ser Gly Gly Gly Gly Gly Gly Gly Gly Gly Ser Ser
                20                  25                  30

Ser Ser Ser Ser Ser Ser Ser Gly Gly Gly Gly Gly Gly Gly Gly
        35                  40                  45

Gly Gly Ser Ser Ser Ser Ser Ser Ser Ser Ser Gly Gly Gly Gly
    50                  55                  60

Gly Gly Gly Gly Gly Gly Ser Ser Ser Ser Ser Ser Ser Ser Ser
65                  70                  75                  80

Gly Gly Gly Gly Gly Gly Gly Gly Gly Ser Ser Ser Ser Ser Ser
                85                  90                  95

Ser Ser Ser Ser Gly Gly Gly Gly Gly Gly Gly Gly Gly Ser Ser
                100                 105                 110

Ser Ser Ser Ser Ser Ser Ser Gly Gly Gly Gly Gly Gly Gly Gly
        115                 120                 125

Gly Gly Ser Ser Ser Ser Ser Ser Ser Ser Ser Gly Gly Gly Gly
    130                 135                 140

Gly Gly Gly Gly Gly Gly Ser Ser Ser Ser Ser Ser Ser Ser Ser
145                 150                 155                 160
```

Gly Gly Gly Gly Gly Gly Gly Gly Ser Ser Ser Ser Ser Ser
                165                 170                 175

Ser Ser Ser Ser Gly Gly Gly Gly Gly Gly Gly Gly Ser Ser
            180                 185                 190

Ser Ser Ser Ser Ser Ser Ser Ser
        195                 200

<210> SEQ ID NO 425
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-10 "Gly Ser Gly
      Gly" repeating units
<220> FEATURE:
<223> OTHER INFORMATION: See specification as filed for detailed
      description of substitutions and preferred embodiments

<400> SEQUENCE: 425

Gly Ser Gly Gly Gly Ser Gly Gly Gly Ser Gly Gly Gly Ser Gly Gly
1               5                   10                  15

Gly Ser Gly Gly Gly Ser Gly Gly Gly Ser Gly Gly Gly Ser Gly Gly
            20                  25                  30

Gly Ser Gly Gly Gly Ser Gly Gly
        35                  40

<210> SEQ ID NO 426
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(10)
<223> OTHER INFORMATION: This region may encompass 1-10 residues
<220> FEATURE:
<221> NAME/KEY: SITE
<222> LOCATION: (11)..(20)
<223> OTHER INFORMATION: This region may encompass 1-10 residues
<220> FEATURE:
<221> NAME/KEY: SITE
<222> LOCATION: (21)..(30)
<223> OTHER INFORMATION: This region may encompass 1-10 residues
<220> FEATURE:
<221> NAME/KEY: SITE
<222> LOCATION: (31)..(40)
<223> OTHER INFORMATION: This region may encompass 1-10 residues
<220> FEATURE:
<221> NAME/KEY: SITE
<222> LOCATION: (41)..(50)
<223> OTHER INFORMATION: This region may encompass 1-10 residues
<220> FEATURE:
<221> NAME/KEY: SITE
<222> LOCATION: (51)..(60)
<223> OTHER INFORMATION: This region may encompass 1-10 residues
<220> FEATURE:
<221> NAME/KEY: SITE
<222> LOCATION: (61)..(70)
<223> OTHER INFORMATION: This region may encompass 1-10 residues
<220> FEATURE:
<221> NAME/KEY: SITE
<222> LOCATION: (71)..(80)
<223> OTHER INFORMATION: This region may encompass 1-10 residues
<220> FEATURE:
<221> NAME/KEY: SITE

```
<222> LOCATION: (81)..(90)
<223> OTHER INFORMATION: This region may encompass 1-10 residues
<220> FEATURE:
<221> NAME/KEY: SITE
<222> LOCATION: (91)..(100)
<223> OTHER INFORMATION: This region may encompass 1-10 residues
<220> FEATURE:
<221> NAME/KEY: SITE
<222> LOCATION: (101)..(110)
<223> OTHER INFORMATION: This region may encompass 1-10 residues
<220> FEATURE:
<221> NAME/KEY: SITE
<222> LOCATION: (111)..(120)
<223> OTHER INFORMATION: This region may encompass 1-10 residues
<220> FEATURE:
<221> NAME/KEY: SITE
<222> LOCATION: (121)..(130)
<223> OTHER INFORMATION: This region may encompass 1-10 residues
<220> FEATURE:
<221> NAME/KEY: SITE
<222> LOCATION: (131)..(140)
<223> OTHER INFORMATION: This region may encompass 1-10 residues
<220> FEATURE:
<221> NAME/KEY: SITE
<222> LOCATION: (141)..(150)
<223> OTHER INFORMATION: This region may encompass 1-10 residues
<220> FEATURE:
<221> NAME/KEY: SITE
<222> LOCATION: (151)..(160)
<223> OTHER INFORMATION: This region may encompass 1-10 residues
<220> FEATURE:
<221> NAME/KEY: SITE
<222> LOCATION: (161)..(170)
<223> OTHER INFORMATION: This region may encompass 1-10 residues
<220> FEATURE:
<221> NAME/KEY: SITE
<222> LOCATION: (171)..(180)
<223> OTHER INFORMATION: This region may encompass 1-10 residues
<220> FEATURE:
<221> NAME/KEY: SITE
<222> LOCATION: (181)..(190)
<223> OTHER INFORMATION: This region may encompass 1-10 residues
<220> FEATURE:
<221> NAME/KEY: SITE
<222> LOCATION: (191)..(200)
<223> OTHER INFORMATION: This region may encompass 1-10 residues
<220> FEATURE:
<221> NAME/KEY: SITE
<222> LOCATION: (201)..(210)
<223> OTHER INFORMATION: This region may encompass 1-10 residues
<220> FEATURE:
<221> NAME/KEY: SITE
<222> LOCATION: (211)..(220)
<223> OTHER INFORMATION: This region may encompass 1-10 residues
<220> FEATURE:
<221> NAME/KEY: SITE
<222> LOCATION: (221)..(230)
<223> OTHER INFORMATION: This region may encompass 1-10 residues
<220> FEATURE:
<221> NAME/KEY: SITE
<222> LOCATION: (231)..(240)
<223> OTHER INFORMATION: This region may encompass 1-10 residues
<220> FEATURE:
<221> NAME/KEY: SITE
<222> LOCATION: (241)..(250)
<223> OTHER INFORMATION: This region may encompass 1-10 residues
<220> FEATURE:
<221> NAME/KEY: SITE
<222> LOCATION: (251)..(260)
<223> OTHER INFORMATION: This region may encompass 1-10 residues
<220> FEATURE:
<221> NAME/KEY: SITE
<222> LOCATION: (261)..(270)
<223> OTHER INFORMATION: This region may encompass 1-10 residues
<220> FEATURE:
<221> NAME/KEY: SITE
<222> LOCATION: (271)..(280)
<223> OTHER INFORMATION: This region may encompass 1-10 residues
<220> FEATURE:
```

```
<221> NAME/KEY: SITE
<222> LOCATION: (281)..(290)
<223> OTHER INFORMATION: This region may encompass 1-10 residues
<220> FEATURE:
<221> NAME/KEY: SITE
<222> LOCATION: (291)..(300)
<223> OTHER INFORMATION: This region may encompass 1-10 residues
<220> FEATURE:
<221> NAME/KEY: SITE
<222> LOCATION: (1)..(300)
<223> OTHER INFORMATION: This sequence may encompass 1-10
      "(Gly)m(Ser)o(Gly)m" repeating units, wherein m = 1 to 10, o = 1
      to 10
<220> FEATURE:
<223> OTHER INFORMATION: See specification as filed for detailed
      description of substitutions and preferred embodiments

<400> SEQUENCE: 426
```

| | | | | | | | | | | | | | | |
|---|---|---|---|---|---|---|---|---|---|---|---|---|---|---|
| Gly | Gly | Gly | Gly | Gly | Gly | Gly | Gly | Gly | Ser | Ser | Ser | Ser | Ser | Ser |
| 1 | | | | 5 | | | | | 10 | | | | | 15 |
| Ser | Ser | Ser | Ser | Gly | Gly | Gly | Gly | Gly | Gly | Gly | Gly | Gly | Gly | Gly |
| | | | 20 | | | | | 25 | | | | | 30 | |
| Gly | Gly | Gly | Gly | Gly | Gly | Ser | Ser | Ser | Ser | Ser | Ser | Ser | Ser | Ser |
| | | | 35 | | | | | 40 | | | | | 45 | |
| Ser | Ser | Gly | Gly | Gly | Gly | Gly | Gly | Gly | Gly | Gly | Gly | Gly | Gly | Gly |
| | 50 | | | | | 55 | | | | | 60 | | | |
| Gly | Gly | Gly | Gly | Gly | Gly | Ser | Ser | Ser | Ser | Ser | Ser | Ser | Ser | Ser |
| 65 | | | | | 70 | | | | | 75 | | | | 80 |
| Gly | Gly | Gly | Gly | Gly | Gly | Gly | Gly | Gly | Gly | Gly | Gly | Gly | Gly | Gly |
| | | | | 85 | | | | | 90 | | | | | 95 |
| Gly | Gly | Gly | Gly | Ser | Ser | Ser | Ser | Ser | Ser | Ser | Ser | Ser | Gly | Gly |
| | | | 100 | | | | | 105 | | | | | 110 | |
| Gly | Gly | Gly | Gly | Gly | Gly | Gly | Gly | Gly | Gly | Gly | Gly | Gly | Gly | Gly |
| | | | 115 | | | | | 120 | | | | | 125 | |
| Gly | Gly | Ser | Ser | Ser | Ser | Ser | Ser | Ser | Ser | Gly | Gly | Gly | Gly | Gly |
| | 130 | | | | | 135 | | | | | 140 | | | |
| Gly | Gly | Gly | Gly | Gly | Gly | Gly | Gly | Gly | Gly | Gly | Gly | Gly | Gly | Gly |
| 145 | | | | | 150 | | | | | 155 | | | | 160 |
| Ser | Ser | Ser | Ser | Ser | Ser | Ser | Ser | Ser | Gly | Gly | Gly | Gly | Gly | Gly |
| | | | | 165 | | | | | 170 | | | | | 175 |
| Gly | Gly | Gly | Gly | Gly | Gly | Gly | Gly | Gly | Gly | Gly | Gly | Gly | Ser | Ser |
| | | | 180 | | | | | 185 | | | | | 190 | |
| Ser | Ser | Ser | Ser | Ser | Ser | Ser | Gly | Gly | Gly | Gly | Gly | Gly | Gly | Gly |
| | | | 195 | | | | | 200 | | | | | 205 | |
| Gly | Gly | Gly | Gly | Gly | Gly | Gly | Gly | Gly | Gly | Ser | Ser | Ser | Ser | Ser |
| | 210 | | | | | 215 | | | | | 220 | | | |
| Ser | Ser | Ser | Ser | Ser | Gly | Gly | Gly | Gly | Gly | Gly | Gly | Gly | Gly | Gly |
| 225 | | | | | 230 | | | | | 235 | | | | 240 |
| Gly | Gly | Gly | Gly | Gly | Gly | Gly | Gly | Gly | Ser | Ser | Ser | Ser | Ser | Ser |
| | | | | 245 | | | | | 250 | | | | | 255 |
| Ser | Ser | Ser | Gly | Gly | Gly | Gly | Gly | Gly | Gly | Gly | Gly | Gly | Gly | Gly |
| | | | 260 | | | | | 265 | | | | | 270 | |
| Gly | Gly | Gly | Gly | Gly | Gly | Gly | Ser | Ser | Ser | Ser | Ser | Ser | Ser | Ser |
| | | | 275 | | | | | 280 | | | | | 285 | |
| Ser | Ser | Gly | Gly | Gly | Gly | Gly | Gly | Gly | Gly | Gly | | | | |
| | 290 | | | | | 295 | | | | | 300 | | | |

```
<210> SEQ ID NO 427
<211> LENGTH: 500
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(10)
<223> OTHER INFORMATION: This region may encompass 1-10 residues
<220> FEATURE:
<221> NAME/KEY: SITE
<222> LOCATION: (11)..(20)
<223> OTHER INFORMATION: This region may encompass 1-10 residues
<220> FEATURE:
<221> NAME/KEY: SITE
<222> LOCATION: (21)..(30)
<223> OTHER INFORMATION: This region may encompass 1-10 residues
<220> FEATURE:
<221> NAME/KEY: SITE
<222> LOCATION: (31)..(40)
<223> OTHER INFORMATION: This region may encompass 1-10 residues
<220> FEATURE:
<221> NAME/KEY: SITE
<222> LOCATION: (41)..(50)
<223> OTHER INFORMATION: This region may encompass 1-10 residues
<220> FEATURE:
<221> NAME/KEY: SITE
<222> LOCATION: (51)..(60)
<223> OTHER INFORMATION: This region may encompass 1-10 residues
<220> FEATURE:
<221> NAME/KEY: SITE
<222> LOCATION: (61)..(70)
<223> OTHER INFORMATION: This region may encompass 1-10 residues
<220> FEATURE:
<221> NAME/KEY: SITE
<222> LOCATION: (71)..(80)
<223> OTHER INFORMATION: This region may encompass 1-10 residues
<220> FEATURE:
<221> NAME/KEY: SITE
<222> LOCATION: (81)..(90)
<223> OTHER INFORMATION: This region may encompass 1-10 residues
<220> FEATURE:
<221> NAME/KEY: SITE
<222> LOCATION: (91)..(100)
<223> OTHER INFORMATION: This region may encompass 1-10 residues
<220> FEATURE:
<221> NAME/KEY: SITE
<222> LOCATION: (101)..(110)
<223> OTHER INFORMATION: This region may encompass 1-10 residues
<220> FEATURE:
<221> NAME/KEY: SITE
<222> LOCATION: (111)..(120)
<223> OTHER INFORMATION: This region may encompass 1-10 residues
<220> FEATURE:
<221> NAME/KEY: SITE
<222> LOCATION: (121)..(130)
<223> OTHER INFORMATION: This region may encompass 1-10 residues
<220> FEATURE:
<221> NAME/KEY: SITE
<222> LOCATION: (131)..(140)
<223> OTHER INFORMATION: This region may encompass 1-10 residues
<220> FEATURE:
<221> NAME/KEY: SITE
<222> LOCATION: (141)..(150)
<223> OTHER INFORMATION: This region may encompass 1-10 residues
<220> FEATURE:
<221> NAME/KEY: SITE
<222> LOCATION: (151)..(160)
<223> OTHER INFORMATION: This region may encompass 1-10 residues
<220> FEATURE:
<221> NAME/KEY: SITE
<222> LOCATION: (161)..(170)
<223> OTHER INFORMATION: This region may encompass 1-10 residues
<220> FEATURE:
<221> NAME/KEY: SITE
<222> LOCATION: (171)..(180)
<223> OTHER INFORMATION: This region may encompass 1-10 residues
<220> FEATURE:
<221> NAME/KEY: SITE
```

```
<222> LOCATION: (181)..(190)
<223> OTHER INFORMATION: This region may encompass 1-10 residues
<220> FEATURE:
<221> NAME/KEY: SITE
<222> LOCATION: (191)..(200)
<223> OTHER INFORMATION: This region may encompass 1-10 residues
<220> FEATURE:
<221> NAME/KEY: SITE
<222> LOCATION: (201)..(210)
<223> OTHER INFORMATION: This region may encompass 1-10 residues
<220> FEATURE:
<221> NAME/KEY: SITE
<222> LOCATION: (211)..(220)
<223> OTHER INFORMATION: This region may encompass 1-10 residues
<220> FEATURE:
<221> NAME/KEY: SITE
<222> LOCATION: (221)..(230)
<223> OTHER INFORMATION: This region may encompass 1-10 residues
<220> FEATURE:
<221> NAME/KEY: SITE
<222> LOCATION: (231)..(240)
<223> OTHER INFORMATION: This region may encompass 1-10 residues
<220> FEATURE:
<221> NAME/KEY: SITE
<222> LOCATION: (241)..(250)
<223> OTHER INFORMATION: This region may encompass 1-10 residues
<220> FEATURE:
<221> NAME/KEY: SITE
<222> LOCATION: (251)..(260)
<223> OTHER INFORMATION: This region may encompass 1-10 residues
<220> FEATURE:
<221> NAME/KEY: SITE
<222> LOCATION: (261)..(270)
<223> OTHER INFORMATION: This region may encompass 1-10 residues
<220> FEATURE:
<221> NAME/KEY: SITE
<222> LOCATION: (271)..(280)
<223> OTHER INFORMATION: This region may encompass 1-10 residues
<220> FEATURE:
<221> NAME/KEY: SITE
<222> LOCATION: (281)..(290)
<223> OTHER INFORMATION: This region may encompass 1-10 residues
<220> FEATURE:
<221> NAME/KEY: SITE
<222> LOCATION: (291)..(300)
<223> OTHER INFORMATION: This region may encompass 1-10 residues
<220> FEATURE:
<221> NAME/KEY: SITE
<222> LOCATION: (301)..(310)
<223> OTHER INFORMATION: This region may encompass 1-10 residues
<220> FEATURE:
<221> NAME/KEY: SITE
<222> LOCATION: (311)..(320)
<223> OTHER INFORMATION: This region may encompass 1-10 residues
<220> FEATURE:
<221> NAME/KEY: SITE
<222> LOCATION: (321)..(330)
<223> OTHER INFORMATION: This region may encompass 1-10 residues
<220> FEATURE:
<221> NAME/KEY: SITE
<222> LOCATION: (331)..(340)
<223> OTHER INFORMATION: This region may encompass 1-10 residues
<220> FEATURE:
<221> NAME/KEY: SITE
<222> LOCATION: (341)..(350)
<223> OTHER INFORMATION: This region may encompass 1-10 residues
<220> FEATURE:
<221> NAME/KEY: SITE
<222> LOCATION: (351)..(360)
<223> OTHER INFORMATION: This region may encompass 1-10 residues
<220> FEATURE:
<221> NAME/KEY: SITE
<222> LOCATION: (361)..(370)
<223> OTHER INFORMATION: This region may encompass 1-10 residues
<220> FEATURE:
<221> NAME/KEY: SITE
<222> LOCATION: (371)..(380)
<223> OTHER INFORMATION: This region may encompass 1-10 residues
<220> FEATURE:
```

<220> FEATURE:
<221> NAME/KEY: SITE
<222> LOCATION: (381)..(390)
<223> OTHER INFORMATION: This region may encompass 1-10 residues
<220> FEATURE:
<221> NAME/KEY: SITE
<222> LOCATION: (391)..(400)
<223> OTHER INFORMATION: This region may encompass 1-10 residues
<220> FEATURE:
<221> NAME/KEY: SITE
<222> LOCATION: (401)..(410)
<223> OTHER INFORMATION: This region may encompass 1-10 residues
<220> FEATURE:
<221> NAME/KEY: SITE
<222> LOCATION: (411)..(420)
<223> OTHER INFORMATION: This region may encompass 1-10 residues
<220> FEATURE:
<221> NAME/KEY: SITE
<222> LOCATION: (421)..(430)
<223> OTHER INFORMATION: This region may encompass 1-10 residues
<220> FEATURE:
<221> NAME/KEY: SITE
<222> LOCATION: (431)..(440)
<223> OTHER INFORMATION: This region may encompass 1-10 residues
<220> FEATURE:
<221> NAME/KEY: SITE
<222> LOCATION: (441)..(450)
<223> OTHER INFORMATION: This region may encompass 1-10 residues
<220> FEATURE:
<221> NAME/KEY: SITE
<222> LOCATION: (451)..(460)
<223> OTHER INFORMATION: This region may encompass 1-10 residues
<220> FEATURE:
<221> NAME/KEY: SITE
<222> LOCATION: (461)..(470)
<223> OTHER INFORMATION: This region may encompass 1-10 residues
<220> FEATURE:
<221> NAME/KEY: SITE
<222> LOCATION: (471)..(480)
<223> OTHER INFORMATION: This region may encompass 1-10 residues
<220> FEATURE:
<221> NAME/KEY: SITE
<222> LOCATION: (481)..(490)
<223> OTHER INFORMATION: This region may encompass 1-10 residues
<220> FEATURE:
<221> NAME/KEY: SITE
<222> LOCATION: (491)..(500)
<223> OTHER INFORMATION: This region may encompass 1-10 residues
<220> FEATURE:
<221> NAME/KEY: SITE
<222> LOCATION: (1)..(500)
<223> OTHER INFORMATION: This sequence may encompass 1-10
       "(Gly)m(Ser)o(Gly)m(Ser)o(Gly)m" repeating units,
       wherein m = 1 to 10, o = 1 to 10
<220> FEATURE:
<223> OTHER INFORMATION: See specification as filed for detailed
       description of substitutions and preferred embodiments

<400> SEQUENCE: 427

Gly Gly Gly Gly Gly Gly Gly Gly Gly Ser Ser Ser Ser Ser Ser
1               5                   10                  15

Ser Ser Ser Ser Gly Gly Gly Gly Gly Gly Gly Gly Gly Ser Ser
            20                  25                  30

Ser Ser Ser Ser Ser Ser Ser Gly Gly Gly Gly Gly Gly Gly Gly
        35                  40                  45

Gly Gly Gly Gly Gly Gly Gly Gly Gly Gly Gly Ser Ser Ser Ser
    50                  55                  60

Ser Ser Ser Ser Ser Gly Gly Gly Gly Gly Gly Gly Gly Gly Gly
65                  70                  75                  80

Ser Ser Ser Ser Ser Ser Ser Ser Gly Gly Gly Gly Gly Gly Gly
                85                  90                  95

Gly Gly Gly Gly Gly Gly Gly Gly Gly Gly Gly Gly Gly Ser Ser
            100                 105                 110

-continued

Ser Ser Ser Ser Ser Ser Ser Gly Gly Gly Gly Gly Gly Gly
        115                 120                 125

Gly Gly Ser Ser Ser Ser Ser Ser Ser Ser Gly Gly Gly Gly
130                 135                 140

Gly Gly Gly Gly Gly Gly Gly Gly Gly Gly Gly Gly Gly Gly
145                 150                 155                 160

Ser Ser Ser Ser Ser Ser Ser Ser Gly Gly Gly Gly Gly
            165                 170                 175

Gly Gly Gly Gly Ser Ser Ser Ser Ser Ser Ser Ser Gly Gly
            180                 185                 190

Gly Gly Gly Gly Gly Gly Gly Gly Gly Gly Gly Gly Gly Gly
            195                 200                 205

Gly Gly Ser Ser Ser Ser Ser Ser Ser Ser Gly Gly Gly Gly
            210                 215                 220

Gly Gly Gly Gly Gly Ser Ser Ser Ser Ser Ser Ser Ser Ser
225                 230                 235                 240

Gly Gly Gly Gly Gly Gly Gly Gly Gly Gly Gly Gly Gly Gly
                    245                 250                 255

Gly Gly Gly Gly Ser Ser Ser Ser Ser Ser Ser Ser Gly Gly
                    260                 265                 270

Gly Gly Gly Gly Gly Gly Gly Ser Ser Ser Ser Ser Ser Ser
            275                 280                 285

Ser Ser Gly Gly Gly Gly Gly Gly Gly Gly Gly Gly Gly Gly
        290                 295                 300

Gly Gly Gly Gly Gly Ser Ser Ser Ser Ser Ser Ser Ser Ser
305                 310                 315                 320

Gly Gly Gly Gly Gly Gly Gly Gly Gly Ser Ser Ser Ser Ser
                    325                 330                 335

Ser Ser Ser Ser Gly Gly Gly Gly Gly Gly Gly Gly Gly Gly
            340                 345                 350

Gly Gly Gly Gly Gly Gly Gly Ser Ser Ser Ser Ser Ser Ser
            355                 360                 365

Ser Ser Gly Gly Gly Gly Gly Gly Gly Gly Gly Ser Ser Ser Ser
        370                 375                 380

Ser Ser Ser Ser Ser Ser Gly Gly Gly Gly Gly Gly Gly Gly
385                 390                 395                 400

Gly Gly Gly Gly Gly Gly Gly Gly Gly Ser Ser Ser Ser Ser
                    405                 410                 415

Ser Ser Ser Ser Gly Gly Gly Gly Gly Gly Gly Gly Gly Ser Ser
            420                 425                 430

Ser Ser Ser Ser Ser Ser Gly Gly Gly Gly Gly Gly Gly
            435                 440                 445

Gly Gly Gly Gly Gly Gly Gly Gly Gly Gly Ser Ser Ser Ser
450                 455                 460

Ser Ser Ser Ser Ser Ser Gly Gly Gly Gly Gly Gly Gly Gly
465                 470                 475                 480

Ser Ser Ser Ser Ser Ser Ser Ser Ser Gly Gly Gly Gly Gly
                    485                 490                 495

Gly Gly Gly Gly
        500

<210> SEQ ID NO 428
<211> LENGTH: 140

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (5)..(14)
<223> OTHER INFORMATION: This region may encompass 1-10 residues
<220> FEATURE:
<221> NAME/KEY: SITE
<222> LOCATION: (19)..(28)
<223> OTHER INFORMATION: This region may encompass 1-10 residues
<220> FEATURE:
<221> NAME/KEY: SITE
<222> LOCATION: (33)..(42)
<223> OTHER INFORMATION: This region may encompass 1-10 residues
<220> FEATURE:
<221> NAME/KEY: SITE
<222> LOCATION: (47)..(56)
<223> OTHER INFORMATION: This region may encompass 1-10 residues
<220> FEATURE:
<221> NAME/KEY: SITE
<222> LOCATION: (61)..(70)
<223> OTHER INFORMATION: This region may encompass 1-10 residues
<220> FEATURE:
<221> NAME/KEY: SITE
<222> LOCATION: (75)..(84)
<223> OTHER INFORMATION: This region may encompass 1-10 residues
<220> FEATURE:
<221> NAME/KEY: SITE
<222> LOCATION: (89)..(98)
<223> OTHER INFORMATION: This region may encompass 1-10 residues
<220> FEATURE:
<221> NAME/KEY: SITE
<222> LOCATION: (103)..(112)
<223> OTHER INFORMATION: This region may encompass 1-10 residues
<220> FEATURE:
<221> NAME/KEY: SITE
<222> LOCATION: (117)..(126)
<223> OTHER INFORMATION: This region may encompass 1-10 residues
<220> FEATURE:
<221> NAME/KEY: SITE
<222> LOCATION: (131)..(140)
<223> OTHER INFORMATION: This region may encompass 1-10 residues
<220> FEATURE:
<221> NAME/KEY: SITE
<222> LOCATION: (1)..(140)
<223> OTHER INFORMATION: This sequence may encompass 1-10
      "Gly Ser Gly Gly (Ser)m" repeating units,
      wherein m = 1 to 10
<220> FEATURE:
<223> OTHER INFORMATION: See specification as filed for detailed
      description of substitutions and preferred embodiments

<400> SEQUENCE: 428

Gly Ser Gly Gly Ser Ser Ser Ser Ser Ser Ser Ser Ser Gly Ser
1               5                   10                  15

Gly Gly Ser Ser Ser Ser Ser Ser Ser Ser Ser Gly Ser Gly Gly
                20                  25                  30

Ser Ser Ser Ser Ser Ser Ser Ser Ser Gly Ser Gly Gly Ser Ser
                35                  40                  45

Ser Ser Ser Ser Ser Ser Ser Gly Ser Gly Gly Ser Ser Ser Ser
    50                  55                  60

Ser Ser Ser Ser Ser Gly Ser Gly Gly Ser Ser Ser Ser Ser Ser
65                  70                  75                  80

Ser Ser Ser Gly Ser Gly Gly Ser Ser Ser Ser Ser Ser Ser Ser
                85                  90                  95

Ser Gly Ser Gly Gly Ser Ser Ser Ser Ser Ser Ser Ser Ser
            100                 105                 110
```

```
Gly Ser Gly Gly Ser Ser Ser Ser Ser Ser Ser Ser Ser Gly Ser
        115                 120                 125

Gly Gly Ser Ser Ser Ser Ser Ser Ser Ser Ser
    130                 135                 140

<210> SEQ ID NO 429
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (4)..(13)
<223> OTHER INFORMATION: This region may encompass 1-10 residues
<220> FEATURE:
<221> NAME/KEY: SITE
<222> LOCATION: (18)..(27)
<223> OTHER INFORMATION: This region may encompass 1-10 residues
<220> FEATURE:
<221> NAME/KEY: SITE
<222> LOCATION: (32)..(41)
<223> OTHER INFORMATION: This region may encompass 1-10 residues
<220> FEATURE:
<221> NAME/KEY: SITE
<222> LOCATION: (46)..(55)
<223> OTHER INFORMATION: This region may encompass 1-10 residues
<220> FEATURE:
<221> NAME/KEY: SITE
<222> LOCATION: (60)..(69)
<223> OTHER INFORMATION: This region may encompass 1-10 residues
<220> FEATURE:
<221> NAME/KEY: SITE
<222> LOCATION: (74)..(83)
<223> OTHER INFORMATION: This region may encompass 1-10 residues
<220> FEATURE:
<221> NAME/KEY: SITE
<222> LOCATION: (88)..(97)
<223> OTHER INFORMATION: This region may encompass 1-10 residues
<220> FEATURE:
<221> NAME/KEY: SITE
<222> LOCATION: (102)..(111)
<223> OTHER INFORMATION: This region may encompass 1-10 residues
<220> FEATURE:
<221> NAME/KEY: SITE
<222> LOCATION: (116)..(125)
<223> OTHER INFORMATION: This region may encompass 1-10 residues
<220> FEATURE:
<221> NAME/KEY: SITE
<222> LOCATION: (130)..(139)
<223> OTHER INFORMATION: This region may encompass 1-10 residues
<220> FEATURE:
<221> NAME/KEY: SITE
<222> LOCATION: (1)..(140)
<223> OTHER INFORMATION: This sequence may encompass 1-10
      "Gly Ser Gly (Ser)m Gly" repeating units,
      wherein m = 1 to 10
<220> FEATURE:
<223> OTHER INFORMATION: See specification as filed for detailed
      description of substitutions and preferred embodiments

<400> SEQUENCE: 429

Gly Ser Gly Ser Ser Ser Ser Ser Ser Ser Ser Ser Gly Gly Ser
1               5                   10                  15

Gly Ser Ser Ser Ser Ser Ser Ser Ser Ser Ser Gly Gly Ser Gly Ser
            20                  25                  30

Ser Ser Ser Ser Ser Ser Ser Ser Gly Gly Ser Gly Ser Ser Ser
        35                  40                  45

Ser Ser Ser Ser Ser Ser Ser Gly Gly Ser Gly Ser Ser Ser Ser Ser
    50                  55                  60
```

Ser Ser Ser Ser Ser Gly Gly Ser Gly Ser Ser Ser Ser Ser Ser Ser
65                  70                  75                  80

Ser Ser Ser Gly Gly Ser Gly Ser Ser Ser Ser Ser Ser Ser
            85                  90                  95

Ser Gly Gly Ser Gly Ser Ser Ser Ser Ser Ser Ser Ser Gly
        100                 105                 110

Gly Ser Gly Ser Ser Ser Ser Ser Ser Ser Ser Gly Gly Ser
        115                 120                 125

Gly Ser Ser Ser Ser Ser Ser Ser Ser Gly
    130                 135                 140

<210> SEQ ID NO 430
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (5)..(14)
<223> OTHER INFORMATION: This region may encompass 1-10 residues
<220> FEATURE:
<221> NAME/KEY: SITE
<222> LOCATION: (19)..(28)
<223> OTHER INFORMATION: This region may encompass 1-10 residues
<220> FEATURE:
<221> NAME/KEY: SITE
<222> LOCATION: (33)..(42)
<223> OTHER INFORMATION: This region may encompass 1-10 residues
<220> FEATURE:
<221> NAME/KEY: SITE
<222> LOCATION: (47)..(56)
<223> OTHER INFORMATION: This region may encompass 1-10 residues
<220> FEATURE:
<221> NAME/KEY: SITE
<222> LOCATION: (61)..(70)
<223> OTHER INFORMATION: This region may encompass 1-10 residues
<220> FEATURE:
<221> NAME/KEY: SITE
<222> LOCATION: (75)..(84)
<223> OTHER INFORMATION: This region may encompass 1-10 residues
<220> FEATURE:
<221> NAME/KEY: SITE
<222> LOCATION: (89)..(98)
<223> OTHER INFORMATION: This region may encompass 1-10 residues
<220> FEATURE:
<221> NAME/KEY: SITE
<222> LOCATION: (103)..(112)
<223> OTHER INFORMATION: This region may encompass 1-10 residues
<220> FEATURE:
<221> NAME/KEY: SITE
<222> LOCATION: (117)..(126)
<223> OTHER INFORMATION: This region may encompass 1-10 residues
<220> FEATURE:
<221> NAME/KEY: SITE
<222> LOCATION: (131)..(140)
<223> OTHER INFORMATION: This region may encompass 1-10 residues
<220> FEATURE:
<221> NAME/KEY: SITE
<222> LOCATION: (1)..(140)
<223> OTHER INFORMATION: This sequence may encompass 1-10
      "Gly Gly Gly Gly (Ser)m" repeating units,
      wherein m = 1 to 10
<220> FEATURE:
<223> OTHER INFORMATION: See specification as filed for detailed
      description of substitutions and preferred embodiments

<400> SEQUENCE: 430

Gly Gly Gly Gly Ser Ser Ser Ser Ser Ser Ser Ser Ser Gly Gly
1               5                   10                  15

```
Gly Gly Ser Ser Ser Ser Ser Ser Ser Ser Gly Gly Gly
        20                  25                  30

Ser Ser Ser Ser Ser Ser Ser Ser Gly Gly Gly Gly Ser Ser
        35                  40                  45

Ser Ser Ser Ser Ser Ser Ser Gly Gly Gly Gly Ser Ser Ser Ser
50                  55                  60

Ser Ser Ser Ser Ser Ser Gly Gly Gly Gly Ser Ser Ser Ser Ser
65                  70                  75                  80

Ser Ser Ser Ser Ser Gly Gly Gly Gly Ser Ser Ser Ser Ser Ser
                85                  90                  95

Ser Ser Gly Gly Gly Gly Ser Ser Ser Ser Ser Ser Ser Ser Ser
            100                 105                 110

Gly Gly Gly Gly Ser Ser Ser Ser Ser Ser Ser Ser Ser Gly Gly
        115                 120                 125

Gly Gly Ser Ser Ser Ser Ser Ser Ser Ser Ser
        130                 135                 140

<210> SEQ ID NO 431
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(100)
<223> OTHER INFORMATION: This sequence may encompass 1-50 "Gly Ser"
      repeating units
<220> FEATURE:
<223> OTHER INFORMATION: See specification as filed for detailed
      description of substitutions and preferred embodiments

<400> SEQUENCE: 431

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser Gly Ser
            20                  25                  30

Gly Ser Gly Ser Gly Ser Gly Ser Gly Ser Gly Ser Gly Ser Gly Ser
        35                  40                  45

Gly Ser Gly Ser Gly Ser Gly Ser Gly Ser Gly Ser Gly Ser Gly Ser
    50                  55                  60

Gly Ser Gly Ser Gly Ser Gly Ser Gly Ser Gly Ser Gly Ser Gly Ser
65                  70                  75                  80

Gly Ser Gly Ser Gly Ser Gly Ser Gly Ser Gly Ser Gly Ser Gly Ser
                85                  90                  95

Gly Ser Gly Ser
            100

<210> SEQ ID NO 432
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(250)
<223> OTHER INFORMATION: This sequence may encompass 1-50 "Gly Ser Gly
      Gly Ser" repeating units
<220> FEATURE:
```

<223> OTHER INFORMATION: See specification as filed for detailed
      description of substitutions and preferred embodiments

<400> SEQUENCE: 432

Gly Ser Gly Gly Ser Gly Ser Gly Ser Gly Ser Gly Ser Gly Ser Gly
1               5                   10                  15

Ser Gly Gly Ser Gly Ser Gly Ser Gly Ser Gly Ser Gly Ser Gly Ser
                20                  25                  30

Gly Gly Ser Gly Ser Gly Ser Gly Ser Gly Ser Gly Ser Gly Ser Gly
            35                  40                  45

Gly Ser Gly Ser Gly Gly Ser Gly Ser Gly Ser Gly Ser Gly Ser Gly
        50                  55                  60

Ser Gly Ser Gly Gly Ser Gly Ser Gly Ser Gly Ser Gly Ser Gly Ser
65                  70                  75                  80

Gly Ser Gly Gly Ser Gly Ser Gly Ser Gly Ser Gly Ser Gly Ser Gly
                85                  90                  95

Ser Gly Gly Ser Gly Ser Gly Ser Gly Ser Gly Ser Gly Ser Gly Ser
                100                 105                 110

Gly Gly Ser Gly Ser Gly Ser Gly Ser Gly Ser Gly Ser Gly Ser Gly
            115                 120                 125

Gly Ser Gly Ser Gly Gly Ser Gly Ser Gly Ser Gly Ser Gly Ser Gly
        130                 135                 140

Ser Gly Ser Gly Gly Ser Gly Ser Gly Ser Gly Ser Gly Ser Gly Ser
145                 150                 155                 160

Gly Ser Gly Gly Ser Gly Ser Gly Gly Ser Gly Ser Gly Ser Gly Ser
                165                 170                 175

Ser Gly Gly Ser Gly Ser Gly Ser Gly Ser Gly Ser Gly Ser Gly Ser
                180                 185                 190

Gly Gly Ser Gly Ser Gly Ser Gly Ser Gly Ser Gly Ser Gly Ser Gly
            195                 200                 205

Gly Ser Gly Ser Gly Ser Gly Ser Gly Ser Gly Ser Gly Ser Gly Gly
        210                 215                 220

Ser Gly Ser Gly Gly Ser Gly Ser Gly Ser Gly Ser Gly Ser Gly Ser
225                 230                 235                 240

Gly Ser Gly Gly Ser Gly Ser Gly Gly Ser
                245                 250

<210> SEQ ID NO 433
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(200)
<223> OTHER INFORMATION: This sequence may encompass 1-50 "Gly Gly Gly
      Ser" repeating units
<220> FEATURE:
<223> OTHER INFORMATION: See specification as filed for detailed
      description of substitutions and preferred embodiments

<400> SEQUENCE: 433

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
                20                  25                  30

Gly Gly Gly Ser Gly Gly Gly Ser Gly Gly Gly Ser Gly Gly Gly Ser
            35                  40                  45

Gly Gly Gly Ser Gly Gly Gly Ser Gly Gly Gly Ser Gly Gly Gly Ser
        50                  55                  60

Gly Gly Gly Ser Gly Gly Gly Ser Gly Gly Gly Ser Gly Gly Gly Ser
65                  70                  75                  80

Gly Gly Gly Ser Gly Gly Gly Ser Gly Gly Gly Ser Gly Gly Gly Ser
                85                  90                  95

Gly Gly Gly Ser Gly Gly Gly Ser Gly Gly Gly Ser Gly Gly Gly Ser
            100                 105                 110

Gly Gly Gly Ser Gly Gly Gly Ser Gly Gly Gly Ser Gly Gly Gly Ser
        115                 120                 125

Gly Gly Gly Ser Gly Gly Gly Ser Gly Gly Gly Ser Gly Gly Gly Ser
    130                 135                 140

Gly Gly Gly Ser Gly Gly Gly Ser Gly Gly Gly Ser Gly Gly Gly Ser
145                 150                 155                 160

Gly Gly Gly Ser Gly Gly Gly Ser Gly Gly Gly Ser Gly Gly Gly Ser
                165                 170                 175

Gly Gly Gly Ser Gly Gly Gly Ser Gly Gly Gly Ser Gly Gly Gly Ser
            180                 185                 190

Gly Gly Gly Ser Gly Gly Gly Ser
        195                 200

<210> SEQ ID NO 434
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(250)
<223> OTHER INFORMATION: This sequence may encompass 1-50 "Gly Gly Gly
      Gly Ser" repeating units
<220> FEATURE:
<223> OTHER INFORMATION: See specification as filed for detailed
      description of substitutions and preferred embodiments

<400> SEQUENCE: 434

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser Gly Gly Gly Gly Ser Gly Gly Gly Gly Ser Gly Gly
            100                 105                 110

Gly Gly Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

```
Ser Gly Gly Gly Gly Ser Gly Gly Gly Ser Gly Gly Gly Ser
145                 150                 155                 160

Gly Gly Gly Gly Ser Gly Gly Gly Ser Gly Gly Gly Ser Gly
                165                 170                 175

Gly Gly Gly Ser Gly Gly Gly Ser Gly Gly Gly Ser Gly Gly
            180                 185                 190

Gly Gly Ser Gly Gly Gly Ser Gly Gly Gly Ser Gly Gly Gly
        195                 200                 205

Gly Ser Gly Gly Gly Ser Gly Gly Gly Ser Gly Gly Gly Gly
    210                 215                 220

Ser Gly Gly Gly Ser Gly Gly Gly Ser Gly Gly Gly Gly Ser
225                 230                 235                 240

Gly Gly Gly Gly Ser Gly Gly Gly Ser
                245                 250

<210> SEQ ID NO 435
<211> LENGTH: 6
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: SITE
<222> LOCATION: (1)..(6)
<223> OTHER INFORMATION: This sequence may encompass 3-6 residues

<400> SEQUENCE: 435

His His His His His His
1               5

<210> SEQ ID NO 436
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 436

His His His His His His
1               5

<210> SEQ ID NO 437
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(10)
<223> OTHER INFORMATION: This sequence may encompass 1-10 residues
<220> FEATURE:
<223> OTHER INFORMATION: See specification as filed for detailed
      description of substitutions and preferred embodiments

<400> SEQUENCE: 437

Gly Gly Gly Gly Gly Gly Gly Gly Gly Gly
1               5                   10

<210> SEQ ID NO 438
<211> LENGTH: 50
<212> TYPE: PRT
```

-continued

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(50)
<223> OTHER INFORMATION: This sequence may encompass 1-50 residues
<220> FEATURE:
<223> OTHER INFORMATION: See specification as filed for detailed
      description of substitutions and preferred embodiments

<400> SEQUENCE: 438

Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Gly Gly
    50
```

IL-2 ORTHOLOGS AND METHODS OF USE

CROSS-REFERENCE TO OTHER APPLICATIONS

This application claims the priority of U.S. Provisional Patent Application Ser. No. 62/948,066 filed Dec. 13, 2019.

STATEMENT REGARDING GOVERNMENT FUNDING

No United States government funding was used in the conception or reduction to practice of the subject matter of the present invention.

REFERENCE TO SUBMISSION OF A SEQUENCE LISTING AS A TEXT FILE

The Sequence Listing written in file 106249-1225734-000710US SL.txt created on Mar. 1, 2021, 291.543 bytes, machine format IBM-PC, MS-Windows operating system, is hereby incorporated by reference in its entirety for all purposes.

BACKGROUND OF THE INVENTION

The controlled manipulation of the differentiation, development and proliferation of cells, particularly engineered immune cells, is of significant clinical interest. T cells have been engineered for use in therapeutic applications such as the recognition and killing of cancer cells, intracellular pathogens and cells involved in autoimmunity. The use of engineered cell therapies in the treatment of cancer is facilitated by the selective activation and expansion of engineered T cells that provide specific functions and are directed to selectively attack cancer cells. In some examples of adoptive immunotherapy, T cells are isolated from the blood of a subject, processed ex vivo, and re-infused into the subject. Compositions and methods that enable selective activation of a targeted engineered cell population are therefore desirable.

A challenge with the manufacture of cell therapy products is that such 'living drugs' require close control of their environment to preserve viability and functionality. In practice, isolated cells, whether derived from a patient (autologous) or from a single donor source (allogeneic), begin to lose function rapidly following removal from the subject or the controlled culture conditions. Successful maintenance of the health and function of isolated cells while outside the subject or controlled culture conditions enables the isolated cells to return to functionality for reinsertion into the cell product manufacturing workflow or into patients.

Additionally, a challenge with the clinical application of engineered T cell therapies is to selectively stimulate these engineered cells to maximize their therapeutic effectiveness. Typical means to provide for the continued maintenance of activated engineered T cell products is the systemic administration of cytokines such as IL2. However, the systemic administration of IL2 is associated with non-specific stimulatory effects beyond the population of engineered cells and is associated, particularly in high doses, and is associated with significant toxicity in human subjects. Furthermore, IL2 has a short lifespan in vivo which requires that the IL-2 be dosed frequently to maintain the engineered T cells in an activated state. Although engineered cells from an initial administration of an initial population may be detectable for months or even years following the administration of the engineered cell product, a significant fraction of these engineered cells lapse into a quiescent state that requires reactivation for them to exhibit significant therapeutic effect. Consequently, a challenge in cell-based therapies is to confer a desired regulatable behavior into the transferred cells that is protected from endogenous signaling pathways, that does not affect non-targeted endogenous cells, and that can be controlled selectively following administration of the engineered cell population to a subject.

CD122 is a component of the intermediate and high affinity IL2 receptor complexes. Sockolosky, et al. (Science (2018) 359: 1037-1042) and Garcia, et al. (United States Patent Application Publication US2018/0228841A1 published Aug. 16, 2018) describe an orthogonal IL2/CD122 ligand/receptor system to facilitate selective stimulation of cells engineered to express the orthogonal CD122 receptor. IL2 muteins that are cognate ligands for the orthogonal receptor are also described. The contact of engineered T cells that express the orthogonal CD122 with a corresponding orthogonal ligand for such orthogonal CD122 ("IL2 orthologs") enables specific activation of such engineered T cells. In particular this orthogonal IL2 receptor ligand complex provides for selective expansion of cells engineered to express the orthogonal receptor in a mixed population of cells, in particular a mixed population of T cells.

IL-2 orthologs with diminished affinity for the non-engineered intermediate affinity (CD122/CD132) IL-2 receptor complex or high-affinity (CD25/CD122/CD132) IL-2 receptor complex are also useful to selectively target the activity of ortholog IL-2 towards cells which exhibit high expression of CD25, e.g. in the treatment of autoimmune disease. IL-2 orthologs with significantly diminished affinity for the native wild-type hCD122 extracellular domain (ECD) but retain binding to the ECD of CD25 may also be used as competitive antagonists of wild-type IL-2 by interfering with the high-affinity IL-2 receptor complex formation and consequently may be employed in the treatment of autoimmune diseases or graft-versus-host (GVH) disease.

The present disclosure is directed to ligands that interact with an orthogonal hCD122 receptor. Specifically provided are hIL-2 orthogonal ligands (hIL2 orthologs) that provide selective binding and signaling via receptors comprising the extracellular domain of a hCD122 orthogonal receptor, in particular the extracellular domain of human CD122 comprising the amino acid substitutions H133D and Y134F. The IL2 activity on cells expressing the wild-type hCD122 of the present hIL2 orthologs is significantly diminished compared to the activity present hIL2 orthologs on cells expressing the orthogonal hCD122. Thus, selective activation and/or expansion of engineered cells expressing a receptor comprising the extracellular domain of orthogonal hIL2 using hIL-2 orthologs on the engineered cell populations is provided.

SUMMARY OF THE INVENTION

The present disclosure relates to human IL2 orthogonal ligands ("hIL2 orthologs") that specifically and selectively bind to the extracellular domain (ECD) a transmembrane polypeptide comprising of a modified hCD122 polypeptide comprising modifications at positions 133 and/or 134 of the ECD of the orthogonal hCD122 polypeptide. In some embodiments, the orthogonal hCD122 polypeptide comprising the amino acid substitutions H133D and Y134F. The binding of the hIL2 ortholog to the modified hCD122 polypeptide participates in the transduction pathway of intracellular signaling resulting in a biological activity of the native intracellular signaling patterns associated with IL2 binding to either the intermediate or high affinity IL2 receptor but which exhibits selectivity to an engineered cell expressing an hCD122 orthogonal receptor. In some embodiments, the hIL2 ortholog is a hIL2 variant of Formula 1 described hereinbelow. The hIL2 orthologs of the present d exhibit significantly reduced binding relative to the extracellular domain of wild-type hCD122, either alone or when hCD122 is present in the form of the endogenous high or intermediate affinity hIL2 receptor relative to the hIL2 ortholog's binding to the hCD122 orthogonal receptor. In some embodiments, the affinity of the hIL2 ortholog for the extracellular domain of the orthogonal hCD122 is comparable to the affinity of wild-type hIL2 for wild-type hCD122. In some embodiments, the affinity of the hIL2 ortholog for the extracellular domain ("ECD") of the orthogonal hCD122 is greater than to the affinity of wild-type hIL2 for extracellular domain of wild-type hCD122. In some embodiments, the affinity of the hIL2 ortholog for the extracellular domain of the orthogonal hCD122 is less than to the affinity of wild-type hIL2 for the extracellular domain of the wild-type hCD122. In one embodiment, the ECD of the orthogonal hCD122 receptor comprises a modified human hCD122 ECD polypeptide comprising the substitutions H133D and Y134F (numbered in accordance with wild-type hCD122) wherein the amino acid sequence of the ECD of the orthogonal hCD122 receptor comprises a 214 amino acid polypeptide having the sequence:

```
                                     (SEQ ID NO: 1)
AVNGTSQFTC FYNSRANISC VWSQDGALQD TSCQVHAWPD

RRRWNQTCEL LPVSQASWAC NLILGAPDSQ KLTTVDIVTL

RVLCREGVRW RVMAIQDFKP FENLRLMAPI SLQVVHVETH

RCNISWEISQ ASDFFERHLE FEARTLSPGH TWEEAPLLTL

KQKQEWICLE TLTPDTQYEF QVRVKPLQGE FTTWSPWSQP

LAFRTKPAAL GKDT
```

In one embodiment, the orthogonal hCD122 receptor is a modified human CD122 having the comprising amino acid sequence (less the signal peptide) of the ECD of hCD122 having substitutions H133D and Y134F (SEQ ID NO:1) and the transmembrane (TM) and intracellular domain (ICD) of the wild-type hCD122 molecule, the orthogonal hCD122 receptor (hoRb) comprising the amino acid sequence:

```
                                     (SEQ ID NO: 2)
AVNGTSQFTC FYNSRANISC VWSQDGALQD TSCQVHAWPD

RRRWNQTCEL LPVSQASWAC NLILGAPDSQ KLTTVDIVTL

RVLCREGVRW RVMAIQDFKP FENLRLMAPI SLQVVHVETH

RCNISWEISQ ASDFFERHLE FEARTLSPGH TWEEAPLLTL

KQKQEWICLE TLTPDTQYEF QVRVKPLQGE FTTWSPWSQP

LAFRTKPAAL GKDTIPWLGH LLVGLSGAFG FIILVYLLIN

CRNTGPWLKK VLKCNTPDPS KFFSQLSSEH GGDVQKWLSS

PFPSSSFSPG GLAPEISPLE VLERDKVTQL LLQQDKVPEP

ASLSSNHSLT SCFTNQGYFF FHLPDALEIE ACQVYFTYDP

YSEEDPDEGV AGAPTGSSPQ PLQPLSGEDD AYCTFPSRDD

LLLFSPSLLG GPSPPSTAPG GSGAGEERMP PSLQERVPRD

WDPQPLGPPT PGVPDLVDFQ PPPELVLREA GEEVPDAGPR

EGVSFPWSRP PGQGEFRALN ARLPLNTDAY LSLQELQGQD

PTHL
```

In one embodiment, the present disclosure provides an hIL2 ortholog, the amino acid sequence of which has at least 80% identity to polypeptide of the Formula #1:

$$
\begin{array}{l}
[(AA1)-(AA2)-(AA3)-(AA4)-(AA5)-(AA6)-(AA7)-(AA8)-(AA9)_i\text{-}T10\text{-}Q11\text{-}L12\text{-} \\
(AA13)\text{-}(AA14)\text{-}(AA15)\text{-}(AA16)\text{-}L17\text{-}(AA18)\text{-}(AA19)\text{-}(AA20)\text{-}L21\text{-}(AA22)\text{-} \\
(AA23)\text{-}I24\text{-}L25\text{-}N26\text{-}(AA27)\text{-}I28\text{-}N29\text{-}N30\text{-}Y31\text{-}K32\text{-}N33\text{-}P34\text{-}K35\text{-}L36\text{-}T37\text{-} \\
(AA38)\text{-}(AA39)\text{-}L40\text{-}T41\text{-}(AA42)\text{-}K43\text{-}F44\text{-}Y45\text{-}M46\text{-}P47\text{-}K48\text{-}K49\text{-}A50\text{-}(AA51)\text{-} \\
E52\text{-}L53\text{-}K54\text{-}(AA55)\text{-}L56\text{-}Q57\text{-}C58\text{-}L59\text{-}E60\text{-}E61\text{-}E62\text{-}L63\text{-}K64\text{-}P65\text{-}L66\text{-}E67\text{-} \\
E68\text{-}V69\text{-}L70\text{-}N71\text{-}L72\text{-}A73\text{-}(AA74)\text{-}S75\text{-}K76\text{-}N77\text{-}F78\text{-}H79\text{-}(AA80\text{-}(AA81)\text{-}P82\text{-} \\
R83\text{-}D84\text{-}(AA85)\text{-}(AA86)\text{-}S87\text{-}N88\text{-}(AA89)\text{-}N90\text{-}(AA91)\text{-}(AA92)\text{-}V93\text{-}L94\text{-}E95\text{-} \\
L96\text{-}(AA97)\text{-}G98\text{-}S99\text{-}E100\text{-}T101\text{-}T102\text{-}F103\text{-}(AA104)\text{-}C105\text{-}E106\text{-}Y107\text{-}A108\text{-} \\
(AA109)\text{-}E110\text{-}T111\text{-}A112\text{-}(AA113)\text{-}I114\text{-}V115\text{-}E116\text{-}F117\text{-}L118\text{-}N119\text{-}R120\text{-} \\
W121\text{-}I122\text{-}T123\text{-}F124\text{-}(AA125)\text{-}(AA126)\text{-}S127\text{-}I128\text{-}I129\text{-}(AA130)\text{-}T131\text{-}L132\text{-} \\
T133]
\end{array}
\quad [1]
$$

wherein:
AA1 is A (wild type) or deleted;
AA2 is P (wild type) or deleted;
AA3 is T (wild type), C, A, G, Q, E, N, D, R, K, P, or deleted;
AA4 is S (wild type) or deleted;
AA5 is S (wild type) or deleted;
AA6 is S (wild type) or deleted;
AA7 is T (wild type) or deleted;
AA8 is K (wild type) or deleted;
AA9 is K (wild type) or deleted;
AA13 is Q (wild type), W or deleted;
AA14 is L (wild type), M, W or deleted;
AA15 is E (wildtype), K, D, T, A, S, Q, H or deleted;
AA16 is H (wildtype), N or Q or deleted;
AA18 is L (wild type) or R, L, G, M, F, E, H, W, K, Q, S, V, I, Y, H, D or T;
AA19 is L (wildtype), A, V, I or deleted;
AA20 is D (wildtype), T, S M L, or deleted;
AA22 is Q (wild type) or F, E, G, A, L, M, F, W, K, S, V, I, Y, H, R, N, D, T, F or deleted;

AA23 is M (wild type), A, W, H, Y, F, Q, S, V, L, T, or deleted;
AA27 IS G (wildtype), K, S or deleted;
AA38 is R (wild type), W or G;
AA39 is M (wildtype), L or V;
AA42 is F (wildtype) or K;
AA51 is T (wildtype), I or deleted
AA55 is H (wildtype) or Y;
AA74 is Q (wild type), N, H, S;
AA80 is L (wild type), F or V;
AA81 is R (wild type), I, D, Y, T or deleted
AA85 is L (wild type) or V;
AA86 is I (wild type) or V;
AA88 is N (wildtype), E or Q or deleted;
AA89 is I (wild type) or V;
AA91 is V (wild type), R or K;
AA92 is I (wild type) or F;
AA97 is K (wild type) or Q;
AA104 is M (wild type) or A;
AA109 is D (wildtype), C or a non-natural amino acid with an activated side chain;
AA113 is T (wild type) or N;
AA125 is C (wild type), A or S;
AA126 is Q (wild type) or H, M, K, C, D, E, G, I, R, S, or T; and/or
AA130 is S (wild type), T or R.

In some embodiments the the present disclosure provides an hIL2 ortholog comprising a IL2 variant polypeptide comprising amino acid modifications at positions: E15, L16, L19, D20, and M23 and optionally Q22. In some embodiments the hIL2 ortholog comprises a IL2 variant polypeptide comprising the amino acid substitutions: L12, Q13, H16, L19, D20, M23, R81, D84, S87, N88, V91, I92 and E95. In some embodiments the the present disclosure provides an hIL2 ortholog comprising a IL2 variant polypeptide comprising amino acid modifications at positions hIL2 ortholog comprises a IL2 variant polypeptide comprising the amino acid substitutions: Q74N, Q74H, Q74S, L80F, L80V, R81D, R81T, L85V, I86V, I89V, and/or I92F. In some embodiments the present disclosure provides an hIL2 ortholog comprises a IL2 variant polypeptide comprising amino acid modifications selected from the following sets of amino acid substitutions:

[E15S-H16Q-L19V-D20L-M23A-L80E-R81D-L85V-I86V-I92F];
[E15S-H16Q-L19V-D20L-Q22K-L80E-R81D-L85V-I86V-I92F];
[E15S-H16Q-L19V-D20L-Q22K-M23A L80E-R81D-L85V-I86V-I92F];
[E15S-H16Q-L19V-D20L-M23A-L80E-R81D-L85V-I86V-I92F-Q126H];
[E15S-H16Q-L19V-D20L-Q22K-L80E-R81D-L85V-I86V-I92F-Q126H];
[E15S-H16Q-L19V-D20L-Q22K-M23A-L80E-R81D-L85V-I86V-I92F-Q126H];
[E15S-H16Q-L19V-D20L-M23A-L80E-R81D-L85V-I86V-I92F-Q126M];
[E15S-H16Q-L19V-D20L-Q22K-L80E-R81D-L85V-I86V-I92F-Q126M]; or
[E15S-H16Q-L19V-D20L-Q22K-M23A-L80E-R81D-L85V-I86V-I92F-Q126M].

In some embodiments the present disclosure provides an hIL2 ortholog comprises a IL2 variant polypeptide comprising amino acid modifications at positions: S4, K8, K9, T10, Q11, Q13, N26, N29, N30, N30, Y31, K35, T37, R38, T41, F42, K43, F44, Y45, M46, K48, K49, K54, E61, E62, K64, P65, E67G, E68, V69, N71, L72, Q74 S75, K76, H79, I89, N90, I92, S99, T101, F103, Y107, I114, I128 and T133. In some embodiments the present disclosure provides an hIL2 ortholog comprises a IL2 variant polypeptide comprising one or more of the amino acid substitutions: S4P, K8R, K9T, T10A, Q11R, Q13R, N26D, N29S, N30S, N30D, N30T, Y31H, Y31C, K35R, T37A, T37R, M46L, K48E, K49R, K49E, K54R, E61D, K64R, E67G, E68D, V69A, N71T, N71A, N71R, A73V, Q74P S75P, K76E, K76R, H79R, I89V, N90H, I92T, S99P, T101A, F103S, I114V, I128T, T133A, and T133N. In some embodiments the present disclosure provides an a IL2 variant polypeptide comprising amino acid modifications selected from the following sets of amino acid substitutions:

[R38A-F42A-Y45A-E62A]; [F42A-Y45A-L72G]; [V69A, Q74P]; [V69A, Q74, T101A]; [V69A, Q74P, I128T]; [N30D, V69A, Q74P, F103S]; [K49E, V69A, A73V, K76E], [V69A, Q74P, T101A, T133N]; [N30S, V69A, Q74P, I128A]; [N30S, V69A, Q74P, I128T]; [K9T, Q11R, K35R, V69A, Q74P], [A1T, M46L, K49R, E61D, V69A, H79R]; [K48E, E68D, N71T, N90H, F103S, I114V]; [S4P T10A, Q11R, V69A, Q74P, T133A]; [N30S, Y31H, K35R, K48E, V69A, Q74P, I92T]; [N30S, E68D, V69A, N71A, Q74P, S75P, K76R, N90H]; [N30S, Y31C, T37A, V69A, A73V, Q74P. H79R, I128T], [N26D, N29S, N30S, K54R, E67G, V69A, Q74P, I92T]; [K8R, Q13R, N26D, N30T, K35R, T37R, V69A, Q74P, I92T], [N29S, Y31H, K35R, T37A, K48E, V69A, N71R, Q74P, I39V] and [T41P-T51P].

In some embodiments the present disclosure provides an hIL2 ortholog comprising a IL2 variant polypeptide comprising amino acid modifications at positions: Q11, L18, Q22, E110, N119, T123, Q126, S127, Q126, S127, I129, S130, and T133. In some embodiments the present disclosure provides an hIL2 ortholog comprising a IL2 variant polypeptide having one or more amino acid substitutions selected from: L18R, L18G, L18M, L18F, L18E, L18H, L18W, L18K, L18Q, L18S, L18V, L18I, L18Y, L18H, L18D, L18T, Q22E, Q22E, Q22E, Q22E, Q22G, Q22E, Q22A, Q22L, Q22M, Q22F, Q22W, Q22K, Q22S, Q22V, Q22I, Q22Y, Q22H, Q22R, Q22N, Q22D, Q22T, Q22F, Q126H, Q126M, Q126K, Q126C, Q126D, Q126E, Q126G, Q126I, Q126R, Q126S, or Q126T. In some embodiments the present disclosure provides an hIL2 ortholog comprising an IL2 variant polypeptide having a set of amino acid substitutions selected from the following sets of amino acid substitutions:

[E15S-H16Q-L18R-L19V-D20L-Q22E-M23A];
[E15S-H16Q-L18R-L19V-D20L-Q22K-M23A];
[E15S-H16Q-L18R-L19V-D20L-M23A];
[E15S-H16Q-L18R-L19V-D20L-Q22K-M23A];
[E15S-H16Q-L18R-L19V-D20L-M23A-Q126H];
[E15S-H16Q-L18R-L19V-D20L-Q22K-M23A-Q126H];
[E15S-H16Q-L18R-L19V-D20L-M23A-Q126K];
[E15S-H16Q-L18R-L19V-D20L-Q22K-M23A-Q126K];
[E15S-H16Q-L19V-D20L-M23A-Q126H];
[E15S-H16Q-L19V-D20L-Q22K-M23A-Q126H];
[E15S-H16Q-L19V-D20L-M23A-Q126K];
[E15S-H16Q-L19V-D20L-Q22K-M23A-Q126K];
[E15S-H16Q-L18R-L19V-D20L-M23A-Q126H];
[E15S-H16Q-L18R-L19V-D20L-Q22K-M23A-Q126H];
[E15S-H16Q-L18R-L19V-D20L-M23A-Q126K];
[E15S-H16Q-L18R-L19V-D20L-Q22K-M23A-Q126K];
[E15S-H16Q-L19V-D20L-Q22K-Q126H];
[E15S-H16Q-L19V-D20L-M23A-Q126M];
[E15S-H16Q-L19V-D20L-Q22K-M23A-Q126M];
[E15S-H16Q-L19V-D20L-Q22K-Q126M];

[desAla1-E15S-H16Q-L19V-D20L-Q126M];
[desAla1-E15S-H16Q-L19V-D20L-Q22K-Q126M];
[desAla1-E15S-H16Q-L19V-D20L-M23A-Q126M];
[desAla1-E15S-H16Q-L19V-D20L-Q22K-M23A-Q126M];
[desAla1-E15S-H16Q-L19V-D20L-Q22K-M23A-Q126M];
[E15S-H16Q-L19V-D20L-M23A-L80E-R81D-I86V-I92F-Q126H];
[E15S-H16Q-L19V-D20L-Q22K-L80E-R81D-I86V-I92F-Q126H];
[E15S-H16Q-L19V-D20L-Q22K-M23A-L80E-R81D-I86V-I92F-Q126H];
[E15S-H16Q-L19V-D20L-M23A-L80E-R81D-I86V-I92F-Q126M];
[E15S-H16Q-L19V-D20L-Q22K-M23A-L80E-R81D-I86V-I92F-Q126M];
[E15S-H16Q-L19V-D20L-M23A-L85V-Q126H];
[E15S-H16Q-L19V-D20L-Q22K-L85V-Q126H];
[E15S-H16Q-L19V-D20L-Q22K-M23A-L85V-Q126H];
[E15S-H16Q-L19V-D20L-M23A-L85V-Q126M];
[E15S-H16Q-L19V-D20L-Q22K-L85V-Q126H]; or
[E15S-H16Q-L19V-D20L-Q22K-M23A-L85V-Q126M].

In some embodiments the present disclosure provides an hIL2 ortholog comprises a IL2 variant polypeptide selected from the group consisting of SEQ ID NOs: 5-138.

In some embodiments the present disclosure provides an hIL2 ortholog is operably linked to at least one carrier molecule. In some embodiments the present disclosure provides an hIL2 ortholog comprising at least one polyethylene glycol (PEG) molecule.

In some embodiments the present disclosure provides an hIL2 ortholog comprises the structure:

[PEG]-[linker]$_n$-[hoIL2]

wherein where n=0 or 1 and hoIL2 is a human orthogonal IL2 polypeptide variant of the Formula 1. In some embodiments PEG has a molecular weight of from between 5 kDa and 80 kDa. In some embodiments the PEG has a molecular weight of approximately 40 kDa. In some embodiments the present disclosure provides an hIL2 ortholog of the above structure wherein the hoIL2 is an IL2 polypeptide variant comprising the set of amino acid substitution -[desAla1-E15S-H16Q-L19V-D20L-Q22K-M23A]. In some embodiments the present disclosure provides an hIL2 ortholog of the above structure wherein the hoIL2 is an IL2 polypeptide variant comprising amino acid sequence:

(SEQ ID NO: 5)
PTSSSTKKTQLQLSQLLVLLKAILNGINNYKNPKLT

RMLTFKFYMPKKATELKHLQCLEEELKPLEEVLNLA

QSKNFHLRPRDLISNINVIVLELKGSETTFMCEYAD

ETATIVEFLNRWITFCQSIISTLT.

In some embodiments the present disclosure provides a nucleic acid sequence encoding an hIL2 ortholog polypeptide of Formula #1.

In some embodiments the present disclosure provides a recombinant vector encoding a nucleic acid sequence encoding an hIL2 ortholog polypeptide of Formula #1A recombinant vector comprising the nucleic acid sequence of claim 22.

In some embodiments the present disclosure provides a method of treating a disease, disorder or condition in a subject suffering therefrom by administering to the subject:

a. an engineered mammalian cell comprising a nucleic acid sequence encoding a transmembrane receptor molecule comprising an extracellular domain (ECD) of an orthogonal hCD122 operably linked to one or more expression control elements capable of effecting the expression and surface presentation of the ECD of the transmembrane receptor molecule; and
b. administering to said subject a therapeutically effective dose of hIL2 ortholog of Formula #1

In some embodiments the present disclosure provides a preparing an engineered T cell product said T cell product comprising at least 20% of an hoCD122 T cell, the method comprising the steps of:

a. isolated a population a population of T cells from a mammalian subject;
b. contacting the isolated a population of T cells ex vivo with recombinant vector comprising a nucleic acid sequence encoding a hoCD122 operably linked to one or more expression control sequences so as to facilitate expression in a mammalian T cell under conditions that permit uptake of the recombinant vector by a T cell;
c. contacting the isolated a population of T cells an effective amount of an hIL2 ortholog of claim 1.

In some embodiments the present disclosure provides a cell population at least 20% engineered hoCD122 T cells.

The present disclosure further provides methods of making the hIL2 orthologs of the present invention. In particular, the present disclosure provides recombinant expression vectors comprising a nucleic acid sequence encoding the hIL2 orthologs operably linked to control elements to provide for expression of the nucleic acid sequence encoding the hIL2 ortholog in a host cell.

The present disclosure further provides a composition comprising a mixed cell population comprising at least 10%, alternatively at least 20%, alternatively at least 30%, alternatively at least 40%, alternatively at least 50%, alternatively at least 60%, alternatively at least 70%, of a T cell (e.g., T cell, CD8+ T cell, Treg, TIL, NK cell, TCR modified cell, CAR-T cell, etc), wherein the T cell has been recombinantly modified to express an orthogonal hCD122 receptor polypeptide. The present disclosure further provides a method of generating a pharmaceutically acceptable dosage form of an engineered cell therapy product the dosage form comprising a population of T cells wherein the population of T cells is substantially enriched for one or more species of engineered T cells, the engineered T cells expressing a receptor comprising the extracellular domain of an hCD122 orthogonal polypeptide, the method comprising the steps culturing the population of T cells comprising engineered T cells expressing a receptor comprising the extracellular domain of an hCD122 orthogonal polypeptide ex vivo in the presence of an hIL2 ortholog of the present invention for a period of time sufficient to enrich the cell population in of one or more such engineered T cells.

In some embodiments, the present disclosure provides a recombinant vector comprising a nucleic acid sequence encoding the hIL2 ortholog described herein operably linked to control elements to facilitate expression and secretion of the hIL2 ortholog from a mammalian cell is administered to the subject to provide for in situ expression of the hIL2 ortholog. In some embodiments, the recombinant vector is administered intratumorally to a subject suffering from cancer. In some embodiments, the recombinant vector is a recombinant viral vector. In some embodiments the recombinant viral vector is a recombinant adeno-associated virus (rAAV) or recombinant adenovirus (rAd), for example in some embodiments, a replication deficient adenovirus derived from human adenovirus serotypes 3 and/or 5. In some embodiments, the replication deficient adenovirus has one or more modifications to the E1 region which interfere with the ability of the virus to initiate the cell cycle and/or apoptotic pathways. The replication deficient adenoviral vector may optionally comprise deletions in the E3 domain. In some embodiments the adenovirus is a replication competent adenovirus. In some embodiments the adenovirus is a replication competent recombinant virus engineered to selectively replicate in neoplastic cells.

The present disclosure further provides methods of preparing a pharmaceutically acceptable dosage form of a cell therapy product comprising at least one (alternatively 2, 3, 4 or more) species of engineered T cells that express a transmembrane receptor protein wherein the extracellular domain of such transmembrane receptor protein comprises the extracellular domain of an hCD122 orthogonal polypeptide wherein the fraction of engineered cells in the cell therapy product comprises at least 20%, alternatively at least 30%, alternatively at least 40%, alternatively at least 50%, alternatively at least 60%, alternatively at least 70%, alternatively at least 80%, or alternatively at least 90% of the total number of cells in the cell therapy product.

In some embodiments a therapeutic method is provided, the method comprising introducing into a subject suffering from disease, disorder or condition a population of engineered cells, said engineered cell population comprising nucleic acid sequence encoding a cell membrane spanning orthogonal receptor polypeptide comprising an ECD of SEQ ID NO:1, a transmembrane domain and an intracellular signaling domain that results in an intracellular signal in response to the binding of a hIL2 ortholog ligand to the ECD of said cell membrane spanning orthogonal receptor polypeptide, said nucleic acid sequence operably linked to expression control elements to facilitate transcription and translation and cell surface presentation of the ECD of said membrane spanning polypeptide in combination with the administration of hCD122 ortholog of the present disclosure. Such cell population may comprise cells which have been modified ex vivo and are autologous or allogeneic with respect to the subject. In some embodiments, the therapeutic method comprises: (1) contacting engineered cell population, the engineered cells expressing a receptor comprising hIL2 orthogonal CD122 ECD ex vivo with an amount of a cognate hIL2 ortholog at a concentration and for a duration of time sufficient to activate said engineered cells; and (2) administering the cell population to the subject; and (3) administering to the subject a cognate hIL2 ortholog in combination with the administration of the engineered cells to the subject. In some embodiments, the subject to which the engineered hIL2 orthogonal CD122 ECD receptor cell population and hIL2 ortholog is suffering from a neoplastic disease. In some embodiments, the orthogonal receptor and ligand are administered in combination with at least one additional/supplemental therapeutic or prophylactic agent.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1 of the attached drawing provides Celltiterglo® values for NKL cells treated with 293 transfection supernatant from experiments as more fully described in Example 7 herein. For NKL cells receiving the indicated dilution of each supernatant, indicated in bold, duplicate Celltiterglo® values are shown in side-by-side columns.

FIG. 2 of the attached drawing provides Celltiterglo® values for NKL cells which have been recombinantly modified to express a hCD122 orthogonal receptor of SEQ ID NO2 ("NKL hoRB cells") treated with 293 transfection supernatants from experiments as described in Example 7. For NKL hoRB cells receiving the indicated dilution of each supernatant, indicated in bold, duplicate Celltiterglo® values are shown in side-by-side columns.

DETAILED DESCRIPTION

In order for the present disclosure to be more readily understood, certain terms and phrases are defined below as well as throughout the specification. The definitions provided herein are non-limiting and should be read in view of the knowledge of one of skill in the art would know.

Before the present methods and compositions are described, it is to be understood that this invention is not limited to particular method or composition described, as such may, of course, vary. It is also to be understood that the terminology used herein is for the purpose of describing particular embodiments only and is not intended to be limiting.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It should be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); pg=picogram; ng=nanogram; µg=microgram; mg=milligram; g=gram; kg=kilogram; dl or dL=deciliter; µl or µL=microliter; ml or mL=milliliter; l or L=liter; µM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; PCR=polymerase chain reaction; NHS=N-hydroxysuccinimide; HSA=human serum albumin; MSA=mouse serum albumin; DMEM=Dulbeco's Modification of Eagle's Medium; GC=genome copy; EDTA=ethylenediaminetetraacetic acid.

It will be appreciated that throughout this disclosure reference is made to amino acids according to the single letter or three letter codes. For the reader's convenience, the single and three letter amino acid codes are provided in Table 1 below:

TABLE 1

Amino Acid Abbreviations

| G | Glycine | Gly |
| P | Proline | Pro |
| A | Alanine | Ala |
| V | Valine | Val |
| L | Leucine | Leu |
| I | Isoleucine | Ile |
| M | Methionine | Met |
| C | Cysteine | Cys |
| F | Phenylalanine | Phe |
| Y | Tyrosine | Tyr |
| W | Tryptophan | Trp |
| H | Histidine | His |
| K | Lysine | Lys |
| R | Arginine | Arg |
| Q | Glutamine | Gln |
| N | Asparagine | Asn |
| E | Glutamic Acid | Glu |
| D | Aspartic Acid | Asp |
| S | Serine | Ser |
| T | Threonine | Thr |

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Unless otherwise indicated, the following terms are intended to have the meaning set forth below. Other terms are defined elsewhere throughout the specification.

Activate: As used herein the term "activate" is used in reference to a receptor or receptor complex to reflect the biological effect, directly and/or by participation in a multicomponent signaling cascade, arising from the binding of an agonist ligand to a receptor responsive to the binding of the ligand. For example, it is said that the binding of an IL2 agonist to its cognate IL2 receptor "activates" the signaling of the receptor to produce one or more intracellular biological effects (e.g., phosphorylation of STAT5).

Activity: As used herein, the term "activity" is used with respect to a molecule to describe a property of the molecule with respect to a test system or biological function such as the degree of binding of the molecule to another molecule. Examples of such biological functions include but are not limited to catalytic activity of a biological agent, the ability to stimulate intracellular signaling, gene expression, cell proliferation, the ability to modulate immunological activity such as inflammatory response. "Activity" is typically expressed as a biological activity per unit of administered agent such as [catalytic activity]/[mg protein], [immunological activity]/[mg protein], international units (IU) of activity, [STAT5 phosphorylation]/[mg protein], [T-cell proliferation]/[mg protein], plaque forming units (pfu), etc. The term "proliferative activity" encompasses an activity that promotes cell division including dysregulated cell division as that observed in neoplastic diseases, inflammatory diseases, fibrosis, dysplasia, cell transformation, metastasis, and angiogenesis.

Administer/Administration: The terms "administration" and "administer" are used interchangeably herein to refer the act of contacting a subject, including contacting a cell, tissue, organ, or biological fluid in vitro, in vivo or ex vivo of the subject, with an agent (e.g. an IL-2 ortholog, a CAR-T cell, a chemotherapeutic agent, an antibody, or modulator or a pharmaceutical formulation comprising one or more of the foregoing). Administration of an agent may be achieved through any of a variety of art recognized methods including but not limited to the topical, intravascular injection (including intravenous or intraarterial infusion), intradermal injection, subcutaneous injection, intramuscular injection, intraperitoneal injection, intracranial injection, intratumoral injection, transdermal, transmucosal, iontophoretic delivery, intralymphatic injection, intragastric infusion, intraprostatic injection, intravesical infusion (e.g., bladder), respiratory inhalers, intraocular injection, intraabdominal injection, intralesional injection, intraovarian injection, intracerebral infusion or injection, intracerebroventricular injection (ICVI), and the like. The term "administration" includes contact of an agent to the cell, tissue or organ as well as the contact of an agent to a fluid, where the fluid is in contact with the cell.

Adverse Event: As used herein, the term "adverse event" refers to any undesirable experience associated with the use of a therapeutic or prophylactic agent in a subject. Adverse events do not have to be caused by the administration of the therapeutic or prophylactic agent (e.g. an hIL2 ortholog) but may arise from unrelated circumstances. Adverse events are typically categorized as mild, moderate, or severe. As used herein, the classification of adverse events as used herein is in accordance with the Common Terminology Criteria for Adverse Events v4.03 (CTCAE) dated Jun. 14, 2010 published by the United States Department of Health and Human services, National Institutes of Health National Cancer Institute.

Affinity: As used herein the term "affinity" refers to the degree of specific binding of a first molecule (e.g. a ligand) to a second molecule (e.g. a receptor) and is measured by the binding kinetics expressed as $K_d$, a ratio of the dissociation constant between the molecule and the its target ($K_{off}$) and the association constant between the molecule and its target ($K_{on}$).

Agonist: As used herein, the term "agonist" refers a first agent that specifically binds a second agent ("target") and interacts with the target to cause or promote an increase in the activation of the target. In some instances, agonists are activators of receptor proteins that modulate cell activation, enhance activation, sensitize cells to activation by a second agent, or up-regulate the expression of one or more genes, proteins, ligands, receptors, biological pathways, that may result in cell proliferation or pathways that result in cell cycle arrest or cell death such as by apoptosis. In some embodiments, an agonist is an agent that binds to a receptor and alters the receptor state resulting in a biological response that mimics the effect of the endogenous ligand of the receptor. The term "agonist" includes partial agonists, full agonists and superagonists. An agonist may be described as a "full agonist" when such agonist which leads to a substantially full biological response (i.e. the response associated with the naturally occurring ligand/receptor binding interaction) induced by receptor under study, or a partial agonist. A "superagonist" is a type of agonist that is capable of producing a maximal response greater than the endogenous agonist for the target receptor, and thus has an activity of more than 100% of the native ligand. A super agonist is typically a synthetic molecule that exhibits greater than 110%, alternatively greater than 120%, alternatively greater than 130%, alternatively greater than 140%, alternatively greater than 150%, alternatively greater than 160%, or alternatively greater than 170% of the response in an evaluable quantitative or qualitative parameter of the naturally occurring form of the molecule when evaluated at similar concentrations in a comparable assay. It should be noted that the biological effects associated with the full agonist may differ in degree and/or in kind from those biological effects of partial or superagonists. In contrast to agonists, antagonists may specifically bind to a receptor but do not result the signal cascade typically initiated by the receptor and may to modify the actions of an agonist at that receptor. Inverse agonists are agents that produce a pharmacological response that is opposite in direction to that of an agonist.

Antagonist: As used herein, the term "antagonist" or "inhibitor" refers a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or down-regulate, e.g., a gene, protein, ligand, receptor, biological pathway including an immune checkpoint pathway, or cell.

Antibody: As used herein, the term "antibody" refers collectively to: (a) glycosylated and non-glycosylated the immunoglobulins (including but not limited to mammalian immunoglobulin classes IgG1, IgG2, IgG3 and IgG4) that specifically binds to target molecule and (b) immunoglobulin derivatives including but not limited to IgG(1-4)deltaC$_H$2, F(ab')2, Fab, ScFv, V$_H$, V$_L$, tetrabodies, triabodies, diabodies, dsFv, F(ab')$_3$, scFv-Fc and (scFv)$_2$ that competes with the immunoglobulin from which it was derived for binding to the target molecule. The term antibody is not restricted to immunoglobulins derived from any particular mammalian species and includes murine, human, equine, camelids, antibodies, human antibodies. The term antibody includes so called "heavy chain antibodies" or "VHHs" or "Nanobodies®" as typically obtained from immunization of camelids (including camels, llamas and alpacas (see, e.g. Hamers-Casterman, et al. (1993) Nature 363:446-448). Antibodies having a given specificity may also be derived from non-mammalian sources such as VHHs obtained from immunization of cartilaginous fishes including, but not limited to, sharks. The term "antibody" encompasses antibodies isolatable from natural sources or from animals following immunization with an antigen and as well as engineered antibodies including monoclonal antibodies, bis-pecific antibodies, tri-specific, chimeric antibodies, humanized antibodies, human antibodies, CDR-grafted, veneered, or deimmunized (e.g., to remove T-cell epitopes) antibodies, camelized (in the case of VHHs), or molecules comprising binding domains of antibodies (e.g. CDRs) in non-immunoglobulin scaffolds. The term "antibody" should not be construed as limited to any particular means of synthesis and includes naturally occurring antibodies isolatable from natural sources and as well as engineered antibodies molecules that are prepared by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries. In one embodiment, an "antibody" is a mammalian immunoglobulin. In some embodiments, the antibody is a "full length antibody" comprising variable and constant domains providing binding and effector functions. The term "single domain antibody" (sdAb) as used herein refers an antibody fragment consisting of a monomeric variable antibody domain that is able to bind selectively to an antigen and compete for binding with the parent antibody from which it is derived. As used herein, the term "VHH" refers to a single domain antibody derived from camelid antibody typically obtained from immunization of camelids (including camels, llamas and alpacas (see, e.g. Hamers-Casterman, et al. (1993) Nature 363:446-448). VHHs are also referred to as heavy chain antibodies or Nanobodies® as Single domain antibodies may also be derived from non-mammalian sources such as VHHs obtained from IgNAR antibodies immunization of cartilaginous fishes including, but not limited to, sharks. The term antibody includes antibody conjugates comprising modifications to prolong duration of action such as fusion proteins or conjugation to polymers (e.g. PEGylated) as described in more detail below.

Biological Sample: As used herein, the term "biological sample" or "sample" refers to a sample obtained or derived from a subject. By way of example, a biological sample comprises a material selected from the group consisting of body fluids, blood, whole blood, plasma, serum, mucus secretions, saliva, cerebrospinal fluid (CSF), bronchoalveolar lavage fluid (BALF), fluids of the eye (e.g., vitreous fluid, aqueous humor), lymph fluid, lymph node tissue, spleen tissue, bone marrow, and an immunoglobulin enriched fraction derived from one or more of these tissues. In some embodiments, the sample is obtained from a subject who has been exposed to a therapeutic treatment regimen including a pharmaceutical formulation of a an hhIL2 ortholog, such as repeatedly exposed to the same drug. In other embodiments, the sample is obtained from a subject who has not recently been exposed to the hIL2 ortholog or obtained from the subject prior to the planned administration of the hIL2 ortholog.

"CAR" or "Chimeric Antigen Receptor": As used herein, the terms "chimeric antigen receptor" and "CAR" are used interchangeably to refer to a chimeric polypeptide comprising multiple functional domains arranged from amino to carboxy terminus in the sequence: (a) an antigen binding domain (ABD), (b) a transmembrane domain (TD); and (c) one or more cytoplasmic signaling domains (CSDs) wherein the foregoing domains may optionally be linked by one or more spacer domains. The CAR may also further comprise a signal peptide sequence which is conventionally removed during post-translational processing and presentation of the CAR on the cell surface of a cell transformed with an expression vector comprising a nucleic acid sequence encoding the CAR. CARs useful in the practice of the present invention are prepared in accordance with principles well known in the art. See e.g., Eshhaar et al. U.S. Pat. No. 7,741,465 B1 issued Jun. 22, 2010; Sadelain, et al (2013) Cancer Discovery 3(4):388-398; Jensen and Riddell (2015) Current Opinions in Immunology 33:9-15; Gross, et al. (1989) PNAS(USA) 86(24):10024-10028; Curran, et al. (2012) J Gene Med 14(6):405-15. Examples of commercially available CAR-T cell products that may be modified to incorporate an orthogonal receptor of the present invention include axicabtagene ciloleucel (marketed as Yescarta® commercially available from Gilead Pharmaceuticals) and tisagenlecleucel (marketed as Kymriah® commercially available from Novartis).

CAR-T Cell: As used herein, the terms "chimeric antigen receptor T-cell" and "CAR-T cell" are used interchangeably to refer to a T-cell that has been recombinantly modified to express a chimeric antigen receptor. As used herein, a CAR-T cell may be engineered to express an hCD122 ortho polypeptide.

CD-122 Ortho: As used herein, the terms "CD122 ortho" or "hoCD122" or "hoIL2Rb" are used interchangeably to refers to a variant of hCD122 polypeptide comprising amino acid substitutions at positions histidine 133 (H133) and tyrosine 134 (Y134) in the ECD of the hCD122 polypeptide. In some embodiments CD-122 ortho comprises the amino acid substitutions at position 133 from histidine to aspartic acid (H133D), glutamic acid (H133E) or lysine (H133K) and/or amino acid substitutions at position 134 to from tyrosine to phenylalanine (Y134F), glutamic acid (Y134E), or arginine (Y134R). In a preferred embodiment, the hCD122 orthogonal receptor is a hCD122 molecule having amino acid substitutions H133D and Y134F. In one embodiment, the hCD122 orthogonal receptor is a polypeptide having the amino acid sequence of Sequence ID NO:2.

CDRs. As used herein, the term "CDR" or "complementarity determining region" is intended to mean the non-contiguous antigen combining sites found within the variable region of both heavy and light chain immunoglobulin polypeptides. CDRs have been described by Kabat et al., *J. Biol. Chem.* 252:6609-6616 (1977); Kabat et al., U.S. Dept. of Health and Human Services, "Sequences of proteins of immunological interest" (1991) (also referred to herein as Kabat 1991); by Chothia et al., *J. Mol. Biol.* 196:901-917 (1987) (also referred to herein as Chothia 1987); and MacCallum et al., *J. Mol. Biol.* 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein.

In the context of the present disclosure, the numbering of the CDR positions is provided according to Kabat numbering conventions.

Comparable: As used herein, the term "comparable" is used to describe the degree of difference in two measurements of an evaluable quantitative or qualitative parameter. For example, where a first measurement of an evaluable quantitative parameter (e.g. the level of IL-2 activity as determined by an CTLL-2 proliferation or phospho-STAT5 assay) and a second measurement of the evaluable parameter do not deviate beyond a range that the skilled artisan would recognize as not producing a statistically significant difference in effect between the two results in the circumstances, the two measurements would be considered "comparable." In some instances, measurements may be considered "comparable" if one measurement deviates from another by less than 35%, alternatively by less than 30%, alternatively by less than 25%, alternatively by less than 20%, alternatively by less than 15%, alternatively by less than 10%, alternatively by less than 7%, alternatively by less than 5%, alternatively by less than 4%, alternatively by less than 3%, alternatively by less than 2%, or by less than 1%. In particular embodiments, one measurement is comparable to a reference standard if it deviates by less than 15%, alternatively by less than 10%, or alternatively by less than 5% from the reference standard.

Derived From: As used herein in the term "derived from", in the context of an amino acid sequence or polynucleotide sequence (e.g., an amino acid sequence "derived from" an IL-2 polypeptide), is meant to indicate that the polypeptide or nucleic acid has a sequence that is based on that of a reference polypeptide or nucleic acid (e.g., a naturally occurring IL-2 polypeptide or an IL-2-encoding nucleic acid), and is not meant to be limiting as to the source or method in which the protein or nucleic acid is made. By way of example, the term "derived from" includes homologs or variants of reference amino acid or DNA sequences.

Effective Concentration (EC): As used herein, the terms "effective concentration" or its abbreviation "EC" are used interchangeably to refer to the concentration of an agent in an amount sufficient to effect a change in a given parameter in a test system. The abbreviation "E" refers to the magnitude of a given biological effect observed in a test system when that test system is exposed to a test agent. When the magnitude of the response is expressed as a factor of the concentration ("C") of the test agent, the abbreviation "EC" is used. In the context of biological systems, the term Emax refers to the maximal magnitude of a given biological effect observed in response to a saturating concentration of an activating test agent. When the abbreviation EC is provided with a subscript (e.g., $EC_{40}$, $EC_{50}$, etc.) the subscript refers to the percentage of the Emax of the biological response observed at that concentration. For example, the concentration of a test agent sufficient to result in the induction of a measurable biological parameter in a test system that is 30% of the maximal level of such measurable biological parameter in response to such test agent, this is referred to as the "$EC_{30}$" of the test agent with respect to such biological parameter. Similarly, the term "$EC_{100}$" is used to denote the effective concentration of an agent that results the maximal (100%) response of a measurable parameter in response to such agent. Similarly, the term $EC_{50}$ (which is commonly used in the field of pharmacodynamics) refers to the concentration of an agent sufficient to results in the half-maximal (50%) change in the measurable parameter. The term "saturating concentration" refers to the maximum possible quantity of a test agent that can dissolve in a standard volume of a specific solvent (e.g., water) under standard conditions of temperature and pressure. In pharmacodynamics, a saturating concentration of a drug is typically used to denote the concentration sufficient of the drug such that all available receptors are occupied by the drug, and $EC_{50}$ is the drug concentration to give the half-maximal effect.

Enriched: As used herein in the term "enriched" refers to a sample is non-naturally manipulated so that a molecule of interest is present in: (a) a greater concentration (e.g., at least 3-fold greater, alternatively at least 5-fold greater, alternatively at least 10-fold greater, alternatively at least 50-fold greater, alternatively at least 100-fold greater, alternatively at least 1000-fold greater) than the concentration of the molecule in the starting sample, such as a biological sample (e.g., a sample in which the molecule naturally occurs or in which it is present after administration); or (b) a concentration greater than the environment in which the molecule was made (e.g., as in a recombinantly modified bacterial or mammalian cell).

Extracellular Domain: As used herein the term "extracellular domain" or its abbreviation "ECD" refers to the portion of a cell surface protein (e.g. a cell surface receptor) which is outside of the plasma membrane of a cell. The ECD may include the entire extra-cytoplasmic portion of a transmembrane protein, a cell surface or membrane associated protein, a secreted protein, a cell surface targeting protein, hCD-122: As used herein the term "hCD122" refers to a naturally occurring human CD122 polypeptide including naturally occurring variants thereof. The amino acid sequence of one naturally occurring hCD122 variant is:

(SEQ ID NO: 3)
```
AVNGTSQFTC FYNSRANISC VWSQDGALQD TSCQVHAWPD

RRRWNQTCEL LPVSQASWAC NLILGAPDSQ KLTTVDIVTL

RVLCREGVRW RVMAIQDFKP FENLRLMAPI SLQVVHVETH

RCNISWEISQ ASHYFERHLE FEARTLSPGH TWEEAPLLTL

KQKQEWICLE TLTPDTQYEF QVRVKPLQGE FTTWSPWSQP

LAFRTKPAAL GKDTIPWLGH LLVGLSGAFG FIILVYLLIN

CRNTGPWLKK VLKCNTPDPS KFFSQLSSEH GGDVQKWLSS

PFPSSSFSPG GLAPEISPLE VLERDKVTQL LLQQDKVPEP

ASLSSNHSLT SCFTNQGYFF FHLPDALEIE ACQVYFTYDP

YSEEDPDEGV AGAPTGSSPQ PLQPLSGEDD AYCTFPSRDD

LLLFSPSLLG GPSPPSTAPG GSGAGEERMP PSLQERVPRD

WDPQPLGPPT PGVPDLVDFQ PPPELVLREA GEEVPDAGPR

EGVSFPWSRP PGQGEFRALN ARLPLNTDAY LSLQELQGQD

PTHL
```

Identity: The term "identity," as used herein in reference to polypeptide or DNA sequences, refers to the subunit sequence identity between two molecules. When a subunit position in both of the molecules is occupied by the same monomeric subunit (i.e., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as the GCS program package (Devereux, et al., (1984) Nucleic Acids Res. 12:387), BLASTP, BLASTN, FASTA (Atschul, et al. (1990) J. Molecular Biol. 215:403-410). Algorithms that are suitable for determining percent sequence identity and sequence similarity are the BLAST and BLAST 2.0 algorithms, which are described in Altschul et al. (1990) *J. Mol. Biol.* 215: 403-410 and Altschul, et al. (1977) *Nucleic Acids Res.* 25: 3389-3402. Software for performing BLAST analyses is publicly available through the National Center for Biotechnology Information (NCBI) web site. The algorithm involves first identifying high scoring sequence pairs (HSPs) by identifying short words of length W of the query sequence, which either match or satisfy some positive-valued threshold score "T" when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (the reward score for a pair of matching residues; always >0) and "N" (the penalty score for mismatching residues; always <0). For amino acid sequences, a scoring matrix is used to calculate the cumulative score. Extension of the word hits in each direction are halted when: (a) the cumulative alignment score falls off by the quantity X from its maximum achieved value; the cumulative score goes to zero or below, due to the accumulation of one or more negative-scoring residue alignments; or (b) the end of either sequence is reached. The BLAST algorithm parameters "W", "T", and "X" determine the sensitivity and speed of the alignment. The BLASTN program (for nucleotide sequences) functions similarly but uses as defaults a word size ("W") of 28, an expectation ("E") of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, (1989) PNAS(USA) 89:10915-10919).

IL-2: As used herein, the term "interleukin-2" or "IL-2" refers to a naturally occurring IL-2 polypeptide that possesses IL-2 activity. In some embodiments, IL-2 refers to mature wild-type human IL-2. Mature wild-type human IL-2 (hIL2) occurs as a 133 amino acid polypeptide (less the signal peptide, consisting of an additional 20 N-terminal amino acids), as described in Fujita, et. al., PNAS USA, 80, 7437-7441 (1983). An amino acid sequence of naturally occurring variant of mature wild-type human IL-2 (hIL2) is:

(SEQ ID NO: 4)
```
APTSSSTKKT QLQLEHLLLD LQMILNGINN YKNPKLTRML

TFKFYMPKKA TELKHLQCLE EELKPLEEVL NLAQSKNFHL

RPRDLISNIN VIVLELKGSE TTFMCEYADE TATIVEFLNR

WITFCQSIIS TLT
```

As used herein, the number of residues is based on the hIL2 sequence UniProt ID P60568 excluding the signal peptide which is the same as that of SEQ ID NO:4.

IL2 Activity: The term "IL2 activity" refers to one or more the biological effects on a cell in response to contacting the cell with an effective amount of an IL2 polypeptide. IL2 Activity may be measured, for example, in a cell proliferation assay using CTLL-2 mouse cytotoxic T cells, see Gearing, A. J. H. and C. B. Bird (1987) in Lymphokines and Interferons, A Practical Approach. Clemens, M. J. et al. (eds): IRL Press. 295. The specific activity of Recombinant Human IL-2 is approximately $2.1 \times 10^4$ IU/µg, which is calibrated against recombinant human IL-2 WHO International Standard (NIBSC code: 86/500). In some embodiments, for example when the hIL2 orthogonal polypeptide of interest exhibits (or is engineered to possess) diminished affinity for CD25, IL2 activity may be assessed in human cells such as YT cells which do not require CD25 to provide signaling through the IL2 receptor but rather are capable of signaling through the intermediate affinity CD122/CD132 receptor. An orthogonal human IL-2 of the present disclosure may have less than 20%, alternatively less than about 10%, alternatively less than about 8%, alternatively less than about 6%, alternatively less than about 4%, alternatively less than about 2%, alternatively less than about 1%, alternatively less than about 0.5% of the activity of WHO International Standard (NIBSC code: 86/500) wild-type mature human IL-2 when evaluated at similar concentrations in a comparable assay.

IL-2 ortholog: As used herein, the term "IL-2 ortholog" refers to a variant of hIL2 derived from an IL-2 parent polypeptide which specifically binds to an orthogonal hCD122 ECD and exhibits significantly reduced binding to the extracellular domain of a wild type hCD122. In some embodiment the hIL2 ortholog exhibits specific binding to a receptor comprising an orthogonal hCD122 ECD and the contacting of a cell expressing a membrane spanning receptor comprising the ECD of an orthogonal hCD122 polypeptide in an amount sufficient to effect a change results in the a signal characteristic of the signal produced by the intracellular domain (ICD) of said membrane spanning receptor. When the membrane spanning receptor comprises an orthogonal hCD122 ECD and hCD122 ICD, the binding of an hIL2 ortholog to such receptor results in an intracellular signal characteristic of the activation of a Cd25/CD122/CD132 high affinity of CD122/CD132 intermediate affinity hIL2 receptor. An IL-2 ortholog exhibits significantly reduced binding to wild-type hCD122. The term hIL2 orthologs includes IL-2 orthogonal variants and modified hIL2 orthologs. In some embodiments, the hIL2 ortholog is derived from a naturally occurring variant of human IL2 and such human IL2 orthologs may be referred to as "hoCD122" or "hoRb." Certain modified IL-2 polypeptides are provided in Garcia, et al. (United States Patent Application Publication US2018/0228842A1 published Aug. 16, 2018). As used herein, the term hIL2 orthologs does not include the modified hIL2 polypeptides described in Garcia, et al United State Patent Application Publication US2018/0228842A1 published Aug. 16, 2018.

In An Amount Sufficient Amount to Effect a Change: As used herein the phrase "in an amount sufficient to effect a change" refers to the amount of a test agent sufficient to provide a detectable difference between a level of an indicator measured before (e.g., a baseline level) and after the application of the test agent to a system such as biological function evaluated in a cell based assay in response to the administration of a quantity of the test agent. "An amount sufficient to effect a change" may be sufficient to be a therapeutically effective amount but "in an amount sufficient to effect a change" may be more or less than a therapeutically effective amount.

In Need of Treatment: The term "in need of treatment" as used herein refers to a judgment made by a physician or other caregiver with respect to a subject that the subject requires or will potentially benefit from treatment. This judgment is made based on a variety of factors that are in the realm of the physician's or caregiver's expertise.

In Need of Prevention: As used herein the term "in need of prevention" refers to a judgment made by a physician or other caregiver with respect to a subject that the subject requires or will potentially benefit from preventative care. This judgment is made based upon a variety of factors that are in the realm of a physician's or caregiver's expertise.

Inhibitor: As used herein the term "inhibitor" refers to a molecule that decreases, blocks, prevents, delays activation of, inactivates, desensitizes, or down-regulates, e.g., a gene, protein, ligand, receptor, or cell. An inhibitor can also be defined as a molecule that reduces, blocks, or inactivates a constitutive activity of a cell or organism.

Intracellular Domain: As used herein the term "intracellular domain" or its abbreviation "ICD" refers to the portion of a cell surface protein (e.g. a cell surface receptor) which is inside of the plasma membrane of a cell. The ICD may include the entire cytoplasmic portion of a transmembrane protein or membrane associated protein, or intracellular protein.

Isolated: As used herein the term "isolated" is used in reference to a polypeptide of interest that, if naturally occurring, is in an environment different from that in which it can naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was made by either synthetic or recombinant means.

Intracellular Domain of the Orthogonal Receptor: As used herein the terms "intracellular domain of the orthogonal receptor" or "ICD-OR" refer to the portion of a transmembrane spanning orthogonal receptor that is inside of the plasma membrane of a cell expressing such transmembrane spanning orthogonal receptor. The ICD-OR may comprise one or more "proliferation signaling domain(s)" or "PSD(s)" which refers to a protein domain which signals the cell to enter mitosis and begin cell growth. Examples include the Janus kinases, including but not limited to, JAK1, JAK2, JAK3, Tyk2, Ptk-2, homologous members of the Janus kinase family from other mammalian or eukaryotic species, the IL-2 receptor β and/or γ chains and other subunits from the cytokine receptor superfamily of proteins that may interact with the Janus kinase family of proteins to transduce a signal, or portions, modifications or combinations thereof. Examples of signals include phosphorylation of one or more STAT molecules including but not limited to one or more of STAT1, STAT3, STAT5a, and/or STAT5b.

Kabat Numbering: The term "Kabat numbering" as used herein is recognized in the art and refers to a system of numbering amino acid residues which are more variable than other amino acid residues (e.g., hypervariable) in the heavy and light chain regions of immunoglobulins (Kabat, et al., (1971) *Ann.* NY Acad. Sci. 190:382-93; Kabat, et al., (1991) *Sequences of Proteins of Immunological Interest*, Fifth Edition, U.S. Department of Health and Human Services, NIH Publication No. 91-3242). For purposes of the present disclosure, the positioning of CDRs in the variable region of an antibody follows Kabat numbering or simply, "Kabat."

Ligand: As used herein, the term "ligand" refers to a molecule that specifically binds a receptor and causes a change in the receptor so as to effect a change in the activity of the receptor or a response in cell that expresses that receptor. In one embodiment, the term "ligand" refers to a molecule or complex thereof that can act as an agonist or antagonist of a receptor. As used herein, the term "ligand" encompasses natural and synthetic ligands. "Ligand" also encompasses small molecules, peptide mimetics of cytokines and antibodies. The complex of a ligand and receptor is termed a "ligand-receptor complex." A ligand may comprise one domain of a polyprotein or fusion protein (e.g., either domain of an antibody/ligand fusion protein).

Metastasis: As used herein the term "metastasis" describes the spread of cancer cell from the primary tumor to surrounding tissues and to distant organs.

Modified IL-2 Ortholog: As used herein the term "modified IL-2 orthologs" is used to refer to IL-2 orthologs that have been modified by one or more modifications such as pegylation, glycosylation (N- and O-linked), acylation, or polysialylation or by conjugation (either chemical or as fusion proteins) with other polypeptide carrier molecules including but not limited to albumin fusion polypeptides comprising serum albumin (e.g., human serum albumin (HSA) or bovine serum albumin (BSA) or and Fc-fusion proteins or with targeting moieties such as IgG comprising hhIL2 orthogonal polypeptide fusion proteins, targeted IL-2 orthogonal polypeptides such as ScFv-hIL2 orthogonal polypeptide fusion proteins and VHH-IL-2 orthogonal polypeptide fusion proteins. Modified hIL2 orthologs may be prepared to order to enhance one or more properties for example, modulating immunogenicity; methods of increasing water solubility, bioavailability, serum half-life, and/or therapeutic half-life; and/or modulating biological activity. Certain modifications can also be useful to, for example, raise of antibodies for use in detection assays (e.g., epitope tags) and to provide for ease of protein purification.

Modulate: As used herein, the terms "modulate", "modulation" and the like refer to the ability of a test agent to affect a response, either positive or negative or directly or indirectly, in a system, including a biological system or biochemical pathway. The term modulator includes both agonists and antagonists.

Neoplastic Disease: As used herein, the term "neoplastic disease" refers to disorders or conditions in a subject arising from cellular hyper-proliferation or unregulated (or dysregulated) cell replication. The term neoplastic disease refers to disorders arising from the presence of neoplasms in the subject. Neoplasms may be classified as: (1) benign (2) pre-malignant (or "pre-cancerous"); and (3) malignant (or "cancerous"). The term "neoplastic disease" includes neoplastic-related diseases, disorders and conditions referring to conditions that are associated, directly or indirectly, with neoplastic disease, and includes, e.g., angiogenesis and precancerous conditions such as dysplasia or smoldering multiple myeloma. Examples of benign disorders arising from dysregulated cell replication include hypertrophic scars such as keloid scars.

N-Terminus: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

Nucleic Acid: The terms "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Numbered in accordance with hIL2: The term "numbered in accordance with hIL2" as used herein refers to the identification of a location of particular amino acid with reference to the position at which that amino acid normally occurs in the sequence of the mature wild type hIL2 (SEQ ID NO: 4). For example, in reference to hIL2, "R81" refers to the eighty-first (numbered from the N-terminus) amino acid, arginine, that occurs in sequence of the mature wild type hIL2. It should be noted that the amino acid sequences of IL2 molecules of different mammalian species have different numbers and sequences of amino acids. Consequently, when referencing a residue in accordance with this convention it is helpful to identify the IL2 species in question.

Numbered in accordance with hCD122: The term "numbered in accordance with hCD122" as used herein refers to the identification of a location of particular amino acid with reference to the position at which that amino acid normally occurs in the sequence of the mature wild type hCD122 molecule, in one embodiment, the hCD122 of SEQ ID NO. 3. For example, in reference to human CD122, H133 refers to the histidine at the one-hundred thirty third (numbered from the N-terminus) amino acid of the sequence of the mature wild type hCD122.

Numbered in accordance with the Extracellular Domain of hCD122: The term "numbered in accordance with extracellular domain of hCD122" or "numbered in accordance with hCD122 ECD" as used herein refers to the identification of a location of particular amino acid with reference to the position at which that amino acid normally occurs in the extracellular domain (ECD) sequence of the mature wild type hCD122 molecules (SEQ ID NO. 3). For example, in reference to human CD122 ECD, H133 refers to the histidine at the one-hundred thirty third (numbered from the N-terminus) amino acid of the sequence of the mature wild type hCD122 ECD.

Operably Linked: The term "operably linked" is used herein to refer to the relationship between molecules, typically polypeptides or nucleic acids, which are arranged in a construct such that each of the functions of the component molecules is retained although the operable linkage may result in the modulation of the activity, either positively or negatively, of the individual components of the construct. For example, the operable linkage of a polyethylene glycol (PEG) molecule to a wild-type protein may result in a construct where the biological activity of the protein is diminished relative to the to the wild-type molecule, however the two are nevertheless considered operably linked. When the term "operably linked" is applied to the relationship of multiple nucleic acid sequences encoding differing functions, the multiple nucleic acid sequences when combined into a single nucleic acid molecule that, for example, when introduced into a cell using recombinant technology, provides a nucleic acid which is capable of effecting the transcription and/or translation of a particular nucleic acid sequence in a cell. For example, the nucleic acid sequence encoding a signal sequence may be considered operably linked to DNA encoding a polypeptide if it results in the expression of a preprotein whereby the signal sequence facilitates the secretion of the polypeptide; a promoter or enhancer is considered operably linked to a coding sequence if it affects the transcription of the sequence; or a ribosome binding site is considered operably linked to a coding sequence if it is positioned so as to facilitate translation. Generally in the context of nucleic acid molecules, the term "operably linked" means that the nucleic acid sequences being linked are contiguous, and, in the case of a secretory leader or associated subdomains of a molecule, contiguous and in reading phase. However, certain genetic elements such as enhancers may function at a distance and need not be contiguous with respect to the sequence to which they provide their effect but nevertheless may be considered operably linked.

Orthogonal hCD122: As used herein the term "orthogonal hCD122" or "CD122 orthogonal receptor" are used interchangeably herein to refer to an hCD122 polypeptide variant comprising amino acid substitutions that result in specific binding to an hhIL2 ortholog but does not specifically bind to a naturally occurring variant of hIL2. In one embodiment, the hCD122 is hCD122 having amino acid modifications at as positions 133 and 134 of Sequence ID NO:4 (the naturally occurring hCD122). In some embodiments, the orthogonal hCD122 comprises is a hCD122 molecule comprising the substitutions H133D and Y134 (Sequence ID NO:2).

Orthogonal Receptor: As used herein the term "orthogonal receptor" refers to a variant of receptor, the orthogonal receptor comprising modifications to the amino acid sequence so that the orthogonal receptor exhibits significantly reduced binding to its cognate ligand but exhibits specific binding for an orthogonal ligand engineered to interact with the orthogonal receptor. In some embodiments, the orthogonal receptor may comprise an extracellular domain that is exhibits significantly reduced binding to its cognate native ligand, while an orthogonal ligand exhibits significantly reduced binding to the ECD of its cognate native receptor(s). In some embodiments, the affinity of the orthogonal ligand for the cognate orthogonal receptor exhibits affinity comparable to the affinity of the native ligand for the native receptor, e.g. having an affinity that is least about 1% of the native cytokine receptor pair affinity, at least about 5%, at least about 10%, at least about 25%, at least about 50%, at least about 75%, at least about 100%, and may be higher, e.g. 2×, 3×, 4×, 5×, 10× or more of the affinity of the native cytokine for the native receptor. An orthogonal receptor may be referred to by the parent molecule from which it was derived (e.g. orthogonal hCD122) or by the cognate ligand from which the orthogonal ligand for the orthogonal receptor was derived (e.g. orthogonal hIL2 receptor).

Ortholog: As used herein the term "ortholog" refers to a ligand component of an orthogonal ligand/receptor pair and refers to a polypeptide incorporating modifications to its primary structure to provide polypeptide variant that exhibits: (a) significantly reduced affinity to its native cognate receptor (i.e., the native receptor for the parent polypeptide from which the ortholog is derived); and (b) specific binding a engineered orthogonal receptor which is a variant of the cognate receptor for the ortholog. Upon binding of the ortholog to the orthogonal receptor (which is expressed on surface of cell which has been modified by recombinant DNA technology to incorporate a nucleic acid sequence encoding the orthogonal receptor operably linked to control elements to effect the expression of the orthogonal receptor in the recombinantly modified cell), the activated orthogonal receptor initiates signaling that is transduced through native cellular elements to provide for a biological activity that mimics that native response of the cognate but which is specific to the recombinantly modified cell population expressing the orthogonal receptor. In some embodiments of the invention, orthologs possess significant selectivity for the orthogonal receptor relative to the cognate receptor and optionally possessing significantly reduced potency with respect to the cognate receptor. Selectivity is typically assessed by activity measured in an assay characteristic of the activity induced in response to ligand/receptor binding. In some embodiments, the ortholog possesses at least 5 fold, alternatively at least 10 fold, alternatively at least 20 fold, alternatively at least 30 fold, alternatively at least 40 fold, alternatively at least 50 fold, alternatively at least 100 fold, alternatively at least 200 fold difference in EC50 increased affinity for the orthogonal receptor as compared to the as measured in the same assay.

Parent Polypeptide: As used herein, the terms "parent polypeptide" or "parent protein" are used interchangeably to designate the source of a second polypeptide (e.g. a derivative or variant) which is modified with respect to a first "parent" polypeptide. In some instances, the parent polypeptide is a wild-type or naturally occurring form of a protein. In some instance, the parent polypeptide may be a modified form a naturally occurring protein that is further modified. The term "parent polypeptide" may refer to the polypeptide itself or compositions that comprise the parent polypeptide (e.g. glycosylated or PEGylated forms and/or fusion proteins comprising the parent polypeptide).

Partial Agonist: As used herein, the term "partial agonist" refers to a molecule that specifically binds that bind to and activate a given receptor but possess only partial activation the receptor relative to a full agonist. Partial agonists may display both agonistic and antagonistic effects. For example when both a full agonist and partial agonist are present, the partial agonist acts as a competitive antagonist by competing with the full agonist for the receptor binding resulting in net decrease in receptor activation relative to the contact of the receptor with the full agonist in the absence of the partial agonist. Partial agonists can be used to activate receptors to give a desired submaximal response in a subject when inadequate amounts of the endogenous ligand are present, or they can reduce the overstimulation of receptors when excess amounts of the endogenous ligand are present. The maximum response ($E_{max}$) produced by a partial agonist is called its intrinsic activity and may be expressed on a percentage scale where a full agonist produced a 100% response. An partial agonist may have greater than 10% but less than 100%, alternatively greater than 20% but less than 100%, alternatively greater than 30% but less than 100%, alternatively greater than 40% but less than 100%, alternatively greater than 50% but less than 100%, alternatively greater than 60% but less than 100%, alternatively greater than 70% but less than 100%, alternatively greater than 80% but less than 100%, or alternatively greater than 90% but less than 100%, of the activity of the reference polypeptide when evaluated at similar concentrations in a given assay system.

PEG-hIL2 Ortholog: As used herein the term "PEG-hIL2 ortholog" refers to a hIL2 ortholog covalently bound to at least one polyethylene glycol (PEG) molecule, the at least one PEG molecule being covalently attached to at least one amino acid residue of an IL-2 ortholog. The PEGylated polypeptide may be further referred to as monopegylated, dipegylated, tripegylated (and so forth) to denote PEG-hIL2 orthologs comprising one, two, three (or more) PEG moieties attached to the IL-2 ortholog, respectively. In some embodiments, the PEG may be covalently attached directly to the IL-2 ortholog (e.g., through a lysine side chain, sulfhydryl group of a cysteine or N-terminal amine) or optionally employ a linker between the PEG and the IL-2 ortholog. In some embodiments the PEG-hIL2 ortholog comprises more than one PEG molecule each of which is attached to a different amino acid residue. In some embodiments, the PEG-hIL2 ortholog is derived from Sequence ID NO:4.

Polypeptide: As used herein the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences; fusion proteins with or without N-terminus methionine residues; fusion proteins with immunologically tagged proteins; fusion proteins of immunologically active proteins (e.g. antigenic diphtheria or tetanus toxin fragments) and the like.

Prevent: As used herein the terms "prevent", "preventing", "prevention" and the like refer to a course of action initiated with respect to a subject prior to the onset of a disease, disorder, condition or symptom thereof so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed due to genetic, experiential or environmental factors to having a particular disease, disorder or condition. In certain instances, the terms "prevent", "preventing", "prevention" are also used to refer to the slowing of the progression of a disease, disorder or condition from a present its state to a more deleterious state.

Receptor: As used herein, the term "receptor" refers to a polypeptide having a domain that specifically binds a ligand that binding of the ligand results in a change to at least one biological property of the polypeptide. In some embodiments, the receptor is a cell surface receptor that comprises and extracellular domain (ECD) and a membrane associated domain which serves to anchor the ECD to the cell surface. In some embodiments of cell surface receptors, the receptor is a membrane spanning polypeptide comprising an intracellular domain (ICD) and extracellular domain (ECD) linked by a membrane spanning domain typically referred to as a transmembrane domain (TM). The binding of a cognate ligand to the receptor results in a conformational change in the receptor resulting in a measurable biological effect. In some instances, where the receptor is a membrane spanning polypeptide comprising an ECD, TM and ICD, the binding of the ligand to the ECD results in a measurable intracellular biological effect mediated by one or more domains of the ICD in response to the binding of the ligand to the ECD. In some embodiments, a receptor is a component of a multicomponent complex to facilitate intracellular signaling. For example, the ligand may bind a cell surface receptor that is not associated with any intracellular signaling alone but upon ligand binding facilitates the formation of a heteromultimeric (including heterodimeric, heterotrimeric, etc.) or homomultimeric (including homodimeric, homotrimeric, homotetrameric, etc.) complex that results in a measurable biological effect in the cell such as activation of an intracellular signaling cascade (e.g. the Jak/STAT pathway). For example, the ligand may bind a cell surface molecule having not associated with any intracellular signaling alone but upon ligand binding facilitates the formation of a heteromultimeric including heterodimeric (e.g. the intermediate affinity hCD122/CD132 hIL2 receptor), heterotrimeric (e.g. the high affinity CD25/CD122/CD132 hIL2 receptor) or homomultimeric (homodimeric, homotrimeric, homotetrameric) complex that results in the activation of an intracellular signaling cascade (e.g. the Jak/STAT pathway). In some embodiments, a receptor is a membrane spanning single chain polypeptide comprising ECD, TM and ICD domains wherein the ECD, TM and ICD domains are derived from the same or differing naturally occurring receptor variants or synthetic functional equivalents thereof.

Recombinant: As used herein, the term "recombinant" is used as an adjective to refer to the method by which a polypeptide, nucleic acid, or cell was modified using recombinant DNA technology. A "recombinant protein" is a protein produced using recombinant DNA technology and is frequently abbreviated with a lower case "r" preceding the protein name to denote the method by which the protein was produced (e.g., recombinantly produced human growth hormone is commonly abbreviated "rhGH"). Similarly a cell is referred to as a "recombinant cell" if the cell has been modified by the incorporation (e.g. transfection, transduction, infection) of exogenous nucleic acids (e.g., ssDNA, dsDNA, ssRNA, dsRNA, mRNA, viral or non-viral vectors, plasmids, cosmids and the like) using recombinant DNA technology. The techniques and protocols for recombinant DNA technology are well known in the art such as those can be found in Sambrook, et al. (1989) Molecular Cloning: A Laboratory Manual (2d ed., Cold Spring Harbor Laboratory Press, Plainview, N.Y.) and other standard molecular biology laboratory manuals.

Response: The term "response," for example, of a cell, tissue, organ, or organism, encompasses a quantitative or qualitative change in a evaluable biochemical or physiological parameter, (e.g., concentration, density, adhesion, proliferation, activation, phosphorylation, migration, enzymatic activity, level of gene expression, rate of gene expression, rate of energy consumption, level of or state of differentiation) where the change is correlated with the activation, stimulation, or treatment, with or contact with exogenous agents or internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects. A "response" may be evaluated in vitro such as through the use of assay systems, surface plasmon resonance, enzymatic activity, mass spectroscopy, amino acid or protein sequencing technologies. A "response" may be evaluated in vivo quantitatively by evaluation of objective physiological parameters such as body temperature, bodyweight, tumor volume, blood pressure, results of X-ray or other imaging technology or qualitatively through changes in reported subjective feelings of well-being, depression, agitation, or pain. In some embodiments, the level of proliferation of CD3 activated primary human T-cells may be evaluated in a bioluminescent assay that generates a luminescent signal that is proportional to the amount of ATP present which is directly proportional to the number of cells present in culture as described in Crouch, et al. (1993) J. Immunol. Methods 160: 81-8 or through the use of commercially available assays such as the CellTiter-Glo® 2.0 Cell Viability Assay or CellTiter-Glo® 3D Cell Viability kits commercially available from Promega Corporation, Madison Wis. 53711 as catalog numbers G9241 and G9681 in substantial accordance with the instructions provided by the manufacturer. In some embodiments, the level of activation of T cells in response to the administration of a test agent may be determined by flow cytometric methods as described as determined by the level of STAT (e.g., STAT1, STAT3, STAT5) phosphorylation in accordance with methods well known in the art. For example, STAT5 phosphorylation may be measured using flow cytometric techniques as described in Horta, et al. supra., Garcia, et al., supra, or commercially available kits such as the Phospho-STAT5 (Tyr694) kit (commercially available from Perkin-Elmer, Waltham Mass. as Part Number 64AT5PEG) in performed in substantial accordance with the instructions provided by the manufacturer.

Significantly Reduced Binding: The term "exhibits significantly reduced binding" is used with respect to a variant of a first molecule (e.g. a ligand) which exhibits a significant reduction in the affinity for a second molecule (e.g. receptor) relative the parent form of the first molecule. As used herein, the term "exhibits significantly reduced binding" is used with respect to the affinity of the binding of the orthogonal ligand to the orthogonal receptor relative to the binding of the orthogonal ligand for the naturally occurring form of its cognate receptor. An orthogonal ligand exhibits significantly reduced binding with respect to the native form of the ligand if the orthogonal ligand binds to the native form of the receptor with less than 20%, alternatively less than about 10%, alternatively less than about 8%, alternatively less than about 6%, alternatively less than about 4%, alternatively less than about 2%, alternatively less than about 1%, alternatively less than about 0.5% of the naturally occurring ligand. Similarly and orthogonal receptor exhibits significantly reduced binding with respect to the native form of the ligand if the native form of the ligand binds to the orthogonal form of the receptor with less than 20%, alternatively less than about 10%, alternatively less than about 8%, alternatively less than about 6%, alternatively less than about 4%, alternatively less than about 2%, alternatively less than about 1%, alternatively less than about 0.5% of the naturally occurring receptor.

Small Molecule(s): The term "small molecules" refers to chemical compounds (typically pharmaceutically active compounds) having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. The term "small molecule" is a term well understood to those of ordinary skill in the pharmaceutical arts and is typically used to distinguish organic chemical compounds from biologics.

Specifically Binds: As used herein the term "specifically binds" refers to the degree of selectivity or affinity for which one molecule binds to another. In the context of binding pairs (e.g. a ligand/receptor, antibody/antigen, antibody/ligand, antibody/receptor binding pairs) a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the first molecule of the binding pair when the affinity of the first molecule for the second molecule is at least two-fold greater, alternatively at least five times greater, alternatively at least ten times greater, alternatively at least 20-times greater, or alternatively at least 100-times greater than the affinity of the first molecule for other components present in the sample. In a particular embodiment, where the first molecule of the binding pair is an antibody, the antibody specifically binds to the second molecule of the binding pair (e.g. a protein, antigen, ligand, or receptor) if the equilibrium dissociation constant between antibody and to the second molecule of the binding pair is greater than about $10^6$M, alternatively greater than about $10^8$ M, alternatively greater than about $10^{10}$ M, alternatively greater than about $10^{11}$ M, alternatively greater than about $10^{10}$ M, greater than about $10^{12}$ M as determined by, e.g., Scatchard analysis (Munsen, et al. 1980 Analyt. Biochem. 107:220-239). In one embodiment where the ligand is an hIL2 ortholog and the receptor comprises an orthogonal hCD122 ECD, the hIL2 ortholog specifically binds if the equilibrium dissociation constant of the hIL2 ortholog/orthogonal hCD122 ECD is greater than about $10^5$M, alternatively greater than about $10^6$ M, alternatively greater than about $10^7$M, alternatively greater than about $10^8$M, alternatively greater than about $10^9$M, alternatively greater than about $10^{10}$ M, or alternatively greater than about $10^{11}$M. Specific binding may be assessed using techniques known in the art including but not limited to competition ELISA assays, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays)) and surface plasmon resonance assays (see, e.g., Drescher et al., (2009) Methods Mol Biol 493:323-343 with commercially available instrumentation such as the Biacore 8+, Biacore 5200, Biacore T200 (GE Healthcare Bio-Sciences, 100 Results Way, Marlborough Mass. 01752).

Subject: The terms "recipient", "individual", "subject", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is a human being.

Suffering From: As used herein, the term "suffering from" refers to a determination made by a physician with respect to a subject based on the available information accepted in the field for the identification of a disease, disorder or condition including but not limited to X-ray, CT-scans, conventional laboratory diagnostic tests (e.g. blood count, etc.), genomic data, protein expression data, immunohistochemistry, that the subject requires or will benefit from treatment. The term suffering from is typically used in conjunction with a particular disease state such as "suffering from a neoplastic disease" refers to a subject which has been diagnosed with the presence of a neoplasm.

Substantially Pure: As used herein, the term "substantially pure" indicates that a component of a composition makes up greater than about 50%, alternatively greater than about 60%, alternatively greater than about 70%, alternatively greater than about 80%, alternatively greater than about 90%, alternatively greater than about 95%, of the total content of the composition. A protein that is "substantially pure" comprises greater than about 50%, alternatively greater than about 60%, alternatively greater than about 70%, alternatively greater than about 80%, alternatively greater than about 90%, alternatively greater than about 95%, of the total content of the composition.

T-cell: As used herein the term "T-cell" or "T cell" is used in its conventional sense to refer to a lymphocytes that differentiates in the thymus, possess specific cell-surface antigen receptors, and include some that control the initiation or suppression of cell-mediated and humoral immunity and others that lyse antigen-bearing cells. In some embodiments the T cell includes without limitation naïve CD8$^+$ T cells, cytotoxic CD8$^+$ T cells, naïve CD4$^+$ T cells, helper T cells, e.g. $T_H1$, $T_H2$, $T_H9$, $T_H11$, $T_H22$, $T_{FH}$; regulatory T cells, e.g. $T_R1$, Tregs, inducible Tregs; memory T cells, e.g. central memory T cells, effector memory T cells, NKT cells, tumor infiltrating lymphocytes (TILs) and engineered variants of such T-cells including but not limited to CAR-T cells, recombinantly modified TILs and TCR-engineered cells.

Terminus/Terminal: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" refers to the position of a first amino acid residue relative to a second amino acid residue in a contiguous polypeptide sequence, the first amino acid being closer to the N-terminus of the polypeptide. "Immediately C-terminal" refers to the position of a first amino acid residue relative to a second amino acid residue in a contiguous polypeptide sequence, the first amino acid being closer to the C-terminus of the polypeptide.

Therapeutically Effective Amount: The phrase "therapeutically effective amount" as used herein in reference to the administration of an agent to a subject, either alone or as part of a pharmaceutical composition or treatment regimen, in a single dose or as part of a series of doses in an amount capable of having any detectable, positive effect on any symptom, aspect, or characteristic of a disease, disorder or condition when administered to the subject. The therapeutically effective amount can be ascertained by measuring relevant physiological effects, and it may be adjusted in connection with a dosing regimen and in response to diagnostic analysis of the subject's condition, and the like. The parameters for evaluation to determine a therapeutically effective amount of an agent are determined by the physician using art accepted diagnostic criteria including but not limited to indicia such as age, weight, sex, general health, ECOG score, observable physiological parameters, blood levels, blood pressure, electrocardiogram, computerized tomography, X-ray, and the like. Alternatively, or in addition, other parameters commonly assessed in the clinical setting may be monitored to determine if a therapeutically effective amount of an agent has been administered to the subject such as body temperature, heart rate, normalization of blood chemistry, normalization of blood pressure, normalization of cholesterol levels, or any symptom, aspect, or characteristic of the disease, disorder or condition, biomarkers (such as inflammatory cytokines, IFN-γ, granzyme, and the like), reduction in serum tumor markers, improvement in Response Evaluation Criteria In Solid Tumors (RECIST), improvement in Immune-Related Response Criteria (irRC), increase in duration of survival, extended duration of progression free survival, extension of the time to progression, increased time to treatment failure, extended duration of event free survival, extension of time to next treatment, improvement objective response rate, improvement in the duration of response, reduction of tumor burden, complete response, partial response, stable disease, and the like that that are relied upon by clinicians in the field for the assessment of an improvement in the condition of the subject in response to administration of an agent. As used herein the terms "Complete Response (CR)," "Partial Response (PR)" "Stable Disease (SD)" and "Progressive Disease (PD)" with respect to target lesions and the terms "Complete Response (CR)," "Incomplete Response/Stable Disease (SD)" and Progressive Disease (PD) with respect to non-target lesions are understood to be as defined in the RECIST criteria. As used herein the terms "immune-related Complete Response (irCR)," "immune-related Partial Response (irPR)," "immune-related Progressive Disease (irPD)" and "immune-related Stable Disease (irSD)" as as defined in accordance with the Immune-Related Response Criteria (irRC). As used herein, the term "Immune-Related Response Criteria (irRC)" refers to a system for evaluation of response to immunotherapies as described in Wolchok, et al. (2009) *Guidelines for the Evaluation of Immune Therapy Activity in Solid Tumors: Immune-Related Response Criteria*, Clinical Cancer Research 15(23): 7412-7420. A therapeutically effective amount may be adjusted over a course of treatment of a subject in connection with the dosing regimen and/or evaluation of the subject's condition and variations in the foregoing factors. In one embodiment, a therapeutically effective amount is an amount of an agent when used alone or in combination with another agent does not result in non-reversible serious adverse events in the course of administration to a mammalian subject.

Transmembrane Domain: The term "transmembrane domain" or "TM" refers to the domain of a membrane spanning polypeptide (e.g. a membrane spanning receptor) which, when the membrane spanning polypeptide is associated with a cell membrane, is which is embedded in the cell membrane and is in peptidyl linkage with the extracellular domain (ECD) and the intracellular domain (ICD) of a membrane spanning polypeptide. A transmembrane domain may be homologous (naturally associated with) or heterologous (not naturally associated with) with either or both of the extracellular and/or intracellular domains. In some embodiments the transmembrane domain is the transmembrane domain natively associated with the ECD domain of the cognate receptor from which the orthogonal receptor is derived. In some embodiments the transmembrane domain is the transmembrane domain natively associated with the ICD domain of the cognate receptor from which the orthogonal receptor is derived. In some embodiments the transmembrane domain is the transmembrane domain natively associated with the proliferation signaling domain. In some embodiments the transmembrane domain is the transmembrane domain natively associated with a different protein. Alternatively, the transmembrane domain of the orthogonal receptor may be an artificial amino acid sequence which spans the plasma membrane. In some embodiments, the transmembrane domain of the orthogonal receptor is the transmembrane domain normally associated with the ICD of the cognate receptor from which the orthogonal receptor is derived.

Treat: The terms "treat", "treating", treatment" and the like refer to a course of action ((such as contacting a subject an hIL-2 orthogolog, a hoRb T cell, a hoCAR-T cell, or a pharmaceutical composition comprising same) alone or in combination with a supplementary agent) that is initiated with respect to a subject in response to a diagnosis that the subject is suffering from a disease, disorder or condition, or a symptom thereof, the course of action being initiated so as to eliminate, reduce, suppress, mitigate, or ameliorate, either temporarily or permanently, at least one of: (a) the underlying causes of such disease, disorder, or condition afflicting a subject; and/or (b) at least one of the symptoms associated with such disease, disorder, or condition. In some embodiments, treating includes a course of action taken with respect to a subject suffering from a disease where the course of action results in the inhibition (e.g., arrests the development of the disease, disorder or condition or ameliorates one or more symptoms associated therewith) of the disease in the subject.

Treg Cell or Regulatory T Cell. The terms "regulatory T cell" or "Treg cell" as used herein refers to a type of $CD4^+$ T cell that can suppress the responses of other T cells including but not limited to effector T cells (Teff). Treg cells are characterized by expression of CD4, the a-subunit of the IL-2 receptor (CD25), and the transcription factor forkhead box P3 (FOXP3) (Sakaguchi, Annu Rev Immunol 22, 531-62 (2004). By "conventional $CD4^+$ T cells" is meant $CD4^+$ T cells other than regulatory T cells.

Variant: The terms "variant", "protein variant" or "variant protein" or "variant polypeptide" are used interchangeably herein to refer to a polypeptide that differs from a parent polypeptide by virtue of at least one amino acid modification, substitution, or deletion. The parent polypeptide may be a naturally occurring or wild-type (WT) polypeptide or may be a modified version of a WT polypeptide. The term variant polypeptide may refer to the polypeptide itself, a composition comprising the polypeptide, or the nucleic acid sequence that encodes it. In some embodiments, the variant polypeptide comprises from about one to about ten, alternatively about one to about eight, alternatively about one to about seven, alternatively about one to about five, alternatively about one to about four, alternatively from about one to about three alternatively from one to two amino acid modifications, substitutions, or deletions, or alternatively a single amino acid amino acid modification, substitution, or deletion compared to the parent polypeptide. A variant may be at least about 99% identical, alternatively at least about 98% identical, alternatively at least about 97% identical, alternatively at least about 95% identical, or alternatively at least about 90% identical to the parent polypeptide from which the variant is derived.

Wild Type: By "wild type" or "WT" or "native" herein is meant an amino acid sequence or a nucleotide sequence that is found in nature, including allelic variations. A WT protein, polypeptide, antibody, immunoglobulin, IgG, etc. has an amino acid sequence or a nucleotide sequence that has not been modified by the hand of man.

hIL2 Orthologs

NOMENCLATURE

The present disclosure provides a variety polypeptide ligands of hIL2 receptor polypeptide variants. The following nomenclature is used herein to refer to substitutions, deletions or insertions. Residues may be designated herein by the one-letter or three-letter amino acid code of the naturally occurring amino acid found in the wild-type molecule but followed by the hIL2 amino acid position of the mature hIL2 molecule, e.g., "Cys125" or "C125" refers to the cysteine residue at position 125 of the wild-type hIL2 molecule. In reference to the hIL2 orthologs, substitutions are designated herein by the one letter amino acid code followed by the hIL2 amino acid position followed by the one letter amino acid code which is substituted. The numbering of the hIL2 orthologs of the present disclosure are numbered in accordance with hIL2. For example, an hIL2 ortholog having the modification "K35A" refers to a substitution of the lysine (K) residue at position 35 of the wild-type hIL2 sequence with an alanine (A) residue at this position. A deletion of an amino acid reside is referred to as "des" followed by the amino acid residue and its position in SEQ ID NO:4. For example the term "des-Ala1" or "ΔA1" "desA1" refers to the deletion of the alanine at position 1 of the polypeptide of wild-type hIL2 sequence. Similarly, in reference to amino acid substitutions in the orthogonal hCD122, amino acid substitutions are designated herein by the one letter amino acid code of the naturally occurring amino acid followed by the number of its position in the wild-type hIL2 sequence followed by the one letter amino acid code of the amino acid which is substituted at that position. The hCD122 modifications to hCD122 incorporated into the orthogonal receptor are numbered in accordance with hCD122. For example, the hCD122 orthogonal receptor having a substitution of the tyrosine residue at position 134 with a phenylalanine residue, the substitution is abbreviated "Y134F." The abbreviation hoRb is used synonomously with hoCD122 to refer to a human CD122 which comprises orthogonal hCD122 receptor. Similarly, the reference to an "hoRb cell" (e.g., an hoRb T cell or hoRb NKL cell) refers to a cell which expresses an orthogonal hCD122 receptor. The term SQVLKA as used herein refers to a hIL2 ortholog comprising the amino acid substitutions: E15S, H16Q, L19V, D20L, Q22K, and M23A.

hIL2 Orthologs

In some embodiments, the present disclosure provides hIL2 orthologs and methods of use thereof, that are cognate ligands of orthogonal receptors comprising a modified hCD122 ECD. In some embodiments, the term hIL2 orthologs refers to hIL2 variants that ligands for a receptor comprising the extracellular domain of human orthogonal hCD122 comprising amino acid substitutions at positions H133 and/or Y134. In some embodiments, the hIL2 orthologs are ligands for an orthogonal receptor comprising the extracellular domain of human hCD122 comprising amino acid substitutions at positions H133 and/or Y134. In some embodiments, the hIL2 orthologs are ligands for a transmembrane receptor comprising the extracellular domain of human CD122 comprising amino acid substitutions at positions H133 and/or Y134 the ICD of which comprises one or more STAT3 binding motifs. In some embodiments, the hIL2 orthologs are ligands for an orthogonal human CD122 comprising amino acid substitutions at positions H133 and Y134. In some embodiments, the hIL2 orthologs are ligands for an orthogonal hCD122 comprising the amino acid substitutions H133D and Y134F.

In various embodiments, the compositions and methods of the present disclosure comprise the use of hIL2 ortholog polypeptides having at least 80%, alternatively 85%, alternatively 90%, alternatively 95%, alternatively 97%, alternatively 99%, identity to polypeptide of the following Formula #1:

$$\left[ \begin{array}{l} \text{(AA1)-(AA2)-(AA3)-(AA4)-(AA5)-(AA6)-(AA7)-(AA8)-(AA9)}_i\text{-T10-Q11-L12-} \\ \text{(AA13)-(AA14)-(AA15)-(AA16)-L17-(AA18)-(AA19)-(AA20)-L21-(AA22)-} \\ \text{(AA23)-I24-L25-N26-(AA27)-I28-N29-N30-Y31-K32-N33-P34-K35-L36-T37-} \\ \text{(AA38)-(AA39)-L40-T41-(AA42)-K43-F44-Y45-M46-P47-K48-K49-A50-(AA51)-} \\ \text{E52-L53-K54-(AA55)-L56-Q57-C58-L59-E60-E61-E62-L63-K64-P65-L66-E67-} \\ \text{E68-V69-L70-N71-L72-A73-(AA74)-S75-K76-N77-F78-H79-(AA80-(AA81)-P82-} \\ \text{R83-D84-(AA85)-(AA86)-S87-N88-(AA89)-N90-(AA91)-(AA92)-V93-L94-E95-} \\ \text{L96-(AA97)-G98-S99-E100-T101-T102-F103-(AA104)-C105-E106-Y107-A108-} \\ \text{(AA109)-E110-T111-A112-(AA113)-I114-V115-E116-F117-L118-N119-R120-} \\ \text{W121-I122-T123-F124-(AA125)-(AA126)-S127-I128-I129-(AA130)-T131-L132-} \\ \text{T133} \end{array} \right] \quad [1]$$

wherein:

AA1 is A (wild type) or deleted;
AA2 is P (wild type) or deleted;
AA3 is T (wild type), C, A, G, Q, E, N, D, R, K, P, or deleted;
AA4 is S (wild type) or deleted;
AA5 is S (wild type) or deleted;
AA6 is S (wild type) or deleted;
AA7 is T (wild type) or deleted;
AA8 is K (wild type) or deleted;
AA9 is K (wild type) or deleted;
AA13 is Q (wild type), W or deleted;
AA14 is L (wild type), M, W or deleted;
AA15 is E (wildtype), K, D, T, A, S, Q, H or deleted;
AA16 is H (wildtype), N or Q or deleted;
AA18 is L (wild type) or R, G, M, F, E, H, W, K, Q, S, V, I, Y, H, D or T;
AA19 is L (wildtype), A, V, I or deleted;
AA20 is D (wildtype), T, S M L, or deleted;
AA22 is Q (wild type) or F, E, G, A, L, M, F, W, K, S, V, I, Y, H, R, N, D, T, F or deleted;
AA23 is M (wild type), A, W, H, Y, F, Q, S, V, L, T, or deleted;
AA27 IS G (wildtype), K, S or deleted;
AA38 is R (wild type), W or G;
AA39 is M (wildtype), L or V;
AA42 is F (wildtype) or K;
AA51 is T (wildtype), I or deleted
AA55 is H (wildtype) or Y;
AA74 is Q (wild type), N, H, S;
AA80 is L (wild type), F or V;
AA81 is R (wild type), I, D, Y, T or deleted
AA85 is L (wild type) or V;
AA86 is I (wild type) or V;
AA88 is N (wildtype), E or Q or deleted;
AA89 is I (wild type) or V;
AA91 is V (wild type), R or K;
AA92 is I (wild type) or F;
AA97 is K (wild type) or Q;
AA104 is M (wild type) or A;
AA109 is D (wildtype), C or a non-natural amino acid with an activated side chain;
AA113 is T (wild type) or N;
AA125 is C (wild type), A or S;
AA126 is Q (wild type) or H, M, K, C, D, E, G, I, R, S, or T; and/or
AA130 is S (wild type), T or R.

A series of hIL2 orthologs of the foregoing Formula 1 (expressed with an additional N-terminal signal peptide of the sequence MYRMQLLSCIALSLALVTNS (SEQ ID NO. 421) of the mature protein sequence) were prepared as provided in Table 2 below in accordance with the Examples and evaluated to their ability to selectively activate NKL cells relative to NKL cells which have been engineered to express an orthogonal CD122 of SEQ ID NO: 2 T cells expressing an orthogonal IL2 receptor comprising the substitutions.

TABLE 2 hIL2 Orthologs

| SEQ ID NO: | Ref# | Name | Modifications Relative to wt hIL2 | Mature Protein Sequence |
|---|---|---|---|---|
| 5 | 001 | -QVLKA | H16Q L19V D20L Q22K M23A | APTSSSTKKTQLQLEQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 6 | 002 | S-VLKA | E15S L19V D20L Q22K M23A | APTSSSTKKTQLQLSHLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 7 | 003 | SQ-LKA | E15S H16Q D20L Q22K M23A | APTSSSTKKTQLQLSQLLLLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |

TABLE 2-continued hIL2 Orthologs

| SEQ ID NO: | Ref# | Name | Modifications Relative to wt hIL2 | Mature Protein Sequence |
|---|---|---|---|---|
| 8 | 004 | SQV-KA | E15S H16Q L19V Q22K M23A | APTSSSTKKTQLQLSQLLVDLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 9 | 005 | SQVL-A | E15S H16Q L19V D20L M23A | APTSSSTKKTQLQLSQLLVLLQAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 10 | 006 | SQVLK- | E15S H16Q L19V D20L Q22K | APTSSSTKKTQLQLSQLLVLLKMILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 11 | 007 | S----- | E15S | APTSSSTKKTQLQLSHLLLDLQMILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 12 | 008 | -Q----- | H16Q | APTSSSTKKTQLQLEQLLLDLQMILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 13 | 009 | --V--- | L19V | APTSSSTKKTQLQLEHLLVDLQMILNGINNYKN PKLTRMLTFKFYMPKKATELKHLQCLEEELKPL EEVLNLAQSKNFHLRPRDLISNINVIVLELKGSE TTFMCEYADETATIVEFLNRWITFCQSIISTLT |
| 14 | 010 | ---L-- | D20L | APTSSSTKKTQLQLEHLLLLLQMILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 15 | 011 | ----K- | Q22K | APTSSSTKKTQLQLEHLLLDLKMILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 16 | 012 | -----A | M23A | APTSSSTKKTQLQLEHLLLDLQAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 17 | 013 | SQ---- | E15S H16Q | APTSSSTKKTQLQLSQLLLDLQMILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 18 | 014 | SQVL-- | E15S H16Q L19V D20L | APTSSSTKKTQLQLSQLLVLLQMILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 19 | 015 | SQVLKA | E15S H16Q L19V D20L Q22K M23A | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 20 | 016 | ΔA1, SQVLKA | desA1 E15S H16Q L19V D20L Q22K M23A | PTSSSTKKTQLQLSQLLVLLKAILNGINNYKNPK LTRMLTFKFYMPKKATELKHLQCLEEELKPLEE VLNLAQSKNFHLRPRDLISNINVIVLELKGSETTF MCEYADETATIVEFLNRWITFCQSIISTLT |
| 21 | 017 | ΔP2, SQVLKA | desP2 E15S H16Q L19V D20L Q22K M23A | ATSSSTKKTQLQLSQLLVLLKAILNGINNYKNPK LTRMLTFKFYMPKKATELKHLQCLEEELKPLEE VLNLAQSKNFHLRPRDLISNINVIVLELKGSETTF MCEYADETATIVEFLNRWITFCQSIISTLT |
| 22 | 018 | ΔT3, SQVLKA | desT3 E15S H16Q L19V D20L Q22K M23A | APSSSTKKTQLQLSQLLVLLKAILNGINNYKNPK LTRMLTFKFYMPKKATELKHLQCLEEELKPLEE VLNLAQSKNFHLRPRDLISNINVIVLELKGSETTF MCEYADETATIVEFLNRWITFCQSIISTLT |

TABLE 2-continued hIL2 Orthologs

| SEQ ID NO: | Ref# | Name | Modifications Relative to wt hIL2 | Mature Protein Sequence |
|---|---|---|---|---|
| 23 | 019 | T3C, SQVLKA | T3C E15S H16Q L19V D20L Q22K M23A | APCSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 24 | 020 | T3A, SQVLKA | T3A E15S H16Q L19V D20L Q22K M23A | APASSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 25 | 021 | T3G, SQVLKA | T3G E15S H16Q L19V D20L Q22K M23A | APGSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 26 | 022 | T3Q, SQVLKA | T3Q E15S H16Q L19V D20L Q22K M23A | APQSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 27 | 023 | T3E, SQVLKA | T3E E15S H16Q L19V D20L Q22K M23A | APESSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 28 | 024 | T3N, SQVLKA | T3N E15S H16Q L19V D20L Q22K M23A | APNSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 29 | 025 | T3D, SQVLKA | T3D E15S H16Q L19V D20L Q22K M23A | APDSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 30 | 026 | T3R, SQVLKA | T3R E15S H16Q L19V D20L Q22K M23A | APRSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 31 | 027 | T3K, SQVLKA | T3K E15S H16Q L19V D20L Q22K M23A | APKSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 32 | 028 | T3P, SQVLKA | T3P E15S H16Q L19V D20L Q22K M23A | APPSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 33 | 029 | ΔS4, SQVLKA | desS4 E15S H16Q L19V D20L Q22K M23A | APTSSTKKTQLQLSQLLVLLKAILNGINNYKNPK LTRMLTFKFYMPKKATELKHLQCLEEELKPLEE VLNLAQSKNFHLRPRDLISNINVIVLELKGSETTF MCEYADETATIVEFLNRWITFCQSIISTLT |
| 34 | 030 | ΔS5, SQVLKA | desS5 E15S H16Q L19V D20L Q22K M23A | APTSSTKKTQLQLSQLLVLLKAILNGINNYKNPK LTRMLTFKFYMPKKATELKHLQCLEEELKPLEE VLNLAQSKNFHLRPRDLISNINVIVLELKGSETTF MCEYADETATIVEFLNRWITFCQSIISTLT |
| 35 | 031 | ΔS6, SQVLKA | desS6 E15S H16Q L19V D20L Q22K M23A | APTSSTKKTQLQLSQLLVLLKAILNGINNYKNPK LTRMLTFKFYMPKKATELKHLQCLEEELKPLEE VLNLAQSKNFHLRPRDLISNINVIVLELKGSETTF MCEYADETATIVEFLNRWITFCQSIISTLT |
| 36 | 032 | ΔT7, SQVLKA | desT7 E15S H16Q L19V D20L Q22K M23A | APTSSSKKTQLQLSQLLVLLKAILNGINNYKNPK LTRMLTFKFYMPKKATELKHLQCLEEELKPLEE VLNLAQSKNFHLRPRDLISNINVIVLELKGSETTF MCEYADETATIVEFLNRWITFCQSIISTLT |
| 37 | 033 | ΔK8, SQVLKA | desK8 E15S H16Q L19V D20L Q22K M23A | APTSSSTKTQLQLSQLLVLLKAILNGINNYKNPK LTRMLTFKFYMPKKATELKHLQCLEEELKPLEE VLNLAQSKNFHLRPRDLISNINVIVLELKGSETTF MCEYADETATIVEFLNRWITFCQSIISTLT |

TABLE 2-continued hIL2 Orthologs

| SEQ ID NO: | Ref# | Name | Modifications Relative to wt hIL2 | Mature Protein Sequence |
|---|---|---|---|---|
| 38 | 034 | ΔK9, SQVLKA | desK9 E15S H16Q L19V D20L Q22K M23A | APTSSSTKTQLQLSQLLVLLKAILNGINNYKNPK LTRMLTFKFYMPKKATELKHLQCLEEELKPLEE VLNLAQSKNFHLRPRDLISNINVIVLELKGSETTF MCEYADETATIVEFLNRWITFCQSIISTLT |
| 39 | 035 | ΔQ13, SQVLKA | desQ13 E15S H16Q L19V D20L Q22K M23A | APTSSSTKKTQLLSQLLVLLKAILNGINNYKNPK LTRMLTFKFYMPKKATELKHLQCLEEELKPLEE VLNLAQSKNFHLRPRDLISNINVIVLELKGSETTF MCEYADETATIVEFLNRWITFCQSIISTLT |
| 40 | 036 | Q13W SQVLKA | Q13W E15S H16Q L19V D20L Q22K M23A | APTSSSTKKTQLWLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 41 | 037 | ΔL14, SQVLKA | desL14 E15S H16Q L19V D20L Q22K M23A | APTSSSTKKTQLQSQLLVLLKAILNGINNYKNPK LTRMLTFKFYMPKKATELKHLQCLEEELKPLEE VLNLAQSKNFHLRPRDLISNINVIVLELKGSETTF MCEYADETATIVEFLNRWITFCQSIISTLT |
| 42 | 038 | L14M, SQVLKA | L14M E15S H16Q L19V D20L Q22K M23A | APTSSSTKKTQLQMSQLLVLLKAILNGINNYKN PKLTRMLTFKFYMPKKATELKHLQCLEEELKPL EEVLNLAQSKNFHLRPRDLISNINVIVLELKGSE TTFMCEYADETATIVEFLNRWITFCQSIISTLT |
| 43 | 039 | L14W, SQVLKA | L14W E15S H16Q L19V D20L Q22K M23A | APTSSSTKKTQLQWSQLLVLLKAILNGINNYKN PKLTRMLTFKFYMPKKATELKHLQCLEEELKPL EEVLNLAQSKNFHLRPRDLISNINVIVLELKGSE TTFMCEYADETATIVEFLNRWITFCQSIISTLT |
| 44 | 041 | KQVLKA | E15K H16Q L19V D20L Q22K M23A | APTSSSTKKTQLQLKQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 45 | 043 | TQVLKA | E15T H16Q L19V D20L Q22K M23A | APTSSSTKKTQLQLTQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 46 | 047 | ΔH16, S_VLKA | desH16 E15S L19V D20L Q22K M23A | APTSSSTKKTQLQLSLLVLLKAILNGINNYKNPK LTRMLTFKFYMPKKATELKHLQCLEEELKPLEE VLNLAQSKNFHLRPRDLISNINVIVLELKGSETTF MCEYADETATIVEFLNRWITFCQSIISTLT |
| 47 | 048 | SNVLKA | E15S H16N L19V D20L Q22K M23A | APTSSSTKKTQLQLSNLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 48 | 050 | L18G, SQVLKA | E15S H16Q L18G L19V D20L Q22K M23A | APTSSSTKKTQLQLSQLGVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 49 | 051 | L18M, SQVLKA | E15S H16Q L18M L19V D20L Q22K M23A | APTSSSTKKTQLQLSQLMVLLKAILNGINNYKN PKLTRMLTFKFYMPKKATELKHLQCLEEELKPL EEVLNLAQSKNFHLRPRDLISNINVIVLELKGSE TTFMCEYADETATIVEFLNRWITFCQSIISTLT |
| 50 | 052 | L18F, SQVLKA | E15S H16Q L18F L19V D20L Q22K M23A | APTSSSTKKTQLQLSQLFVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 51 | 053 | L18E, SQVLKA | E15S H16Q L18E L19V D20L Q22K M23A | APTSSSTKKTQLQLSQLEVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 52 | 054 | L18H, SQVLKA | E15S H16Q L18H L19V D20L Q22K M23A | APTSSSTKKTQLQLSQLHVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |

TABLE 2-continued hIL2 Orthologs

| SEQ ID NO: | Ref# | Name | Modifications Relative to wt hIL2 | Mature Protein Sequence |
|---|---|---|---|---|
| 53 | 055 | L18W, SQVLKA | E15S H16Q L18W L19V D20L Q22K M23A | APTSSSTKKTQLQLSQLWVLLKAILNGINNYKN PKLTRMLTFKFYMPKKATELKHLQCLEEELKPL EEVLNLAQSKNFHLRPRDLISNINVIVLELKGSE TTFMCEYADETATIVEFLNRWITFCQSIISTLT |
| 54 | 056 | L18K, SQVLKA | E15S H16Q L18K L19V D20L Q22K M23A | APTSSSTKKTQLQLSQLKVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 55 | 057 | L18Q, SQVLKA | E15S H16Q L18Q L19V D20L Q22K M23A | APTSSSTKKTQLQLSQLQVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 56 | 058 | L18S, SQVLKA | E15S H16Q L18S L19V D20L Q22K M23A | APTSSSTKKTQLQLSQLSVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 57 | 059 | L18V, SQVLKA | E15S H16Q L18V L19V D20L Q22K M23A | APTSSSTKKTQLQLSQLVVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 58 | 060 | L18I, SQVLKA | E15S H16Q L18I L19V D20L Q22K M23A | APTSSSTKKTQLQLSQLIVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 59 | 061 | L18Y, SQVLKA | E15S H16Q L18Y L19V D20L Q22K M23A | APTSSSTKKTQLQLSQLYVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 60 | 062 | L18H, SQVLKA | E15S H16Q L18H L19V D20L Q22K M23A | APTSSSTKKTQLQLSQLHVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 61 | 063 | L18D, SQVLKA | E15S H16Q L18D L19V D20L Q22K M23A | APTSSSTKKTQLQLSQLDVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 62 | 064 | L18T, SQVLKA | E15S H16Q L18T L19V D20L Q22K M23A | APTSSSTKKTQLQLSQLTVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 63 | 065 | ΔL19, SQ_LKA | desL19 E15S H16Q D20L Q22K M23A | APTSSSTKKTQLQLSQLLLLKAILNGINNYKNPK LTRMLTFKFYMPKKATELKHLQCLEEELKPLEE VLNLAQSKNFHLRPRDLISNINVIVLELKGSETTF MCEYADETATIVEFLNRWITFCQSIISTLT |
| 64 | 067 | SQILKA | E15S H16Q L19I D20L Q22K M23A | APTSSSTKKTQLQLSQLLILLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 65 | 068 | ΔD20, SQVKA | desD20 E15S H16Q L19V Q22K M23A | APTSSSTKKTQLQLSQLLVLKAILNGINNYKNPK LTRMLTFKFYMPKKATELKHLQCLEEELKPLEE VLNLAQSKNFHLRPRDLISNINVIVLELKGSETTF MCEYADETATIVEFLNRWITFCQSIISTLT |
| 66 | 070 | SQVSKA | E15S H16Q L19V D20S Q22K M23A | APTSSSTKKTQLQLSQLLVSLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 67 | 073 | SQVLFA | E15S H16Q L19V D20L Q22F M23A | APTSSSTKKTQLQLSQLLVLLFAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |

TABLE 2-continued hIL2 Orthologs

| SEQ ID NO: | Ref# | Name | Modifications Relative to wt hIL2 | Mature Protein Sequence |
|---|---|---|---|---|
| 68 | 074 | SQVLEA | E15S H16Q L19V D20L Q22E M23A | APTSSSTKKTQLQLSQLLVLLEAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 69 | 075 | SQVLGA | E15S H16Q L19V D20L Q22G M23A | APTSSSTKKTQLQLSQLLVLLGAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 70 | 076 | SQVLAA | E15S H16Q L19V D20L Q22A M23A | APTSSSTKKTQLQLSQLLVLLAAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 71 | 077 | SQVLLA | E15S H16Q L19V D20L Q22L M23A | APTSSSTKKTQLQLSQLLVLLLAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 72 | 078 | SQVLMA | E15S H16Q L19V D20L Q22M M23A | APTSSSTKKTQLQLSQLLVLLMAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 73 | 079 | SQVLFA | E15S H16Q L19V D20L Q22F M23A | APTSSSTKKTQLQLSQLLVLLFAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 74 | 080 | SQVLWA | E15S H16Q L19V D20L Q22W M23A | APTSSSTKKTQLQLSQLLVLLWAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 75 | 081 | SQVLSA | E15S H16Q L19V D20L Q22S M23A | APTSSSTKKTQLQLSQLLVLLSAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 76 | 082 | SQVLVA | E15S H16Q L19V D20L Q22V M23A | APTSSSTKKTQLQLSQLLVLLVAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 77 | 083 | SQVLIA | E15S H16Q L19V D20L Q22I M23A | APTSSSTKKTQLQLSQLLVLLIAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 78 | 084 | SQVLYA, E116G | E15S H16Q L19V D20L Q22Y M23A E116G | APTSSSTKKTQLQLSQLLVLLYAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 79 | 085 | SQVLHA | E15S H16Q L19V D20L Q22H M23A | APTSSSTKKTQLQLSQLLVLLHAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 80 | 086 | SQVLRA | E15S H16Q L19V D20L Q22R M23A | APTSSSTKKTQLQLSQLLVLLRAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 81 | 087 | SQVLNA | E15S H16Q L19V D20L Q22N M23A | APTSSSTKKTQLQLSQLLVLLNAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 82 | 088 | SQVLDA | E15S H16Q L19V D20L Q22D M23A | APTSSSTKKTQLQLSQLLVLLDAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |

TABLE 2-continued hIL2 Orthologs

| SEQ ID NO: | Ref# | Name | Modifications Relative to wt hIL2 | Mature Protein Sequence |
|---|---|---|---|---|
| 83 | 089 | SQVLTA | E15S H16Q L19V D20L Q22T M23A | APTSSSTKKTQLQLSQLLVLLTAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 84 | 090 | ΔM23, SQVLK- | desM23 E15S H16Q L19V D20L Q22K | APTSSSTKKTQLQLSQLLVLLKILNGINNYKNPK LTRMLTFKFYMPKKATELKHLQCLEEELKPLEE VLNLAQSKNFHLRPRDLISNINVIVLELKGSETTF MCEYADETATIVEFLNRWITFCQSIISTLT |
| 85 | 091 | SQVLKW | E15S H16Q L19V D20L Q22K M23W | APTSSSTKKTQLQLSQLLVLLKWILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 86 | 092 | SQVLKH | E15S H16Q L19V D20L Q22K M23H | APTSSSTKKTQLQLSQLLVLLKHILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 87 | 093 | SQVLKY | E15S H16Q L19V D20L Q22K M23Y | APTSSSTKKTQLQLSQLLVLLKYILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 88 | 094 | SQVLKF | E15S H16Q L19V D20L Q22K M23F | APTSSSTKKTQLQLSQLLVLLKFILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 89 | 095 | SQVLKQ | E15S H16Q L19V D20L Q22K M23Q | APTSSSTKKTQLQLSQLLVLLKQILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 90 | 096 | SQVLKS | E15S H16Q L19V D20L Q22K M23S | APTSSSTKKTQLQLSQLLVLLKSILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 91 | 097 | SQVLKV | E15S H16Q L19V D20L Q22K M23V | APTSSSTKKTQLQLSQLLVLLKVILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 92 | 098 | SQVLKL | E15S H16Q L19V D20L Q22K M23L | APTSSSTKKTQLQLSQLLVLLKLILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 93 | 099 | SQVLKT | E15S H16Q L19V D20L Q22K M23T | APTSSSTKKTQLQLSQLLVLLKTILNGINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 94 | 100 | ΔG27, SQVLKA | desG27 E15S H16Q L19V D20L Q22K M23A | APTSSSTKKTQLQLSQLLVLLKAILNINNYKNPK LTRMLTFKFYMPKKATELKHLQCLEEELKPLEE VLNLAQSKNFHLRPRDLISNINVIVLELKGSETTF MCEYADETATIVEFLNRWITFCQSIISTLT |
| 95 | 101 | G27K, SQVLKA | E15S H16Q L19V D20L Q22K M23A G27K | APTSSSTKKTQLQLSQLLVLLKAILNKINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 96 | 102 | G27S, SQVLKA | E15S H16Q L19V D20L Q22K M23A G27S | APTSSSTKKTQLQLSQLLVLLKAILNSINNYKNP KLTRMLTFKFYMPKKATELKHLQCLEEELKPLE EVLNLAQSKNFHLRPRDLISNINVIVLELKGSET TFMCEYADETATIVEFLNRWITFCQSIISTLT |
| 97 | 103 | R38W, SQVLKA | E15S H16Q L19V D20L Q22K M23A R38W | APTSSSTKKTQLQLSQLLVLLKAILNGINNYKNP KLTWMLTFKFYMPKKATELKHLQCLEEELKPL EEVLNLAQSKNFHLRPRDLISNINVIVLELKGSE TTFMCEYADETATIVEFLNRWITFCQSIISTLT |

TABLE 2-continued hIL2 Orthologs

| SEQ ID NO: | Ref# | Name | Modifications Relative to wt hIL2 | Mature Protein Sequence |
|---|---|---|---|---|
| 98 | 104 | R38G, SQVLKA | E15S H16Q L19V D20L Q22K M23A R38G | APTSSSTKKTQLQLSQLLVLLKAILNGINNYKNP KLTGMLTFKFYMPKKATELKHLQCLEEELKPLE EVLNLAQSKNFHLRPRDLISNINVIVLELKGSET TFMCEYADETATIVEFLNRWITFCQSIISTLT |
| 99 | 105 | M39L, SQVLKA | E15S H16Q L19V D20L Q22K M23A M39L | APTSSSTKKTQLQLSQLLVLLKAILNGINNYKNP KLTRLLTFKFYMPKKATELKHLQCLEEELKPLE EVLNLAQSKNFHLRPRDLISNINVIVLELKGSET TFMCEYADETATIVEFLNRWITFCQSIISTLT |
| 101 | 106 | M39V, SQVLKA | E15S H16Q L19V D20L Q22K M23A M39V | APTSSSTKKTQLQLSQLLVLLKAILNGINNYKNP KLTRVLTFKFYMPKKATELKHLQCLEEELKPLE EVLNLAQSKNFHLRPRDLISNINVIVLELKGSET TFMCEYADETATIVEFLNRWITFCQSIISTLT |
| 101 | 107 | F42K, SQVLKA | E15S H16Q L19V D20L Q22K M23A F42K | APTSSSTKKTQLQLSQLLVLLKAILNGINNYKNP KLTRMLTKKFYMPKKATELKHLQCLEEELKPLE EVLNLAQSKNFHLRPRDLISNINVIVLELKGSET TFMCEYADETATIVEFLNRWITFCQSIISTLT |
| 102 | 108 | ΔT51, SQVLKA | desT51 E15S H16Q L19V D20L Q22K M23A | APTSSSTKKTQLQLSQLLVLLKAILNGINNYKNP KLTRMLTFKFYMPKKA ELKHLQCLEEELKPLEEVLNLAQSKNFHLRPRD LISNINVIVLELKGSETTFMCEYADETATIVEFLN RWITFCQSIISTLT |
| 103 | 109 | T51I, SQVLKA | E15S H16Q L19V D20L Q22K M23A T51I | APTSSSTKKTQLQLSQLLVLLKAILNGINNYKNP KLTRMLTFKFYMPKKAIELKHLQCLEEELKPLE EVLNLAQSKNFHLRPRDLISNINVIVLELKGSET TFMCEYADETATIVEFLNRWITFCQSIISTLT |
| 104 | 110 | H55Y, SQVLKA | E15S H16Q L19V D20L Q22K M23A H55Y | APTSSSTKKTQLQLSQLLVLLKAILNGINNYKNP KLTRMLTFKFYMPKKATELKYLQCLEEELKPLE EVLNLAQSKNFHLRPRDLISNINVIVLELKGSET TFMCEYADETATIVEFLNRWITFCQSIISTLT |
| 105 | 111 | Q74N, SQVLKA | E15S H16Q L19V D20L Q22K M23A Q74N | APTSSSTKKTQLQLSQLLVLLKAILNGINNYKNP KLTRMLTFKFYMPKKATELKHLQCLEEELKPLE EVLNLANSKNFHLRPRDLISNINVIVLELKGSET TFMCEYADETATIVEFLNRWITFCQSIISTLT |
| 106 | 112 | Q74H, SQVLKA | E15S H16Q L19V D20L Q22K M23A Q74H | APTSSSTKKTQLQLSQLLVLLKAILNGINNYKNP KLTRMLTFKFYMPKKATELKHLQCLEEELKPLE EVLNLAHSKNFHLRPRDLISNINVIVLELKGSET TFMCEYADETATIVEFLNRWITFCQSIISTLT |
| 107 | 113 | Q74S, SQVLKA | E15S H16Q L19V D20L Q22K M23A Q74S | APTSSSTKKTQLQLSQLLVLLKAILNGINNYKNP KLTRMLTFKFYMPKKATELKHLQCLEEELKPLE EVLNLASSKNFHLRPRDLISNINVIVLELKGSETT FMCEYADETATIVEFLNRWITFCQSIISTLT |
| 108 | 114 | L80F, SQVLKA | E15S H16Q L19V D20L Q22K M23A L80F | APTSSSTKKTQLQLSQLLVLLKAILNGINNYKNP KLTRMLTFKFYMPKKATELKHLQCLEEELKPLE EVLNLAQSKNFHFRPRDLISNINVIVLELKGSETT FMCEYADETATIVEFLNRWITFCQSIISTLT |
| 109 | 115 | L80V, SQVLKA | E15S H16Q L19V D20L Q22K M23A L80V | APTSSSTKKTQLQLSQLLVLLKAILNGINNYKNP KLTRMLTFKFYMPKKATELKHLQCLEEELKPLE EVLNLAQSKNFHVRPRDLISNINVIVLELKGSET TFMCEYADETATIVEFLNRWITFCQSIISTLT |
| 110 | 116 | ΔR81, SQVLKA | desR81 E15S H16Q L19V D20L Q22K M23A | APTSSSTKKTQLQLSQLLVLLKAILNGINNYKNP KLTRMLTFKFYMPKKATELKHLQCLEEELKPLE EVLNLAQSKNFHLPRDLISNINVIVLELKGSETTF MCEYADETATIVEFLNRWITFCQSIISTLT |
| 111 | 117 | R81I, SQVLKA | E15S H16Q L19V D20L Q22K M23A R81I | APTSSSTKKTQLQLSQLLVLLKAILNGINNYKNP KLTRMLTFKFYMPKKATELKHLQCLEEELKPLE EVLNLAQSKNFHLIPRDLISNINVIVLELKGSETT FMCEYADETATIVEFLNRWITFCQSIISTLT |

TABLE 2-continued hIL2 Orthologs

| SEQ ID NO: | Ref# | Name | Modifications Relative to wt hIL2 | Mature Protein Sequence |
|---|---|---|---|---|
| 112 | 118 | R81D, SQVLKA | E15S H16Q L19V D20L Q22K M23A R81D | APTSSSTKKTQLQLSQLLVLLKAILNGINNYKNP KLTRMLTFKFYMPKKATELKHLQCLEEELKPLE EVLNLAQSKNFHLDPRDLISNINVIVLELKGSET TFMCEYADETATIVEFLNRWITFCQSIISTLT |
| 113 | 119 | R81Y, SQVLKA | E15S H16Q L19V D20L Q22K M23A R81Y | APTSSSTKKTQLQLSQLLVLLKAILNGINNYKNP KLTRMLTFKFYMPKKATELKHLQCLEEELKPLE EVLNLAQSKNFHLYPRDLISNINVIVLELKGSET TFMCEYADETATIVEFLNRWITFCQSIISTLT |
| 114 | 121 | L85V, SQVLKA | E15S H16Q L19V D20L Q22K M23A L85V | APTSSSTKKTQLQLSQLLVLLKAILNGINNYKNP KLTRMLTFKFYMPKKATELKHLQCLEEELKPLE EVLNLAQSKNFHLRPRDVISNINVIVLELKGSET TFMCEYADETATIVEFLNRWITFCQSIISTLT |
| 115 | 122 | I86V, SQVLKA | E15S H16Q L19V D20L Q22K M23A I86V | APTSSSTKKTQLQLSQLLVLLKAILNGINNYKNP KLTRMLTFKFYMPKKATELKHLQCLEEELKPLE EVLNLAQSKNFHLRPRDLVSNINVIVLELKGSET TFMCEYADETATIVEFLNRWITFCQSIISTLT |
| 116 | 123 | Δ88N, SQVLKA | E15S H16Q L19V D20L Q22K M23A desN88 | APTSSSTKKTQLQLSQLLVLLKAILNGINNYKNP KLTRMLTFKFYMPKKATELKHLQCLEEELKPLE EVLNLAQSKNFHLRPRDLIS INVIVLELKGSETTFMCEYADETATIVEFLNRWI TFCQSIISTLT |
| 117 | 124 | N88E, SQVLKA | E15S H16Q L19V D20L Q22K M23A N88E | APTSSSTKKTQLQLSQLLVLLKAILNGINNYKNP KLTRMLTFKFYMPKKATELKHLQCLEEELKPLE EVLNLAQSKNFHLRPRDLISEINVIVLELKGSETT FMCEYADETATIVEFLNRWITFCQSIISTLT |
| 118 | 125 | N88Q, SQVLKA | E15S H16Q L19V D20L Q22K M23A N88Q | APTSSSTKKTQLQLSQLLVLLKAILNGINNYKNP KLTRMLTFKFYMPKKATELKHLQCLEEELKPLE EVLNLAQSKNFHLRPRDLISQINVIVLELKGSET TFMCEYADETATIVEFLNRWITFCQSIISTLT |
| 119 | 127 | V91R, SQVLKA | E15S H16Q L19V D20L Q22K M23A V91R | APTSSSTKKTQLQLSQLLVLLKAILNGINNYKNP KLTRMLTFKFYMPKKATELKHLQCLEEELKPLE EVLNLAQSKNFHLRPRDLISNINRIVLELKGSETT FMCEYADETATIVEFLNRWITFCQSIISTLT |
| 120 | 128 | V91K, SQVLKA | E15S H16Q L19V D20L Q22K M23A V91K | APTSSSTKKTQLQLSQLLVLLKAILNGINNYKNP KLTRMLTFKFYMPKKATELKHLQCLEEELKPLE EVLNLAQSKNFHLRPRDLISNINKIVLELKGSET TFMCEYADETATIVEFLNRWITFCQSIISTLT |
| 121 | 129 | I92F, SQVLKA | E15S H16Q L19V D20L Q22K M23A I92F | APTSSSTKKTQLQLSQLLVLLKAILNGINNYKNP KLTRMLTFKFYMPKKATELKHLQCLEEELKPLE EVLNLAQSKNFHLRPRDLISNINVFVLELKGSET TFMCEYADETATIVEFLNRWITFCQSIISTLT |
| 122 | 130 | K97Q, SQVLKA | E15S H16Q L19V D20L Q22K M23A K97Q | APTSSSTKKTQLQLSQLLVLLKAILNGINNYKNP KLTRMLTFKFYMPKKATELKHLQCLEEELKPLE EVLNLAQSKNFHLRPRDLISNINVIVLELQGSET TFMCEYADETATIVEFLNRWITFCQSIISTLT |
| 123 | 131 | M104A, SQVLKA | E15S H16Q L19V D20L Q22K M23A M104A | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFACEYADETATIVEFLNRWITFCQSIISTLT |
| 124 | 132 | D109C, SQVLKA | E15S H16Q L19V D20L Q22K M23A D109C | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYACETATIVEFLNRWITFCQSIISTLT |
| 125 | 133 | T113N, SQVLKA | E15S H16Q L19V D20L Q22K M23A T113N | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETANIVEFLNRWITFCQSIISTLT |

TABLE 2-continued hIL2 Orthologs

| SEQ ID NO: | Ref# | Name | Modifications Relative to wt hIL2 | Mature Protein Sequence |
|---|---|---|---|---|
| 126 | 134 | C125A, SQVLKA | E15S H16Q L19V D20L Q22K M23A C125A | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFAQSIISTLT |
| 127 | 135 | C125S, SQVLKA | E15S H16Q L19V D20L Q22K M23A C125S | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFSQSIISTLT |
| 128 | 136 | Q126H, SQVLKA | E15S H16Q L19V D20L Q22K M23A Q126H | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCHSIISTLT |
| 129 | 137 | Q126M, SQVLKA | E15S H16Q L19V D20L Q22K M23A Q126M | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCMSIISTLT |
| 130 | 138 | Q126K, SQVLKA | E15S H16Q L19V D20L Q22K M23A Q126K | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCKSIISTLT |
| 131 | 139 | Q126C, SQVLKA | E15S H16Q L19V D20L Q22K M23A Q126C | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCCSIISTLT |
| 132 | 140 | Q126D, SQVLKA | E15S H16Q L19V D20L Q22K M23A Q126D | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCDSIISTLT |
| 133 | 141 | Q126E, SQVLKA | E15S H16Q L19V D20L Q22K M23A Q126E | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCESIISTLT |
| 134 | 142 | Q126G, SQVLKA | E15S H16Q L19V D20L Q22K M23A Q126G | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCGSIISTLT |
| 135 | 143 | Q126I, SQVLKA | E15S H16Q L19V D20L Q22K M23A Q126I | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCISIISTLT |
| 136 | 144 | Q126R, SQVLKA | E15S H16Q L19V D20L Q22K M23A Q126R | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCRSIISTLT |
| 137 | 145 | Q126S, SQVLKA | E15S H16Q L19V D20L Q22K M23A Q126S | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCSSIISTLT |
| 138 | 146 | Q126T, SQVLKA | E15S H16Q L19V D20L Q22K M23A Q126T | APTSSSTKKTQLQLSQLLVLLKAILNGINNYKNP KLTRMLTFKFYMPKKATELKHLQCLEEELKPLE EVLNLAQSKNFHLRPRDLISNINVIVLELKGSET TFMCEYADETATIVEFLNRWITFCTSIISTLT |

The activity of the foregoing hIL2 orthologs was evaluated for their ability to activate NKL and hoRb NKL cells in substantial accordance with the teaching herein below dilutions. The results of these experiments are provided in FIGS. 1 and 2 of the attached drawings and in Table 3 below:

TABLE 3

Proliferative Activity of hIL2 Orthologs on hoCD122 NKL cells v. NKL Cells

| SEQ ID NO | Mutant # | NKL Proliferation Signal cts/min | NKL Ortho Proliferation Signal | Relative Proliferation Fold Change | Dilution |
|---|---|---|---|---|---|
| 20 | 16 | 11290 | 33439 | 2.96 | 1:2 |
|  |  | 15321 | 27747 | 1.81 | 1:10 |
|  |  | 14397 | 13824 | 0.96 | 1:50 |
| 21 | 17 | 14514 | 63991 | 4.41 | 1:2 |
|  |  | 16305 | 61911 | 3.80 | 1:10 |
|  |  | 15733 | 27785 | 1.77 | 1:50 |
| 22 | 18 | 15205 | 60773 | 4.00 | 1:2 |
|  |  | 17304 | 64585 | 3.73 | 1:10 |
|  |  | 16255 | 32287 | 1.99 | 1:50 |
| 23 | 19 | 13346 | 60626 | 4.54 | 1:2 |
|  |  | 17004 | 70804 | 4.16 | 1:10 |
|  |  | 17168 | 35301 | 2.06 | 1:50 |
| 24 | 20 | 17687 | 69148 | 3.91 | 1:2 |
|  |  | 18869 | 79543 | 4.22 | 1:10 |
|  |  | 17596 | 46983 | 2.67 | 1:50 |
| 25 | 21 | 14942 | 58905 | 3.94 | 1:2 |
|  |  | 17779 | 66909 | 3.76 | 1:10 |
|  |  | 16747 | 32200 | 1.92 | 1:50 |
| 26 | 22 | 15597 | 65319 | 4.19 | 1:2 |
|  |  | 18280 | 73740 | 4.03 | 1:10 |
|  |  | 18054 | 34763 | 1.93 | 1:50 |
| 27 | 23 | 17301 | 68608 | 3.97 | 1:2 |
|  |  | 19419 | 75040 | 3.86 | 1:10 |
|  |  | 18178 | 37407 | 2.06 | 1:50 |
| 28 | 24 | 16135 | 62428 | 3.87 | 1:2 |
|  |  | 19760 | 65663 | 3.32 | 1:10 |
|  |  | 17742 | 31375 | 1.77 | 1:50 |
| 29 | 25 | 12176 | 49755 | 4.09 | 1:2 |
|  |  | 13388 | 53895 | 4.03 | 1:10 |
|  |  | 11903 | 27904 | 2.34 | 1:50 |
| 30 | 26 | 14052 | 58383 | 4.15 | 1:2 |
|  |  | 14043 | 40680 | 2.90 | 1:10 |
|  |  | 13313 | 19342 | 1.45 | 1:50 |
| 31 | 27 | 12359 | 42918 | 3.47 | 1:2 |
|  |  | 14355 | 35526 | 2.47 | 1:10 |
|  |  | 13265 | 18371 | 1.38 | 1:50 |
| 32 | 28 | 9175 | 55355 | 6.03 | 1:2 |
|  |  | 11584 | 56868 | 4.91 | 1:10 |
|  |  | 11286 | 32736 | 2.90 | 1:50 |
| 33 | 29 | 12703 | 51159 | 4.03 | 1:2 |
|  |  | 13769 | 42300 | 3.07 | 1:10 |
|  |  | 12021 | 21368 | 1.78 | 1:50 |
| 34 | 30 | 13166 | 58054 | 4.41 | 1:2 |
|  |  | 15087 | 57368 | 3.80 | 1:10 |
|  |  | 13754 | 30580 | 2.22 | 1:50 |
| 35 | 31 | 11759 | 54377 | 4.62 | 1:2 |
|  |  | 13828 | 50211 | 3.63 | 1:10 |
|  |  | 13162 | 25401 | 1.93 | 1:50 |
| 36 | 32 | 15203 | 55447 | 3.65 | 1:2 |
|  |  | 15635 | 51908 | 3.32 | 1:10 |
|  |  | 14368 | 25282 | 1.76 | 1:50 |
| 37 | 33 | 14709 | 52082 | 3.54 | 1:2 |
|  |  | 15971 | 43484 | 2.72 | 1:10 |
|  |  | 15099 | 21672 | 1.44 | 1:50 |
| 38 | 34 | 13448 | 55505 | 4.13 | 1:2 |
|  |  | 13960 | 61288 | 4.39 | 1:10 |
|  |  | 12991 | 31595 | 2.43 | 1:50 |
| 39 | 35 | 12976 | 26668 | 2.06 | 1:2 |
|  |  | 14898 | 20740 | 1.39 | 1:10 |
|  |  | 14846 | 11770 | 0.79 | 1:50 |
| 40 | 36 | 11087 | 13735 | 1.24 | 1:2 |
|  |  | 15364 | 12919 | 0.84 | 1:10 |
|  |  | 13859 | 8726 | 0.63 | 1:50 |
| 41 | 37 | 13329 | 31787 | 2.38 | 1:2 |
|  |  | 14639 | 23481 | 1.60 | 1:10 |
|  |  | 14126 | 12167 | 0.86 | 1:50 |
| 42 | 38 | 15198 | 57185 | 3.76 | 1:2 |
|  |  | 15817 | 54533 | 3.45 | 1:10 |
|  |  | 13528 | 26727 | 1.98 | 1:50 |
| 43 | 39 | 12437 | 50303 | 4.04 | 1:2 |
|  |  | 15903 | 45080 | 2.83 | 1:10 |
|  |  | 15069 | 20889 | 1.39 | 1:50 |
| 44 | 41 | 13914 | 71249 | 5.12 | 1:2 |
|  |  | 15513 | 67638 | 4.36 | 1:10 |
|  |  | 14815 | 38935 | 2.63 | 1:50 |
| 45 | 43 | 14568 | 50423 | 3.46 | 1:2 |
|  |  | 17486 | 57880 | 3.31 | 1:10 |
|  |  | 15855 | 27801 | 1.75 | 1:50 |
| 46 | 47 | 15842 | 20855 | 1.32 | 1:2 |
|  |  | 16921 | 14245 | 0.84 | 1:10 |
|  |  | 15861 | 9764 | 0.62 | 1:50 |
| 47 | 48 | 15894 | 46760 | 2.94 | 1:2 |
|  |  | 18183 | 39738 | 2.19 | 1:10 |
|  |  | 16805 | 18332 | 1.09 | 1:50 |
| 48 | 50 | 14669 | 15397 | 1.05 | 1:2 |
|  |  | 16085 | 13421 | 0.83 | 1:10 |
|  |  | 15206 | 8641 | 0.57 | 1:50 |
| 49 | 51 | 11549 | 42731 | 3.70 | 1:2 |
|  |  | 16148 | 43886 | 2.72 | 1:10 |
|  |  | 14258 | 22100 | 1.55 | 1:50 |
| 50 | 52 | 12620 | 48563 | 3.85 | 1:2 |
|  |  | 15644 | 39424 | 2.52 | 1:10 |
|  |  | 14855 | 19352 | 1.30 | 1:50 |
| 51 | 53 | 14506 | 8261 | 0.57 | 1:2 |
|  |  | 16289 | 9063 | 0.56 | 1:10 |
|  |  | 15779 | 8115 | 0.51 | 1:50 |
| 52 | 54 | 12284 | 32164 | 2.62 | 1:2 |
|  |  | 16415 | 27614 | 1.68 | 1:10 |
|  |  | 15166 | 13909 | 0.92 | 1:50 |
| 53 | 55 | 11964 | 18701 | 1.56 | 1:2 |
|  |  | 15427 | 16963 | 1.10 | 1:10 |
|  |  | 15163 | 10726 | 0.71 | 1:50 |
| 54 | 56 | 14228 | 22200 | 1.56 | 1:2 |
|  |  | 16729 | 20183 | 1.21 | 1:10 |
|  |  | 15170 | 11463 | 0.76 | 1:50 |
| 55 | 57 | 12082 | 47459 | 3.93 | 1:2 |
|  |  | 16495 | 41174 | 2.50 | 1:10 |
|  |  | 15136 | 21381 | 1.41 | 1:50 |
| 56 | 58 | 11308 | 27160 | 2.40 | 1:2 |
|  |  | 13796 | 21520 | 1.56 | 1:10 |
|  |  | 13477 | 11506 | 0.85 | 1:50 |
| 57 | 59 | 13097 | 17769 | 1.36 | 1:2 |
|  |  | 14608 | 13969 | 0.96 | 1:10 |
|  |  | 13961 | 8670 | 0.62 | 1:50 |
| 58 | 60 | 11620 | 23840 | 2.05 | 1:2 |
|  |  | 14893 | 20537 | 1.38 | 1:10 |
|  |  | 13821 | 11018 | 0.80 | 1:50 |
| 59 | 61 | 11148 | 37259 | 3.34 | 1:2 |
|  |  | 12930 | 26982 | 2.09 | 1:10 |
|  |  | 12473 | 14806 | 1.19 | 1:50 |
| 60 | 62 | 11959 | 32614 | 2.73 | 1:2 |
|  |  | 13404 | 23272 | 1.74 | 1:10 |
|  |  | 13261 | 12409 | 0.94 | 1:50 |
| 61 | 63 | 10603 | 6383 | 0.60 | 1:2 |
|  |  | 13815 | 8157 | 0.59 | 1:10 |
|  |  | 13317 | 7465 | 0.56 | 1:50 |
| 62 | 64 | 10516 | 24970 | 2.37 | 1:2 |
|  |  | 13432 | 20059 | 1.49 | 1:10 |
|  |  | 12998 | 11344 | 0.87 | 1:50 |
| 63 | 65 | 13174 | 6436 | 0.49 | 1:2 |
|  |  | 14721 | 9117 | 0.62 | 1:10 |
|  |  | 14404 | 8467 | 0.59 | 1:50 |
| 64 | 67 | 13796 | 55309 | 4.01 | 1:2 |
|  |  | 15267 | 52537 | 3.44 | 1:10 |
|  |  | 14636 | 24499 | 1.67 | 1:50 |

TABLE 3-continued

Proliferative Activity of hIL2 Orthologs on hoCD122 NKL cells v. NKL Cells

| SEQ ID NO | Mutant # | NKL Proliferation Signal cts/min | NKL Ortho Proliferation Signal | Relative Proliferation Fold Change | Dilution |
|---|---|---|---|---|---|
| 65 | 68 | 12926 | 6786 | 0.52 | 1:2 |
|  |  | 16040 | 9389 | 0.59 | 1:10 |
|  |  | 15423 | 8687 | 0.56 | 1:50 |
| 66 | 70 | 59557 | 59470 | 1.00 | 1:2 |
|  |  | 42545 | 73657 | 1.73 | 1:10 |
|  |  | 23632 | 45032 | 1.91 | 1:50 |
| 67 | 73 | 13546 | 16646 | 1.23 | 1:2 |
|  |  | 14734 | 12280 | 0.83 | 1:10 |
|  |  | 14101 | 8499 | 0.60 | 1:50 |
| 68 | 74 | 11816 | 21060 | 1.78 | 1:2 |
|  |  | 15275 | 18219 | 1.19 | 1:10 |
|  |  | 14206 | 9479 | 0.67 | 1:50 |
| 69 | 75 | 12255 | 13518 | 1.10 | 1:2 |
|  |  | 14129 | 11701 | 0.83 | 1:10 |
|  |  | 14485 | 8727 | 0.60 | 1:50 |
| 70 | 76 | 13851 | 14570 | 1.05 | 1:2 |
|  |  | 16489 | 11844 | 0.72 | 1:10 |
|  |  | 15281 | 9399 | 0.62 | 1:50 |
| 71 | 77 | 10941 | 16408 | 1.50 | 1:2 |
|  |  | 15123 | 16082 | 1.06 | 1:10 |
|  |  | 14493 | 8571 | 0.59 | 1:50 |
| 72 | 78 | 14622 | 20542 | 1.40 | 1:2 |
|  |  | 17357 | 18647 | 1.07 | 1:10 |
|  |  | 16948 | 11010 | 0.65 | 1:50 |
| 73 | 79 | 16218 | 19987 | 1.23 | 1:2 |
|  |  | 18720 | 14095 | 0.75 | 1:10 |
|  |  | 17534 | 10015 | 0.57 | 1:50 |
| 74 | 80 | 12257 | 14033 | 1.14 | 1:2 |
|  |  | 16880 | 11123 | 0.66 | 1:10 |
|  |  | 16584 | 8874 | 0.54 | 1:50 |
| 75 | 81 | 7643 | 16014 | 2.10 | 1:2 |
|  |  | 10421 | 12984 | 1.25 | 1:10 |
|  |  | 10247 | 7839 | 0.77 | 1:50 |
| 76 | 82 | 12955 | 10804 | 0.83 | 1:2 |
|  |  | 13827 | 8605 | 0.62 | 1:10 |
|  |  | 12919 | 6586 | 0.51 | 1:50 |
| 77 | 83 | 11761 | 13004 | 1.11 | 1:2 |
|  |  | 13772 | 10709 | 0.78 | 1:10 |
|  |  | 12870 | 6782 | 0.53 | 1:50 |
| 78 | 84 | 10892 | 13205 | 1.21 | 1:2 |
|  |  | 14094 | 11634 | 0.83 | 1:10 |
|  |  | 13332 | 8394 | 0.63 | 1:50 |
| 79 | 85 | 15316 | 53023 | 3.46 | 1:2 |
|  |  | 16010 | 26042 | 1.63 | 1:10 |
|  |  | 15303 | 13269 | 0.87 | 1:50 |
| 80 | 86 | 14043 | 60823 | 4.33 | 1:2 |
|  |  | 16878 | 68450 | 4.06 | 1:10 |
|  |  | 15056 | 34281 | 2.28 | 1:50 |
| 81 | 87 | 11124 | 50560 | 4.55 | 1:2 |
|  |  | 12142 | 36485 | 3.00 | 1:10 |
|  |  | 12372 | 17317 | 1.40 | 1:50 |
| 82 | 88 | 13762 | 35108 | 2.55 | 1:2 |
|  |  | 13790 | 22737 | 1.65 | 1:10 |
|  |  | 12245 | 11592 | 0.95 | 1:50 |
| 83 | 89 | 11630 | 26364 | 2.27 | 1:2 |
|  |  | 14002 | 19385 | 1.38 | 1:10 |
|  |  | 12843 | 7649 | 0.60 | 1:50 |
| 84 | 90 | 9645 | 27637 | 2.87 | 1:2 |
|  |  | 13246 | 18989 | 1.43 | 1:10 |
|  |  | 12208 | 8951 | 0.73 | 1:50 |
| 85 | 91 | 14650 | 51969 | 3.55 | 1:2 |
|  |  | 14296 | 35992 | 2.52 | 1:10 |
|  |  | 13462 | 17860 | 1.33 | 1:50 |
| 86 | 92 | 11117 | 44420 | 4.00 | 1:2 |
|  |  | 14496 | 39187 | 2.70 | 1:10 |
|  |  | 12461 | 18514 | 1.49 | 1:50 |
| 87 | 93 | 14904 | 52383 | 3.51 | 1:2 |
|  |  | 16631 | 43832 | 2.64 | 1:10 |
|  |  | 15863 | 21862 | 1.38 | 1:50 |
| 88 | 94 | 18416 | 65107 | 3.54 | 1:2 |
|  |  | 17875 | 44692 | 2.50 | 1:10 |
|  |  | 16292 | 23226 | 1.43 | 1:50 |
| 89 | 95 | 16752 | 74288 | 4.43 | 1:2 |
|  |  | 17805 | 82001 | 4.61 | 1:10 |
|  |  | 16276 | 49574 | 3.05 | 1:50 |
| 90 | 96 | 11739 | 56202 | 4.79 | 1:2 |
|  |  | 14877 | 59385 | 3.99 | 1:10 |
|  |  | 13750 | 29007 | 2.11 | 1:50 |
| 91 | 97 | 13742 | 63408 | 4.61 | 1:2 |
|  |  | 15956 | 66142 | 4.15 | 1:10 |
|  |  | 14936 | 29859 | 2.00 | 1:50 |
| 92 | 98 | 12716 | 59665 | 4.69 | 1:2 |
|  |  | 15304 | 67053 | 4.38 | 1:10 |
|  |  | 14498 | 32715 | 2.26 | 1:50 |
| 93 | 99 | 13128 | 61425 | 4.68 | 1:2 |
|  |  | 14049 | 63448 | 4.52 | 1:10 |
|  |  | 13347 | 33416 | 2.50 | 1:50 |
| 94 | 100 | 14140 | 46551 | 3.29 | 1:2 |
|  |  | 15302 | 31408 | 2.05 | 1:10 |
|  |  | 14020 | 14616 | 1.04 | 1:50 |
| 95 | 101 | 12378 | 36298 | 2.93 | 1:2 |
|  |  | 15802 | 30577 | 1.94 | 1:10 |
|  |  | 14743 | 15178 | 1.03 | 1:50 |
| 96 | 102 | 11613 | 48857 | 4.21 | 1:2 |
|  |  | 13925 | 40967 | 2.94 | 1:10 |
|  |  | 13560 | 20710 | 1.53 | 1:50 |
| 97 | 103 | 13389 | 36697 | 2.74 | 1:2 |
|  |  | 15773 | 23763 | 1.51 | 1:10 |
|  |  | 14922 | 11507 | 0.77 | 1:50 |
| 98 | 104 | 11262 | 20088 | 1.78 | 1:2 |
|  |  | 15198 | 18115 | 1.19 | 1:10 |
|  |  | 14644 | 9740 | 0.67 | 1:50 |
| 99 | 105 | 12872 | 57571 | 4.47 | 1:2 |
|  |  | 15491 | 44060 | 2.84 | 1:10 |
|  |  | 14627 | 21801 | 1.49 | 1:50 |
| 100 | 106 | 15750 | 42790 | 2.72 | 1:2 |
|  |  | 16892 | 31264 | 1.85 | 1:10 |
|  |  | 16607 | 15331 | 0.92 | 1:50 |
| 101 | 107 | 14238 | 11882 | 0.83 | 1:2 |
|  |  | 17401 | 10462 | 0.60 | 1:10 |
|  |  | 16713 | 8733 | 0.52 | 1:50 |
| 102 | 108 | 12160 | 12147 | 1.00 | 1:2 |
|  |  | 14210 | 10083 | 0.71 | 1:10 |
|  |  | 13405 | 7781 | 0.58 | 1:50 |
| 103 | 109 | 14233 | 50765 | 3.57 | 1:2 |
|  |  | 14367 | 37908 | 2.64 | 1:10 |
|  |  | 13262 | 18506 | 1.40 | 1:50 |
| 104 | 110 | 12633 | 47057 | 3.72 | 1:2 |
|  |  | 15843 | 37066 | 2.34 | 1:10 |
|  |  | 14553 | 17789 | 1.22 | 1:50 |
| 105 | 111 | 13034 | 55149 | 4.23 | 1:2 |
|  |  | 14919 | 47442 | 3.18 | 1:10 |
|  |  | 13569 | 22641 | 1.67 | 1:50 |
| 106 | 112 | 14984 | 58345 | 3.89 | 1:2 |
|  |  | 15836 | 50345 | 3.18 | 1:10 |
|  |  | 14399 | 22979 | 1.60 | 1:50 |
| 107 | 113 | 13433 | 54620 | 4.07 | 1:2 |
|  |  | 15733 | 65670 | 4.17 | 1:10 |
|  |  | 14336 | 35047 | 2.44 | 1:50 |
| 108 | 114 | 14432 | 61200 | 4.24 | 1:2 |
|  |  | 16348 | 67761 | 4.14 | 1:10 |
|  |  | 14651 | 33242 | 2.27 | 1:50 |
| 109 | 115 | 14672 | 62456 | 4.26 | 1:2 |
|  |  | 16489 | 51561 | 3.13 | 1:10 |
|  |  | 15442 | 24341 | 1.58 | 1:50 |
| 110 | 116 | 12883 | 62380 | 4.84 | 1:2 |
|  |  | 16845 | 68836 | 4.09 | 1:10 |
|  |  | 15192 | 31880 | 2.10 | 1:50 |
| 111 | 117 | 13744 | 52806 | 3.84 | 1:2 |
|  |  | 15045 | 57953 | 3.85 | 1:10 |
|  |  | 14183 | 27287 | 1.92 | 1:50 |
| 112 | 118 | 19746 | 71838 | 3.64 | 1:2 |
|  |  | 16964 | 73760 | 4.35 | 1:10 |
|  |  | 14482 | 44423 | 3.07 | 1:50 |

TABLE 3-continued

Proliferative Activity of hIL2 Orthologs on hoCD122 NKL cells v. NKL Cells

| SEQ ID NO | Mutant # | NKL Proliferation Signal cts/min | NKL Ortho Proliferation Signal | Relative Proliferation Fold Change | Dilution |
|---|---|---|---|---|---|
| 113 | 119 | 16432 | 59763 | 3.64 | 1:2 |
|  |  | 16784 | 77926 | 4.64 | 1:10 |
|  |  | 14404 | 49457 | 3.43 | 1:50 |
| 114 | 121 | 14304 | 56313 | 3.94 | 1:2 |
|  |  | 14834 | 49554 | 3.34 | 1:10 |
|  |  | 14135 | 24202 | 1.71 | 1:50 |
| 115 | 122 | 10440 | 39923 | 3.82 | 1:2 |
|  |  | 14232 | 38044 | 2.67 | 1:10 |
|  |  | 12979 | 18379 | 1.42 | 1:50 |
| 116 | 123 | 10882 | 4610 | 0.42 | 1:2 |
|  |  | 12687 | 7474 | 0.59 | 1:10 |
|  |  | 11598 | 6688 | 0.58 | 1:50 |
| 117 | 124 | 13165 | 6411 | 0.49 | 1:2 |
|  |  | 13474 | 7086 | 0.53 | 1:10 |
|  |  | 12791 | 6479 | 0.51 | 1:50 |
| 118 | 125 | 11513 | 4981 | 0.43 | 1:2 |
|  |  | 13037 | 6955 | 0.53 | 1:10 |
|  |  | 12398 | 6244 | 0.50 | 1:50 |
| 119 | 127 | 9932 | 8526 | 0.86 | 1:2 |
|  |  | 10456 | 5585 | 0.53 | 1:10 |
|  |  | 10090 | 4416 | 0.44 | 1:50 |
| 120 | 128 | 6963 | 5176 | 0.74 | 1:2 |
|  |  | 8289 | 5206 | 0.63 | 1:10 |
|  |  | 9382 | 4940 | 0.53 | 1:50 |
| 121 | 129 | 13891 | 32233 | 2.32 | 1:2 |
|  |  | 14731 | 27033 | 1.84 | 1:10 |
|  |  | 13864 | 12751 | 0.92 | 1:50 |
| 122 | 130 | 16092 | 52990 | 3.29 | 1:2 |
|  |  | 15233 | 55372 | 3.64 | 1:10 |
|  |  | 13269 | 25150 | 1.90 | 1:50 |
| 123 | 131 | 12261 | 47557 | 3.88 | 1:2 |
|  |  | 15753 | 54802 | 3.48 | 1:10 |
|  |  | 14118 | 29487 | 2.09 | 1:50 |
| 124 | 132 | 11394 | 47798 | 4.20 | 1:2 |
|  |  | 13698 | 44151 | 3.22 | 1:10 |
|  |  | 13348 | 20374 | 1.52 | 1:50 |
| 125 | 133 | 12764 | 47432 | 3.71 | 1:2 |
|  |  | 14164 | 48815 | 3.45 | 1:10 |
|  |  | 13064 | 21356 | 1.63 | 1:50 |
| 126 | 134 | 10628 | 41984 | 3.95 | 1:2 |
|  |  | 13997 | 50413 | 3.60 | 1:10 |
|  |  | 11700 | 22800 | 1.95 | 1:50 |
| 127 | 135 | 11227 | 48166 | 4.29 | 1:2 |
|  |  | 13134 | 59512 | 4.53 | 1:10 |
|  |  | 12291 | 27806 | 2.26 | 1:50 |
| 128 | 136 | 11988 | 43616 | 3.64 | 1:2 |
|  |  | 15116 | 28971 | 1.92 | 1:10 |
|  |  | 14513 | 15807 | 1.09 | 1:50 |
| 129 | 137 | 9890 | 19801 | 2.00 | 1:2 |
|  |  | 14489 | 18666 | 1.29 | 1:10 |
|  |  | 13147 | 9763 | 0.74 | 1:50 |
| 130 | 138 | 11958 | 6514 | 0.54 | 1:2 |
|  |  | 14104 | 7927 | 0.56 | 1:10 |
|  |  | 13240 | 6978 | 0.53 | 1:50 |
| 131 | 139 | 14812 | 6557 | 0.44 | 1:2 |
|  |  | 15356 | 8208 | 0.53 | 1:10 |
|  |  | 14649 | 7195 | 0.49 | 1:50 |
| 132 | 140 | 12048 | 4645 | 0.39 | 1:2 |
|  |  | 15294 | 7556 | 0.49 | 1:10 |
|  |  | 13970 | 6378 | 0.46 | 1:50 |
| 133 | 141 | 10476 | 10620 | 1.01 | 1:2 |
|  |  | 12737 | 8599 | 0.68 | 1:10 |
|  |  | 12278 | 6804 | 0.55 | 1:50 |
| 134 | 142 | 12806 | 5739 | 0.45 | 1:2 |
|  |  | 14651 | 7220 | 0.49 | 1:10 |
|  |  | 13319 | 6047 | 0.45 | 1:50 |
| 135 | 143 | 10571 | 40003 | 3.78 | 1:2 |
|  |  | 14275 | 35628 | 2.50 | 1:10 |
|  |  | 13362 | 16693 | 1.25 | 1:50 |
| 136 | 144 | 11784 | 13914 | 1.18 | 1:2 |
|  |  | 12870 | 9670 | 0.75 | 1:10 |
|  |  | 11644 | 6647 | 0.57 | 1:50 |
| 137 | 145 | 13359 | 9459 | 0.71 | 1:2 |
|  |  | 13868 | 7878 | 0.57 | 1:10 |
|  |  | 12614 | 6308 | 0.50 | 1:50 |
| 138 | 146 | 13448 | 5983 | 0.44 | 1:2 |
|  |  | 14275 | 6752 | 0.47 | 1:10 |
|  |  | 12782 | 5181 | 0.41 | 1:50 |

The IL2 orthologs were evaluated for activity in CD4 positive human T cell clone 3F8 cells as more fully described in Example 8. The resulting data from these experiments is provided in Table 4 below.

TABLE 4

Proliferative Activity of hIL2 Orthologs on hoCD122 3F8 cells v 3F8 Cells

| Sequence ID | Mutant # | 3F8 Proliferation Signal cts/min | 3F8 Ortho Proliferation Signal cts/min | Relative Proliferation Fold Change | Dilution |
|---|---|---|---|---|---|
| 20 | 16 | 190 | 32446 | 170.77 | 1:02 |
|  |  | 966 | 21870 | 22.64 | 1:10 |
|  |  | 698 | 8148 | 11.67 | 1:50 |
| 21 | 17 | 1172 | 40086 | 34.2 | 1:02 |
|  |  | 1058 | 31048 | 29.35 | 1:10 |
|  |  | 1176 | 12364 | 10.51 | 1:50 |
| 22 | 18 | 1274 | 38872 | 30.51 | 1:02 |
|  |  | 2308 | 34780 | 15.07 | 1:10 |
|  |  | 2126 | 15990 | 7.52 | 1:50 |
| 23 | 19 | 948 | 33054 | 34.87 | 1:02 |
|  |  | 2640 | 33654 | 12.75 | 1:10 |
|  |  | 1224 | 14650 | 11.97 | 1:50 |
| 24 | 20 | 2416 | 41406 | 17.14 | 1:02 |
|  |  | 3580 | 39262 | 10.97 | 1:10 |
|  |  | 2240 | 19454 | 8.68 | 1:50 |
| 25 | 21 | 1556 | 31754 | 20.41 | 1:02 |
|  |  | 1254 | 24386 | 19.45 | 1:10 |
|  |  | 1324 | 9456 | 7.14 | 1:50 |
| 26 | 22 | 574 | 39196 | 68.29 | 1:02 |
|  |  | 1144 | 32216 | 28.16 | 1:10 |
|  |  | 824 | 14180 | 17.21 | 1:50 |
| 27 | 23 | 1738 | 36116 | 20.78 | 1:02 |
|  |  | 796 | 36222 | 45.51 | 1:10 |
|  |  | 1182 | 18896 | 15.99 | 1:50 |
| 28 | 24 | 16510 | 34194 | 2.07 | 1:02 |
|  |  | 9126 | 27244 | 2.99 | 1:10 |
|  |  | 2390 | 9790 | 4.1 | 1:50 |
| 29 | 25 | 952 | 33412 | 35.1 | 1:02 |
|  |  | 1886 | 35028 | 18.57 | 1:10 |
|  |  | 704 | 13374 | 19 | 1:50 |
| 30 | 26 | 3428 | 28888 | 8.43 | 1:02 |
|  |  | 1262 | 16752 | 13.27 | 1:10 |
|  |  | 1128 | 5984 | 5.3 | 1:50 |
| 31 | 27 | 568 | 28890 | 50.86 | 1:02 |
|  |  | 2052 | 15082 | 7.35 | 1:10 |
|  |  | 774 | 7148 | 9.24 | 1:50 |
| 32 | 28 | 1078 | 36522 | 33.88 | 1:02 |
|  |  | 928 | 39744 | 42.83 | 1:10 |
|  |  | 494 | 19040 | 38.54 | 1:50 |
| 33 | 29 | 20690 | 41050 | 1.98 | 1:02 |
|  |  | 11516 | 29554 | 2.57 | 1:10 |
|  |  | 1176 | 13948 | 11.86 | 1:50 |
| 34 | 30 | 14128 | 40508 | 2.87 | 1:02 |
|  |  | 2634 | 39450 | 14.98 | 1:10 |
|  |  | 582 | 22902 | 39.35 | 1:50 |

TABLE 4-continued

Proliferative Activity of hIL2 Orthologs on hoCD122 3F8 cells v 3F8 Cells

| Sequence ID | Mutant # | 3F8 Proliferation Signal cts/min | 3F8 Ortho Proliferation Signal cts/min | Relative Proliferation Fold Change | Dilution |
|---|---|---|---|---|---|
| 35 | 31 | 494 | 40440 | 81.86 | 1:02 |
|  |  | 1404 | 35202 | 25.07 | 1:10 |
|  |  | 696 | 15794 | 22.69 | 1:50 |
| 36 | 32 | 832 | 40844 | 49.09 | 1:02 |
|  |  | 1346 | 29186 | 21.68 | 1:10 |
|  |  | 698 | 10672 | 15.29 | 1:50 |
| 37 | 33 | 858 | 42550 | 49.59 | 1:02 |
|  |  | 1182 | 30142 | 25.5 | 1:10 |
|  |  | 1130 | 12316 | 10.9 | 1:50 |
| 38 | 34 | 1810 | 39790 | 21.98 | 1:02 |
|  |  | 1076 | 45440 | 42.23 | 1:10 |
|  |  | 1002 | 24362 | 24.31 | 1:50 |
| 39 | 35 | 370 | 37642 | 101.74 | 1:02 |
|  |  | 1104 | 26132 | 23.67 | 1:10 |
|  |  | 1628 | 12416 | 7.63 | 1:50 |
| 40 | 36 | 182 | 26986 | 148.27 | 1:02 |
|  |  | 760 | 16898 | 22.23 | 1:10 |
|  |  | 590 | 6424 | 10.89 | 1:50 |
| 41 | 37 | 242 | 30270 | 125.08 | 1:02 |
|  |  | 924 | 24488 | 26.5 | 1:10 |
|  |  | 614 | 8132 | 13.24 | 1:50 |
| 42 | 38 | 974 | 39816 | 40.88 | 1:02 |
|  |  | 1218 | 41530 | 34.1 | 1:10 |
|  |  | 1528 | 18514 | 12.12 | 1:50 |
| 43 | 39 | 534 | 35346 | 66.19 | 1:02 |
|  |  | 1134 | 36034 | 31.78 | 1:10 |
|  |  | 828 | 13628 | 16.46 | 1:50 |
| 44 | 41 | 7242 | 35180 | 4.86 | 1:02 |
|  |  | 9488 | 36794 | 3.88 | 1:10 |
|  |  | 1046 | 24030 | 22.97 | 1:50 |
| 45 | 43 | 11192 | 29098 | 2.6 | 1:02 |
|  |  | 2238 | 35886 | 16.03 | 1:10 |
|  |  | 1952 | 16972 | 8.69 | 1:50 |
| 46 | 47 | 678 | 2364 | 3.49 | 1:02 |
|  |  | 2624 | 4418 | 1.68 | 1:10 |
|  |  | 1256 | 1670 | 1.33 | 1:50 |
| 47 | 48 | 3412 | 31378 | 9.2 | 1:02 |
|  |  | 2788 | 32746 | 11.75 | 1:10 |
|  |  | 3972 | 19016 | 4.79 | 1:50 |
| 48 | 50 | 712 | 37660 | 52.89 | 1:02 |
|  |  | 1524 | 25864 | 16.97 | 1:10 |
|  |  | 2570 | 9752 | 3.79 | 1:50 |
| 49 | 51 | 764 | 41998 | 54.97 | 1:02 |
|  |  | 2208 | 48472 | 21.95 | 1:10 |
|  |  | 2246 | 37170 | 16.55 | 1:50 |
| 50 | 52 | 908 | 49780 | 54.82 | 1:02 |
|  |  | 2430 | 40804 | 16.79 | 1:10 |
|  |  | 2542 | 29982 | 11.79 | 1:50 |
| 51 | 53 | 610 | 6094 | 9.99 | 1:02 |
|  |  | 2540 | 2354 | 0.93 | 1:10 |
|  |  | 2576 | 1982 | 0.77 | 1:50 |
| 52 | 54 | 1366 | 32926 | 24.1 | 1:02 |
|  |  | 4212 | 29950 | 7.11 | 1:10 |
|  |  | 3328 | 29722 | 8.93 | 1:50 |
| 53 | 55 | 266 | 36764 | 138.21 | 1:02 |
|  |  | 762 | 32848 | 43.11 | 1:10 |
|  |  | 756 | 9568 | 12.66 | 1:50 |
| 54 | 56 | 280 | 45378 | 162.06 | 1:02 |
|  |  | 862 | 42754 | 49.6 | 1:10 |
|  |  | 1392 | 20368 | 14.63 | 1:50 |
| 55 | 57 | 368 | 40786 | 110.83 | 1:02 |
|  |  | 708 | 57226 | 80.83 | 1:10 |
|  |  | 948 | 44728 | 47.18 | 1:50 |
| 56 | 58 | 234 | 43268 | 184.91 | 1:02 |
|  |  | 546 | 48596 | 89 | 1:10 |
|  |  | 564 | 23614 | 41.87 | 1:50 |
| 57 | 59 | 262 | 36538 | 139.46 | 1:02 |
|  |  | 1532 | 29456 | 19.23 | 1:10 |
|  |  | 824 | 9918 | 12.04 | 1:50 |
| 58 | 60 | 454 | 36884 | 81.24 | 1:02 |
|  |  | 1250 | 37306 | 29.84 | 1:10 |
|  |  | 1758 | 19380 | 11.02 | 1:50 |
| 59 | 61 | 222 | 47570 | 214.28 | 1:02 |
|  |  | 510 | 51420 | 100.82 | 1:10 |
|  |  | 440 | 28182 | 64.05 | 1:50 |
| 60 | 62 | 238 | 49984 | 210.02 | 1:02 |
|  |  | 586 | 51554 | 87.98 | 1:10 |
|  |  | 686 | 28784 | 41.96 | 1:50 |
| 61 | 63 | 476 | 44038 | 92.52 | 1:02 |
|  |  | 610 | 49584 | 81.29 | 1:10 |
|  |  | 888 | 25250 | 28.43 | 1:50 |
| 62 | 64 | 29818 | 61054 | 2.05 | 1:02 |
|  |  | 8262 | 51812 | 6.27 | 1:10 |
|  |  | 1864 | 25654 | 13.76 | 1:50 |
| 63 | 65 | 666 | 736 | 1.11 | 1:02 |
|  |  | 842 | 1068 | 1.27 | 1:10 |
|  |  | 776 | 1538 | 1.98 | 1:50 |
| 64 | 67 | 842 | 38522 | 45.75 | 1:02 |
|  |  | 1338 | 45738 | 34.18 | 1:10 |
|  |  | 590 | 20288 | 34.39 | 1:50 |
| 65 | 68 | 670 | 1014 | 1.51 | 1:02 |
|  |  | 936 | 1266 | 1.35 | 1:10 |
|  |  | 822 | 1366 | 1.66 | 1:50 |
| 66 | 70 | 58180 | 47276 | 0.81 | 1:02 |
|  |  | 46084 | 56580 | 1.23 | 1:10 |
|  |  | 25656 | 33070 | 1.29 | 1:50 |
| 67 | 73 | 7510 | 65214 | 8.68 | 1:02 |
|  |  | 7730 | 42872 | 5.55 | 1:10 |
|  |  | 730 | 10104 | 13.84 | 1:50 |
| 68 | 74 | 1014 | 33384 | 32.92 | 1:02 |
|  |  | 1120 | 31604 | 28.22 | 1:10 |
|  |  | 958 | 12568 | 13.12 | 1:50 |
| 69 | 75 | 242 | 18038 | 74.54 | 1:02 |
|  |  | 586 | 9166 | 15.64 | 1:10 |
|  |  | 454 | 2296 | 5.06 | 1:50 |
| 70 | 76 | 230 | 15926 | 69.24 | 1:02 |
|  |  | 724 | 7288 | 10.07 | 1:10 |
|  |  | 684 | 2936 | 4.29 | 1:50 |
| 71 | 77 | 330 | 19746 | 59.84 | 1:02 |
|  |  | 750 | 9734 | 12.98 | 1:10 |
|  |  | 674 | 3152 | 4.68 | 1:50 |
| 72 | 78 | 328 | 20772 | 63.33 | 1:02 |
|  |  | 764 | 11060 | 14.48 | 1:10 |
|  |  | 642 | 3798 | 5.92 | 1:50 |
| 73 | 79 | 252 | 7800 | 30.95 | 1:02 |
|  |  | 612 | 5398 | 8.82 | 1:10 |
|  |  | 930 | 2176 | 2.34 | 1:50 |
| 74 | 80 | 538 | 7842 | 14.58 | 1:02 |
|  |  | 1334 | 4472 | 3.35 | 1:10 |
|  |  | 780 | 714 | 0.92 | 1:50 |
| 75 | 81 | 188 | 21956 | 116.79 | 1:02 |
|  |  | 606 | 14492 | 23.91 | 1:10 |
|  |  | 676 | 4058 | 6 | 1:50 |
| 76 | 82 | 422 | 8534 | 20.22 | 1:02 |
|  |  | 582 | 5586 | 9.6 | 1:10 |
|  |  | 882 | 1852 | 2.1 | 1:50 |
| 77 | 83 | 41410 | 18632 | 0.45 | 1:02 |
|  |  | 8742 | 10500 | 1.2 | 1:10 |
|  |  | 4528 | 3498 | 0.77 | 1:50 |
| 78 | 84 | 422 | 12516 | 29.66 | 1:02 |
|  |  | 820 | 8026 | 9.79 | 1:10 |
|  |  | 920 | 2508 | 2.73 | 1:50 |
| 79 | 85 | 406 | 32554 | 80.18 | 1:02 |
|  |  | 622 | 35052 | 56.35 | 1:10 |
|  |  | 740 | 19090 | 25.8 | 1:50 |
| 80 | 86 | 778 | 33426 | 42.96 | 1:02 |
|  |  | 834 | 32330 | 38.76 | 1:10 |
|  |  | 650 | 19616 | 30.18 | 1:50 |

TABLE 4-continued

Proliferative Activity of hIL2 Orthologs on hoCD122 3F8 cells v 3F8 Cells

| Sequence ID | Mutant # | 3F8 Proliferation Signal cts/min | 3F8 Ortho Proliferation Signal cts/min | Relative Proliferation Fold Change | Dilution |
|---|---|---|---|---|---|
| 81 | 87 | 406 | 32554 | 80.18 | 1:02 |
|  |  | 622 | 35052 | 56.35 | 1:10 |
|  |  | 740 | 19090 | 25.8 | 1:50 |
| 82 | 88 | 778 | 33426 | 42.96 | 1:02 |
|  |  | 834 | 32330 | 38.76 | 1:10 |
|  |  | 650 | 19616 | 30.18 | 1:50 |
| 83 | 89 | 52640 | 24098 | 0.46 | 1:02 |
|  |  | 1390 | 15108 | 10.87 | 1:10 |
|  |  | 1102 | 6552 | 5.95 | 1:50 |
| 84 | 90 | 482 | 6222 | 12.91 | 1:02 |
|  |  | 554 | 4414 | 7.97 | 1:10 |
|  |  | 1038 | 2926 | 2.82 | 1:50 |
| 85 | 91 | 1134 | 40826 | 36 | 1:02 |
|  |  | 1320 | 32596 | 24.69 | 1:10 |
|  |  | 596 | 20466 | 34.34 | 1:50 |
| 86 | 92 | 644 | 25662 | 39.85 | 1:02 |
|  |  | 1184 | 17254 | 14.57 | 1:10 |
|  |  | 1364 | 18676 | 13.69 | 1:50 |
| 87 | 93 | 1324 | 39110 | 29.54 | 1:02 |
|  |  | 1014 | 50650 | 49.95 | 1:10 |
|  |  | 810 | 24570 | 30.33 | 1:50 |
| 88 | 94 | 982 | 42072 | 42.84 | 1:02 |
|  |  | 994 | 48458 | 48.75 | 1:10 |
|  |  | 1206 | 21008 | 17.42 | 1:50 |
| 89 | 95 | 1470 | 45652 | 31.06 | 1:02 |
|  |  | 3196 | 64050 | 20.04 | 1:10 |
|  |  | 1122 | 33140 | 29.54 | 1:50 |
| 90 | 96 | 482 | 43790 | 90.85 | 1:02 |
|  |  | 952 | 55494 | 58.29 | 1:10 |
|  |  | 1098 | 26628 | 24.25 | 1:50 |
| 91 | 97 | 1256 | 45292 | 36.06 | 1:02 |
|  |  | 1822 | 52956 | 29.06 | 1:10 |
|  |  | 1014 | 21036 | 20.75 | 1:50 |
| 92 | 98 | 934 | 40160 | 43 | 1:02 |
|  |  | 2418 | 36988 | 15.3 | 1:10 |
|  |  | 1646 | 8934 | 5.43 | 1:50 |
| 93 | 99 | 2032 | 46428 | 22.85 | 1:02 |
|  |  | 990 | 54366 | 54.92 | 1:10 |
|  |  | 754 | 28502 | 37.8 | 1:50 |
| 94 | 100 | 270 | 28366 | 105.06 | 1:02 |
|  |  | 720 | 21874 | 30.38 | 1:10 |
|  |  | 662 | 6734 | 10.17 | 1:50 |
| 95 | 101 | 222 | 37776 | 170.16 | 1:02 |
|  |  | 494 | 23668 | 47.91 | 1:10 |
|  |  | 1322 | 10340 | 7.82 | 1:50 |
| 96 | 102 | 428 | 40248 | 94.04 | 1:02 |
|  |  | 1050 | 34698 | 33.05 | 1:10 |
|  |  | 620 | 15244 | 24.59 | 1:50 |
| 97 | 103 | 428 | 40386 | 94.36 | 1:02 |
|  |  | 718 | 41110 | 57.26 | 1:10 |
|  |  | 1126 | 24154 | 21.45 | 1:50 |
| 98 | 104 | 572 | 27176 | 47.51 | 1:02 |
|  |  | 1492 | 32146 | 21.55 | 1:10 |
|  |  | 1682 | 14170 | 8.42 | 1:50 |
| 99 | 105 | 174 | 31194 | 179.28 | 1:02 |
|  |  | 320 | 24550 | 76.72 | 1:10 |
|  |  | 328 | 12162 | 37.08 | 1:50 |
| 100 | 106 | 266 | 29250 | 109.96 | 1:02 |
|  |  | 446 | 22884 | 51.31 | 1:10 |
|  |  | 578 | 9634 | 16.67 | 1:50 |
| 101 | 107 | 236 | 10272 | 43.53 | 1:02 |
|  |  | 454 | 5764 | 12.7 | 1:10 |
|  |  | 714 | 1572 | 2.2 | 1:50 |
| 102 | 108 | 168 | 9936 | 59.14 | 1:02 |
|  |  | 810 | 7068 | 8.73 | 1:10 |
|  |  | 486 | 1056 | 2.17 | 1:50 |
| 103 | 109 | 288 | 31874 | 110.67 | 1:02 |
|  |  | 468 | 20154 | 43.06 | 1:10 |
|  |  | 744 | 11580 | 15.56 | 1:50 |
| 104 | 110 | 390 | 24590 | 63.05 | 1:02 |
|  |  | 1258 | 29534 | 23.48 | 1:10 |
|  |  | 988 | 16534 | 16.73 | 1:50 |
| 105 | 111 | 294 | 34188 | 116.29 | 1:02 |
|  |  | 376 | 36390 | 96.78 | 1:10 |
|  |  | 1252 | 21878 | 17.47 | 1:50 |
| 106 | 112 | 542 | 35072 | 64.71 | 1:02 |
|  |  | 670 | 28718 | 42.86 | 1:10 |
|  |  | 400 | 21180 | 52.95 | 1:50 |
| 107 | 113 | 1946 | 36418 | 18.71 | 1:02 |
|  |  | 574 | 32526 | 56.67 | 1:10 |
|  |  | 802 | 27108 | 33.8 | 1:50 |
| 108 | 114 | 36986 | 37234 | 1.01 | 1:02 |
|  |  | 9570 | 26788 | 2.8 | 1:10 |
|  |  | 1534 | 25830 | 16.84 | 1:50 |
| 109 | 115 | 1142 | 34936 | 30.59 | 1:02 |
|  |  | 916 | 34830 | 38.02 | 1:10 |
|  |  | 648 | 21180 | 32.69 | 1:50 |
| 110 | 116 | 616 | 28566 | 46.37 | 1:02 |
|  |  | 824 | 32178 | 39.05 | 1:10 |
|  |  | 916 | 21964 | 23.98 | 1:50 |
| 111 | 117 | 716 | 40050 | 55.94 | 1:02 |
|  |  | 944 | 46042 | 48.77 | 1:10 |
|  |  | 424 | 20930 | 49.36 | 1:50 |
| 112 | 118 | 5226 | 39266 | 7.51 | 1:02 |
|  |  | 2208 | 30026 | 13.6 | 1:10 |
|  |  | 902 | 10356 | 11.48 | 1:50 |
| 113 | 119 | 8646 | 35822 | 4.14 | 1:02 |
|  |  | 2778 | 45996 | 16.56 | 1:10 |
|  |  | 936 | 16464 | 17.59 | 1:50 |
| 114 | 121 | 1110 | 44280 | 39.89 | 1:02 |
|  |  | 926 | 41336 | 44.64 | 1:10 |
|  |  | 1316 | 18888 | 14.35 | 1:50 |
| 115 | 122 | 42504 | 33968 | 0.8 | 1:02 |
|  |  | 8668 | 32580 | 3.76 | 1:10 |
|  |  | 4116 | 15076 | 3.66 | 1:50 |
| 116 | 123 | 188 | 486 | 2.59 | 1:02 |
|  |  | 730 | 580 | 0.79 | 1:10 |
|  |  | 500 | 666 | 1.33 | 1:50 |
| 117 | 124 | 326 | 326 | 1 | 1:02 |
|  |  | 490 | 588 | 1.2 | 1:10 |
|  |  | 590 | 850 | 1.44 | 1:50 |
| 118 | 125 | 514 | 644 | 1.25 | 1:02 |
|  |  | 1086 | 914 | 0.84 | 1:10 |
|  |  | 1802 | 1074 | 0.6 | 1:50 |
| 119 | 127 | 350 | 12460 | 35.6 | 1:02 |
|  |  | 512 | 5136 | 10.03 | 1:10 |
|  |  | 972 | 2852 | 2.93 | 1:50 |
| 120 | 128 | 278 | 3724 | 13.4 | 1:02 |
|  |  | 688 | 992 | 1.44 | 1:10 |
|  |  | 644 | 804 | 1.25 | 1:50 |
| 120 | 129 | 370 | 29694 | 80.25 | 1:02 |
|  |  | 630 | 36294 | 57.61 | 1:10 |
|  |  | 1132 | 20880 | 18.45 | 1:50 |
| 122 | 130 | 388 | 35556 | 91.64 | 1:02 |
|  |  | 1232 | 40094 | 32.54 | 1:10 |
|  |  | 596 | 19732 | 33.11 | 1:50 |
| 123 | 131 | 1200 | 29296 | 24.41 | 1:02 |
|  |  | 1126 | 42372 | 37.63 | 1:10 |
|  |  | 682 | 27098 | 39.73 | 1:50 |
| 124 | 132 | 346 | 29070 | 84.02 | 1:02 |
|  |  | 662 | 34022 | 51.39 | 1:10 |
|  |  | 800 | 18576 | 23.22 | 1:50 |
| 125 | 133 | 798 | 31632 | 39.64 | 1:02 |
|  |  | 854 | 33140 | 38.81 | 1:10 |
|  |  | 1074 | 13616 | 12.68 | 1:50 |
| 126 | 134 | 60850 | 43706 | 0.72 | 1:02 |
|  |  | 10198 | 44558 | 4.37 | 1:10 |
|  |  | 4690 | 24848 | 5.3 | 1:50 |

TABLE 4-continued

Proliferative Activity of hIL2 Orthologs on hoCD122 3F8 cells v 3F8 Cells

| Sequence ID | Mutant # | 3F8 Proliferation Signal cts/min | 3F8 Ortho Proliferation Signal cts/min | Relative Proliferation Fold Change | Dilution |
|---|---|---|---|---|---|
| 127 | 135 | 258 | 36230 | 140.43 | 1:02 |
|  |  | 676 | 45002 | 66.57 | 1:10 |
|  |  | 968 | 26082 | 26.94 | 1:50 |
| 128 | 136 | 202 | 36514 | 180.76 | 1:02 |
|  |  | 714 | 38610 | 54.08 | 1:10 |
|  |  | 1294 | 18738 | 14.48 | 1:50 |
| 129 | 137 | 214 | 33064 | 154.5 | 1:02 |
|  |  | 596 | 33160 | 55.64 | 1:10 |
|  |  | 538 | 17086 | 31.76 | 1:50 |
| 130 | 138 | 296 | 2718 | 9.18 | 1:02 |
|  |  | 342 | 2492 | 7.29 | 1:10 |
|  |  | 640 | 964 | 1.51 | 1:50 |
| 131 | 139 | 198 | 452 | 2.28 | 1:02 |
|  |  | 838 | 574 | 0.68 | 1:10 |
|  |  | 534 | 748 | 1.4 | 1:50 |
| 132 | 140 | 470 | 294 | 0.63 | 1:02 |
|  |  | 922 | 368 | 0.4 | 1:10 |
|  |  | 896 | 544 | 0.61 | 1:50 |
| 133 | 141 | 162 | 20968 | 129.43 | 1:02 |
|  |  | 436 | 14648 | 33.6 | 1:10 |
|  |  | 416 | 2664 | 6.4 | 1:50 |
| 134 | 142 | 218 | 1536 | 7.05 | 1:02 |
|  |  | 516 | 1104 | 2.14 | 1:10 |
|  |  | 738 | 838 | 1.14 | 1:50 |
| 135 | 143 | 912 | 27352 | 29.99 | 1:02 |
|  |  | 2388 | 26954 | 11.29 | 1:10 |
|  |  | 1094 | 9508 | 8.69 | 1:50 |
| 136 | 144 | 45710 | 22440 | 0.49 | 1:02 |
|  |  | 12602 | 18114 | 1.44 | 1:10 |
|  |  | 2720 | 3714 | 1.37 | 1:50 |
| 137 | 145 | 494 | 9536 | 19.3 | 1:02 |
|  |  | 778 | 2872 | 3.69 | 1:10 |
|  |  | 516 | 826 | 1.6 | 1:50 |
| 139 | 146 | 12206 | 3382 | 0.28 | 1:02 |
|  |  | 3484 | 1882 | 0.54 | 1:10 |
|  |  | 686 | 1316 | 1.92 | 1:50 |

As demonstrated by the above data, the hIL2 orthologs of the Formula 1 selectively activate hoCD122 human T cells relative to the human T cells that do no express an orthogonal receptor (NKL cells).

Conservative Amino Acid Substitutions

In some embodiments, the the hIL2 ortholog of Formula 1 may optionally comprise one or more conservative amino acid substitutions Such conservative substitutions include those described by Dayhoff in The Atlas of Protein Sequence and Structure 5 (1978), and by Argos in EMBO J., 8:779-785 (1989). Conservative substitutions are generally made in accordance with the following Table 4:

TABLE 4

Conservative Amino Acid Substitutions

| Wild type Residue | Substitution(s) |
|---|---|
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |

TABLE 4-continued

Conservative Amino Acid Substitutions

| Wild type Residue | Substitution(s) |
|---|---|
| Lys | Arg, Gln, Glu, Met, Leu, Ile |
| Phe | Met, Leu, Tyr, Trp |
| Ser | Thr |
| Thr | Ser |
| Trp | Tyr, Phe |
| Tyr | Trp, Phe |
| Val | Ile, Leu |

Substantial changes in function or immunological identity may be made by selecting amino acid substitutions that are less conservative than those indicated in Table 4. For example substitutions may be made which more significantly affect the structure of the polypeptide backbone or disrupt secondary or tertiary elements including the substitution of an amino acid with a small uncharged side chain (e.g. glycine) with a large charge bulky side chain (asparagine). In particular, substitution of those hIL2 residues which are involved in the amino acids that interact with one or more of CD25, CD122 and/or CD123 as may be discerned from the crystal structure of hIL2 in association with its receptors as described in Wang, et al (2005) Science 310: 1159-1163. Modifications to the primary structure as provided above may optionally further comprise modifications including but not limited to the substitutions: N30E; K32E; N33D; P34G; T37I, M39Q, F42Y, F44Y, P47G, T51I, E52K, L53N, Q57E, M104A (see U.S. Pat. No. 5,206,344).

Cys125:

In some embodiments, the present disclosure provides hIL2 orthologs of Formula 1 containing modifications that facilitate recombinant expression in bacterial cells by eliminating the unpaired cysteine residue at position 125 by the substitution of C125A or C125S. In some embodiments, the hIL2 orthologs of the present invention comprise one of the following sets of amino acid modifications:

[E15S-H16Q-L19V-D20L-Q22K-M23A-C125S];
[E15S-H16Q-L19V-D20L-Q22K-C125S];
[E15S-H16Q-L19V-D20L-M23A-C125S];
[E15S-H16Q-L19V-D20L-C125S];
[E15S-H16Q-L19V-D20L-Q22K-M23A-C125A];
[E15S-H16Q-L19V-D20L-M23A-C125A];
[E15S-H16Q-L19V-D20L-Q22K-C125A];
[E15S-H16Q-L19V-D20L-C125A];
[desAla1-E15S-H16Q-L19V-D20L-Q22K-M23A-C125S];
[desAla1-E15S-H16Q-L19V-D20L-Q22K-C125S];
[desAla1-E15S-H16Q-L19V-D20L-C125S];
[desAla1-E15S-H16Q-L19V-D20L-Q22K-M23A-C125A];
[desAla1-E15S-H16Q-L19V-D20L-Q22K-C125A];
[desAla1-E15S-H16Q-L19V-D20L-C125A];
[desAla1-E15S-H16Q-L19V-D20L-Q22K-M23A];
[desAla1-E15S-H16Q-L19V-D20L-M23A];
[desAla1-E15S-H16Q-L19V-D20L-Q22K]; or
[desAla1-E15S-H16Q-L19V-D20L].

Mutations to Enhance hCD122 Affinity

In some embodiments, hIL-2 orthologs of Formula 1 contain one or more mutations in positions of the hIL-2 sequence that either contact hCD122 or alter the orientation of other positions contacting hCD122, that modify the binding affinity of the hIL-2 ortholog for hCD122. hIL-2 residues that have been identified as being involved in the binding of hIL2 to hCD122 include L12, Q13, H16, L19, D20, M23, R81, D84, S87, N88, V91, I92, and E95. In some embodiments, the hIL2 ortholog comprises one or more of the amino acid substitutions: Q74N, Q74H, Q74S, L80F, L80V, R81D, R81T, L85V, I86V, I89V, and/or I92F or combinations thereof. In some embodiments, the hIL2 ortholog comprises one or more of the amino acid substitutions: L80F, R81D, L85V, I86V and I92F. In some embodiments, the hIL2 ortholog comprises one or more of the amino acid substitutions: N74Q, L80F, R81D, L85V, I86V, I89V, and I92F. In some embodiments, the hIL2 ortholog comprises one or more of the amino acid substitutions: Q74N, L80V, R81T, L85V, I86V, and I92F. In some embodiments, the hIL2 ortholog comprises one or more of the amino acid substitutions: Q74H, L80F, R81D, L85V, I86V and I92F. In some embodiments, the hIL2 ortholog comprises one or more of the amino acid substitutions: Q74S, L80F, R81D, L85V, I86V and I92F. In some embodiments, the hIL2 ortholog comprises one or more of the amino acid substitutions: Q74N, L80F, R81D, L85V, I86V and I92F. In some embodiments, the hIL2 ortholog comprises one or more of the amino acid substitutions: Q74S, R81T, L85V, and I92F. In some embodiments, the hIL2 orthologs comprise the set of mutations [L80E-R81D-L85V-I86V-I92F] that have been identified as increasing affinity of hIL2 to hCD122. In some embodiments, the present disclosure provides hIL2 orthologs which are hIL2 polypeptides comprise one of the following sets of amino acid modifications:

[E15S-H16Q-L19V-D20L-M23A-L80E-R81D-L85V-I86V-I92F];
[E15S-H16Q-L19V-D20L-Q22K-L80E-R81D-L85V-I86V-I92F];
[E15S-H16Q-L19V-D20L-Q22K-M23A L80E-R81D-L85V-I86V-I92F];
[E15S-H16Q-L19V-D20L-M23A-L80E-R81D-L85V-I86V-I92F-Q126H];
[E15S-H16Q-L19V-D20L-Q22K-L80E-R81D-L85V-I86V-I92F-Q126H];
[E15S-H16Q-L19V-D20L-Q22K-M23A-L80E-R81D-L85V-I86V-I92F-Q126H];
[E15S-H16Q-L19V-D20L-M23A-L80E-R81D-L85V-I86V-I92F-Q126M];
[E15S-H16Q-L19V-D20L-Q22K-L80E-R81D-L85V-I86V-I92F-Q126M]; or
[E15S-H16Q-L19V-D20L-Q22K-M23A-L80E-R81D-L85V-I86V-I92F-Q126M].

In some embodiments, hIL-2 orthologs of Formula 1 comprise the substitution L85V that has been identified as increasing affinity of hIL2 to hCD122. In some embodiments, the present disclosure provides hIL2 orthologs which are hIL2 polypeptides comprising one of the following sets of amino acid modifications:

[E15S-H16Q-L19V-D20L-M23A-L85V];
[E15S-H16Q-L19V-D20L-Q22K-M23A-L85V];
[E15S-H16Q-L19V-D20L-M23A-L85V];
[E15S-H16Q-L19V-D20L-Q22K-M23A-L85V];
[E15S-H16Q-L19V-D20L-M23A-L85V-Q126H];
[E15S-H16Q-L19V-D20L-Q22K-M23A-L85V-Q126H];
[E15S-H16Q-L19V-D20L-M23A-L85V-Q126M]; or
[E15S-H16Q-L19V-D20L-Q22K-M23A-L85V-Q126M].

Modifications to Modulate CD25 Affinity

In some embodiments, hIL-2 orthologs of Formula 1 contain one or more mutations in positions of the hIL-2 ortholog that modulate the binding affinity for hCD25. The mutations regions of hIL2 in close proximity to hCD25 as part of the trimeric IL2 receptor complex based on the crystal structure of IL2 in association with the IL2 receptor (Wang, et al (2005) Science 310:1159). In some embodiments, hIL-2 orthologs of Formula 1 contain modifications at one or more positions selected from S4, K8, K9, T10, Q11, Q13, N26, N29, N30, N30, Y31, K35, T37, R38, T41, F42, K43, F44, Y45, M46, K48, K49, K54, E61, E62, K64, P65, E67G, E68, V69, N71, L72, Q74 S75, K76, H79, I89, N90, I92, S99, T101, F103, Y107, I114, I128 and T133. Examples of amino acid substitutions which may be incorporated into the hIL2 ortholog sequence include one or more substitutions selected from S4P, K8R, K9T, T10A, Q11R, Q13R, N26D, N29S, N30S, N30D, N30T, Y31H, Y31C, K35R, T37A, T37R, M46L, K48E, K49R, K49E, K54R, E61D, K64R, E67G, E68D, V69A, N71T, N71A, N71R, A73V, Q74P S75P, K76E, K76R, H79R, I89V, N90H, I92T, S99P, T101A, F103S, I114V, I128T, T133A, and T133N. In some embodiments, the hIL2 orthologs of the present disclosure comprise one or more of the point mutations of S4P, K8R, K9T, T10A, Q11R, Q13R, N26D, N29S, N30S, N30D, N30T, Y31H, Y31C, K35R, T37A, T37R, M46L, K48E, K49R, K49E, K54R, E61D, K64R, E67G, E68D, V69A, N71T, N71A, N71R, A73V, Q74P, S75P, K76E, K76R, H79R, I89V, N90H, I92T, S99P, T101A, F103S, I114V, I128T, T133A, and T133N (Wittrup, et al supra), R38A, F41A and/or F42A (Suave, et al (1991) PNAS(USA)88: 4636-4640); P65L (Chen et al. Cell Death and Disease (2018) 9:989); F42A/G/S/T/Q/E/N/R/K, Y45A/G/S/T/Q/E/N/D/R/K and/or L72G/A/S/T/Q/E/N/D/R/K (Ast, et al United States Patent Application Publication 2012/0244112 A1 published Sep. 27, 2012; U.S. Pat. No. 9,266,938 B2 issued Feb. 23, 2016).

In addition to point mutations, combinations of the foregoing modifications may be employed to modulate the binding of the hIL-2 orthologs of Formula 1 to CD25. In some embodiments, the hIL-2 orthologs of the present disclosure comprise one or more of the following sets of amino acid substitutions: [R38A-F42A-Y45A-E62A] (Carmenate, et al (2013) J Immunol 190:6230-6238); [F42A-Y45A-L72G] (Roche RG7461 (R06874281); [V69A, Q74P]; [V69A, Q74, T101A]; [V69A, Q74P, I128T]; [N30D, V69A, Q74P, F1035]; [K49E, V69A, A73V, K76E], [V69A, Q74P, T101A, T133N]; [N30S, V69A, Q74P, I128A]; [N30S, V69A, Q74P, I128T]; [K9T, Q11R, K35R, V69A, Q74P], [A1T, M46L, K49R, E61D, V69A, H79R]; [K48E, E68D, N71T, N90H, F103S, I114V]; [S4P T10A, Q11R, V69A, Q74P, T133A]; [N30S, Y31H, K35R, K48E, V69A, Q74P, I92T]; [N30S, E68D, V69A, N71A, Q74P, S75P, K76R, N90H]; [N30S, Y31C, T37A, V69A, A73V, Q74P, H79R, I128T], [N26D, N29S, N30S, K54R, E67G, V69A, Q74P, I92T]; [K8R, Q13R, N26D, N30T, K35R, T37R, V69A, Q74P, I92T] and [N29S, Y31H, K35R, T37A, K48E, V69A, N71R, Q74P, I39V] (Wittrup et al., U.S. Pat. No. 7,569,215 issued Aug. 4, 2009); and/or [T41P-T51P] (Chang, et al (1995) Molecular Pharmacology 47:206-211).

In some embodiments, the present disclosure provides hIL-2 orthologs of Formula 1 comprising one of the following sets of amino acid modifications:

[E15S-H16Q-L19V-D20L-M23A-R38A-F42A-Y45A-E62A];
[E15S-H16Q-L19V-D20L-M23A-R38A-F42A-Y45A-E62A];
[E15S-H16Q-L19V-D20L-Q22K-M23A-R38A-F42A-Y45A-E62A];
[E15S-H16Q-L19V-D20L-M23A-R38A-F42A-Y45A-E62A-Q126H];
[E15S-H16Q-L19V-D20L-M23A-R38A-F42A-Y45A-E62A-Q126H];

[E15S-H16Q-L19V-D20L-Q22K-M23A-R38A-F42A-Y45A-E62A-Q126H];
[E15S-H16Q-L19V-D20L-M23A-V69A];
[E15S-H16Q-L19V-D20L-Q22K-M23A-V69A];
[E15S-H16Q-L19V-D20L-M23A-Q74P];
[E15S-H16Q-L19V-D20L-Q22K-M23A-Q74P];
[E15S-H16Q-L19V-D20L-M23A-R38A-F42A-Y45A-E62A-Q126M]; or
[E15S-H16Q-L19V-D20L-M23A-R38A-F42A-Y45A-E62A-Q126M].

Modifications to Modulate CD132 Affinity

In some embodiments of the invention, the hIL-2 orthologs of the present disclosure contain one or more mutations that modulate the binding to hIL-2 ortholog to CD132. Exemplary hIL-2 orthologs contain one or more mutations in positions of the hIL-2 sequence that either contact CD132 or alter the orientation of other positions contacting hCD122, resulting in an altered binding to CD132. hIL-2 residues that are identified modulating the affinity of hIL2 to CD132 include Q11, L18 (e.g. L18R), Q22 (e.g. Q22E), E110, N119, T123, Q126 (e.g. Q126K/H), 5127, 1129, 5130, and T133. In some embodiments, the present disclosure provides hIL2 orthologs which are hIL2 polypeptides comprising one the following sets of amino acid modifications:

[E15S-H16Q-L18R-L19V-D20L-Q22E-M23A];
[E15S-H16Q-L18R-L19V-D20L-Q22K-M23A];
[E15S-H16Q-L18R-L19V-D20L-M23A];
[E15S-H16Q-L18R-L19V-D20L-Q22K-M23A];
[E15S-H16Q-L18R-L19V-D20L-M23A-Q126H];
[E15S-H16Q-L18R-L19V-D20L-Q22K-M23A-Q126H];
[E15S-H16Q-L18R-L19V-D20L-M23A-Q126K];
[E15S-H16Q-L18R-L19V-D20L-Q22K-M23A-Q126K];
[E15S-H16Q-L19V-D20L-M23A-Q126H];
[E15S-H16Q-L19V-D20L-Q22K-M23A-Q126H];
[E15S-H16Q-L19V-D20L-M23A-Q126K];
[E15S-H16Q-L19V-D20L-Q22K-M23A-Q126K];
[E15S-H16Q-L18R-L19V-D20L-M23A-Q126H];
[E15S-H16Q-L18R-L19V-D20L-Q22K-M23A-Q126H];
[E15S-H16Q-L18R-L19V-D20L-M23A-Q126K];
[E15S-H16Q-L18R-L19V-D20L-Q22K-M23A-Q126K];
[E15S-H16Q-L19V-D20L-Q22K-Q126H];
[E15S-H16Q-L19V-D20L-M23A-Q126M];
[E15S-H16Q-L19V-D20L-Q22K-M23A-Q126M];
[E15S-H16Q-L19V-D20L-Q22K-Q126M];
[desAla1-E15S-H16Q-L19V-D20L-Q126M];
[desAla1-E15S-H16Q-L19V-D20L-Q22K-Q126M];
[desAla1-E15S-H16Q-L19V-D20L-M23A-Q126M];
[desAla1-E15S-H16Q-L19V-D20L-Q22K-M23A-Q126M];
[desAla1-E15S-H16Q-L19V-D20L-Q22K-M23A-Q126M];
[E15S-H16Q-L19V-D20L-M23A-L80E-R81D-I86V-I92F-Q126H];
[E15S-H16Q-L19V-D20L-Q22K-L80E-R81D-I86V-I92F-Q126H];
[E15S-H16Q-L19V-D20L-Q22K-M23A-L80E-R81D-I86V-I92F-Q126H];
[E15S-H16Q-L19V-D20L-M23A-L80E-R81D-I86V-I92F-Q126M];
[E15S-H16Q-L19V-D20L-Q22K-M23A-L80E-R81D-I86V-I92F-Q126M];
[E15S-H16Q-L19V-D20L-M23A-L85V-Q126H];
[E15S-H16Q-L19V-D20L-Q22K-L85V-Q126H];
[E15S-H16Q-L19V-D20L-Q22K-M23A-L85V-Q126H];
[E15S-H16Q-L19V-D20L-M23A-L85V-Q126M];
[E15S-H16Q-L19V-D20L-Q22K-L85V-Q126H]; or
[E15S-H16Q-L19V-D20L-Q22K-M23A-L85V-Q126M].

Removal of Glycosylation Site

The hIL2 orthologs of the present disclosure may further or optionally provide elimination of the O-glycosylation site at position Thr3 of the to facilitate the production of an aglycosylated hIL2 ortholog variant when the ortholog expressed in mammalian cells such as CHO or HEK cells. Thus, in certain embodiments the hIL2 orthologs further comprise a modification which eliminates the O-glycosylation site of IL-2 at a position corresponding to residue 3 of human IL-2. In one embodiment said modification which eliminates the 0-glycosylation site of IL-2 at a position corresponding to residue 3 of human IL-2 is an amino acid substitution. Exemplary amino acid substitutions include T3A, T3G, T3Q, T3E, T3N, T3D, T3R, T3K, and T3P which removes the glycosylation site at position 3 without eliminating biological activity (see U.S. Pat. No. 5,116,943; Weiger et al., (1989) Eur. J. Biochem., 180:295-300). In a specific embodiment, said modification is the amino acid substitution T3A. In some embodiments, the present disclosure provides hIL2 orthologs which are hIL2 polypeptides comprising one of the following sets of amino acid modifications:

[T3A-E15S-H16Q-L19V-D20L-Q22K-M23A-C125S];
[T3A-E15S-H16Q-L19V-D20L-Q22K-C125S];
[T3A-E15S-H16Q-L19V-D20L-M23A-C125S];
[T3A-E15S-H16Q-L19V-D20L-C125S];
[T3A-E15S-H16Q-L19V-D20L-Q22K-M23A-C125A];
[T3A-E15S-H16Q-L19V-D20L-M23A-C125A];
[T3A-E15S-H16Q-L19V-D20L-Q22K-C125A];
[T3A-E15S-H16Q-L19V-D20L-C125A];
[T3A-E15S-H16Q-L19V-D20L-Q22K-M23A];
[T3A-E15S-H16Q-L19V-D20L-M23A];
[T3A-E15S-H16Q-L19V-D20L-Q22K];
[T3A-E15S-H16Q-L19V-D20L];
[desAla1-T3A-E15S-H16Q-L19V-D20L-Q22K-M23A-C125S];
[desAla1-T3A-E15S-H16Q-L19V-D20L-M23A-C125S];
[desAla1-T3A-E15S-H16Q-L19V-D20L-Q22K-C125S];
[desAla1-T3A-E15S-H16Q-L19V-D20L-C125S];
[desAla1-T3A-E15S-H16Q-L19V-D20L-Q22K-M23A-C125A];
[desAla1-T3A-E15S-H16Q-L19V-D20L-M23A-C125A];
[desAla1-T3A-E15S-H16Q-L19V-D20L-Q22K-C125A];
[desAla1-T3A-E15S-H16Q-L19V-D20L-C125A];
[desAla1-T3A-E15S-H16Q-L19V-D20L-Q22K-M23A];
[desAla1-T3A-E15S-H16Q-L19V-D20L-M23A];
[desAla1-T3A-E15S-H16Q-L19V-D20L-Q22K]; or
[desAla1-T3A-E15S-H16Q-L19V-D20L].

N Terminal Deletions:

The IL-2 orthologs may further comprise elimination of N-terminal amino acids at one or more of positions 1-9, alternatively positions 1-8, alternatively positions 1-7 alternatively positions 1-6, alternatively positions 1-5, alternatively positions 1-4, alternatively positions des1-3, alternatively positions 1-2 while retaining hIL2 ortholog activity. In some embodiments, the present disclosure provides hIL2 orthologs which are hIL2 polypeptides comprising one of the following sets of amino acid modifications:

[desAla1-E15S-H16Q-L18R-L19V-D20L-Q22E-M23A];
[desAla1-E15S-H16Q-L18R-L19V-D20L-Q22K-M23A];
[desAla1-E15S-H16Q-L18R-L19V-D20L-M23A];
[desAla1-E15S-H16Q-L18R-L19V-D20L-Q22K-M23A];

[desAla1-E15S-H16Q-L18R-L19V-D20L-M23A-Q126H];
[desAla1-E15S-H16Q-L18R-L19V-D20L-Q22K-M23A-Q126H];
[desAla1-E15S-H16Q-L18R-L19V-D20L-M23A-Q126K];
[desAla1-E15S-H16Q-L18R-L19V-D20L-Q22K-M23A-Q126K];
[desAla1-E15S-H16Q-L19V-D20L-M23A-Q126H];
[desAla1-E15S-H16Q-L19V-D20L-Q22K-M23A-Q126H];
[desAla1-E15S-H16Q-L19V-D20L-M23A-Q126K];
[desAla1-E15S-H16Q-L19V-D20L-Q22K-M23A-Q126K];
[desAla1-E15S-H16Q-L18R-L19V-D20L-M23A-Q126H];
[desAla1-E15S-H16Q-L18R-L19V-D20L-Q22K-M23A-Q126H];
[desAla1-E15S-H16Q-L18R-L19V-D20L-M23A-Q126K];
[desAla1-desPro2-E15S-H16Q-L19V-D20L-Q22K-M23A];
[desAla1-desPro2-E15S-H16Q-L19V-D20L-Q22K];
[desAla1-desPro2-E15S-H16Q-L19V-D20L-M23A];
[desAla1-desPro2-E15S-H16Q-L19V-D20L];
[desAla1-desPro2-desThr3-E15S-H16Q-L19V-D20L-Q22K-M23A];
[desAla1-desPro2-desThr3-E15S-H16Q-L19V-D20L-Q22K];
[desAla1-desPro2-desThr3-E15S-H16Q-L19V-D20L-M23A];
[desAla1-desPro2-desThr3-E15S-H16Q-L19V-D20L];
[desAla1-desPro2-desThr3-desSer4-E15S-H16Q-L19V-D20L-Q22K-M23A];
[desAla1-desPro2-desThr3-desSer4-E15S-H16Q-L19V-D20L-Q22K];
[desAla1-desPro2-desThr3-desSer4-E15S-H16Q-L19V-D20L-M23A];
[desAla1-desPro2-desThr3-desSer4-E15S-H16Q-L19V-D20L];
[desAla1-desPro2-desThr3-desSer4-desSer5-E15S-H16Q-L19V-D20L-Q22K-M23A];
[desAla1-desPro2-desThr3-desSer4-desSer5-E15S-H16Q-L19V-D20L-Q22K];
[desAla1-desPro2-desThr3-desSer4-desSer5-E15S-H16Q-L19V-D20L-M23A];
[desAla1-desPro2-desThr3-desSer4-desSer5-E15S-H16Q-L19V-D20L];
[desAla1-desPro2-desThr3-desSer4-desSer5-desSer6-E15S-H16Q-L19V-D20L-Q22K-M23A];
[desAla1-desPro2-desThr3-desSer4-desSer5-desSer6-E15S-H16Q-L19V-D20L-Q22K];
[desAla1-desPro2-desThr3-desSer4-desSer5-desSer6-E15S-H16Q-L19V-D20L-M23A];
or
[desAla1-desPro2-desThr3-desSer4-desSer5-desSer6-E15S-H16Q-L19V-D20L].

In some embodiments, the hIL2 orthologs may comprise deletion of the first two amino acids (desAla1-desPro2) as well as substitution of the Thr3 glycosylation with a cysteine residue to facilitate for selective N-terminal modification, especially PEGylation of the sulfhydryl group of the cysteine (See, e.g. Katre, et al. U.S. Pat. No. 5,206,344 issued Apr. 27, 1993). In some embodiments, the present disclosure provides hIL2 orthologs which are hIL2 polypeptides comprising one of the following sets of amino acid modifications:

[desAla1-desPro2-T3C-E15S-H16Q-L19V-D20L-Q22K-M23A-C125S];
[desAla1-desPro2-T3C-E15S-H16Q-L19V-D20L-Q22K-C125S];
[desAla1-desPro2-T3C-E15S-H16Q-L19V-D20L-M23A-C125S];
[desAla1-desPro2-T3C-E15S-H16Q-L19V-D20L-C125S];
[desAla1-desPro2-T3C-E15S-H16Q-L19V-D20L-Q22K-M23A-C125A];
[desAla1-desPro2-T3C-E15S-H16Q-L19V-D20L-Q22K-C125A];
[desAla1-desPro2-T3C E15S-H16Q-L19V-D20L-M23A-C125A];
[desAla1-desPro2-T3C-E15S-H16Q-L19V-D20L-C125A];
[desAla1-desPro2-T3C-E15S-H16Q-L19V-D20L-Q22K-M23A];
[desAla1-desPro2-T3C-E15S-H16Q-L19V-D20L-Q22K];
[desAla1-desPro2-T3C-E15S-H16Q-L19V-D20L-M23A]; or
[desAla1-desPro2-T3C-E15S-H16Q-L19V-D20L].

In some embodiments, the hIL2 orthologs of the present disclosure comprise a deletion of the alanine at position 1 ("desAla1") hIL2 orthologs. In some embodiments, the present disclosure provides des-Ala1-hIL2 orthologs comprising one of the following sets of amino acid modifications:

[desAla1-E15S-H16Q-L19V-D20L];
[desAla1-E15S-H16Q-L19V-D20L-Q22K];
[desAla1-E15S-H16Q-L19V-D20L-Q22K-M23A];
[desAla1-E15S-H16Q-L19V-D20L-Q126H];
[desAla1-E15S-H16Q-L19V-D20L-Q22K-Q126H];
[desAla1-E15S-H16Q-L19V-D20L-Q22K-M23A-Q126H];
[desAla1-E15S-H16Q-L19V-D20L-Q126M];
[desAla1-E15S-H16Q-L19V-D20L-Q22K-Q126H];
[desAla1-E15S-H16Q-L19V-D20L-Q22K-M23A-Q126H];
[desAla1-E15S-H16Q-L19V-D20L-C125A];
[desAla1-E15S-H16Q-L19V-D20L-Q22K-C125A];
[desAla1-E15S-H16Q-L19V-D20L-Q22K-M23A-C125A];
[desAla1-E15S-H16Q-L19V-D20L-C125A-Q126H];
[desAla1-E15S-H16Q-L19V-D20L-Q22K-C125A-Q126H];
[desAla1-E15S-H16Q-L19V-D20L-Q22K-M23A-C125A-Q126H];
[desAla1-E15S-H16Q-L19V-D20L-C125A-Q126M];
[desAla1-E15S-H16Q-L19V-D20L-Q22K-C125A-Q126H];
[desAla1-E15S-H16Q-L19V-D20L-Q22K-M23A-C125A-Q126H];
[desAla1-E15S-H16Q-L19V-D20L-C125S];
[desAla1-E15S-H16Q-L19V-D20L-Q22K-C125S];
[desAla1-E15S-H16Q-L19V-D20L-Q22K-M23A-C125S];
[desAla1-E15S-H16Q-L19V-D20L-C125S-Q126H];
[desAla1-E15S-H16Q-L19V-D20L-Q22K-C125S-Q126H];
[desAla1-E15S-H16Q-L19V-D20L-Q22K-M23A-C125S-Q126H];
[desAla1-E15S-H16Q-L19V-D20L-C1255-Q126M];
[desAla1-E15S-H16Q-L19V-D20L-Q22K-C125S-Q126M]; or

[desAla1-E15S-H16Q-L19V-D20L-Q22K-M23A-C125S-Q126M].

Modifications to Minimize Vascular Leak Syndrome

In some embodiments of the disclosure, the hIL2 ortholog comprises amino acid substitutions to avoid vascular leak syndrome. Epstein, et al., U.S. Pat. No. 7,514,073B2 issued Apr. 7, 2009. Examples of such modifications which may be incorporated into the hIL2 orthologs of the present disclosure include one or more of R38W, R38G, R39L, R39V, F42K, and/or H55Y.

Oxidation Stabilized M104A:

In some embodiments of the disclosure, the hIL2 ortholog may comprise a modification at position M104. In one embodiment the substitution of methionine 104 with an alanine residue (M104A) to provide a more oxidation-resistant ortholog (Koths, et al. U.S. Pat. No. 4,752,585 issued Jun. 21, 1988).

Affinity Maturation:

some embodiments, the hIL2 orthologs of the present disclosure may be affinity matured to enhance their activity with respect to the orthogonal hCD122. An "affinity matured" polypeptide is one having one or more alteration(s) in one or more residues which results in an improvement in the affinity of the orthogonal polypeptide for the cognate orthogonal receptor, or vice versa, compared to a parent polypeptide which does not possess those alteration(s). Affinity maturation can be done to increase the binding affinity of the hIL2 ortholog by at least about 10%, alternatively at least about 50%, alternatively at least about 100% alternatively at least about 150%, or from 1 to 5 fold as compared to the "parent" polypeptide. An engineered hIL2 ortholog of the present invention activates its cognate orthogonal receptor, as discussed above, but has significantly reduced binding and activation of the native receptor when assessed by ELISA and/or FACS analysis using sufficient amounts of the molecules under suitable assay conditions.

Modifications to Extend Duration of Action In Vivo

In some embodiments the hIL-2 orthologs of the present disclosure may comprise modifications to provide for an extended lifetime in vivo and/or extended duration of action in a subject. In some embodiments, the hIL-2 orthologs of the present disclosure possess a plasma half-life in a human subject of greater than 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, 10 days, 14 days, or 30 days. Such extended-life hIL2 orthologs may be achieved by primary sequence modifications and/or conjugation to carrier molecules.

Primary Sequence Modifications to Extend Duration of Action hIL-2 orthologs of the present disclosure may comprise amino acid substitutions that result in prolonged in vivo lifetime. Examples of positions where amino acid substitutions may be incorporated into the hIL-2 orthologs to provide for extended in vivo duration include one or more of positions V111, R117 and/or T133. In some embodiments, the hIL2 orthologs of the present disclosure comprise one or more of V111R, R117K and/or T133N modifications. Dakshinamurthi, et al. (2009) International Journal of Bioinformatics Research 1(2):4-13

Carrier Molecules

In some embodiments the hIL2 ortholog is modified to provide an extended duration of action in a subject which may be achieve through conjugation to carrier molecules to provide desired pharmacological properties such as extended half-life. In one embodiment, the hIL2 ortholog may comprise a functional domain of a chimeric polypeptide. In some embodiments, the hIL2 ortholog can be covalently linked to the Fc domain of IgG, albumin, or other molecules to extend its half-life, e.g. by pegylation, glycosylation, and the like as known in the art.

Fc Fusions

In some embodiments, the hIL2 orthologs of the present disclosure are operably linked to a functional domain of an Fc-fusion chimeric polypeptide molecule. Fc fusion conjugates have been shown to increase the systemic half-life of biopharmaceuticals, and thus the biopharmaceutical product can require less frequent administration. Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates. The "Fc region" useful in the preparation of Fc fusions can be a naturally occurring or synthetic polypeptide that is homologous to an IgG C-terminal domain produced by digestion of IgG with papain. IgG Fc has a molecular weight of approximately 50 kDa. The hIL2 orthologs may provide the entire Fc region, or a smaller portion that retains the ability to extend the circulating half-life of a chimeric polypeptide of which it is a part. In addition, full-length or fragmented Fc regions can be variants of the wild-type molecule. In a typical presentation, each monomer of the dimeric Fc is carries a heterologous polypeptide, the heterologous polypeptides being the same or different.

In some embodiments, when the hIL2 ortholog is to be administered in the format of an Fc fusion, particularly in those situations when the polypeptide chains conjugated to each subunit of the Fc dimer are different, the Fc fusion may be engineered to possess a "knob-into-hole modification." The knob-into-hole modification is more fully described in Ridgway, et al. (1996) Protein Engineering 9(7):617-621 and U.S. Pat. No. 5,731,168, issued Mar. 24, 1998. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g. tyrosine or tryptophan) creating a projection from the surface ("knob") and ii) in the CH3 domain of a second heavy chain, an amino acid residue is replaced with an amino acid residue having a smaller side chain (e.g. alanine or threonine), thereby generating a cavity ("hole") within at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 and Y349 which results in a stabilizing disulfide bridge between the two antibody heavy chains in the Fe region (Carter, et al. (2001) Immunol Methods 248, 7-15). The knob-into-hole format is used to facilitate the expression of a first polypeptide (e.g. an hIL2 ortholog) on a first Fc monomer with a "knob" modification and a second polypeptide on the second Fc monomer possessing a "hole" modification to facilitate the expression of heterodimeric polypeptide conjugates.

The Fc region can be "lytic" or "non-lytic," but is typically non-lytic. A non-lytic Fc region typically lacks a high affinity Fc receptor binding site and a Clq binding site. The high affinity Fc receptor binding site of murine IgG Fc includes the Leu residue at position 235 of IgG Fc. Thus, the Fc receptor binding site can be inhibited by mutating or deleting Leu 235. For example, substitution of Glu for Leu 235 inhibits the ability of the Fc region to bind the high affinity Fc receptor. The murine Clq binding site can be functionally destroyed by mutating or deleting the Glu 318, Lys 320, and Lys 322 residues of IgG. For example, substitution of Ala residues for Glu 318, Lys 320, and Lys 322 renders IgG1 Fc unable to direct antibody-dependent complement lysis. In contrast, a lytic IgG Fc region has a high affinity Fc receptor binding site and a Clq binding site. The high affinity Fc receptor binding site includes the Leu residue at position 235 of IgG Fc, and the Clq binding site includes the Glu 318, Lys 320, and Lys 322 residues of IgG 1. Lytic IgG Fc has wild type residues or conservative amino acid substitutions at these sites. Lytic IgG Fc can target cells for antibody dependent cellular cytotoxicity or complement directed cytolysis (CDC). Appropriate mutations for human IgG are also known (see, e.g., Morrison et al., The Immunologist 2:119-124, 1994; and Brekke et al., The Immunologist 2: 125, 1994). In some embodiments, the Fc domain monomer comprises at least one mutation relative to a wild-type human IgG1, IgG2, or IgG4 Fc region as described in U.S. Pat. No. 10,259,859 B2, the entire teaching of which is herein incorporated by reference. In some embodiments, the polypeptide exhibits a reduction of phagocytosis in a phagocytosis assay compared to a polypeptide with a wild-type human IgG Fc region. In some embodiments, the Fc domain monomer is linked to a second polypeptide comprising a second Fc domain monomer to form an Fc domain dimer.

PEGylation:

In some embodiments, the hIL2 ortholog of the present disclosure may be conjugated to one or more water-soluble polymers. Examples of water soluble polymers useful in the practice of the present invention include polyethylene glycol (PEG), poly-propylene glycol (PPG), polysaccharides (polyvinylpyrrolidone, copolymers of ethylene glycol and propylene glycol, poly(oxyethylated polyol), polyolefinic alcohol), polysaccharides), poly-alpha-hydroxy acid), polyvinyl alcohol (PVA), polyphosphazene, polyoxazolines (POZ), poly(N-acryloylmorpholine), or a combination thereof.

In some embodiments the hIL2 ortholog is operably linked to one or more polyethylene glycol molecules or "PEGylated." Although the method or site of PEG attachment to hIL2 ortholog may vary, in certain embodiments the PEGylation does not alter, or only minimally alters, the activity of the hIL2 ortholog.

In some embodiments, selective PEGylation of the hIL2 ortholog (for example by the incorporation of non-natural amino acids having side chains to facilitate selective PEG conjugation chemistries as described Ptacin, et al (PCT International Application No. PCT/US2018/045257 filed Aug. 3, 2018 and published Feb. 7, 2019 as International Publication Number WO 2019/028419A1 may be employed to generate an hIL2 ortholog with having reduced affinity for one or more subunits (e.g. CD25, CD132) of an hIL2 receptor complex. For example, an hIL2 ortholog incorporating non-natural amino acids having a PEGylatable specific moiety at those sequences or residues of hIL2 identified as interacting with CD25 including amino acids 34-45, 61-72 and 105-109 provides an hIL2 ortholog having modulated binding to CD25. Similarly, an hIL2 ortholog incorporating non-natural amino acids having a PEGylatable specific moiety at those sequences or residues of hIL2 identified as interacting with hCD132 including but not limited to amino acids 18, 22, 109, 126, and/or 133 provides an hIL2 ortholog with modulated binding affinity for hCD132.

In certain embodiments, the increase in half-life is greater than any decrease in biological activity. PEGs suitable for conjugation to a polypeptide sequence are generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure.

A molecular weight of the PEG useful in the context of the hIL2 orthologs of the present disclosure is not restricted to any particular range. The PEG component of the PEG-hIL2 ortholog can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa. Linear or branched PEG molecules having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, alternatively about 30,000 to about 40,000 daltons. In one embodiment of the invention, the PEG is a 40 kD branched PEG comprising two 20 kD arms.

The present disclosure also contemplates compositions wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGs suitable for conjugation to a IL2 ortholog polypeptide are generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbons.

Two widely used first generation activated monomethoxy PEGs (mPEGs) are succinimdyl carbonate PEG (SC-PEG;

see, e.g., Zalipsky, et al. (1992) Biotehnol. Appl. Biochem 15:100-114) and benzotriazole carbonate PEG (BTC-PEG; see, e.g., Dolence, et al. U.S. Pat. No. 5,650,234), which react preferentially with lysine residues to form a carbamate linkage but are also known to react with histidine and tyrosine residues. Use of a PEG-aldehyde linker targets a single site on the N-terminus of a polypeptide through reductive amination.

Pegylation may occur at the α-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General pegylation strategies known in the art can be applied herein.

The PEG can be bound to an hIL2 ortholog of the present disclosure via a terminal reactive group (a "spacer") which mediates a bond between the free amino or carboxyl groups of one or more of the polypeptide sequences and polyethylene glycol. A PEG having the spacer which can be bound to the free amino group includes N-hydroxysuccinylimide polyethylene glycol, which can be prepared by activating succinic acid ester of polyethylene glycol with N-hydroxysuccinylimide.

In some embodiments, the PEGylation of hIL2 orthologs is facilitated by the incorporation of non-natural amino acids bearing unique side chains to facilitate site specific PEGylation. The incorporation of non-natural amino acids into polypeptides to provide functional moieties to achieve site specific pegylation of such polypeptides is known in the art. See e.g. Ptacin, et al (PCT International Application No. PCT/US2018/045257 filed Aug. 3, 2018 and published Feb. 7, 2019 as International Publication Number WO 2019/028419A1. In one embodiment, the hIL2 orthologs of the present invention incorporate a non-natural amino acid at position D109 of the hIL2 ortholog. In one embodiment of the invention the hIL2 ortholog is a PEGylated at position 109 of the hIL2 ortholog to a PEG molecule having a molecular weight of about 20 kD, alternatively about 30 kD, alternatively about 40 kD.

The PEG conjugated to the polypeptide sequence can be linear or branched. Branched PEG derivatives, "star-PEGs" and multi-armed PEGs are contemplated by the present disclosure. Specific embodiments PEGs useful in the practice of the present invention include a 10 kDa linear PEG-aldehyde (e.g., Sunbright® ME-100AL, NOF America Corporation, One North Broadway, White Plains, N.Y. 10601 USA), 10 kDa linear PEG-NETS ester (e.g., Sunbright® ME-100CS, Sunbright® ME-100AS, Sunbright® ME-100GS, Sunbright® ME-100HS, NOF), a 20 kDa linear PEG-aldehyde (e.g. Sunbright® ME-200AL, NOF, a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 kDA PEG-aldehyde comprising two 10 kDA linear PEG molecules (e.g., Sunbright® GL2-200AL3, NOF), a 20 kDa 2-arm branched PEG-NETS ester the 20 kDA PEG-NETS ester comprising two 10 kDA linear PEG molecules (e.g., Sunbright® GL2-200TS, Sunbright® GL200GS2, NOF), a 40 kDa 2-arm branched PEG-aldehyde the 40 kDA PEG-aldehyde comprising two 20 kDA linear PEG molecules (e.g., Sunbright® GL2-400AL3), a 40 kDa 2-arm branched PEG-NETS ester the 40 kDA PEG-NHS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NETS ester.

In one embodiment, the hIL2 ortholog of the present disclosure comprises the structure:
[PEG]-[linker]$_n$-[hoIL2]
where n=0 or 1.

In embodiment, the hIL2 ortholog of the present disclosure comprises the structure:
[PEG]-[linker]$_n$-[desAla1-E15S-H16Q-L19V-D20L-Q22K-M23A]
where n=0 or 1.

In one embodiment, the hIL2 ortholog of the present disclosure comprises the structure:
[40 kDa-PEG]-[linker]$_n$-[hoIL2],
where n=0 or 1.

In embodiment, the hIL2 ortholog of the present disclosure comprises the structure:
[40 kDa-PEG]-[linker]$_n$-[desAla1-E15S-H16Q-L19V-D20L-Q22K-M23A]
where n=0 or 1.

In one embodiment, the hIL2 ortholog of the present disclosure comprises the structure:
[40 kDa-branched PEG]-[linker-]$_n$-[hoIL2],
where n=0 or 1.

In embodiment, the hIL2 ortholog of the present disclosure comprises the structure:
[40 KD-branched PEG]-[linker]$_n$-[desAla1-E15S-H16Q-L19V-D20L-Q22K-M23A],
where n=0 or 1.

In another embodiment, the hIL2 ortholog comprises the structure:

(SEQ ID NO: 5)
[PEG]-(linker)$_n$-[PTSSSTKKTQLQLSQLLVLLKAILNGIN

NYKNPKLTRMLTFKFYMPKKATELKHLQCLEEELKPLEEVLNLAQ

SKNFHLRPRDLISNINVIVLELKGSETTFMCEYADETATIVEFLN

RWITFCQSIISTLT], where n=0 or 1.

In another embodiment, the hIL2 ortholog comprises the structure:

(SEQUENCE ID NO:5)
[40 kDa-PEG]-(linker)$_n$-[PTSSSTKKTQLQLSQLLVLL

KAILNGINNYKNPKLTRMLTFKFYMPKKATELKHLQCLEEELKP

LEEVLNLAQSKNFHLRPRDLISNINVIVLELKGSETTFMCEYAD

ETATIVEFLNRWITFCQSIISTLT], where n=0 or 1.

Suitable linkers include "flexible linkers" which are generally of sufficient length to permit some movement between the modified polypeptide sequences and the linked components and molecules. The linker molecules are generally from about 6-50 atoms long. The linker may also be, for example aryl acetylene, ethelyene glycol oligomers containing 2-10 monomer units, diamines, diacids, amino acids or combinations thereof. Suitable linkers can be readily selected and can be of an suitable length such as 1 amino acid (e.g. glycine), 2, 3, 4, 5, 6, 7, 8, 9, 10, 10-20, 20-30, 30-50 or more than 50 amino acids.

Examples of flexible linkers include glycine polymers (G)n, glycine-alanine polymers, alanine-serine polymers, glycine-serine polymers (for example GmSo)n, (GSGG)n, (GmSoGm)n, (GmSoGmSoGm)n, (GSGGSm)n, (GSGSmG)n and (GGGGSm)n and combinations thereof, where m, n and o are each independently selected from an integer of at least 1 to 10, e.g. 1-18, 2-16, 3-14, 4-12, 5-10, 1, 2, 3, 4, 5, 6, 7, 8, 9 or 10) or other flexible linkers. Glycine and glycine serine polymers are relatively unstructured, and therefore may serve as a neutral tether between components include, but are not limited to GGGSG (SEQ ID NO:139), GGSGG (SEQ ID NO:140), GSGSG (SEQ ID NO:141), GSGGG (SEQ ID NO:142), GGGGSG (SEQ ID NO:143). Additional examples of flexible linkers include glycine polymers (G)n or glycine-serine polymers (e.g. GS)n, GSGGS)n, GGGS)n andGGGGS)n wherein n=1-50, for example, 1, 2, 3, 4, 5, 6, 7, 8, 9, 10, 10-20, 20-30, 30-50 G linker. Exemplary flexible linkes include but are not limited to GGGGS (SEQ ID NO:144), GGGGS (SEQ ID NO:145), GGSG (SEQ ID NO:146), GGSGG (SEQ ID NO:147), GSGSG (SEQ ID NO:148), GSGGG (SEQ ID NO:149), GGGGSG (SEQ ID NO:150) and GSSSG (SEQ ID NO:151). A multimer (e.g, 1, 2, 3, 4, 5, 6, 7, 8, 9, 10, 10-20, 20-30, 30-50) of these linker sequences may be linked together to provide flexible linkers that may be used to conjugate a therlogous amino acid sequence to the polypeptides disclosed herein or a PEG molecule. Alternative to a polypeptide linker, the linker can be a chemical linker e.g. a PEG-aldehyde linker.

Acetylated:

In some embodiments, the IL-2 ortholog is acetylated at the N-terminus by enzymatic reaction with N-terminal acetyltransferase and, for example, acetyl CoA. Alternatively, or in addition to N-terminal aceylation, the IL-2 ortholog can be acetylated at one or more lysine residues, e.g. by enzymatic reaction with a lysine acetyltransferase. See, for example Choudhary et al. (2009) Science 325 (5942):834-840.

Flag Tags

In some embodiments, the IL-2 ortholog is modified to include an additional polypeptide sequence that functions as an antigenic tag, such as a FLAG sequence. FLAG sequences are recognized by biotinylated, highly specific, anti-FLAG antibodies, as described herein (see e.g., Blanar et al. (1992) Science 256:1014 and LeClair, et al. (1992) PNAS-USA 89:8145). In some embodiments, the IL-2 ortholog polypeptide further comprises a C-terminal c-myc epitope tag.

Albumin Fusions:

In some embodiments, the IL-2 ortholog is conjugated to albumin referred to herein as an "IL2 ortholog albumin fusion." The term "albumin" as used in the context hIL2 ortholog albumin fusions include albumins such as human serum albumin (HSA), cyno serum albumin, and bovine serum albumin (BSA). In some embodiments, the HSA the HSA comprises a C34S or K573P amino acid substitution relative to the wild type HSA sequence According to the present disclosure, albumin can be conjugated to a hIL2 ortholog at the carboxyl terminus, the amino terminus, both the carboxyl and amino termini, and internally (see, e.g., U.S. Pat. Nos. 5,876,969 and 7,056,701). In the HSA-hIL2 ortholog polypeptide conjugates contemplated by the present disclosure, various forms of albumin can be used, such as albumin secretion pre-sequences and variants thereof, fragments and variants thereof, and HSA variants. Such forms generally possess one or more desired albumin activities. In additional embodiments, the present disclosure involves fusion proteins comprising a hIL2 ortholog polypeptide fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. In some embodiments, the indirect fusion is effected by a linker such as a peptide linker or modified version thereof as more fully discussed below.

Alternatively, the hIL2 ortholog albumin fusion comprises hIL2 orthologs that are fusion proteins which comprise an albumin binding domain (ABD) polypeptide sequence and an hIL2 ortholog polypeptide. As alluded to above, fusion proteins which comprise an albumin binding domain (ABD) polypeptide sequence and an hIL2 ortholog polypeptide can, for example, be achieved by genetic manipulation, such that the nucleic acid coding for HSA, or a fragment thereof, is joined to the nucleic acid coding for the one or more hIL2 ortholog sequences. In some embodiments, the albumin-binding peptide comprises the amino acid sequence: DICLPRWGCLW (SEQ ID NO:152).

His Tags

In some embodiment, the hIL2 orthologs (including fusion proteins of such IL-2 orthologs) of the present invention are expressed as a fusion protein with one or more transition metal chelating polypeptide sequences. The incorporation of such a transition metal chelating domain facilitates purification immobilized metal affinity chromatography (IMAC) as described in Smith, et al. U.S. Pat. No. 4,569,794 issued Feb. 11, 1986. Examples of transition metal chelating polypeptides useful in the practice of the present invention are described in Smith, et al. supra and Dobeli, et al. U.S. Pat. No. 5,320,663 issued May 10, 1995, the entire teachings of which are hereby incorporated by reference. Particular transition metal chelating polypeptides useful in the practice of the present invention are peptides comprising 3-6 contiguous histidine residues such as a six-histidine peptide $(His)_6$ and are frequently referred to in the art as "His-tags."

The foregoing fusion proteins may be readily produced by recombinant DNA methodology by techniques known in the art by constructing a recombinant vector comprising a nucleic acid sequence comprising a nucleic acid sequence encoding the hIL2 ortholog in frame with a nucleic acid sequence encoding the fusion partner either at the N-terminus or C-terminus of the hIL2 ortholog, the sequence optionally further comprising a nucleic acid sequence in frame encoding a linker or spacer polypeptide.

Targeted hIL2 Ortholog Molecules

In some embodiments, the hIL2 ortholog is provided as a fusion protein with a polypeptide sequence ("targeting domain") to facilitate selective binding to particular cell type or tissue expressing a cell surface molecule that specifically binds to such targeting domain, optionally incorporating a linker molecule between the hIL2 ortholog sequence and the sequence of the targeting domain of the fusion protein. In one embodiment, the targeting domain of the hIL2 ortholog fusion protein specifically binds to a cell surface molecule of the cell type that is targeted by the CAR-T cell expressing the orthogonal hCD122. For example, in the event that the orthogonal hCD122 CAR-T cell comprises a CAR with an ECD that specifically bind to CD-19, the targeting domain of the hIL2 ortholog fusion protein may also bind to CD-19. Examples of targeting domains would include ligands for cell surface receptors or specific binding molecules antibodies. In one embodiment, the hIL2 ortholog fusion protein comprises a molecule that specifically binds to the same cell type for which the engineered cell expressing the orthogonal ligand (e.g., and hoRb CAR-T cell) is targeted. In one embodiment wherein the ECD of the CAR of an hoRb CAR-T cell specifically binds to CD-19, the IL-2 ortholog may be provided as a fusion protein with a CD-19 targeting moiety. For example, in one embodiment wherein the ECD of the CAR of an hoRb CAR-T cell is an scFv molecule that provides specific binding to CD-19, the IL-2 ortholog is provided as a fusion protein with a CD-19 targeting moiety such as a single chain antibody (e.g., an scFv or VHH) that specifically binds to CD-19. In one embodiment, the fusion protein comprises an IL-10 ortholog and the anti-CD19 scFv FMC63 (Nicholson, et al. (1997) Mol Immunol 34: 1157-1165). Similarly, in some embodiments wherein the ECD of the CAR of an hoRb CAR-T cell specifically binds to BCMA, the IL-2 ortholog is provided as a fusion protein with a BCMA targeting moiety, such as antibody comprising the CDRs of anti-BMCA antibodies as described in in Kalled, et al (U.S. Pat. No. 9,034,324 issued May 9, 2015) or antibodies comprising the CDRs as described in Brogdon, et al (U.S. Pat. No. 10,174,095 issued Jan. 8, 2019). In some embodiments, wherein the ECD of the CAR of an hoRb CAR-T cell specifically binds to GD2, the IL-2 ortholog is provided as a fusion protein with a GD2 targeting moiety, such as an antibody comprising the CDRs of described in Cheung, et al (U.S. Pat. No. 9,315,585 issued Apr. 19, 2016) or the CDRs derived from ME36.1 (Thurin et al (1987) Cancer Research 47:1229-1233), 14G2a, 3F8 (Cheung, et al 1985 Cancer Research 45:2642-2649), hu14.18, 8B6, 2E12, or ic9.

In some embodiments, the targeting moiety of the hIL2 ortholog fusion protein is the same as that provided by the CAR-T cell expressing an orthogonal hCD122 or it may be different, in particular it may be directed to an alternative antigen expressed on the tumor cell type targeted by the CAR. For example, in the context of a orthogonal hCD122 scfv 14G2a GD2 targeted CAR-T cell, the hIL2 ortholog may be provided in a targeted fusion construct comprising specific binding domain of another GD2 tumor antigen.

In an alternative embodiment, the targeted hIL2 orthologs of the present disclosure may be administered in combination with CAR-T cell therapy to provide targeted delivery of the hIL2 ortholog to the CAR-T cell based on an extracellular receptor of the CAR-T cell such as by and anti-FMC63 antibody to target the hIL2 activity to the CAR-T cells and rejuvenate exhausted CAR-T cells in vivo. Consequently, embodiments of the present disclosure include targeted delivery of hIL2 orthologs by conjugation of such hIL2 orthologs to antibodies or ligands that are designed to interact with specific cell surface molecules of CAR-T cells. An example of such a molecule would an anti-FMC63-hIL2 ortholog.

In other embodiments, the chimeric polypeptide includes the mutant IL-2 polypeptide and a heterologous polypeptide that functions to enhance expression or direct cellular localization of the mutant IL-2 polypeptide, such as the Aga2p agglutinin subunit (see, e.g., Boder and Wittrup, Nature Biotechnol. 15:553-7, 1997).

Protein Transduction Domain Fusion Proteins:

In some embodiments, the hIL2 ortholog may optionally comprise a "Protein Transduction Domain" or "PTD." A PTD is a polypeptide, polynucleotide, carbohydrate, or organic or inorganic molecule that facilitates traversing a lipid bilayer, micelle, cell membrane, organelle membrane, or vesicle membrane. The incorporation of a PTD into an hIL2 ortholog facilitates the molecule traversing a membrane. In some embodiments, a PTD is covalently linked to the amino or carboxy terminus of an hIL2 ortholog. In some embodiments, the PTD is incorporated as part of an PTD-IL2 ortholog fusion protein, either at the N or C terminus of the molecule.

Exemplary protein transduction domains include, but are not limited to, a minimal decapeptide protein transduction domain (corresponding to residues 47-57 of HIV-1 TAT); a polyarginine sequence comprising a number of arginine residues sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); a *Drosophila Antennapedia* protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008), Transportan (as described in Wierzbicki, et al., (2014) Folio Histomchemica et Cytobiologica 52(4): 270-280 and Pooga, et a (1998) FASEB J 12(1)67-77 and commercially available from AnaSpec as Catalog No. AS-61256); KALA (as described in Wyman et al., (1997) Biochemistry 36(10) 3008-3017 and commercially available from AnaSpec as Catalog No. AS-65459); Antennapedia Peptide (as described in Pietersz et al., (2001) Vaccine 19:1397 and commercially available from AnaSpec as Catalog No. AS-61032); TAT 47-57 (commercially available from AnaSpec as Catalog No. AS-60023).

Preparation of hIL2 Orthologs

The hIL2 orthologs may be produced by any conventional method including recombinant or solid phase synthesis.

Solid Phase Chemical Synthesis:

In addition to generating mutant polypeptides via expression of nucleic acid molecules that have been altered by recombinant molecular biological techniques, subject hIL2 orthologs can be chemically synthesized. Chemically synthesized polypeptides are routinely generated by those of skill in the art. Chemical synthesis includes direct synthesis of a peptide by chemical means of the protein sequence encoding for an hIL2 ortholog exhibiting the properties described.

In some embodiments, the hIL2 orthologs of the present disclosure may be prepared by chemical synthesis. The chemical synthesis of the hIL2 orthologs of may proceed via liquid-phase or solid-phase. Solid-phase peptide synthesis (SPPS) allows the incorporation of unnatural amino acids and/or peptide/protein backbone modification. Various forms of SPPS are available for synthesizing hIL2 orthologs of the present disclosure are known in the art (e.g., Ganesan A. (2006) Mini Rev. Med. Chem. 6:3-10; and Camarero J. A. et al., (2005) Protein Pept Lett. 12:723-8). In the course of chemical synthesis, the alpha functions and any reactive side chains may be protected with acid-labile or base-labile groups that are stable under the conditions for linking amide bonds but can readily be cleaved without impairing the peptide chain that has formed.

In the solid phase synthesis, either the N-terminal or C-terminal amino acid may be coupled to a suitable support material. Suitable support materials are those which are inert towards the reagents and reaction conditions for the stepwise condensation and cleavage reactions of the synthesis process and which do not dissolve in the reaction media being used. Examples of commercially available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like. The successive coupling of the protected amino acids can be carried out according to conventional methods in peptide synthesis, typically in an automated peptide synthesizer.

At the end of the solid phase synthesis, the peptide is cleaved from the support material while simultaneously cleaving the side chain protecting groups. The peptide obtained can be purified by various chromatographic methods including but not limited to hydrophobic adsorption chromatography, ion exchange chromatography, distribution chromatography, high pressure liquid chromatography (HPLC) and reversed-phase HPLC.

Recombinant Production:

In some embodiments, the hIL2 ortholog (or fusion proteins comprising the hIL2 ortholog) is produced by recombinant methods. A nucleic acid sequence encoding the desired hIL2 ortholog polypeptide (optionally comprising a secretion leader sequence or signal peptide) is introduced into an expression vector into the cell to be engineered, nucleic acid sequence being operably linked to one or more expression control sequences encoding by the vector and functional in the target host cell. The recombinant hIL2 ortholog may be recovered through disruption of the host cell or from the cell medium if a secretion leader sequence (signal peptide) is incorporated into the polypeptide. The recombinant hIL2 ortholog may be purified and concentrated for further use including incorporation. The process for the recombinant production of hIL2 polypeptides is known in the art and described in Fernandes and Taforo, U.S. Pat. No. 4,604,377 issued Aug. 5, 1986 and hIL2 orthologs in Mark, et al., U.S. Pat. No. 4,512,584 issued May 21, 1985, Gillis, U.S. Pat. No. 4,401,756 issued Aug. 30, 1983 the entire teachings of which are herein incorporated by reference.

DNA encoding an hIL2 ortholog may be obtained from various sources as designed during the engineering process. Amino acid sequence variants of the hIL2 polypeptides to the produce the hIL2 orthologs of the present disclosure are prepared by introducing appropriate nucleotide changes into the coding sequence, as described herein. Such variants represent insertions, substitutions, and/or specified deletions of, residues as noted. Any combination of insertion, substitution, and/or specified deletion is made to arrive at the final construct, provided that the final construct possesses the desired biological activity as defined herein.

Construction of Nucleic Acid Sequences Encoding the hIL2 Ortholog

In some embodiments, the hIL2 ortholog is produced by recombinant methods using a nucleic acid sequence encoding the hIL2 ortholog (or fusion protein comprising the hIL2 ortholog). The nucleic acid sequence encoding the desired hIL2 ortholog can be synthesized by chemical means using an oligonucleotide synthesizer.

The nucleic acid molecules are not limited to sequences that encode polypeptides; some or all of the non-coding sequences that lie upstream or downstream from a coding sequence (e.g., the coding sequence of hIL2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The nucleic acid molecules encoding the hIL2 ortholog (and fusions thereof) may contain naturally occurring sequences or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an anti-sense strand).

Nucleic acid sequences encoding the hIL2 ortholog may be obtained from various commercial sources that provide custom made nucleic acid sequences. Amino acid sequence variants of the hIL2 polypeptides to the produce the hIL2 orthologs of the present disclosure are prepared by introducing appropriate nucleotide changes into the coding sequence based on the genetic code which is well known in the art. Such variants represent insertions, substitutions, and/or specified deletions of, residues as noted. Any combination of insertion, substitution, and/or specified deletion is made to arrive at the final construct, provided that the final construct possesses the desired biological activity as defined herein.

Methods for constructing a DNA sequence encoding the hIL2 orthologs and expressing those sequences in a suitably transformed host include, but are not limited to, using a PCR-assisted mutagenesis technique. Mutations that consist of deletions or additions of amino acid residues to an hIL2 polypeptide can also be made with standard recombinant techniques. In the event of a deletion or addition, the nucleic acid molecule encoding hIL2 is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

An hIL2 ortholog of the present disclosure may be produced recombinantly not only directly, but also as a fusion polypeptide with a heterologous polypeptide, e.g. a signal sequence or other polypeptide having a specific cleavage site at the N-terminus or C-terminus of the mature hIL2 ortholog. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. In some embodiments, the signal sequence is the signal sequence that is natively associated with the hIL2 ortholog (i.e. the human IL2 signal sequence). The inclusion of a signal sequence depends on whether it is desired to secrete the hIL2 ortholog from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild type IL2 signal sequence be used. Alternatively, heterologous mammalian signal sequences may be suitable, such as signal sequences from secreted polypeptides of the same or related species, as well as viral secretory leaders, for example, the herpes simplex gD signal. When the recombinant host cell is a yeast cell such as *Saccharomyces cerevisiae*, the alpha mating factor secretion signal sequence may be employed to achieve extracellular secretion of the IL2 ortholog into the culture medium as described in Singh, U.S. Pat. No. 7,198,919 B1 issued Apr. 3, 2007.

Codon Optimization:

In some embodiments, the nucleic acid sequence encoding the recombinant protein (IL2 ortholog, orthogonal hCD122, or CAR) may be "codon optimized" to facilitate expression in a particular host cell type. Techniques for codon optimization in a wide variety of expression systems, including mammalian, yeast and bacterial host cells, are well known in the and there are online tools to provide for a codon optimized sequences for expression in a variety of host cell types. See e.g. Hawash, et al., (2017) 9:46-53 and Mauro and Chappell in *Recombinant Protein Expression in Mammalian Cells: Methods and Protocols*, edited by David Hacker (Human Press New York). Additionally, there are a variety of web based on-line software packages that are freely available to assist in the preparation of codon optimized nucleic acid sequences.

Expression Vectors:

Once assembled (by synthesis, site-directed mutagenesis or another method), the nucleic acid sequence encoding an hIL2 ortholog is inserted into an expression vector. A variety of expression vectors for uses in various host cells are available and are typically selected based on the host cell for expression. The vector components generally include, but are not limited to, one or more of the following: an origin of replication, one or more marker genes, an enhancer element, a promoter, and a transcription termination sequence. Vectors include viral vectors, plasmid vectors, integrating vectors, and the like. Plasmids are examples of non-viral vectors. In order to facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, and magnetic fields (electroporation).

An hIL2 ortholog may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. In mammalian cell expression the native signal sequence may be used, or other mammalian signal sequences may be suitable, such as signal sequences from secreted polypeptides of the same or related species, as well as viral secretory leaders, for example, the herpes simplex gD signal.

Selectable Marker

Expression vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Regulatory Control Sequences:

Expression vectors for hIL2 orthologs of the present disclosure contain a regulatory sequence that is recognized by the host organism and is operably linked to nucleic acid sequence encoding the hIL2 ortholog. The terms "regulatory control sequence," "regulatory sequence" or "expression control sequence" are used interchangeably herein to refer to promoters, enhancers, and other expression control elements (e.g., polyadenylation signals). See, for example, Goeddel (1990) in Gene Expression Technology: Methods in Enzymology 185 (Academic Press, San Diego Calif. USA Regulatory sequences include those that direct constitute expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. In selecting an expression control sequence, a variety of factors understood by one of skill in the art are to be considered. These include, for example, the relative strength of the sequence, its controllability, and its compatibility with the actual DNA sequence encoding the subject hIL2 ortholog, particularly as regards potential secondary structures.

Promoters

In some embodiments, the regulatory sequence is a promoter, which is selected based on, for example, the cell type in which expression is sought. Expression vectors will contain a promoter that is recognized by the host organism and is operably linked to an orthogonal protein coding sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known. For example the T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

Transcription from vectors in mammalian host cells may be controlled, for example, by promoters obtained from the genomes of viruses such as polyoma virus, fowlpox virus, adenovirus (such as human adenovirus serotype 5), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication.

Enhancers

Transcription by higher eukaryotes is often increased by inserting an enhancer sequence into the vector and operably linked to the nucleic acid sequence encoding the hIL2 ortholog. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence but is preferably located at a site 5' from the promoter. Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Additional examples of marker or reporter genes include beta-lactamase, chloramphenicol acetyltransferase (CAT), adenosine deaminase (ADA), dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). Those of skill in the art can readily determine whether a given regulatory element or selectable marker is suitable for use in a particular experimental context.

Proper assembly of the expression vector can be confirmed by nucleotide sequencing, restriction mapping, and expression of a biologically active polypeptide in a suitable host.

Host Cells for Production of hIL2 Orthologs

In one embodiment, the present disclosure further a recombinant cell comprising a nucleic acid sequence encoding an hIL2 ortholog. The cell may be a prokaryotic or eukaryotic. A cell of the present disclosure is a transfected cell, i.e., a cell into which a nucleic acid molecule, for example a nucleic acid molecule encoding a mutant hIL2 polypeptide, has been introduced by means of recombinant DNA techniques. The progeny of such a cell are also considered within the scope of the present disclosure.

Host cells for expression of the hIL2 ortholog are typically selected in accordance with their compatibility with the chosen expression vector, the toxicity of the product coded for by the DNA sequences of this invention, their secretion characteristics, their ability to fold the polypeptides correctly, their fermentation or culture requirements, and the ease of purification of the products coded for by the DNA sequences. Suitable host cells for cloning or expressing the DNA in the vectors herein are the prokaryote, yeast, or higher eukaryote cells.

In some embodiments the host cell for recombinant production of the hIL2 orthologs are eukaryotic cells, such as yeast or human cells. Suitable eukaryotic host cells include insect cells (examples of Baculovirus vectors available for expression of proteins in cultured insect cells (e.g., 519 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast S. cerenvisiae include pYepSecl (Baldari et al. (1987) EMBO J. 6:229-234), pMfa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) EMBO J. 6:187:195)).

Examples of useful mammalian host cell lines are mouse L cells (L-M[TK-], ATCC#CRL-2648), monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

In some embodiments, hIL2 orthologs obtained will be glycosylated or unglycosylated depending on the host organism used to produce the mutein. If bacteria are chosen as the host then the hIL2 ortholog produced will be unglycosylated. Eukaryotic cells, on the other hand, may glycosylate the hIL2 orthologs and perhaps not in the same way as native-IL2 is glycosylated.

For other additional expression systems for both prokaryotic and eukaryotic cells, see Chapters 16 and 17 of Sambrook et al. (1989) Molecular Cloning: A Laboratory Manual (2nd ed., Cold Spring Harbor Laboratory Press, Plainview, N.Y.). See, Goeddel (1990) in Gene Expression Technology: Methods in Enzymology 185 (Academic Press, San Diego, Calif.).

Transfection:

The nucleic acid expression constructs encoding the hIL2 ortholog is introduced into host cells to thereby produce the hIL2 orthologs disclosed herein or to produce biologically active muteins thereof. Vector DNA can be introduced into prokaryotic or eukaryotic cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals.

In order to facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, and magnetic fields (electroporation).

Cell Culture:

Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression and will be apparent to the ordinarily skilled artisan.

Recovery of Recombinant Proteins:

Recombinantly produced hIL2 ortholog polypeptides can be recovered from the culture medium as a secreted polypeptide if a secretion leader sequence is employed. Alternatively, the hIL2 ortholog polypeptides can also be recovered from host cell lysates. A protease inhibitor, such as phenyl methyl sulfonyl fluoride (PMSF) may be employed during the recovery phase from cell lysates to inhibit proteolytic degradation during purification, and antibiotics may be included to prevent the growth of adventitious contaminants. In some embodiments, the hIL2 ortholog is produced in *E. coli* in which the overexpression of the hIL2 ortholog which is sequestered in inclusion bodies. Techniques for the isolation and solubilization of inclusion bodies and recovery of active proteins are well known in the art.

Various purification steps are known in the art and find use, e.g. affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural specific binding of one molecular species to separate and purify a second species from a mixture. Antibodies are commonly used in affinity chromatography. Size selection steps may also be used, e.g. gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column.

The orthogonal hIL2 ortholog may be concentrated, filtered, dialyzed, etc., using methods known in the art. For therapeutic applications, the hIL2 ortholog can be administered to a mammal comprising the appropriate engineered orthogonal receptor. Administration may be intravenous, as a bolus or by continuous infusion over a period of time. Alternative routes of administration include intramuscular, intraperitoneal, intra-cerebrospinal, subcutaneous, intra-articular, intrasynovial, intrathecal, oral, topical, or inhalation routes. The orthogonal hIL2 orthologs also are suitably administered by intratumoral, peritumoral, intralesional, or perilesional routes or to the lymph, to exert local as well as systemic therapeutic effects.

Routes of Administration of hIL2 Orthologs:

In embodiments of the therapeutic methods of the present disclosure involve the administration of a pharmaceutical formulation comprising an hIL2 ortholog (and/or nucleic acids encoding the hIL2 ortholog) to a subject in need of treatment. Administration to the subject may be achieved by intravenous, as a bolus or by continuous infusion over a period of time. Alternative routes of administration include intramuscular, intraperitoneal, intra-cerobrospinal, subcutaneous, intra-articular, intrasynovial, intrathecal, oral, topical, or inhalation routes. The hIL2 orthologs also are suitably administered by intratumoral, peritumoral, intralesional, intranodal or perilesional routes or to the lymph, to exert local as well as systemic therapeutic effects.

In some embodiments, subject hIL2 orthologs (and/or nucleic acids encoding the hIL2 ortholog) can be incorporated into compositions, including pharmaceutical compositions. Such compositions typically include the polypeptide or nucleic acid molecule and a pharmaceutically acceptable carrier. A pharmaceutical composition is formulated to be compatible with its intended route of administration and is compatible with the therapeutic use for which the hIL2 ortholog is to be administered to the subject in need of treatment or prophyaxis.

Formulations of hIL2 Orthologs

In some embodiments, the present disclosure provides a pharmaceutically acceptable formulation of a hIL2 ortholog. The preferred formulation depends on the intended mode of administration and therapeutic application. Pharmaceutically acceptable formulations of hIL2 orthologs comprise physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of polypeptides include polysaccharides such as sodium carboxymethylcellulose or methylcellulose, polyvinylpyrrolidone, polyacrylates, polyoxyethylene-polyoxypropylene-block polymers, PEG, polymeric amino acids, amino acid copolymers, and lipid aggregates (such as oil droplets or liposomes).

The formulation may also comprise pharmaceutically-acceptable, non-toxic carriers, excipients, stabilizers or diluents, which are defined as vehicles commonly used to formulate pharmaceutical compositions for animal or human administration. The diluent is selected so as not to affect the biological activity of the combination. Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration are typically sterile. Sterilization of the compositions of the present invention may readily accomplished by filtration through sterile filtration membranes.

Typically, formulations are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science (1990) 249: 1527 and Hanes, Advanced Drug Delivery Reviews (1997) 28: 97-119. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

In some embodiments, the methods of the present disclosure involve the parental administration of a hIL2 ortholog. Examples of parenteral routes of administration include, for example, intravenous, intradermal, subcutaneous, transdermal (topical), transmucosal, and rectal administration. Parenteral formulations comprise solutions or suspensions used for parenteral application can include vehicles the carriers and buffers. Pharmaceutical formulations for parenteral administration include sterile aqueous solutions (where water soluble) or dispersions and sterile powders for the extemporaneous preparation of sterile injectable solutions or dispersion. The parenteral preparation can be enclosed in ampoules, disposable syringes or multiple dose vials made of glass or plastic. In one embodiment, the formulation is provided in a prefilled syringe for parenteral administration Oral formulations, if used, may include one or more an inert diluents and/or edible carriers. For the purpose of oral therapeutic administration, the a hIL2 ortholog may be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the formulation. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

In the event of administration by inhalation, subject hIL2 orthologs, or the nucleic acids encoding them, are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration of the subject hIL2 orthologs or nucleic acids can also be by transmucosal or transdermal formulations. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories suppositories (e.g., with conventional suppository bases such as cocoa butter and other glycerides) or retention enemas for rectal delivery. For transdermal administration, the active compounds are formulated into ointments, salves, gels, or creams as generally known in the art and may incorporate permeation enhancers such as ethanol or lanolin.

In some embodiments, the hIL2 ortholog the formulation is an extended release formulation to provide extended delivery of the hIL2 ortholog agent over a period of hours or days. Examples of extended release formulations of the injectable compositions can be brought about by including in the composition an agent which delays absorption, for example, aluminum monostearate and gelatin. In one embodiment, the subject hIL2 orthologs or nucleic acids are prepared with carriers that will protect the mutant IL-2 polypeptides against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. Liposomal suspensions can also be used as pharmaceutically acceptable carriers.

Engineered hoCD122 Cells:

The preparation of recombinant cells useful in the practice of the present invention is achieved by transforming isolated with an expression vector comprising a nucleic acid sequence encoding an hCD122 orthogonal receptor. The hIL2 orthologs of the present invention may be employed in methods of selectively expanding such engineered hoRb cells (e.g., human T-cells) which have been engineered to express a corresponding orthogonal hCD122 receptor. T-cells useful for engineering with the constructs described herein include naïve T-cells, central memory T-cells, effector memory T-cells or combination thereof. T cells for engineering as described above are collected from a subject or a donor may be separated from a mixture of cells by techniques that enrich for desired cells or may be engineered and cultured without separation. Alternatively, the T cells for engineering may be separated from other cells. Techniques providing accurate separation include fluorescence activated cell sorters. The cells may be selected against dead cells by employing dyes associated with dead cells (e.g., propidium iodide). The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum (FCS). The collected and optionally enriched cell population may be used immediately for genetic modification or may be frozen at liquid nitrogen temperatures and stored, being thawed and capable of being reused. The cells will usually be stored in 10% DMSO, 50% FCS, 40% RPMI 1640 medium.

In some embodiments, the engineered cells comprise a complex mixture of immune cells, e.g., tumor infiltrating lymphocytes (TILs) isolated from an individual in need of treatment. See, for example, Yang and Rosenberg (2016) Adv Immunol. 130:279-94, "Adoptive T Cell Therapy for Cancer; Feldman et al (2015) Seminars in Oncol. 42(4):626-

39 "Adoptive Cell Therapy-Tumor-Infiltrating Lymphocytes, T-Cell Receptors, and Chimeric Antigen Receptors"; Clinical Trial NCT01174121, "Immunotherapy Using Tumor Infiltrating Lymphocytes for Patients With Metastatic Cancer"; Tran et al. (2014) Science 344(6184)641-645, "Cancer immunotherapy based on mutation-specific CD4+ T cells in a patient with epithelial cancer".

CAR-T Cells

In one embodiment of the invention the hoRb cell is a T-cell (e.g., human T-cell) which has been modified to surface express a chimeric antigen receptor (a "hoCAR-T cell"). As used herein, the term antigen binding domain (ABD) refers to a polypeptide that specifically binds to an antigen expressed on the surface of a target cell. The ABD may be any polypeptide that specifically binds to one or more antigens expressed on the surface of a target cell. CARs further comprise a transmembrane domain joining the ABD (or linker, if employed) to the intracellular cytoplasmic domain of the CAR. The transmembrane domain is comprised of any polypeptide sequence which is thermodynamically stable in a eukaryotic cell membrane. The transmembrane spanning domain may be derived from the transmembrane domain of a naturally occurring membrane spanning protein or may be synthetic. In designing synthetic transmembrane domains, amino acids favoring alpha-helical structures are preferred. Transmembrane domains useful in construction of CARs are comprised of approximately 10, 11, 12, 13, 14, 15, 16, 17, 18, 19, 20, 21, 22, 22, 23, or 24 amino acids favoring the formation having an alpha-helical secondary structure. Amino acids having a to favor alpha-helical conformations are well known in the art. See, e.g Pace, et al. (1998) Biophysical Journal 75: 422-427. Amino acids that are particularly favored in alpha helical conformations include methionine, alanine, leucine, glutamate, and lysine. In some embodiments, the CAR transmembrane domain may be derived from the transmembrane domain from type I membrane spanning proteins, such as CD3, CD4, CD8, CD28, etc.

The cytoplasmic domain (ICD) of the CAR polypeptide comprises one or more intracellular signal domains. In one embodiment, the intracellular signal domains comprise the cytoplasmic sequences of the T-cell receptor (TCR) and co-receptors that initiate signal transduction following antigen receptor engagement and functional derivatives and sub-fragments thereof. A cytoplasmic signaling domain, such as those derived from the T cell receptor zeta-chain, is employed as part of the CAR in order to produce stimulatory signals for T lymphocyte proliferation and effector function following engagement of the chimeric receptor with the target antigen. Examples of cytoplasmic signaling domains include but are not limited to the cytoplasmic domain of CD27, the cytoplasmic domain S of CD28, the cytoplasmic domain of CD137 (also referred to as 4-1BB and TNFRSF9), the cytoplasmic domain of CD278 (also referred to as ICOS), p110α, β, or δ catalytic subunit of PI3 kinase, the human CD3 ζ-chain, cytoplasmic domain of CD134 (also referred to as OX40 and TNFRSF4), FcεR1γ and β chains, MB1 (Igα) chain, B29 (Igβ) chain, etc.), CD3 polypeptides (δ, Δ and ε), syk family tyrosine kinases (Syk, ZAP 70, etc.), src family tyrosine kinases (Lck, Fyn, Lyn, etc.) and other molecules involved in T-cell transduction, such as CD2, CD5 and CD28.

In some embodiments, the CAR may also provide a co-stimulatory domain. The term "co-stimulatory domain", refers to a stimulatory domain, typically an endodomain, of a CAR that provides a secondary non-specific activation mechanism through which a primary specific stimulation is propagated. The co-stimulatory domain refers to the portion of the CAR which enhances the proliferation, survival or development of memory cells. Examples of co-stimulation include antigen nonspecific T cell co-stimulation following antigen specific signaling through the T cell receptor and antigen nonspecific B cell co-stimulation following signaling through the B cell receptor. Co-stimulation, e.g., T cell co-stimulation, and the factors involved have been described in Chen & Flies. (2013) Nat Rev Immunol 13(4):227-42. In some embodiments of the present disclosure, the CSD comprises one or more of members of the TNFR superfamily, CD28, CD137 (4-1BB), CD134 (OX40), Dap10, CD27, CD2, CD5, ICAM-1, LFA-1 (CD11a/CD18), Lck, TNFR-I, TNFR-II, Fas, CD30, CD40 or combinations thereof. CARs are often referred to as first, second, third or fourth generation. The term first-generation CAR refers to a CAR wherein the cytoplasmic domain transmits the signal from antigen binding through only a single signaling domain, for example a signaling domain derived from the high-affinity receptor for IgE FcεR1γ or the CD3ζ chain. The domain contains one or three immunoreceptor tyrosine-based activating motif(s) [ITAM(s)] for antigen-dependent T-cell activation. The ITAM-based activating signal endows T-cells with the ability to lyse the target tumor cells and secret cytokines in response to antigen binding. Second-generation CARs include a co-stimulatory signal in addition to the CD3 ζ signal. Coincidental delivery of the delivered co-stimulatory signal enhances cytokine secretion and antitumor activity induced by CAR-transduced T-cells. The co-stimulatory domain is usually be membrane proximal relative to the CD3ζ domain. Third-generation CARs include a tripartite signaling domain, comprising for example a CD28, CD3ζ, OX40 or 4-1BB signaling region. In fourth generation, or "armored car" CAR T-cells are further modified to express or block molecules and/or receptors to enhance immune activity such as the expression of IL-12, IL-18, IL-7, and/or IL-10; 4-1BB ligand, CD-40 ligand.

Examples of intracellular signaling domains comprising may be incorporated into the hoCAR-T cell useful in the practice of the present invention include (amino to carboxy): CD3ζ; CD28-41BB-CD3ζ; CD28-OX40-CD3ζ; CD28-41BB-CD3ζ; 41BB-CD-28-CD3ζ and 41BB-CD3ζ.

The term CAR includes CAR variants including but not limited split CARs, ON-switch CARS, bispecific or tandem CARs, inhibitory CARs (iCARs) and induced pluripotent stem (iPS) CAR-T cells.

The term "Split CARs" refers to CARs wherein the extracellular portion, the ABD and the cytoplasmic signaling domain of a CAR are present on two separate molecules. CAR variants also include ON-switch CARs which are conditionally activatable CARs, e.g., comprising a split CAR wherein conditional hetero-dimerization of the two portions of the split CAR is pharmacologically controlled. CAR molecules and derivatives thereof (i.e., CAR variants) are described, e.g., in PCT Application Nos. US2014/016527, US1996/017060, US2013/063083; Fedorov et al. *Sci Transl Med* (2013); 5(215):215ra172; Glienke et al. *Front Pharmacol* (2015) 6:21; Kakarla & Gottschalk 52 *Cancer J* (2014) 20(2):151-5; Riddell et al. *Cancer J* (2014) 20(2):141-4; Pegram et al. *Cancer J* (2014) 20(2):127-33; Cheadle et al. *Immunol Rev* (2014) 257(1):91-106; Barrett et al. *Annu Rev Med* (2014) 65:333-47; Sadelain et al. *Cancer Discov* (2013) 3(4):388-98; Cartellieri et al., *J Biomed Biotechnol* (2010) 956304; the disclosures of which are incorporated herein by reference in their entirety.

The term "bispecific or tandem CARs" refers to CARs which include a secondary CAR binding domain that can either amplify or inhibit the activity of a primary CAR.

The term "inhibitory chimeric antigen receptors" or "iCARs" are used interchangeably herein to refer to a CAR where binding iCARs use the dual antigen targeting to shut down the activation of an active CAR through the engagement of a second suppressive receptor equipped with inhibitory signaling domains of a secondary CAR binding domain results in inhibition of primary CAR activation. Inhibitory CARs (iCARs) are designed to regulate CAR-T cells activity through inhibitory receptors signaling modules activation. This approach combines the activity of two CARs, one of which generates dominant negative signals limiting the responses of CAR-T cells activated by the activating receptor. iCARs can switch off the response of the counteracting activator CAR when bound to a specific antigen expressed only by normal tissues. In this way, iCARs-T cells can distinguish cancer cells from healthy ones, and reversibly block functionalities of transduced T cells in an antigen-selective fashion. CTLA-4 or PD-1 intracellular domains in iCARs trigger inhibitory signals on T lymphocytes, leading to less cytokine production, less efficient target cell lysis, and altered lymphocyte motility. The term "tandem CAR" or "TanCAR" refers to CARs which mediate bispecific activation of T cells through the engagement of two chimeric receptors designed to deliver stimulatory or costimulatory signals in response to an independent engagement of two different tumor associated antigens.

Typically, the chimeric antigen receptor T-cells (CAR-T cells) are T-cells which have been recombinantly modified by transduction with an expression vector encoding a CAR in substantial accordance with the teaching above.

In some embodiments, hoCAR-T cell is allogeneic with respect to the individual that is treated. Graham et al. (2018) Cell 7(10) E155. In some embodiments an allogeneic engineered T cell is fully HLA matched. However not all patients have a fully matched donor and a cellular product suitable for all patients independent of HLA type provides an alternative.

Because the hoCAR-T cell be derived from a subject's own T-cells, the population of the cells to be administered is to the subject is necessarily variable, the response to such agents can vary and thus involves the ongoing monitoring and management of therapy related toxicities which are managed with a course of pharmacologic immunosuppression or B cell depletion prior to the administration of the hoCAR-T cell product. Usually, at least $1 \times 10^6$ hoCAR-T cell/kg will be administered, at least $1 \times 10^7$ hoCAR-T cell/kg, at least $1 \times 10^8$ hoCAR-T cells/kg, at least $1 \times 10^9$ hoCAR-T cell/kg, at least $1 \times 10^{10}$ hoCAR-T cells/kg, or more, usually being limited by the number of T cells that are obtained during collection. The engineered hoCAR-T cells may be infused to the subject in any physiologically acceptable medium by any convenient route of administration, normally intravascularly, although they may also be introduced by other routes, where the cells may find an appropriate site for growth If the hoCAR-T cells are allogeneic T cells, such cells may be modified to reduce graft versus host disease. For example, the engineered cells of the present invention may be TCRαβ receptor knock-outs achieved by gene editing techniques. TCRαβ is a heterodimer and both alpha and beta chains need to be present for it to be expressed. A single gene codes for the alpha chain (TRAC), whereas there are 2 genes coding for the beta chain, therefore TRAC loci KO has been deleted for this purpose. A number of different approaches have been used to accomplish this deletion, e.g. CRISPR/Cas9; meganuclease; engineered I-CreI homing endonuclease, etc. See, for example, Eyquem et al. (2017) Nature 543:113-117, in which the TRAC coding sequence is replaced by a CAR coding sequence; and Georgiadis et al. (2018) Mol. Ther. 26:1215-1227, which linked CAR expression with TRAC disruption by clustered regularly interspaced short palindromic repeats (CRISPR)/Cas9 without directly incorporating the CAR into the TRAC loci. An alternative strategy to prevent GVHD modifies T cells to express an inhibitor of TCRαβ signaling, for example using a truncated form of CD3ζ as a TCR inhibitory molecule.

In one embodiment, the present disclosure provides a method of selectively expanding a population of engineered cells expressing an orthogonal hCD122 receptor from a mixed cell population, the method comprising contacting the mixed cell population with an hIL2 ortholog of the present disclosure under conditions that facilitate the proliferation of the engineered cell. In one embodiment when the orthogonal hCD122 receptor expressing CAR-T cell, the orthogonal receptor expressing CAR-T cells may also be selectively expanded from the background or mixed population of transduced and non-transduced cells through the use of the hIL2 orthologs described herein. Expansion of the T cells for therapeutic applications typically involves culturing the cells in contact with a surface providing an agent that stimulates a CD3 TCR complex associated signal and an agent that stimulates a co-stimulatory molecule on the surface of the T-cell. In conventional practice, engineered T-cells are stimulated prior to administration of the cell therapy product by contacting with CD3/D28, particularly in the preparation of CAR-T cells for use in clinical applications. A wide variety or commercially available products are available to facilitate bead-based activation of T-cells including but not limited to the Invitrogen® CTS Dynabeads® CD3/28 (Life Technologies, Inc. Carlsbad Calif.) or Miltenyi MACS® GMP ExpAct Treg beads or Miltenyi MACS GMP TransAct™ CD3/28 beads (Miltenyi Biotec, Inc.). Conditions appropriate for T-cell culture are well known in the art. Lin, et al. (2009) Cytotherapy 11(7):912-922; Smith, et al. (2015) Clinical & Translational Immunology 4:e31 published online 16 Jan. 2015. The target cells are maintained under conditions necessary to support growth, for example, an appropriate temperature (e.g., 37° C.) and atmosphere (e.g., air plus 5% $CO_2$). Wherein the mixed cell population containing engineered T cells expressing the hCD122 orthogonal receptor is cultured in the presence of a concentration of the hIL2 ortholog. In some embodiments for at least 2 hours, alternatively at least 3 hours, alternatively at least 4 hours, alternatively at least 6 hours, alternatively at least 8 hours, alternatively at least 12 hours, alternatively at least 24 hours, alternatively at least 48 hours, alternatively at least 72 hours, or more. The concentration of the hIL2 ortholog in such ex vivo situations is sufficient to induce cellular proliferation in the cell population. T cell proliferation can be readily assessed by microscopic methods and the determination of the optimal concentration of the hIL2 ortholog will depend upon the relative activity of the hIL2 ortholog for the orthogonal hCD122 receptor.

In one embodiment, the present disclosure provides for a method making an engineered cell product substantially enriched for engineered hoCD122 expressing cells, the method comprising the steps of: (a) obtaining a biological sample comprising T-cells; (b) contacting said biological sample with a recombinant vector encoding an hoCD122 receptor; (c) contacting the biological sample an hIL2 ortholog for a period of time sufficient to expand the engineered hoCD122 expressing cells. The duration of contact and culture may be modified depending on the degree to which the population is to be enriched.

Where the cells are to be contacted with the hIL2 ortholog in vitro, the hIL2 ortholog is added to the engineered cells in a dose and for a period of time sufficient to activate signaling from the hoCD122 receptor, which may utilize the native cellular machinery, e.g. accessory proteins, co-receptors, and the like. Any suitable culture medium may be used. The cells thus activated may be used for any desired purpose, including experimental purposes relating to determination of antigen specificity, cytokine profiling, and the like, and for delivery in vivo.

Where the contacting is performed in vivo, an effective dose of engineered cells, including without limitation CAR-T cells modified to express an orthogonal hoCD122 receptor, are infused to the recipient, in combination with or prior to administration of the orthogonal cytokine, e.g. IL-2 and allowed to contact T cells in their native environment, e.g. in lymph nodes, etc. Dosage and frequency may vary depending on the agent; mode of administration; nature of the hIL2 ortholog, and the like. It will be understood by one of skill in the art that such guidelines will be adjusted for the individual circumstances. The dosage may also be varied for route of administration, e.g. intramuscular, intraperitoneal, intradermal, subcutaneous, intravenous infusion and the like. Generally at least about $10^4$ engineered cells/kg are administered, at least about $10^5$ engineered cells/kg; at least about $10^6$ engineered cells/kg, at least about $10^7$ engineered cells/kg, or more.

Where the engineered cells that are modified to express the hoCD122 are T cells, an enhanced immune response may be manifest as an increase in the cytolytic response of T cells towards the target cells present in the recipient, e.g. towards elimination of tumor cells, infected cells; decrease in symptoms of autoimmune disease; and the like. In some embodiments when the engineered T cell population is to be administered to a subject, the subject is provided with immunosuppressive course of therapy prior to or in combination with the administration of the engineered T cell population. Examples of such immunosuppressive regimens include but are not limited to systemic corticosteroids (e.g., methylprednisolone). Therapies for B cell depletion include intravenous immunoglobulin (IVIG) by established clinical dosing guidelines to restore normal levels of serum immunoglobulin levels. In some embodiments, prior to administration of the CAR-T cell therapy of the present invention, the subject may optionally be subjected to a lymphodepleting regimen. One example of a such lymphodepleting regimen consists of the administration to the subject of fludarabine (30 mg/m$^2$ intravenous daily for 4 days) and cyclophosphamide (500 mg/m$^2$ IV daily for 2 days starting with the first dose of fludarabine).

Engineered hoCD122 cells can be provided in pharmaceutical compositions suitable for therapeutic use, e.g. for human treatment. Therapeutic formulations comprising such cells can be frozen, or prepared for administration with physiologically acceptable carriers, excipients or stabilizers (Remington's Pharmaceutical Sciences 16th edition, Osol, A. Ed. (1980)), in the form of aqueous solutions. The hoCD122 cells will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The hoCD122 cells can be administered by any suitable means, usually parenteral. Parenteral infusions include intramuscular, intravenous (bolus or slow infusion), intraarterial, intraperitoneal, intrathecal or subcutaneous administration. In the typical practice, the engineered T cells are infused to the subject in a physiologically acceptable medium, normally intravascularly, although they may also be introduced into any other convenient site, where the cells may find an appropriate site for growth. Usually, at least $1 \times 10^5$ cells/kg will be administered, at least $1 \times 10^6$ cells/kg, at least $1 \times 10^7$ cells/kg, at least $1 \times 10^8$ cells/kg, at least $1 \times 10^9$ cells/kg, or more, usually being limited by the number of T cells that are obtained during collection.

For example, typical ranges for the administration of cells modified to express the a orthogonal hCD122 receptor for use in the practice of the present invention range from about $1 \times 10^5$ to $5 \times 10^8$ viable cells per kg of subject body weight per course of therapy. Consequently, adjusted for body weight, typical ranges for the administration of viable cells in human subjects ranges from approximately $1 \times 10^6$ to approximately $1 \times 10^{13}$ viable cells, alternatively from approximately $5 \times 10^6$ to approximately $5 \times 10^{12}$ viable cells, alternatively from approximately $1 \times 10^7$ to approximately $1 \times 10^{12}$ viable cells, alternatively from approximately $5 \times 10^7$ to approximately $1 \times 10^{12}$ viable cells, alternatively from approximately $1 \times 10^8$ to approximately $1 \times 10^{12}$ viable cells, alternatively from approximately $5 \times 10^8$ to approximately $1 \times 10^{12}$ viable cells, alternatively from approximately $1 \times 10^9$ to approximately $1 \times 10^{12}$ viable cells per course of therapy. In one embodiment, the dose of the cells is in the range of $2.5$-$5 \times 10^9$ viable cells per course of therapy.

A course of therapy with an hIL2 ortholog and/or hoCD122 cell may comprise a single dose or in multiple doses over a period of time. In some embodiments, the hoCD122 cells are administered in a single dose. In some embodiments, the hoCD122 cells are administered in two or more split doses administered over a period of 1, 2, 3, 4, 5, 6, 7, 8, 9, 10, 11, 12, 13, 14, 21, 28, 30, 60, 90, 120 or 180 days. The quantity of engineered hoCD122 cells administered in such split dosing protocols may be the same in each administration or may be provided at different levels. Multi-day dosing protocols over time periods may be provided by the skilled artisan (e.g. physician) monitoring the administration of the cells taking into account the response of the subject to the treatment including adverse effects of the treatment and their modulation as discussed above.

The compositions and methods of the present disclosure also provide a method for the treatment of a subject with a hoCD122 cell therapy (especially CAR T cell therapy) in the absence of prior lymphodepletion. Lymphodepletion is typically performed in a subject in conjunction with CAR T cell therapy because the subsequent administration of the mixed cell population and the administration of non-specific agents (e.g. hIL2) to expand the engineered cell population in the subject in combination with the administration of the cell therapy product acts results in significant systemic toxicity (including cytokine release syndrome or "cytokine storm") arising from the widespread proliferation and activation of immune cells by administration of agents that result in widespread activation as well as the presence of a substantial fraction of non-engineered cells in the cell therapy product itself. The methods and compositions of the present disclosure obviate this significant hurdle by both (or either) providing a substantially purified population of engineered cells largely devoid of contamination by non-engineered cells when the foregoing ex vivo method is employed and/or the selective activation and expansion of the engineered T cells with the hIL2 orthologs of the present invention which provide substantially reduced off-target effects of non-specific proliferative agents such as IL2.

For example, in the current clinical practice of CAR-T cell therapy, CAR-T cells are commonly administered in combination with lymphodepletion (e.g. by administration of Alemtuzumab (monoclonal anti-CD52), purine analogs, and the like) to facilitate expansion of the CAR-T cells to prior to host immune recovery. In some embodiments, the CAR-T cells may be modified for resistance to Alemtuzumab. In one aspect of the invention, the lymphodepletion currently employed in association with CAR-T therapy may be obviated or reduced by the orthogonal ligand expressing CAR-Ts of the present invention. As noted above, the lymphodepletion is commonly employed to enable expansion of the CAR-T cells. However, the lymphodepletion is also associated with major side effects of CAR-T cell therapy. Because the orthogonal ligand provides a means to selectively expand a particular T-cell population, the need for lymphodepletion prior to administration of the orthogonal ligand expressing CAR-Ts may be reduced. The present invention enables the practice of CAR-T cell therapy without or with reduced lymphodepletion prior to administration of the orthogonal ligand expressing CAR-Ts. In one embodiment, the present disclosure provides a method of treating a subject suffering from a disease, disorder or condition amendable to treatment with CAR-T cell therapy (e.g. cancer) by the administration of a orthogonal ligand expressing CAR-Ts in the absence of lymphodepletion prior to administration of the orthogonal ligand CAR-Ts.

In one embodiment, the present disclosure provides for a method of treatment of a mammalian subject suffering from a neoplastic disease, the method comprising the steps of (a) obtaining a biological sample comprising T-cells from the individual; (b) enriching the biological sample for the presence of T-cells; (c) transfecting the T-cells with one or more expression vectors comprising a nucleic acid sequence encoding a CAR and a nucleic acid sequence encoding an orthogonal hCD122 receptor, the antigen targeting domain of the CAR being capable of binding to at least one antigen present on a neoplastic cell; (d) contacting the population cells comprising the orthogonal receptor expressing CAR-T cells ex vivo with an hIL2 ortholog such that the population of cells is enriched for the hoCD122 expressing CAR T cells, (e) administering a pharmaceutically effective amount of the orthogonal receptor expressing CAR-T cells to the mammal; and (f) modulating the growth of the orthogonal hCD122 receptor expressing CAR-T cells by the administration of a therapeutically effective amount of an hIL2 ortholog that binds selectively to the orthogonal hCD122 receptor expressed on the CAR-T cell. In the foregoing method, when the nucleic acid sequences encoding the CAR and the orthogonal hCD122 receptor are provided on the same vector, the sequences may optionally be provided in polycistronic format the nucleic acid sequences separated by an intervening sequence such as IRES or T2A sequence. In one embodiment, the foregoing method is associated with lymphodepletion or immunosuppression of the mammal prior to the initiation of the course of CAR-T cell therapy. In another embodiment, the foregoing method is practiced in the absence of lymphodepletion and/or immunosuppression of the mammal.

Administration of Viral or Non-Viral Vectors Encoding the hIL2 Ortholog:

Alternative to the administration of a hIL2 ortholog protein, the hIL2 ortholog may be provided to a subject by the administration of a nucleic acid construct encoding the hIL2 ortholog to the subject to achieve continuous exposure of the subject to the selective hIL2 ortholog. The administration of a recombinant vector encoding the hIL2 ortholog provides for extended delivery of the hIL2 ortholog to the subject and prolonged activation of the corresponding cells engineered to express the cognate orthogonal receptor associated with such hIL2 ortholog.

Non-Viral Vectors:

In one embodiment, the hIL2 ortholog may be administered to a subject in the form of nucleic acid expression construct for the hIL2 ortholog in a non-viral vector may be provided in a non-viral delivery system. Non-viral delivery systems are typically complexes to facilitate transduction of the target cell with a nucleic acid cargo wherein the nucleic acid is complexed with agents such as cationic lipids (DOTAP, DOTMA), surfactants, biologicals (gelatin, chitosan), metals (gold, magnetic iron) and synthetic polymers (PLG, PEI, PAMAM). Numerous embodiments of non-viral delivery systems are well known in the art including lipidic vector systems (Lee et al. (1997) Critical Reviews of Therapeutic Drug Carrier Systems 14:173-206); polymer coated liposomes (Marin et al., U.S. Pat. No. 5,213,804, issued May 25, 1993; Woodle, et al., U.S. Pat. No. 5,013,556, issued May 7, 1991); cationic liposomes (Epand et al., U.S. Pat. No. 5,283,185, issued Feb. 1, 1994; Jessee, J. A., U.S. Pat. No. 5,578,475, issued Nov. 26, 1996; Rose et al, U.S. Pat. No. 5,279,833, issued Jan. 18, 1994; Gebeyehu et al., U.S. Pat. No. 5,334,761, issued Aug. 2, 1994). In one embodiment, the nucleic acid sequence in the non-viral vector system encoding the hIL2 receptor is under control of a regulatable promoter, inducible promoter, tissue specific or tumor specific promoter, or temporally regulated promoter.

Viral Vectors:

In another embodiment, hIL2 ortholog may be administered to a subject in the form of nucleic acid expression construct in viral vector encoding the hIL2 ortholog. The terms "viral vector" and "virus" are used interchangeably herein to refer to any of the obligate intracellular parasites having no protein-synthesizing or energy-generating mechanism. The viral genome may be RNA or DNA contained with a coated structure of protein of a lipid membrane. The terms virus(es) and viral vector(s) are used interchangeably herein. The viruses useful in the practice of the present invention include recombinantly modified enveloped or nonenveloped DNA and RNA viruses, preferably selected from baculoviridiae, parvoviridiae, picornoviridiae, herpesviridiae, poxviridae, or adenoviridiae. The viruses are modified by recombinant DNA techniques to include expression of exogenous transgenes (e.g. a nucleic acid sequence encoding the hIL2 ortholog) and may be engineered to be replication deficient, conditionally replicating or replication competent. Minimal vector systems in which the viral backbone contains only the sequences need for packaging of the viral vector and may optionally include a transgene expression cassette may also be employed. The term "replication deficient" refers to vectors that are highly attenuated for replication in a wild type mammalian cell. In order to produce such vectors in quantity, a producer cell line is generally created by co-transfection with a helper virus or genomically modified to complement the missing functions. The term "replication competent viral vectors" refers to a viral vector that is capable of infection, DNA replication, packaging and lysis of an infected cell. The term "conditionally replicating viral vectors" is used herein to refer to replication competent vectors that are designed to achieve selective expression in particular cell types. Such conditional replication may be achieved by operably linking tissue specific, tumor specific or cell type specific or other selectively induced regulatory control sequences to early genes (e.g., the E1 gene of adenoviral vectors). Infection of the subject with the recombinant virus or non-viral vector can provide for long term expression of the hIL2 ortholog in the subject and provide continuous selective maintenance of the engineered T cells expressing the hCD122 orthogonal receptor. In one embodiment, the nucleic acid sequence in the viral vector system encoding the hIL2 ortholog is under control of a regulatable promoter, inducible promoter, tissue specific or tumor specific promoter, or temporally regulated promoter.

Therapeutic Combinations:

The compositions and methods of the present disclosure may be combined with additional therapeutic agents. For example, when the disease, disorder or condition to be treated is a neoplastic disease (e.g. cancer) the methods of the present disclosure may be combined with conventional chemotherapeutic agents or other biological anti-cancer drugs such as checkpoint inhibitors (e.g. PD1 or PDL1 inhibitors) or therapeutic monoclonal antibodies (e.g. Avastin, Herceptin).

Examples of chemical agents identified in the art as useful in the treatment of neoplastic disease, include without limitation, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon.

The compositions of the present disclosure may be administered in combination with one or more additional therapeutic agents selected from the group consisting of tyrosine-kinase inhibitors, such as Imatinib mesylate (marketed as Gleevec®, also known as STI-571), Gefitinib (Iressa®, also known as ZD1839), Erlotinib (marketed as Tarceva®), Sorafenib (Nexavar®), Sunitinib (Sutent®), Dasatinib (Sprycel®), Lapatinib (Tykerb®), Nilotinib (Tasigna®), and Bortezomib (Velcade®), Jakafi® (ruxolitinib); Janus kinase inhibitors, such as tofacitinib; ALK inhibitors, such as crizotinib; Bcl-2 inhibitors, such as obatoclax, venclexta, and gossypol; FLT3 inhibitors, such as midostaurin (Rydapt®), IDH inhibitors, such as AG-221, PARP inhibitors, such as Iniparib and Olaparib; PI3K inhibitors, such as perifosine; VEGF Receptor 2 inhibitors, such as Apatinib; AN-152 (AEZS-108) doxorubicin linked to [D-Lys(6)]-LHRH; Braf inhibitors, such as vemurafenib, dabrafenib, and LGX818; MEK inhibitors, such as trametinib; CDK inhibitors, such as PD-0332991 and LEE011; Hsp90 inhibitors, such as salinomycin; and/or small molecule drug conjugates, such as Vintafolide; serine/threonine kinase inhibitors, such as Temsirolimus (Torisel®), everolimus (Afinitor®), Vemurafenib (Zelboraf®), Trametinib (Mekinist), and Dabrafenib (Tafinlar®).

In some embodiments, particularly where the tumor antigen binding portion of the CAR is directed against BCMA, the engineered CAR-T cell is administered in combination with a γ-Secretase Inhibitor (GSI) as described in Pont, et al. (2019) "γ-secretase inhibition increases efficacy of BCMA-specific chimeric antigen receptor T cells in multiple myeloma" Blood https://doi.org/10.1182/blood.2019000050.

Examples of biological agents identified in the art as useful in the treatment of neoplastic disease, include without limitation, cytokines or cytokine antagonists such as IL-12, INFα, or anti-epidermal growth factor receptor, radiotherapy, irinotecan; tetrahydrofolate antimetabolites such as pemetrexed; antibodies against tumor antigens, a complex of a monoclonal antibody and toxin, a T-cell adjuvant, bone marrow transplant, or antigen presenting cells (e.g., dendritic cell therapy), anti-tumor vaccines, replication competent viruses, signal transduction inhibitors (e.g., Gleevec® or Herceptin®) or an immunomodulator to achieve additive or synergistic suppression of tumor growth, cyclooxygenase-2 (COX-2) inhibitors, steroids, TNF antagonists (e.g., Remicade® and Enbrel®), interferon-β1a (Avonex®), and interferon-β1b (Betaseron®) as well as combinations of one or more of the foregoing as practiced in known chemotherapeutic treatment regimens readily appreciated by the skilled clinician in the art.

Tumor specific monoclonal antibodies that can be administered in combination with an engineered cell may include, without limitation, Rituximab (marketed as MabThera or Rituxan), Alemtuzumab, Panitumumab, Ipilimumab (Yervoy), etc.

In some embodiments the compositions and methods of the present disclosure may be combined with immune checkpoint therapy. Examples of immune checkpoint therapies include inhibitors of the binding of PD1 to PDL1 and/or PDL2. PD1 to PDL1 and/or PDL2 inhibitors are well known in the art. Examples of commercially available monoclonal antibodies that interfere with the binding of PD1 to PDL1 and/or PDL2 include nivolumab (Opdivo®, BMS-936558, MDX1106, commercially available from BristolMyers Squibb, Princeton N.J.), pembrolizumab (Keytruda®MK-3475, lambrolizumab, commercially available from Merck and Company, Kenilworth N.J.), and atezolizumab (Tecentriq®, Genentech/Roche, South San Francisco Calif.). Additional examples of PD1 inhibitory antibodies include but are not limited to durvalumab (MEDI4736, Medimmune/AstraZeneca), pidilizumab (CT-011, CureTech), PDR001 (Novartis), BMS-936559 (MDX1105, Bristol Myers Squibb), and avelumab (MSB0010718C, Merck Serono/Pfizer) and SHR-1210 (Incyte). Additional antibody PD1 pathway inhibitors are described in U.S. Pat. No. 8,217,149 (Genentech, Inc) issued Jul. 10, 2012; U.S. Pat. No. 8,168,757 (Merck Sharp and Dohme Corp.) issued May 1, 2012, U.S. Pat. No. 8,008,449 (Medarex) issued Aug. 30, 2011, U.S. Pat. No. 7,943,743 (Medarex, Inc) issued May 17, 2011. Additionally, small molecule PD1 to PDL1 and/or PDL2 inhibitors are known in the art. See, e.g. Sasikumar, et al as WO2016142833A1 and Sasikumar, et al. WO2016142886A2, BMS-1166 and BMS-1001 (Skalniak, et al (2017) Oncotarget 8(42): 72167-72181).

The invention now being fully described, it will be apparent to one of ordinary skill in the art that various

EXAMPLES

The following examples are presented in order to more fully illustrate the preferred embodiments of the invention. They should in no way, however, be construed as limiting the broad scope of the invention.

Example 1. Generation of the Human IL2 Expression Vector pcDNA3.1/Hygro(+)-huIL2

The human IL2 DNA ORF (Genbank NM_000586.3) was synthesized (Life Technologies GeneArt Service, Carlsbad, Calif.), and amplified via PCR using Platinum SuperFi II DNA polymerase kit (item #12361050, ThermoFisher) following the manufacturer's protocol, and using primers:

```
                                      (SEQ ID NO: 153)
5' TATAGTCAGCGCCACcCATGTACAGGATGCAACTCCTGTC 3'
``` which incorporates and NheI restriction site, and

```
                                      (SEQ ID NO: 154)
5' TATAGGGCCCTATCAAGTCAGTGTTGAGATG 3'
``` which incorporates an ApaI restriction site. The PCR fragment was visualized on a 1% agarose gel (item #54803, Lonza, Rockland, Me.), excised from the gel and purified using a QIAquick PCR Purification kit (item #28106, Qiagen, Germany) according to the manufacturer's protocol. The purified PCR fragment and mammalian expression vector pcDNA 3.1/Hygro(+) (#V87020, ThermoFisher) were digested with NheI and ApaI (#R0111S and #R0114L, New England Biolabs, Ipswich, Mass.) restriction enzymes. The expression vector was further treated with a Quick Dephosphorylation kit (#M0508L, New England Biolabs) according to the manufacturer's protocol. The PCR fragment was ligated into pcDNA 3.1/Hygro(+) using the Rapid DNA Ligation Kit (#11635379001, Sigma Aldrich, St. Louis, Mo.) following the manufacturer's protocol, transformed into One Shot TOP10 Chemically Competent E. coli (#C404006, Life Technologies, Carlsbad, Calif.), plated onto LB Agar plates containing 100 ug/ml carbenicillin (#L1010, Teknova, Hollister, Calif.), and grown overnight at 37 C.

The following day individual bacterial colonies were picked and used to start a 3 ml bacterial culture in LB Broth (#10855-001, Life Technologies) with 100 ug/ml ampicillin (#A9626, Teknova). The cultures were grown overnight at 37 C.

The following day the E. coli were pelleted (6,000 rpm, 10 minutes, tabletop centrifuge #5424, Eppendorf, Hauppauge, N.Y.), and the DNA expression vector isolated using QIAprep Spin Miniprep Kit (#27106, Qiagen). The plasmid DNA was sequence verified (MCLab, South San Francisco, Calif.).

Example 2. Generation of the Human IL2 ORTHO Expression Vector pcDNA3.1/Hygro(+)-huIL2-ORTHO An expression vector which introduced six mutations into the human IL2 ORF (E35S, H36Q, L39V, D40L, Q42K and M43A; all numbering is based on the full length human IL2 ORF NM 000586.3 numbering) was assembled in substantial accordance with the teaching of Example 1 for the human IL2 expression vector in pcDNA3.1/Hygro(+), with the following exceptions: The initial template DNA used for PCR was synthesized with the E35S, H36Q, L39V, D40L, Q42K and M43A mutations.

Example 3. Introduction of Mutations into pcDNA3.1/Hygro(+)-huIL2 or Back-Mutations into pcDNA3.1/Hygro(+)-huIL2 IRTHO Expression Vectors All mutations or back-mutations (reverting a mutation in pcDNA3.1/hygro(+)-huIL2-ORTHO back to match the wild type human IL2 ORF) were introduced into the pcDNA3.1/Hygro(+)-huIL2 or pcDNA3.1/Hygro(+)-huIL2-ORTHO expression vectors using a Quik Change II Site Directed Mutagenesis Kit (#200524, Agilent Technologies, Santa Clara, Calif.) in substantial accordance with the manufacturer's protocol.

Table 5 lists the mutations generated, the template into which the mutation was introduced, and the primer sets used to introduce the mutation. The transformation of the Quik Change PCR reactions into E. coli, as well as the isolation and sequence analysis of the plasmid DNA, was performed using substantially the same protocol as in the generation of the pcDNA3.1/Hygro-huIL2 expression vector. The abbreviations for the templates are: Template 1=pcDNA3.1/hygro(+)-huIL2; Template 2=pcDNA3.1/Hygro(+)-huIL2 ORTHO.

TABLE 5

QuikChange Mutagenesis and Sequence Information Regarding Mutations

| Ref# | Name | Modifications Relative wthIL2 | Primer Set Sequences 5' → 3' | Template |
|---|---|---|---|---|
| 5 | -QVLKA | H16Q L19V D20L Q22K M23A | CAAAGAAAACACAGCTACAACTGGAGCAGTTACTGG TGCTCTTAAAGGC (SEQ ID NO: 155) GCCTTTAAGAGCACCAGTAACTGCTCCAGTTGTAGCT GTGTTTTCTTTG (SEQ ID NO: 156) | 2 |
| 6 | S-VLKA | E15S L19V D20L Q22K M23A | CAGCTACAACTGAGCCATTTACTGGTGCTCTTAAA (SEQ ID NO: 157) TTTAAGAGCACCAGTAAATGGCTCAGTTGTAGCTG (SEQ ID NO: 158) | 2 |
| 7 | SQ-LKA | E15S H16Q D20L Q22K M23A | CTGAGCCAGTTACTGCTGCTCTTAAAGGCC (SEQ ID NO: 159) GGCCTTTAAGAGCAGCAGTAACTGGCTCAG (SEQ ID NO: 160) | 2 |

TABLE 5-continued

QuikChange Mutagenesis and Sequence Information Regarding Mutations

| Ref# | Name | Modifications Relative wthIL2 | Primer Set Sequences 5' → 3' | Template |
|---|---|---|---|---|
| 8 | SQV-KA | E15S H16Q L19V Q22K M23A | AACTGAGCCAGTTACTGGTGGATTTAAAGGCCATTTT GAATG(SEQ ID NO: 161) CATTCAAAATGGCCTTTAAATCCACCAGTAACTGGCT CAGTT (SEQ ID NO: 162) | 2 |
| 9 | SQVL-A | E15SH16Q L19V D20L M23A | TGAGCCAGTTACTGGTGCTCTTACAGGCCATTTTGA (SEQ ID NO: 163) TCAAAATGGCCTGTAAGAGCACCAGTAACTGGCTCA (SEQ ID NO: 164) | 2 |
| 10 | SQVLK- | E15S H16Q L19V D20L Q22K | CTGGTGCTCTTAAAGATGATTTTGAATGGAATTAA (SEQ ID NO: 165) TTAATTCCATTCAAAATCATCTTTAAGAGCACCAG (SEQ ID NO: 166) | 2 |
| 11 | S----- | E15S | CACAGCTACAACTGTCGCATTTACTGCTGG (SEQ ID NO: 167) CCAGCAGTAAATGCGACAGTTGTAGCTGTG (SEQ ID NO: 168) | 1 |
| 12 | -Q----- | H16Q | GCTACAACTGGAGCAGTTACTGCTGGATTTAC (SEQ ID NO: 169) GTAAATCCAGCAGTAACTGCTCCAGTTGTAGC (SEQ ID NO: 170) | 1 |
| 13 | --V--- | L19V | CTGGAGCATTACTGGTGGATTTACAGATGATTTTG (SEQ ID NO: 171) CAAAATCATCTGTAAATCCACCAGTAATGCTCCAG (SEQ ID NO: 172) | 1 |
| 14 | ---L-- | D20L | GAGCATTACTGCTGCTATTACAGATGATTTTG (SEQ ID NO: 173) CAAAATCATCTGTAATAGCAGCAGTAAATGCTC (SEQ ID NO: 174) | 1 |
| 15 | ----K- | Q22K | CATTTACTGCTGGATTTAAAGATGATTTTGAATGG (SEQ ID NO: 175) CCATTCAAAATCATCTTTAAATCCAGCAGTAAATG (SEQ ID NO: 176) | 1 |
| 16 | -----A | M23A | CTGGAGCATTTACTGCTGGATTTACAGGCGATTTTGA ATGGAATTAATAATTACA (SEQ ID NO: 177) TGTAATTATTAATTCCATTCAAAATCGCCTGTAAATC CAGCAGTAAATGCTCCAG (SEQ ID NO: 178) | 1 |
| 17 | SQ---- | E15S H16Q | CAAAGAAAACACAGCTACAACTGAGCCAGTTACTGC TGGATTTACAGATG (SEQ ID NO: 179) CATCTGTAAATCCAGCAGTAACTGGCTCAGTTGTAGC TGTGTTTTCTTTG (SEQ ID NO: 180) | 1 |
| 18 | SQVL-- | E15S H16Q L19V D20L | CCATTCAAAATCATCTGTAAGAGCACCAGTAACTGGC TCAGTTGTAGCTG (SEQ ID NO: 181) CAACTGAGCCAGTTACTGGTGCTCTTAAAGGCCATTT TGAATGGAATTAATAATTACAAG (SEQ ID NO: 182) | 1 |
| 20 | ΔA1, SQVLKA | desA1 E15S H16Q L19V D20L Q22K M23A | CTTGTCACAAACAGTCCTACTTCAAGTTC (SEQ ID NO: 183) GAACTTGAAGTAGGACTGTTTGTGACAAG (SEQ ID NO: 184) | 2 |
| 21 | ΔP2, SQVLKA | desP2E15S H16QL19V D20L Q22K M23A | CACAAACAGTGCAACTTCAAGTTCTAC (SEQ ID NO: 185) GTAGAACTTGAAGTTGCACTGTTTGTG (SEQ ID NO: 186) | 2 |
| 018 | ΔT3, SQVLKA | desT3 E15S H16QL19V D20L Q22K M23A | CAAACAGTGCACCTTCAAGTTCTACAAAG (SEQ ID NO: 187) CTTTGTAGAACTTGAAGGTGCACTGTTTG (SEQ ID NO: 188) | 2 |
| 019 | T3C, SQVLKA | T3C E15S H16Q L19V D20L Q22K M23A | CAAACAGTGCACCTTGTTCAAGTTCTACA (SEQ ID NO: 189) TGTAGAACTTGAACAAGGTGCACTGTTTG (SEQ ID NO: 190) | 2 |

TABLE 5-continued

QuikChange Mutagenesis and Sequence Information Regarding Mutations

| Ref# | Name | Modifications Relative wthIL2 | Primer Set Sequences 5' → 3' | Template |
|---|---|---|---|---|
| 020 | T3A, SQVLKA | T3A E15S H16Q L19V D20L Q22K M23A | CAAACAGTGCACCTGCTTCAAGTTCTAC (SEQ ID NO: 191) GTAGAACTTGAAGCAGGTGCACTGTTTG (SEQ ID NO: 192) | 2 |
| 021 | T3G, SQVLKA | T3G E15S H16Q L19V D20L Q22K M23A | CAAACAGTGCACCTGGTTCAAGTTCTAC (SEQ ID NO: 193) GTAGAACTTGAACCAGGTGCACTGTTTG (SEQ ID NO: 194) | 2 |
| 022 | T3Q, SQVLKA | T3Q E15S H16 QL19V D20L Q22K M23A | CAAACAGTGCACCTCAGTCAAGTTCTACAAAG (SEQ ID NO: 195) CTTTGTAGAACTTGACTGAGGTGCACTGTTTG (SEQ ID NO: 196) | 2 |
| 023 | T3E, SQVLKA | T3E E15S H16Q L19V D20L Q22K M23A | CAAACAGTGCACCTGAGTCAAGTTCTACAAAG (SEQ ID NO: 197) CTTTGTAGAACTTGACTCAGGTGCACTGTTTG (SEQ ID NO: 198) | 2 |
| 024 | T3N, SQVLKA | T3N E15S H16Q L19V D20L Q22K M23A | CAAACAGTGCACCTAATTCAAGTTCTACAAAG (SEQ ID NO: 199) CTTTGTAGAACTTGAATTAGGTGCACTGTTTG (SEQ ID NO: 200) | 2 |
| 025 | T3D, SQVLKA | T3D E15S H16Q L19V D20L Q22K M23A | AAACAGTGCACCTGATTCAAGTTCTACAAAG (SEQ ID NO: 201) CTTTGTAGAACTTGAATCAGGTGCACTGTTTG (SEQ ID NO: 202) | 2 |
| 026 | T3R, SQVLKA | T3R E15S H16Q L19V D20L Q22K M23A | CAAACAGTGCACCTAGGTCAAGTTCTACAAAG (SEQ ID NO: 203) CTTTGTAGAACTTGACCTAGGTGCACTGTTTG (SEQ ID NO: 204) | 2 |
| 027 | T3K, SQVLKA | T3K E15S H16Q L19V D20L Q22K M23A | CAAACAGTGCACCTAAGTCAAGTTCTACAAAG (SEQ ID NO: 205) CTTTGTAGAACTTGACTTAGGTGCACTGTTTG (SEQ ID NO: 206) | 2 |
| 028 | T3P, SQVLKA | T3P E15S H16Q L19V D20L Q22K M23A | CAAACAGTGCACCTCCTTCAAGTTCTAC (SEQ ID NO: 207) GTAGAACTTGAAGGAGGTGCACTGTTTG (SEQ ID NO: 208) | 2 |
| 029 | ΔS4, SQVLKA | desS4 E15S H16Q L19V D20L Q22K M23A | CAGTGCACCTACTAGTTCTACAAAGA (SEQ ID NO: 209) TCTTTGTAGAACTAGTAGGTGCACTG (SEQ ID NO: 210) | 2 |
| 030 | ΔS5, SQVLKA | desS5 E15S H16Q L19V D20L Q22K M23A | GTGCACCTACTTCATCTACAAAGAAAAC (SEQ ID NO: 211) GTTTTCTTTGTAGATGAAGTAGGTGCAC (SEQ ID NO: 212) | 2 |
| 031 | ΔS6, SQVLKA | desS6 E15S H16Q L19V D20L Q22K M23A | CACCTACTTCAAGTACAAAGAAAACACAG (SEQ ID NO: 213) CTGTGTTTTCTTTGTACTTGAAGTAGGTG (SEQ ID NO: 214) | 2 |
| 032 | ΔT7, SQVLKA | desT7 E15S H16Q L19V D20L Q22K M23A | CTACTTCAAGTTCTAAGAAAACACAGCT (SEQ ID NO: 215) AGCTGTGTTTTCTTAGAACTTGAAGTAG (SEQ ID NO: 216) | 2 |
| 033 | ΔK8, SQVLKA | desK8 E15S H16Q L19V D20L Q22K M23A | CTTCAAGTTCTACAAAAACACAGCTACAAC (SEQ ID NO: 217) GTTGTAGCTGTGTTTTTGTAGAACTTGAAG (SEQ ID NO: 218) | 2 |

TABLE 5-continued

QuikChange Mutagenesis and Sequence Information Regarding Mutations

| Ref# | Name | Modifications Relative wthIL2 | Primer Set Sequences 5' → 3' | Template |
|---|---|---|---|---|
| 034 | ΔK9, SQVLKA | desK9 E15S H16Q L19V D20L Q22K M23A | CAAGTTCTACAAAGACACAGCTACAACTG (SEQ ID NO: 219)<br>CAGTTGTAGCTGTGTCTTTGTAGAACTTG (SEQ ID NO: 220) | 2 |
| 035 | ΔQ13, SQVLKA | desQ13 E15S H16Q L19V D20L Q22K M23A | GAAAACACAGCTACTGAGCCAGTTACTG (SEQ ID NO: 221)<br>CAGTAACTGGCTCAGTAGCTGTGTTTTC (SEQ ID NO: 222) | 2 |
| 036 | Q13W SQVLKA | Q13W E15S H16Q L19V D20L Q22K M23A | GAAAACACAGCTATGGCTGAGCCAGTTAC (SEQ ID NO: 223)<br>GTAACTGGCTCAGCCATAGCTGTGTTTTC (SEQ ID NO: 224) | 2 |
| 037 | ΔL14, SQVLKA | desL14 E15S H16Q L19V D20L Q22K M23A | AAACACAGCTACAAAGCCAGTTACTGGTGC (SEQ ID NO: 225)<br>GCACCAGTAACTGGCTTTGTAGCTGTGTTT (SEQ ID NO: 226) | 2 |
| 038 | L14M, SQVLKA | L14M E15S H16Q L19V D20L Q22K M23A | AAACACAGCTACAAATGAGCCAGTTACTG (SEQ ID NO: 227)<br>CAGTAACTGGCTCATTTGTAGCTGTGTTT (SEQ ID NO: 228) | 2 |
| 039 | L14W, SQVLKA | L14W E15S H16Q L19V D20L Q22K M23A | AAACACAGCTACAATGGAGCCAGTTACTGG (SEQ ID NO: 229)<br>CCAGTAACTGGCTCCATTGTAGCTGTGTTT (SEQ ID NO: 230) | 2 |
| 041 | KQVLKA | E15K H16Q L19V D20L Q22K M23A | CACAGCTACAACTGAAGCAGTTACTGGTGC (SEQ ID NO: 231)<br>GCACCAGTAACTGCTTCAGTTGTAGCTGTG (SEQ ID NO: 232) | 2 |
| 043 | TQVLKA | E15T H16Q L19V D20L Q22K M23A | CACAGCTACAACTGACCCAGTTACTGGTGCTC (SEQ ID NO: 233)<br>GAGCACCAGTAACTGGGTCAGTTGTAGCTGTG (SEQ ID NO: 234) | 2 |
| 047 | ΔH16, S_VLKA | desH16 E15S L19V D20L Q22K M23A | GCTACAACTGAGCTTACTGGTGCTCTTA (SEQ ID NO: 235)<br>TAAGAGCACCAGTAAGCTCAGTTGTAGC (SEQ ID NO: 236) | 2 |
| 048 | SNVLKA | E15S H16N L19V D20L Q22K M23A | GCTACAACTGAGCAACTTACTGGTGCTC (SEQ ID NO: 237)<br>GAGCACCAGTAAGTTGCTCAGTTGTAGC (SEQ ID NO: 238) | 2 |
| 050 | L18G, SQVLKA | E15S H16Q L18G L19V D20L Q22K M23A | AACTGAGCCAGTTAGGGGTGCTCTTAAAGG (SEQ ID NO: 239)<br>CCTTTAAGAGCACCCCTAACTGGCTCAGTT (SEQ ID NO: 240) | 2 |
| 051 | L18M, SQVLKA | E15S H16Q L18M L19V D20L Q22K M23A | CAACTGAGCCAGTTAATGGTGCTCTTAAAGGC (SEQ ID NO: 241)<br>GCCTTTAAGAGCACCATTAACTGGCTCAGTTG (SEQ ID NO: 242) | 2 |
| 052 | L18F, SQVLKA | E15S H16Q L18F L19V D20L Q22K M23A | AACTGAGCCAGTTATTCGTGCTCTTAAAGGC (SEQ ID NO: 243)<br>GCCTTTAAGAGCACGAATAACTGGCTCAGTT (SEQ ID NO: 244) | 2 |
| 053 | L18E, SQVLKA | E15S H16Q L18E L19V D20L Q22K M23A | CAACTGAGCCAGTTAGAGGTGCTCTTAAAGGC (SEQ ID NO: 245)<br>GCCTTTAAGAGCACCTCTAACTGGCTCAGTTG (SEQ ID NO: 246) | 2 |

TABLE 5-continued

QuikChange Mutagenesis and Sequence Information Regarding Mutations

| Ref# | Name | Modifications Relative wthIL2 | Primer Set Sequences 5' → 3' | Template |
|---|---|---|---|---|
| 054 | L18H, SQVLKA | E15S H16Q L18H L19V D20L Q22K M23A | ACTGAGCCAGTTACACGTGCTCTTAAAGGC (SEQ ID NO: 247) GCCTTTAAGAGCACGTGTAACTGGCTCAGT (SEQ ID NO: 248) | 2 |
| 055 | L18W, SQVLKA | E15S H16Q L18W L19V D20L Q22K M23A | AACTGAGCCAGTTATGGGTGCTCTTAAAGG (SEQ ID NO: 249) CCTTTAAGAGCACCCATAACTGGCTCAGTT (SEQ ID NO: 250) | 2 |
| 056 | L18K, SQVLKA | E15S H16Q L18K L19V D20L Q22K M23A | CAACTGAGCCAGTTAAAGGTGCTCTTAAAGGC (SEQ ID NO: 251) GCCTTTAAGAGCACCTTTAACTGGCTCAGTTG (SEQ ID NO: 252) | 2 |
| 057 | L18Q, SQVLKA | E15S H16Q L18Q L19V D20L Q22K M23A | CTGAGCCAGTTACAGGTGCTCTTAAAG (SEQ ID NO: 253) CTTTAAGAGCACCTGTAACTGGCTCAG (SEQ ID NO: 254) | 2 |
| 058 | L18S, SQVLKA | E15S H16Q L18S L19V D20L Q22K M23A | CAACTGAGCCAGTTAAGCGTGCTCTTAAAGGC (SEQ ID NO: 255) GCCTTTAAGAGCACGCTTAACTGGCTCAGTTG (SEQ ID NO: 256) | 2 |
| 059 | L18V, SQVLKA | E15S H16Q L18V L19V D20L Q22K M23A | CAACTGAGCCAGTTAGTGGTGCTCTTAAAGG (SEQ ID NO: 257) CCTTTAAGAGCACCACTAACTGGCTCAGTTG (SEQ ID NO: 258) | 2 |
| 060 | L18I, SQVLKA | E15S H16Q L18I L19V D20L Q22K M23A | CAACTGAGCCAGTTAATCGTGCTCTTAAAGGC (SEQ ID NO: 259) GCCTTTAAGAGCACGATTAACTGGCTCAGTTG (SEQ ID NO: 260) | 2 |
| 061 | L18Y, SQVLKA | E15S H16Q L18YL19V D20L Q22K M23A | CAACTGAGCCAGTTATACGTGCTCTTAAAGGC (SEQ ID NO: 261) GCCTTTAAGAGCACGTATAACTGGCTCAGTTG (SEQ ID NO: 262) | 2 |
| 062 | L18H, SQVLKA | E15S H16Q L18H L19V D20L Q22K M23A | CTGAGCCAGTTACACGTGCTCTTAAAGG (SEQ ID NO: 263) CCTTTAAGAGCACGTGTAACTGGCTCAG (SEQ ID NO: 264) | 2 |
| 063 | L18D, SQVLKA | E15S H16Q L18D L19V D20L Q22K M23A | CAACTGAGCCAGTTAGACGTGCTCTTAAAGGC (SEQ ID NO: 265) GCCTTTAAGAGCACGTCTAACTGGCTCAGTTG (SEQ ID NO: 266) | 2 |
| 064 | L18T, SQVLKA | E15S H16Q L18T L19V D20L Q22K M23A | CAACTGAGCCAGTTAACGGTGCTCTTAAAGGC (SEQ ID NO: 267) GCCTTTAAGAGCACCGTTAACTGGCTCAGTTG (SEQ ID NO: 268) | 2 |
| 065 | ΔL19, SQ_LKA | desL19 E15S H16Q D20L Q22K M23A | CTGAGCCAGTTACTGCTCTTAAAGGCCATT (SEQ ID NO: 269) AATGGCCTTTAAGAGCAGTAACTGGCTCAG (SEQ ID NO: 270) | 2 |
| 067 | SQILKA | E15S H16Q L19I D20L Q22K M23A | CTGAGCCAGTTACTGATCCTCTTAAAGGCCAT (SEQ ID NO: 271) ATGGCCTTTAAGAGGATCAGTAACTGGCTCAG (SEQ ID NO: 272) | 2 |
| 068 | ΔD20, SQV_KA | desD20 E15S H16Q L19V Q22K M23A | GCCAGTTACTGGTGTTAAAGGCCATTTTG (SEQ ID NO: 273) CAAAATGGCCTTTAACACCAGTAACTGGC (SEQ ID NO: 274) | 2 |
| 070 | SQVSKA | E15S H16Q L19V D20s Q22K M23A | GCCAGTTACTGGTGTCCTTAAAGGCCATTTTG (SEQ ID NO: 275) CAAAATGGCCTTTAAGGACACCAGTAACTGGC (SEQ ID NO:276) | 2 |

TABLE 5-continued

QuikChange Mutagenesis and Sequence Information Regarding Mutations

| Ref# | Name | Modifications Relative wthIL2 | Primer Set Sequences 5' → 3' | Template |
|---|---|---|---|---|
| 073 | SQVLFA | E15S H16Q<br>L19V D20L<br>Q22F M23A | TACTGGTGCTCTTATTCGCCATTTTGAATGG<br>(SEQ ID NO: 277)<br>CCATTCAAAATGGCGAATAAGAGCACCAGTA<br>(SEQ ID NO: 278) | 2 |
| 074 | SQVLEA | E15S H16Q<br>L19V D20L<br>Q22E M23A | TACTGGTGCTCTTAGAGGCCATTTTGAATGG<br>(SEQ ID NO: 279)<br>CCATTCAAAATGGCCTCTAAGAGCACCAGTA<br>(SEQ ID NO: 280) | 2 |
| 075 | SQVLGA | E15S H16Q<br>L19V D20L<br>Q22G M23A | TTACTGGTGCTCTTAGGGGCCATTTTGAATGG<br>(SEQ ID NO: 281)<br>CCATTCAAAATGGCCCCTAAGAGCACCAGTAA<br>(SEQ ID NO: 282) | 2 |
| 076 | SQVLAA | E15S H16Q<br>L19V D20L<br>Q22A M23A | TACTGGTGCTCTTAGCGGCCATTTTGAATG<br>(SEQ ID NO: 283)<br>CATTCAAAATGGCCGCTAAGAGCACCAGTA<br>(SEQ ID NO: 284) | 2 |
| 077 | SQVLLA | E15S H16Q<br>L19V D20L<br>Q22L M23A | TACTGGTGCTCTTACTGGCCATTTTGAATG<br>(SEQ ID NO: 285)<br>CATTCAAAATGGCCAGTAAGAGCACCAGTA<br>(SEQ ID NO: 286) | 2 |
| 078 | SQVLMA | E15S H16Q<br>L19V D20L<br>Q22M M23A | TACTGGTGCTCTTAATGGCCATTTTGAATG<br>(SEQ ID NO: 287)<br>CATTCAAAATGGCCATTAAGAGCACCAGTA<br>(SEQ ID NO: 288) | 2 |
| 079 | SQVLFA | E15S H16Q<br>L19V D20L<br>Q22F M23A | TACTGGTGCTCTTATTCGCCATTTTGAATGG<br>(SEQ ID NO: 289)<br>CCATTCAAAATGGCGAATAAGAGCACCAGTA<br>(SEQ ID NO: 290) | 2 |
| 080 | SQVLWA | E15S H16Q<br>L19V D20L<br>Q22W M23A | TACTGGTGCTCTTATGGGCCATTTTGAATG<br>(SEQ ID NO: 291)<br>CATTCAAAATGGCCCATAAGAGCACCAGTA<br>(SEQ ID NO: 292) | 2 |
| 081 | SQVLSA | E15S H16Q<br>L19V D20L<br>Q22S M23A | TACTGGTGCTCTTAAGCGCCATTTTGAATGG<br>(SEQ ID NO: 293)<br>CCATTCAAAATGGCGCTTAAGAGCACCAGTA<br>(SEQ ID NO: 294) | 2 |
| 082 | SQVLVA | E15S H16Q<br>L19V D20L<br>Q22V M23A | TACTGGTGCTCTTAGTGGCCATTTTGAATG<br>(SEQ ID NO: 295)<br>CATTCAAAATGGCCACTAAGAGCACCAGTA<br>(SEQ ID NO: 296) | 2 |
| 083 | SQVLIA | E15S H16Q<br>L19V D20L<br>Q22I M23A | TACTGGTGCTCTTAATCGCCATTTTGAATGG<br>(SEQ ID NO: 297)<br>CCATTCAAAATGGCGATTAAGAGCACCAGTA<br>(SEQ ID NO: 298) | 2 |
| 084 | SQVLYA,<br>E116G | E15S H16Q<br>L19V D20L<br>Q22Y M23A<br>E116G | TACTGGTGCTCTTATACGCCATTTTGAATGG<br>(SEQ ID NO: 299)<br>CCATTCAAAATGGCGTATAAGAGCACCAGTA<br>(SEQ ID NO: 300) | 2 |
| 085 | SQVLHA | E15S H16Q<br>L19V D20L<br>Q22H M23A | TACTGGTGCTCTTACACGCCATTTTGAATGG<br>(SEQ ID NO: 301)<br>CCATTCAAAATGGCGTGTAAGAGCACCAGTA<br>(SEQ ID NO: 302) | 2 |
| 086 | SQVLRA | E15S H16Q<br>L19V D20L<br>Q22R M23A | TACTGGTGCTCTTACGGGCCATTTTGAATG<br>(SEQ ID NO: 303)<br>CATTCAAAATGGCCCGTAAGAGCACCAGTA<br>(SEQ ID NO: 304) | 2 |

TABLE 5-continued

QuikChange Mutagenesis and Sequence Information Regarding Mutations

| Ref# | Name | Modifications Relative wthIL2 | Primer Set Sequences 5' → 3' | Template |
|---|---|---|---|---|
| 087 | SQVLNA | E15S H16Q<br>L19V D20L<br>Q22N M23A | CTGGTGCTCTTAAACGCCATTTTGAATGG<br>(SEQ ID NO: 305)<br>CCATTCAAAATGGCGTTTAAGAGCACCAG<br>(SEQ ID NO: 306) | 2 |
| 088 | SQVLDA | E15S H16Q<br>L19V D20L<br>Q22D M23A | TACTGGTGCTCTTAGACGCCATTTTGAATGG<br>(SEQ ID NO: 307)<br>CCATTCAAAATGGCGTCTAAGAGCACCAGTA<br>(SEQ ID NO: 308) | 2 |
| 089 | SQVLTA | E15S H16Q<br>L19V D20L<br>Q22T M23A | TACTGGTGCTCTTAACGGCCATTTTGAATGG<br>(SEQ ID NO: 309)<br>CCATTCAAAATGGCCGTTAAGAGCACCAGTA<br>(SEQ ID NO: 310) | 2 |
| 090 | ΔM23,<br>SQVLK- | desM23 E15S<br>H16Q L19V<br>D20L Q22K | CTGGTGCTCTTAAAGATTTTGAATGGAATTAA<br>(SEQ ID NO: 311)<br>TTAATTCCATTCAAAATCTTTAAGAGCACCAG<br>(SEQ ID NO: 312) | 2 |
| 091 | SQVLKW | E15S H16Q<br>L19V D20L<br>Q22K M23w | CTGGTGCTCTTAAAGTGGATTTTGAATGGAAT<br>(SEQ ID NO: 313)<br>ATTCCATTCAAAATCCACTTTAAGAGCACCAG<br>(SEQ ID NO: 314) | 2 |
| 092 | SQVLKH | E15S H16Q<br>L19V D20L<br>Q22K M23H | TGGTGCTCTTAAAGCACATTTTGAATGGAA<br>(SEQ ID NO: 315)<br>TTCCATTCAAAATGTGCTTTAAGAGCACCA<br>(SEQ ID NO: 316) | 2 |
| 093 | SQVLKY | E15S H16Q<br>L19V D20L<br>Q22K M23Y | GGTGCTCTTAAAGTACATTTTGAATGGAA<br>(SEQ ID NO: 317)<br>TTCCATTCAAAATGTACTTTAAGAGCACC<br>(SEQ ID NO: 318) | 2 |
| 094 | SQVLKF | E15S H16Q<br>L19V D20L<br>Q22K M23F | CTGGTGCTCTTAAAGTTCATTTTGAATGGAAT<br>(SEQ ID NO: 319)<br>ATTCCATTCAAAATGAACTTTAAGAGCACCAG<br>(SEQ ID NO: 320) | 2 |
| 095 | SQVLKQ | E15S H16Q<br>L19V D20L<br>Q22K M23Q | TGGTGCTCTTAAAGCAGATTTTGAATGG<br>(SEQ ID NO: 321)<br>CCATTCAAAATCTGCTTTAAGAGCACCA<br>(SEQ ID NO: 322) | 2 |
| 096 | SQVLKS | E15S H16Q<br>L19V D20L<br>Q22K M23S | GGTGCTCTTAAAGAGCATTTTGAATGGA<br>(SEQ ID NO: 323)<br>TCCATTCAAAATGCTCTTTAAGAGCACC<br>(SEQ ID NO: 324) | 2 |
| 097 | SQVLKV | E15S H16Q<br>L19V D20L<br>Q22K M23V | GGTGCTCTTAAAGGTCATTTTGAATGGAA<br>(SEQ ID NO: 325)<br>TTCCATTCAAAATGACCTTTAAGAGCACC<br>(SEQ ID NO: 326) | 2 |
| 098 | SQVLKL | E15S H16Q<br>L19V D20L<br>Q22K M23L | CTGGTGCTCTTAAAGCTCATTTTGAATGGAAT<br>(SEQ ID NO: 327)<br>ATTCCATTCAAAATGAGCTTTAAGAGCACCAG<br>(SEQ ID NO: 328) | 2 |
| 099 | SQVLKT | E15S H16Q<br>L19V D20L<br>Q22K M23T | GGTGCTCTTAAAGACCATTTTGAATGG<br>(SEQ ID NO: 329)<br>CCATTCAAAATGGTCTTTAAGAGCACC<br>(SEQ ID NO: 330) | 2 |
| 100 | ΔG27,<br>SQVLKA | desG27 E15S<br>H16Q L19V<br>D20L Q22K<br>M23A | GGCCATTTTGAATATTAATAATTACAAG<br>(SEQ ID NO: 331)<br>CTTGTAATTATTAATATTCAAAATGGCC<br>(SEQ ID NO: 332) | 2 |

TABLE 5-continued

QuikChange Mutagenesis and Sequence Information Regarding Mutations

| Ref# | Name | Modifications Relative wthIL2 | Primer Set Sequences 5' → 3' | Template |
|---|---|---|---|---|
| 101 | G27K, SQVLKA | E15S H16Q L19V D20L Q22K M23A G27K | GGCCATTTTGAATAAAATTAATAATTAC (SEQ ID NO: 333) GTAATTATTAATTTTATTCAAAATGGCC (SEQ ID NO: 334) | 2 |
| 102 | G27S, SQVLKA | E15S H16Q L19V D20L Q22K M23A G27S | GGCCATTTTGAATTCAATTAATAATTAC (SEQ ID NO: 335) GTAATTATTAATTGAATTCAAAATGGCC (SEQ ID NO: 336) | 2 |
| 103 | R38W, SQVLKA | E15S H16Q L19V D20L Q22K M23A R38W | ATCCCAAACTCACCTGGATGCTCACATTT (SEQ ID NO: 337) AAATGTGAGCATCCAGGTGAGTTTGGGAT (SEQ ID NO: 338) | 2 |
| 104 | R38G, SQVLKA | E15S H16Q L19V D20L Q22K M23A R38G | ATCCCAAACTCACCGGGATGCTCACATTT (SEQ ID NO: 339) AAATGTGAGCATCCCGGTGAGTTTGGGAT (SEQ ID NO: 340) | 2 |
| 105 | M39L, SQVLKA | E15S H16Q L19V D20L Q22K M23A M39L | CCAAACTCACCAGGCTGCTCACATTTAAG (SEQ ID NO: 341) CTTAAATGTGAGCAGCCTGGTGAGTTTGG (SEQ ID NO: 342) | 2 |
| 106 | M39V, SQVLKA | E15S H16Q L19V D20L Q22K M23A M39V | CCAAACTCACCAGGGTGCTCACATTTAAG (SEQ ID NO: 343) CTTAAATGTGAGCACCCTGGTGAGTTTGG (SEQ ID NO: 344) | 2 |
| 107 | F42K, SQVLKA | E15S H16Q L19V D20L Q22K M23A F42K | CCAGGATGCTCACAAAGAAGTTTTACATGCC (SEQ ID NO: 345) GGCATGTAAAACTTCTTTGTGAGCATCCTGG (SEQ ID NO: 346) | 2 |
| 108 | ΔT51, SQVLKA | desT51 E15S H16Q L19V D20L Q22K M23A | TGCCCAAGAAGGCCGAACTGAAACATCT (SEQ ID NO: 347) AGATGTTTCAGTTCGGCCTTCTTGGGCA (SEQ ID NO: 348) | 2 |
| 109 | T51I, SQVLKA | E15S H16Q L19V D20L Q22K M23A T51I | GCCCAAGAAGGCCATAGAACTGAAACATC (SEQ ID NO: 349) GATGTTTCAGTTCTATGGCCTTCTTGGGC (SEQ ID NO: 350) | 2 |
| 110 | H55Y, SQVLKA | E15S H16Q L19V D20L Q22K M23A H55Y | CCACAGAACTGAAATATCTTCAGTGTCTA (SEQ ID NO: 351) TAGACACTGAAGATATTTCAGTTCTGTGG (SEQ ID NO: 352) | 2 |
| 111 | Q74N, SQVLKA | E15S H16Q L19V D20L Q22K M23A Q74N | GCTAAATTTAGCTAACAGCAAAAACTTTC (SEQ ID NO: 353) GAAAGTTTTTGCTGTTAGCTAAATTTAGC (SEQ ID NO: 354) | 2 |
| 112 | Q74H, SQVLKA | E15S H16Q L19V D20L Q22K M23A Q74H | CTAAATTTAGCTCACAGCAAAAACTTTC (SEQ ID NO: 355) GAAAGTTTTTGCTGTGAGCTAAATTTAG (SEQ ID NO: 356) | 2 |
| 113 | Q74S, SQVLKA | E15S H16Q L19V D20L Q22K M23A Q74S | GTGCTAAATTTAGCTTCAAGCAAAAACTTTC (SEQ ID NO: 357) GAAAGTTTTTGCTTGAAGCTAAATTTAGCAC (SEQ ID NO: 358) | 2 |
| 114 | L80F, SQVLKA | E15S H16Q L19V D20L Q22K M23A L80F | CAAAAACTTTCACTTCAGACCCAGGGACTT (SEQ ID NO: 359) AAGTCCCTGGGTCTGAAGTGAAAGTTTTTG (SEQ ID NO: 360) | 2 |
| 115 | L80V, SQVLKA | E15S H16Q L19V D20L Q22K M23A L80V | CAAAAACTTTCACGTAAGACCCAGGGAC (SEQ ID NO: 361) GTCCCTGGGTCTTACGTGAAAGTTTTTG (SEQ ID NO: 362) | 2 |

TABLE 5-continued

QuikChange Mutagenesis and Sequence Information Regarding Mutations

| Ref# | Name | Modifications Relative wthIL2 | Primer Set Sequences 5' → 3' | Template |
|---|---|---|---|---|
| 116 | ΔR81, SQVLKA | desR81 E15S H16Q L19V D20L Q22K M23A | AAAAACTTTCACTTACCCAGGGACTTAATC (SEQ ID NO: 363) GATTAAGTCCCTGGGTAAGTGAAAGTTTTT (SEQ ID NO: 364) | 2 |
| 117 | R81I, SQVLKA | E15S H16Q L19V D20L Q22K M23A R81I | AACTTTCACTTAATACCCAGGGACTTA (SEQ ID NO: 365) TAAGTCCCTGGGTATTAAGTGAAAGTT (SEQ ID NO: 366) | 2 |
| 118 | R81D, SQVLKA | E15S H16Q L19V D20L Q22K M23A R81D | AAAACTTTCACTTAGACCCCAGGGACTTAAT (SEQ ID NO: 367) ATTAAGTCCCTGGGGTCTAAGTGAAAGTTTT (SEQ ID NO: 368) | 2 |
| 119 | R81Y, SQVLKA | E15S H16Q L19V D20L Q22K M23A R81Y | AAAACTTTCACTTATACCCCAGGGACTTAAT (SEQ ID NO: 369) ATTAAGTCCCTGGGGTATAAGTGAAAGTTTT (SEQ ID NO: 370) | 2 |
| 121 | L85V, SQVLKA | E15S H16Q L19V D20L Q22K M23A L85V | TAAGACCCAGGGACGTAATCAGCAATATC (SEQ ID NO: 371) GATATTGCTGATTACGTCCCTGGGTCTTA (SEQ ID NO: 372) | 2 |
| 122 | I86V, SQVLKA | E15S H16Q L19V D20L Q22K M23A I86V | GACCCAGGGACTTAGTCAGCAATATCAAC (SEQ ID NO: 373) GTTGATATTGCTGACTAAGTCCCTGGGTC (SEQ ID NO: 374) | 2 |
| 123 | ΔN88, SQVLKA | E15S H16Q L19V D20L Q22K M23A desN88 | GGGACTTAATCAGCATCAACGTAATAGT (SEQ ID NO: 375) ACTATTACGTTGATGCTGATTAAGTCCC (SEQ ID NO: 376) | 2 |
| 124 | N88E, SQVLKA | E15S H16Q L19V D20L Q22K M23A N88E | GGGACTTAATCAGCGAGATCAACGTAATAG (SEQ ID NO: 377) CTATTACGTTGATCTCGCTGATTAAGTCCC (SEQ ID NO: 378) | 2 |
| 125 | N88Q, SQVLKA | E15S H16Q L19V D20L Q22K M23A N88Q | GGGACTTAATCAGCGAGATCAACGTAATAG (SEQ ID NO: 379) CTATTACGTTGATCTGGCTGATTAAGTCCC (SEQ ID NO: 380) | 2 |
| 127 | V91R, SQVLKA | E15S H16Q L19V D20L Q22K M23A V91R | CAGCAATATCAACCGAATAGTTCTGGAAC (SEQ ID NO: 381) GTTCCAGAACTATTCGGTTGATATTGCTG (SEQ ID NO: 382) | 2 |
| 128 | V91K, SQVLKA | E15S H16Q L19V D20L Q22K M23A V91K | TCAGCAATATCAACAAGATAGTTCTGGAACT (SEQ ID NO: 383) AGTTCCAGAACTATCTTGTTGATATTGCTGA (SEQ ID NO: 384) | 2 |
| 129 | I92F, SQVLKA | E15S H16Q L19V D20L Q22K M23A I92F | GCAATATCAACGTATTCGTTCTGGAACTAAAG (SEQ ID NO: 385) CTTTAGTTCCAGAACGAATACGTTGATATTGC (SEQ ID NO: 386) | 2 |
| 130 | K97Q, SQVLKA | E15S H16Q L19V D20L Q22K M23A K97Q | TAGTTCTGGAACTACAGGGATCTGAAACA (SEQ ID NO: 387) TGTTTCAGATCCCTGTAGTTCCAGAACTA (SEQ ID NO: 388) | 2 |
| 131 | M104A, SQVLKA | E15S H16Q L19V D20L Q22K M23A M104A | CTGAAACAACATTCGCGTGTGAATATGCTG (SEQ ID NO: 389) CAGCATATTCACACGCGAATGTTGTTTCAG (SEQ ID NO: 390) | 2 |
| 132 | D109C, SQVLKA | E15S H16Q L19V D20L Q22K M23A D109C | GTGTGAATATGCTTGTGAGACAGCAACC (SEQ ID NO: 391) GGTTGCTGTCTCACAAGCATATTCACAC (SEQ ID NO: 392) | 2 |

TABLE 5-continued

QuikChange Mutagenesis and Sequence Information Regarding Mutations

| Ref# | Name | Modifications Relative wthIL2 | Primer Set Sequences 5' → 3' | Template |
|------|------|-------------------------------|------------------------------|----------|
| 133 | T113N, SQVLKA | E15S H16Q L19V D20L Q22K M23A T113N | GATGAGACAGCAAACATTGTAGAATTTC (SEQ ID NO: 393) GAAATTCTACAATGTTTGCTGTCTCATC (SEQ ID NO: 394) | 2 |
| 134 | C125A, SQVLKA | E15S H16Q L19V D20L Q22K M23A C125A | GATGGATTACCTTTGCTCAAAGCATCATC (SEQ ID NO: 395) GATGATGCTTTGAGCAAAGGTAATCCATC (SEQ ID NO: 396) | 2 |
| 135 | C125S, SQVLKA | E15S H16Q L19V D20L Q22K M23A C125S | ATGGATTACCTTTTCTCAAAGCATCATCTC (SEQ ID NO: 397) GAGATGATGCTTTGAGAAAAGGTAATCCAT (SEQID NO:398) | 2 |
| 136 | Q126H, SQVLKA | E15S H16Q L19V D20L Q22K M23A Q126H | TTACCTTTTGTCACAGCATCATCTCAAC (SEQ ID NO: 399) GTTGAGATGATGCTGTGACAAAAGGTAA (SEQ ID NO:400) | 2 |
| 137 | Q126M, SQVLKA | E15S H16Q L19V D20L Q22K M23A Q126M | GGATTACCTTTTGTATGAGCATCATCTCAAC (SEQ ID NO: 401) GTTGAGATGATGCTCATACAAAAGGTAATCC (SEQ ID NO: 402) | 2 |
| 138 | Q126K, SQVLKA | E15S H16Q L19V D20L Q22K M23A Q126K | GGATTACCTTTTGTAAAAGCATCATCTC (SEQ ID NO: 403) GAGATGATGCTTTTACAAAAGGTAATCC (SEQ ID NO: 404) | 2 |
| 139 | Q126C, SQVLKA | E15S H16Q L19V D20L Q22K M23A Q126C | GGATTACCTTTTGTTGCAGCATCATCTCAAC (SEQ ID NO: 405) GTTGAGATGATGCTGCAACAAAAGGTAATCC (SEQ ID NO: 406) | 2 |
| 140 | Q126D, SQVLKA | E15S H16Q L19V D20L Q22K M23A Q126D | GGATTACCTTTTGTGACAGCATCATCTCAAC (SEQ ID NO: 407) GTTGAGATGATGCTGTCACAAAAGGTAATCC (SEQ ID NO: 408) | 2 |
| 141 | Q126E, SQVLKA | E15S H16Q L19V D20L Q22K M23A Q126E | GGATTACCTTTTGTGAAAGCATCATCTCA (SEQ ID NO: 409) TGAGATGATGCTTTCACAAAAGGTAATCC (SEQ ID NO: 410) | 2 |
| 142 | Q126G, SQVLKA | E15S H16Q L19V D20L Q22K M23A Q126G | GGATTACCTTTTGTGGAAGCATCATCTCAAC (SEQ ID NO: 411) GTTGAGATGATGCTTCCACAAAAGGTAATCC (SEQ ID NO: 412) | 2 |
| 143 | Q126I, SQVLKA | E15S H16Q L19V D20L Q22K M23A Q126I | GGATTACCTTTTGTATAAGCATCATCTCAAC (SEQ ID NO: 413) GTTGAGATGATGCTTATACAAAAGGTAATCC (SEQ ID NO: 414) | 2 |
| 144 | Q126R, SQVLKA | E15S H16Q L19V D20L Q22K M23A Q126R | GGATTACCTTTTGTCGAAGCATCATCTCAAC (SEQ ID NO: 415) GTTGAGATGATGCTTCGACAAAAGGTAATCC (SEQ ID NO: 416) | 2 |
| 145 | Q126S, SQVLKA | E15S H16Q L19V D20L Q22K M23A Q126S | GGATTACCTTTTGTTCAAGCATCATCTCAAC (SEQ ID NO: 417) GTTGAGATGATGCTTGAACAAAAGGTAATCC (SEQ ID NO: 418) | 2 |
| 146 | Q126T, SQVLKA | E15S H16Q L19V D20L Q22K M23A Q126T | GGATTACCTTTTGTACAAGCATCATCTCAAC (SEQ ID NO: 419) GTTGAGATGATGCTTGTACAAAAGGTAATCC (SEQ ID NO: 420) | 2 |

Example 4. Transient Transfections in HEK293 Cells

All expression vectors were transiently transfected into HEK293 cells (#CRL-1573, ATCC, Manassas, Va.). ~1E6 HEK293 cells were plated into each well of a 6 well tissue culture plate in 2 ml of DMEM (#10569044, Life Technologies) supplemented with 10% Fetal Bovine serum (#SH30071.03, Fisher Scientific, Chicago, Ill.), and grown overnight at 37 C and 5% $CO_2$.

The next day the cells were transfected using Lipofectamine 3000 Reagent (#L3000150, Life Technologies) following the manufacturer's protocol, using 2.5 ug DNA, 5 ul P3000 reagent, and 7.5 ul Lipofectamine 3000 per transfection. The transfected cells were grown at 37 C, 5% CO2 for 48-72 hours and then the conditioned media was harvested.

Example 5. Analysis of Protein Expression

Protein expression for some mutant proteins was measured by ELISA using the Human IL2 V-PLEX ELISA kit (#K151QQD-4, Mesoscale Diagnostics, Baltimore, Md.) following the manufacturer's protocol (transfected media was diluted 1:4 initially, then 1:2 serially). The plate was read on a Meso Quickplex SQ120 (Mesoscale Diagnostics) using the manufacture's preprogrammed setting for this ELISA kit. The human IL2 standard in the kit was used to compute an approximate expression level in the conditioned media samples. Table 6 below details the approximate expression levels for the proteins expressed.

TABLE 6

Expression Levels of Human IL2 Orthologs

| Full ORF # | 35 | 36 | 39 | 40 | 42 | 43 | |
|---|---|---|---|---|---|---|---|
| Mature Peptide # | 15 | 16 | 19 | 20 | 22 | 23 | |
| Wild Type human IL2 Residue | E | H | L | D | Q | M | Expression Level in Transient Transfection (ng/ml) |
| WT IL2 | E | H | L | D | Q | M | 1000 |
| SQVLKA | S | Q | V | L | K | A | 325 |
| -QVLKA | E | Q | V | L | K | A | 75 |
| S-VLKA | S | H | V | L | K | A | 325 |
| SQ-LKA | S | Q | L | L | K | A | 350 |
| SQV-KA | S | Q | V | D | K | A | 325 |
| SQVL-A | S | Q | V | L | Q | A | 225 |
| SQVLK- | S | Q | V | L | K | M | 325 |
| S----- | S | H | L | D | Q | M | 650 |
| -Q---- | E | Q | L | D | Q | M | 1000 |
| --V--- | E | H | V | D | Q | M | 650 |
| ---L-- | E | H | L | L | Q | M | 650 |
| ----K- | E | H | L | D | K | M | 900 |
| -----A | E | H | L | D | Q | A | 1400 |
| SQ---- | S | Q | L | D | Q | M | 625 |
| SQVL-- | S | Q | V | L | Q | M | 225 |

Example 7. Evaluation of Activity of Orthologs in Cell Lines Expressing hoCD122

The IL2 orthologs were evaluated for activity in NKL cells (Robertson, et al (1996) Experimental Hematology 24(3):406-15). To generate the cell line that expresses the human orthogonal hCD122 (hoNKL hoRB), NKL cells were infected with a retrovirus encoding the hoRB hCD122 and co-expressing YFP (MSCV-hoRb-IRES-YFP) in accordance with procedures known in the art.

NKL and NKL hoRB cells were contacted with supernatants from 293 cells transfected with hIL2 orthologs as follows: Cells were seeded in growth medium consisting of RPMI 1640 (ThermoFisher), 10 percent fetal bovine serum (ThermoFisher), 1 percent penicillin/streptomycin (ThermoFisher), 1 percent glutamax (ThermoFisher) at 0.5 million cells per ml. After two days of culture, cells were seeded into 96-well plates (Falcon) at 25 thousand cells per well in 100 µl growth medium. Two-fold or five-fold serial dilutions of transfected 293 cell supernatants were made in growth medium and 100 µl of each dilution was added in duplicate to plates of NKL and NKL hoRB cells at final titrations ranging from 1:2 to 1:31,250. Plates were transferred to a humidified incubator (ThermoFisher) and incubated at 37 degrees centigrade, 5 percent carbon dioxide for three days.

Plates were removed from the incubator and kept at room temperature for 30 minutes. Plates were centrifuged 5 minutes at 400×g and supernatants discarded. Cells were lysed by adding 50 µl per well of a 1:1 dilution of Celltiterglo (Promega) in PBS. Cell lysates were mixed on an orbital shaker (VWR Scientific) for two minutes at 600 rpm then held at room temperature for 10 minutes. Lysates were transferred to black, clear bottom 96 well plates (Costar) and luminescence for NKL cell lysates (FIG. 1) and NKL hoRB cell lysates (FIG. 2) were read as counts per second in an Envision 2103 Multilabel Plate Reader (Perkin Elmer).

To compare the effect of each IL-2 variant upon NKL cell and NKL hoRB cell proliferation, celltiterglo values for cells treated with the supernatants were compared to those obtained for control cells treated with growth medium alone, with 293 supernatant from empty-vector transfection, wild-type IL-2 transfection, or supernatant from human orthogonal IL-2 transfection. The data from these experiments is presented in FIGS. 1 and 2 of the accompanying drawings.

Example 8. Evaluation of Activity of Orthologs in Cell Lines Expressing hoCD122

The IL2 orthologs were evaluated for activity in CD4 positive human T cell clone 3F8 cells. The CD4 positive T cell clone 3F8 was generated by activation of PBMC of a healthy donor with the EBV transformed B cell line JY in two successive rounds of Mixed Leukocyte Reactions followed by single cell cloning by limited dilution as described (Yssel and Spits (2002) Current Protocols in Immunology 7.19.1-7.19.12). The CD4 positive T cell clone 3F8 expresses CD25 and CD122 and proliferates in response to IL-2. To generate the cell line that expresses the human orthogonal hCD122 (ho3F8 hoRB), 3F8 cells were infected with a retrovirus encoding the hoRB hCD122 and co-expressing YFP (MSCV-hoRb-IRES-YFP) in accordance with procedures known in the art.

3F8 and 3F8 hoRb cells were contacted with supernatants from 293 cells transfected with hIL2 orthologs as follows: Cells were grown in growth medium consisting of Yssel's medium (Iscove's modified Dulbecco's Medium (ThermoFisher), 0.25% w/v percent human albumin (Sigma), 1 percent penicillin/streptomycin (ThermoFisher), 1 percent ITS-X Insulin, Transferrin, Selenium (Gibco), 30 mg/L Tansferrin (Roche), 2 mg/L Palmitic Acid (Sigma), 1 percent LA-OA-Albumin Linoleic Acid, Oleic Acid (Sigma), 1 percent human serum (Gemini) (Yssel et al (1984) J Immunol Methods 72: 219-227) at 0.2 million cells per ml with 50 Gy irradiated JY cells at 0.1 million cells per well and 40 Gy irradiated allogeneic PBMC at 1 million cells per mL. After ten days of culture and expansion with human IL-2 at 100 pM, cells were washed and seeded into black, clear bottom 96 well plates (Costar) at 50 thousand cells per well in 50 µl growth medium. Two-fold serial dilutions of transfected 293 cell supernatants were made in growth medium and 50 µl of each dilution was added to plates of 3F8 and 3F8 hoRB cells at final titrations ranging from 1:2 to 1:31250. Plates were transferred to a humidified incubator (ThermoFisher) and incubated at 37 degrees centigrade, 5 percent carbon dioxide for three days.

Plates were removed from the incubator and kept at room temperature for 30 minutes. Cells were lysed by adding 100 µl per well of Celltiterglo (Promega. Cell lysates were mixed on an orbital shaker (VWR Scientific) for two minutes at 600 rpm then held at room temperature for 10 minutes. Luminescence for 3F8 cell lysates (FIG. 1) and 3F8 hoRB cell lysates (FIG. 2) were read as counts per second in an Envision 2103 Multilabel Plate Reader (Perkin Elmer).

To compare the effect of each IL-2 variant upon 3F8 cell and 3F8 hoRB cell proliferation, celltiterglo values for cells treated with the supernatants were compared to those obtained for control cells treated with growth medium alone, with 293 supernatant from empty-vector transfection, wild-type IL-2 transfection, or supernatant from human orthogonal IL-2 transfection. The data from these experiments is presented in Table 4.

We claim:

1. A human IL-2 (hIL2) ortholog polypeptide consisting of the amino acid sequence set forth in SEQ ID NO:20, wherein polyethylene glycol (PEG) is linked to the amino terminus of the polypeptide and the PEG is a 40 kD branched PEG comprising two 20 kD arms.

2. A pharmaceutical formulation comprising the hIL2 ortholog polypeptide of claim 1.

* * * * *